US012780779B2

(12) United States Patent
Chu et al.

(10) Patent No.: US 12,780,779 B2
(45) Date of Patent: Nov. 3, 2026

(54) CXCR6 SULFONAMIDE COMPOUNDS

(71) Applicant: CHEMOCENTRYX, INC., San Carlos, CA (US)

(72) Inventors: Hiufung Chu, Brookline, MA (US); Pingchen Fan, Hayward, CA (US); Yandong Li, San Diego, CA (US); Viengkham Malathong, Mountain View, CA (US); Jay Powers, Sisters, OR (US); Hiroko Tanaka, Mountain View, CA (US); Yibin Zeng, Foster City, CA (US); Penglie Zhang, Foster City, CA (US)

(73) Assignee: CHEMOCENTRYX, INC., San Carlos, CA (US)

( * ) Notice: Subject to any disclaimer, the term of this patent is extended or adjusted under 35 U.S.C. 154(b) by 0 days.

(21) Appl. No.: 18/186,265

(22) Filed: Mar. 20, 2023

(65) Prior Publication Data

US 2023/0339851 A1 Oct. 26, 2023

Related U.S. Application Data

(60) Provisional application No. 63/321,818, filed on Mar. 21, 2022.

(51) Int. Cl.

| | |
|---|---|
| *C07C 311/44* | (2006.01) |
| *A61P 35/00* | (2006.01) |
| *C07C 211/60* | (2006.01) |
| *C07C 311/46* | (2006.01) |
| *C07D 207/16* | (2006.01) |
| *C07D 207/22* | (2006.01) |
| *C07D 211/60* | (2006.01) |
| *C07D 211/62* | (2006.01) |
| *C07D 213/81* | (2006.01) |
| *C07D 231/14* | (2006.01) |
| *C07D 233/60* | (2006.01) |
| *C07D 233/64* | (2006.01) |
| *C07D 233/90* | (2006.01) |
| *C07D 237/24* | (2006.01) |
| *C07D 239/28* | (2006.01) |
| *C07D 261/18* | (2006.01) |
| *C07D 265/30* | (2006.01) |
| *C07D 275/03* | (2006.01) |

(Continued)

(52) U.S. Cl.

CPC .......... *C07C 311/44* (2013.01); *C07D 207/16* (2013.01); *C07D 207/22* (2013.01); *C07D 211/60* (2013.01); *C07D 211/62* (2013.01); *C07D 213/81* (2013.01); *C07D 231/14* (2013.01); *C07D 233/90* (2013.01); *C07D 237/24* (2013.01); *C07D 239/28* (2013.01); *C07D 261/18* (2013.01); *C07D 265/30* (2013.01); *C07D 275/03* (2013.01); *C07D 295/195* (2013.01); *C07D 307/16* (2013.01); *C07D 307/24* (2013.01); *C07D 307/68* (2013.01); *C07D 309/06* (2013.01); *C07D 309/08* (2013.01); *C07D 309/10* (2013.01); *C07D 309/28* (2013.01); *C07D 317/60* (2013.01); *C07D 317/66* (2013.01); *C07D 319/12* (2013.01); *C07D 335/02* (2013.01); *C07D 471/08* (2013.01); *C07D 493/08* (2013.01); *C07C 2601/02* (2017.05); *C07C 2601/04* (2017.05); *C07C 2601/08* (2017.05); *C07C 2601/14* (2017.05); *C07C 2601/16* (2017.05); *C07C 2601/18* (2017.05); *C07C 2602/08* (2017.05); *C07C 2602/18* (2017.05); *C07C 2602/42* (2017.05)

(58) Field of Classification Search

None

See application file for complete search history.

(56) References Cited

U.S. PATENT DOCUMENTS 4,166,452 A 9/1979 Generales, Jr.
4,256,108 A 3/1981 Theeuwes (Continued)

FOREIGN PATENT DOCUMENTS

KR 10-2009-0071679 A 7/2009
WO 90/13332 A1 11/1990

(Continued)

OTHER PUBLICATIONS

RN329901-65-7, registry database compound, 2001.*

(Continued)

*Primary Examiner* — Sun Jae Yoo
(74) *Attorney, Agent, or Firm* — Cindy Kan

(57) ABSTRACT

Provided are sulfonamide compounds having formula (I):

(I)

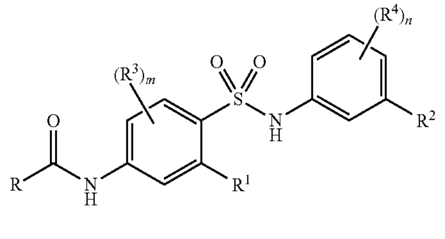

or a pharmaceutically acceptable salt thereof, wherein R, $R^1$, $R^2$, $R^3$, $R^4$ and the subscripts n and m have the meanings provided in the specification. The compounds are useful for treating diseases and conditions associated with CXCR6 activity.

26 Claims, No Drawings

(51) Int. Cl.

| | |
|---|---|
| ***C07D 295/195*** | (2006.01) |
| ***C07D 307/16*** | (2006.01) |
| ***C07D 307/24*** | (2006.01) |
| ***C07D 307/68*** | (2006.01) |
| ***C07D 309/06*** | (2006.01) |
| ***C07D 309/08*** | (2006.01) |
| ***C07D 309/10*** | (2006.01) |
| ***C07D 309/28*** | (2006.01) |
| ***C07D 317/46*** | (2006.01) |
| ***C07D 317/48*** | (2006.01) |
| ***C07D 317/60*** | (2006.01) |
| ***C07D 317/66*** | (2006.01) |
| ***C07D 319/12*** | (2006.01) |
| ***C07D 335/02*** | (2006.01) |
| ***C07D 471/08*** | (2006.01) |
| ***C07D 493/08*** | (2006.01) |

(56) References Cited

U.S. PATENT DOCUMENTS

| | | | |
|---|---|---|---|
| 4,265,874 | A | 5/1981 | Bonsen et al. |
| 4,733,655 | A | 3/1988 | Smal |
| 4,800,882 | A | 1/1989 | Gianturco |
| 4,886,062 | A | 12/1989 | Wiktor |
| 5,102,417 | A | 4/1992 | Palmaz et al. |
| 5,419,760 | A | 5/1995 | Narciso |
| 5,429,634 | A | 7/1995 | Narciso |
| 5,833,651 | A | 11/1998 | Donovan et al. |
| 6,388,131 | B2 | 5/2002 | Medina et al. |
| 6,451,339 | B2 | 9/2002 | Patel et al. |
| 6,770,729 | B2 | 8/2004 | Van Antwerp |
| 2004/0243225 | A1 | 12/2004 | Ragheb et al. |
| 2009/0093485 | A1 | 4/2009 | Bladh et al. |
| 2011/0243844 | A1 | 10/2011 | McCauley |
| 2021/0120811 | A1 | 4/2021 | Krause et al. |

FOREIGN PATENT DOCUMENTS

| | | | |
|---|---|---|---|
| WO | 91/12779 | A1 | 9/1991 |
| WO | 01/17955 | A2 | 3/2001 |
| WO | 2008/064116 | A2 | 5/2008 |
| WO | 2008/146272 | A2 | 12/2008 |
| WO | 2013/127268 | A1 | 9/2013 |
| WO | 2020/243415 | A2 | 12/2020 |
| WO | WO-2023059914 | A1 * | 4/2023 |

OTHER PUBLICATIONS

RN329901-65-7-properties, 2024, registry database compound abstract of properties.*

RN 1388996-23-3, registry database compound, 2012.*

RN 1388996-23-3-properties, registry database compound properties, 2012.*

2761485-20-3, registry database compound, Jul. 7, 2022.*

RN 2419474-87-4, registry database compound, Jun. 5, 2020.*

RN 1607183-50-5, registry database compound, 2014.*

RN 1606237-66-4, registry database compound, 2014.*

"2-amino-N-[3-chloro-4-[[(2-chlorophenyl)amino]sulfonyl]phenyl]-propanamide", CAS Registry Number: 1576417-66-7, Mar. 31, 2014.

"3-amino-N-[3-chloro-4-[[(2-chlorophenyl)amino]sulfonyl]phenyl]-2,2-dimethyl-propanamide", CAS Registry Number: 1590585-08-2, Apr. 25, 2014.

"N-[3-chloro-4-[[(2-chlorophenyl)amino]sulfonyl]phenyl]-2-piperidinecarboxamide", CAS Registry Number: 1582899-29-3, Apr. 10, 2014.

"N-[4-[[(2-methoxyphenyl)amino]sulfonyl]-3,5-dimethylphenyl]-acetamide", CAS Registry Number: 1311928-38-7, Jul. 7, 2011.

"Pubchem CID 146090366", Create date: Jun. 5, 2020.

Berge et al., "Pharmaceutical salts", Journal of Pharmaceutical Sciences, vol. 66(1), pp. 1-19(1977).

Engers, D.W., et al.; "Synthesis and SAR of novel 4-(phenylsulfamoyl)phenylacetamide mGlu4 positive allosteric modulators (PAMs) identified by functional high-throughput screening (HTS)", Bioorganic & Medicinal Chemistry Letters, vol. 20(17), pp. 5175-5178(2010).

International Preliminary Report on Patentability received for PCT Patent Application No. PCT/US23/64686, mailed on Oct. 3, 2024, 7 pages.

International Search Report and Written Opinion received for PCT Patent Application No. PCT/US23/064686, mailed on Aug. 23, 2023, 9 pages.

* cited by examiner

CXCR6 SULFONAMIDE COMPOUNDS

CROSS-REFERENCES TO RELATED APPLICATIONS

This application claims the benefit of priority under 35 U.S.C. § 119(e) to U.S. Provisional Application Ser. No. 63/321,818 filed Mar. 21, 2022, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

CXCR6 is the seven transmembrane domain G protein-coupled receptor (GPCR) target for the natural ligand, CXCL16, a chemokine that exists in both membrane-anchored and soluble forms. CXCR6 is a transmembrane protein abundantly expressed on the surface of dendritic cells and by CD4+ T cells, CD8+ T cells, natural killer T (NKT) cells and natural killer (NK) cells. The CXCR6/CXCL16 axis plays a critical role in pro-inflammatory and pro-fibrotic events in liver and kidney. Knockout mouse studies indicate that CXCR6 and CXCL16 contribute to pro-inflammatory cytokine expression in liver and kidney. CXCR6-deficient mice were protected from liver fibrosis and CXCL16 deficiency resulted in protection from hypertensive renal injury and fibrosis.

In chronic liver injury, the production of the soluble form of CXCL16 from sinusoidal epithelial cells is increased. The secretion of CXCL16 promotes NKT cells expressing CXCR6 to migrate to the liver. The transmembrane form of CXCL16 functions as an adhesion molecule, anchoring activated NKT cells. NKT cells secrete pro-inflammatory cytokines TNF-α and IFN-γ leading to increased levels of CXCL16 and attract more NKT cells in a positive feedback loop. In this way, CXCR6 and its ligand CXCL16 promote liver fibrosis. In mice with diet-induced hepatic injury, the administration of an anti-CXCL16a antibody blocked the accumulation of hepatic NKT cells and pro-inflammatory cytokines. In liver tissue taken from patients with liver disease, hepatic CXCR6 and CXCL16 mRNA expression is upregulated independent of the underlying etiology of liver disease, such as viral hepatitis, alcoholism, or cholestatic disorders.

CXCL16 expression has been demonstrated in a variety of tissues and cells including activated endothelial cells. Additionally, it was shown that CXCL16 functions as a potent and direct activator of NF-κB and induces κB-dependent pro-inflammatory gene transcription through interaction with heterotrimeric G-proteins triggering downstream PI3K, PDK-1, Akt, and IKB kinase (IKK) signal transduction events. Through a cytokine antibody array, it was shown that CXCL16 protein production was increased in aggressive prostate cancer cells compared to the less aggressive prostate cancer cells or benign prostate cells. It was also found that both IL-1β and TNFa significantly induced CXCL16 production by LNCaP and PC3 cells, thereby indicating inflammatory cytokines may play a role in CXCL16 induction. CXCR6 and CXCL16 are highly expressed in many types of human cancers, including prostate cancer, papillary thyroid carcinoma, non-small cell lung carcinoma, gastric cancer and hepatocellular carcinoma (HCC) and are consistently expressed in hepatoma cell lines. CXCR6 expression profile is low in normal hepatocytes, increases in noninvasive HCC cells, and reaches highest levels in invasive HCCs. Upregulation of CXCR6 receptor contributes to a pro-inflammatory tumor microenvironment that promotes metastasis and has been identified as an independent predictor for increased recurrence and poor survival in patients with HCCs. Knockdown of CXCR6 receptor inhibits HCC cell invasion in vitro and inhibits tumorigenicity, neutrophil recruitment, angiogenesis, and metastasis of hepatoma cells in vivo.

Recently, the Kuchroo group discovered that the most active type of T cell in autoimmune diseases is a subset of Th17 cells that express CXCR6. Th17 cells in general are responsible for a wide variety of autoimmune diseases including rheumatoid arthritis, multiple sclerosis, plaque psoriasis, pustular psoriasis, inflammatory bowel disease, asthma, diabetes, and systemic lupus erythematosus, among others. The CXCR6-expressing population of Th17 cells displays markers demonstrating that these cells are more activated than Th17 cells lacking CXCR6. The CXCR6-expressors display a different trafficking pattern than CXCR6-deficient Th17 cells, accumulating within tissues at sites of autoimmune inflammation.

Based on importance of CXCR6 receptor in pro-inflammatory, autoimmune and pro-fibrotic events in liver, kidney, and heart, the compounds which inhibit CXCR6 receptor activity are considered to be useful in treating, amelioration of the symptoms, or preventing inflammation, liver, renal, and heart injury and fibrosis including non-alcoholic fatty liver disease (NAFLD), acute kidney injury, and reperfusion injury. Additionally, small molecule antagonists to CXCR6/CXCL16 signaling may provide a venue to ameliorate tumor progression and metastasis. Finally, an inhibitor of CXCR6 is considered useful in ameliorating Th17-mediated autoimmune diseases, which include rheumatoid arthritis, multiple sclerosis, plaque psoriasis, pustular psoriasis, inflammatory bowel disease, asthma, diabetes, and systemic lupus erythematosus.

Accordingly, described herein are CXCR6 receptor inhibitor compounds, as well as methods of treating diseases or conditions mediated by CXCR6/CXCL16 signaling pathway in a mammal in need thereof.

BRIEF SUMMARY OF THE INVENTION

In one aspect, provided herein are compounds of formula (I):

(I)

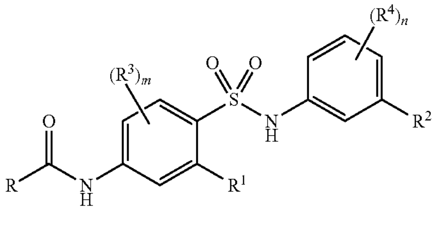

or a pharmaceutically acceptable salt thereof, wherein R, $R^1$, $R^2$, $R^3$, $R^4$ and the subscripts n and m have the meanings provided below.

In a related aspect, provided herein is a pharmaceutical composition comprising a compound of any of formulae (I), (Ia), (Ia1), (Ia2), (Ia3), or (Ia4), or a pharmaceutically acceptable salt thereof, and at least one pharmaceutically acceptable excipient.

In some embodiments, the compound of any of formulae (I), (Ia), (Ia1), (Ia2), (Ia3), or (Ia4), or a pharmaceutically acceptable salt thereof, is formulated for administration to a mammal by intravenous administration, subcutaneous administration, oral administration, inhalation, nasal administration, transdermal administration, or ophthalmic administration. In some embodiments, the compound of any of formulae (I), (Ia), (Ia1), (Ia2), (Ia3), or (Ia4), or a pharmaceutically acceptable salt thereof, is in the form of a tablet, a pill, a capsule, a liquid, a suspension, a gel, a dispersion, a solution, an emulsion, an ointment, or a lotion.

In another aspect, described herein is a method of treating a disease or condition mediated by CXCR6/CXCL16 signaling pathway in a mammal in need thereof comprising administering a CXCR6 inhibitor compound as described herein, or a pharmaceutically acceptable salt, solvate, or N-oxide thereof, to the mammal in need thereof.

In some embodiments, the disease or condition is cancer. In some embodiments, the cancer is hepatocellular carcinoma. In some embodiments, the cancer is prostate cancer. In some embodiments, the cancer is gastric adenocarcinoma. In some embodiments, the cancer is bladder cancer. In some embodiments, the cancer is papillary thyroid carcinoma. In some embodiments, the cancer is non-small cell lung carcinoma. In some embodiments, the disease or condition is autoimmune hepatitis. In some embodiments, the disease or condition is a kidney injury or lung injury. In some embodiments, the kidney injury is acute kidney injury. In some embodiments, the disease or condition is a myocardial ischemia or reperfusion injury. In some embodiments, the disease or condition is an inflammatory disease or condition.

In still another aspect, provided herein is the use of a CXCR6 inhibitor compound as described herein, or a pharmaceutically acceptable salt, solvate, or N-oxide thereof, in the manufacture of a medicament for the treatment or amelioration of the symptoms of a disease or condition that is mediated by CXCR6/CXCL16 signaling pathway.

BRIEF DESCRIPTION OF THE DRAWINGS

Not Applicable

DETAILED DESCRIPTION OF THE INVENTION

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one or two double bonds between ring vertices. "Cycloalkyl" is also meant to refer to bicyclic and polycyclic hydrocarbon rings such as, for example, bicyclo[2.2.1]heptane, bicyclo[2.2.2]octane, etc. The terms "heterocycloalkane," "heterocycloalkyl," "heterocyclyl," and "heterocyclic ring" refers to a cycloalkyl group wherein one to five of the carbon ring vertices are replaced by heteroatoms selected from N, O, and S, wherein the nitrogen and sulfur atoms are optionally oxidized, and the nitrogen atom(s) are optionally quaternized. The heterocycloalkane may be indicated as a monocyclic, a bicyclic or a polycylic ring system. Non limiting examples of heterocycloalkane groups include pyrrolidine, imidazolidine, pyrazolidine, butyrolactam, valerolactam, imidazolidinone, hydantoin, dioxolane, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkane group can be attached to the remainder of the molecule through a ring carbon or a heteroatom.

As used herein, the term "6- to 12-membered fused or bridged carbocyclic or heterocyclic ring" refers to a ring system having the indicated number of ring vertices (e.g., 6- to 12) and which includes bridged systems (e.g., norbornanyl for a carbocyclic system, and quinuclidinyl for a heterocyclic system) as well as fused systems. The ring systems can contain 0, 1 or 2 double bonds. Additionally, for these non-aromatic systems, a fused ring is meant to include a single atom shared by two ring (e.g., a spriocyclic system). Examples include the following:

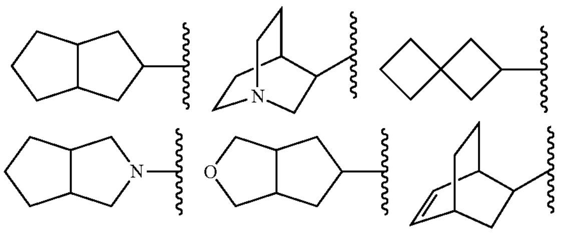

When the terms "bridged cycloalkyl" or "bridged cycloalkenyl" are used, the ring systems are saturated and unsaturated ring systems respectively, having the indicated number of carbon atom ring vertices (no heteroatoms as ring vertices). Examples include norbornanyl, bicyclo[2.2.2]oct-2-enyl, bicyclo[2.2.1]heptanyl, and the like.

The term "alkylene" by itself or as part of another substituent means a divalent radical derived from an alkane, as exemplified by $—CH_2CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "∿", that intersects a single, double or triple bond in any chemical structure depicted herein, represents the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like. Similarly, the term "haloalkoxy," is meant to include monohaloalkoxy and polyhaloalkoxy. For example, the term "$C_{1-6}$ haloalkoxy" is meant to include trifluoromethoxy, 2,2,2-trifluoroethoxy, and 4-chlorobutoxy.

Terms such as "hydroxyalkyl," are meant to include monohydroxyalkyl and polyhydroxyalkyl. For example, the term "$C_{1-6}$ hydroxyalkyl" is meant to refer to an alkyl group having from one to six carbon atoms, and one or more hydroxy groups (generally one or two hydroxy groups) as substituents. For example, 4-hydroxybutyl, 3-hydroxypropyl, and the like.

Compound terms such as "alkoxyalkyl" and "alkoxyalkoxy," are used in their conventional sense and refer to groups having the indicated number of carbon atoms and attached to the remainder of the molecule through the second listed component of the compound group. For example, a $C_{1-4}$alkoxy$C_{1-4}$alkyl group refers to methoxymethyl, ethoxymethyl, and 2-(n-butoxy)ethyl. Similarly, a $C_{1-4}$alkoxy$C_{1-4}$alkoxy group refers to methoxymethoxy, ethoxymethoxy, and 3-(n-propoxy)propoxy, and the like.

The term "aryl" means, unless otherwise stated, a polyunsaturated, aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below. A "5- or 6-membered heteroaryl" group refers to a group above, which is monocyclic and has 5 or 6 ring vertices.

As used herein, the term "heteroatom" is meant to include oxygen (O), nitrogen (N), sulfur (S) and silicon (Si).

More specifically, the phrase "4- to 7-membered heterocyclic ring having 1 or 2 heteroatoms as ring vertices selected from N, O and S" refers to a single ring having 4 to 7 ring vertices, wherein 1 or 2 of the ring vertices are heteroatoms (N, O, or S). Examples of such rings include morpholine, pyrrolidine, tetrahydrofuran, thiomorpholine, piperidine, piperazine, and the like. The ring may have 0 or 1 double bond between ring vertices.

The phrase "bicyclic 9- or 10-membered fused aromatic or heteroaromatic ring having 0 to 4 heteroatoms as ring vertices selected from N, O and S" refers to a ring system in which two adjacent ring vertices of a first ring are also adjacent ring vertices of a second ring, and wherein at least one of the two rings is aromatic. In some embodiments, both rings have aromatic character (e.g., naphthalene, quinolone, quinazoline, benzimidazole, benzothiophene, benzopyrazole). In some embodiments, only one ring is aromatic (e.g., indane, 1,2,3,4-tetrahydronaphthalene, 5,6,7,8-tetrahydroquinoline, 1,2,3,4-tetrahydroisoquinoline).

The phrase "monocyclic 5- or 6-membered aromatic or heteroaromatic ring having 0 to 3 heteroatoms as ring vertices selected from N, O and S" refers to a single ring which is aromatic (phenyl) or heteroaromatic (e.g., pyridine, thiophene, furan, pyrimidine, pyrazine).

A "3- to 6-membered spirocyclic ring" as a substituent refers to a group having two points of attachment to a carbon atom that is a ring vertex or part of an alkylene group. For example, the group:

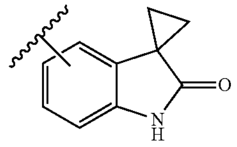

is a bicyclic 9- or 10-membered fused aromatic or heteroaromatic ring having 1 heteroatom as a ring vertex, and which is substituted with a 3-membered spirocyclic ring and oxo.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium (2H) or carbon-13 ($^{13}C$). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The term "and acid isosteres" means, unless otherwise stated, a group which can replace a carboxylic acid, having an acidic functionality and steric and electronic characteristics that provide a level of activity (or other compound characteristic such as solubility) similar to a carboxylic acid. Representative acid isosteres include, hydroxamic acids, sulfonic acids, sulfinic acids, sulfonamides, acyl-sulfonamides, phosphonic acids, phosphinic acids, phosphoric acids, tetrazole, and oxo-oxadiazoles.

Compounds of the invention having formula I can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more a bonds. Rotamers are conformers that differ by rotation about only a single a bond.

General

The present invention derives from the discovery that compounds of formula I act as potent antagonists of the CXCR6 receptor. The compounds have in vivo anti-inflammatory activity and have superior pharmacokinetic properties. Accordingly, the compounds provided herein are useful in pharmaceutical compositions, methods for the treatment of CXCR6-mediated diseases, and as controls in assays for the identification of competitive CXCR6 antagonists.

III. Compounds

In one aspect, provided herein are compounds of formula (I):

(I)

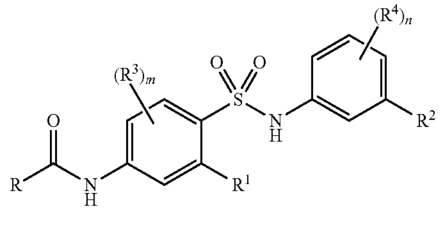

or a pharmaceutically acceptable salt thereof, wherein:

R is a member selected from the group consisting of:

i) $C_{1-8}$ alkyl and $C_{2-8}$ alkenyl, each of which is unsubstituted or substituted with $R^5$, $R^6$ and/or $R^7$;

ii) $C_{3-7}$ cycloalkyl, having 0, 1 or 2 double bonds between ring vertices and which is substituted with 0 to 4 $R^d$;

iii) 4- to 7-membered monocyclic heterocyclic ring having 1 or 2 heteroatoms as ring vertices selected from N, O, S and $S(O)_2$, having 0, 1 or 2 double bonds between ring vertices and which is substituted with 0 to 4 $R^d$;

iv) 6- to 12-membered fused or bridged carbocyclic or heterocyclic ring having 1 to 2 heteroatoms as ring vertices selected from N, O, S and $S(O)_2$, each of which has 0, 1 or 2 double bonds between ring vertices and is substituted with 0 to 4 $R^d$;

(v) phenyl or —CO-phenyl, each of which is substituted with 0 to 4 $R^a$;

(vi) 5- or 6-membered heteroaryl ring, substituted with 0 to 3 $R^a$;

(vii) bicyclic 9- or 10-membered fused aromatic or heteroaromatic ring having 0 to 4 heteroatoms as ring vertices selected from N, O, S and $S(O)_2$, and which is substituted with 0 to 5 $R^a$;

$R^1$ is a member selected from the group consisting of halogen, CN, $C_{1-8}$ alkyl, $C_{1-8}$ haloalkyl, $C_{1-4}$ alkoxy$C_{1-4}$ alkyl, $C_{2-8}$ alkenyl, $C_{2-8}$ alkynyl, $C_{3-8}$ cycloalkyl, OH, and O—$R^{1a}$, wherein each $R^{1a}$ is independently selected from the group consisting of $C_{1-8}$ alkyl, $C_{1-8}$ haloalkyl, and $C_{3-8}$ cycloalkyl, and wherein each $R^{1a}$ is substituted with 0 to 4 members selected from the group consisting of halogen, CN, OH, amino, $C_{1-4}$ alkylamino, and di$C_{1-4}$ alkylamino;

$R^2$ is a member selected from the group consisting of H, halogen, CN, $C_{1-8}$ alkyl, $C_{1-8}$ haloalkyl, $C_{1-8}$ hydroxyalkyl, $C_{2-8}$ alkenyl, $C_{2-8}$ alkynyl, $C_{3-8}$ cycloalkyl, —$NH_2$, —NH($C_{1-4}$ alkyl), —N($C_{1-4}$ alkyl)$_2$, OH, and O—$R^{2a}$, wherein each $R^{2a}$ is independently selected from the group consisting of $C_{1-8}$ alkyl, $C_{1-8}$ haloalkyl, and $C_{3-8}$ cycloalkyl, and wherein each $R^{2a}$ is substituted with 0 to 4 members selected from the group consisting of halogen, CN, OH, amino, $C_{1-4}$ alkylamino, and di$C_{1-4}$ alkylamino;

the subscript m is 0, 1, 2 or 3;

each $R^3$ is a member selected from the group consisting of halogen, CN, $C_{1-6}$ alkyl, $C_{1-6}$ haloalkyl, $C_{1-6}$ hydroxyalkyl, $C_{3-6}$ cycloalkyl, $C_{1-6}$ alkoxy, and $C_{1-6}$ haloalkoxy; the subscript n is 0, 1, 2, 3 or 4;

each $R^4$ is a member selected from the group consisting of halogen, CN, $C_{1-6}$ alkyl, $C_{2-8}$ alkenyl, $C_{1-6}$ haloalkyl, $C_{1-6}$ hydroxyalkyl, $C_{3-6}$ cycloalkyl, $C_{1-6}$ alkoxy, and $C_{1-6}$ haloalkoxy; or $R^4$ when attached to a carbon adjacent to the carbon atom bearing $R^2$ is optionally combined with $R^2$ to form a 5- or 6-membered heterocyclic ring having 1 to 2 heteroatoms as ring vertices selected from N and O, and is substituted with 0 to 4 halogen;

and when $R^2$ is H, then n is 1, 2, 3 or 4;

$R^5$, $R^6$ and $R^7$ are each independently selected from the group consisting of OH, $C_{1-6}$ alkyl, $C_{1-6}$ haloalkyl, $C_{1-6}$ hydroxyalkyl, $C_{1-6}$ alkoxy, $C_{2-8}$ alkenyl, $C_{2-8}$ alkynyl, $C_{1-4}$ alkoxy$C_{1-4}$ alkoxy, —X—Y, —X—$CO_2R^b$, —X—$NR^bR^c$, —X—$NR^bCOR^c$, —X—$NR^bCO_2R^c$, —X—$NR^bS(O)_2R^c$, —X—$NR^bCONR^bR^c$, and —X—$CONR^bR^c$, wherein each X is a bond or $C_{1-4}$ alkylene, and each Y is phenyl, $C_{3-7}$ cycloalkyl, $C_{5-7}$ cycloalkenyl, $C_6$-8 bridged cycloalkyl, $C_6$-8 bridged cycloalkenyl, a 4- to 7-membered heterocyclic ring having 1 or 2 heteroatoms as ring vertices selected from N, O, S and $S(O)_2$, and having 0 or 1 double bonds between ring vertices, a 6- to 12-membered fused or bridged heterocyclic ring having 1 to 2 heteroatoms as ring vertices selected from N, O, S and $S(O)_2$, and having 0, 1 or 2 double bonds between ring vertices, or a 5- or 6-membered heteroaryl ring having 1 to 3 heteroatoms as ring vertices selected from N, O, and S; and wherein each Y is unsubstituted or substituted with 1 to 4 $R^d$; or two of $R^5$, $R^6$ and $R^7$ are joined to form $C_{3-6}$ cycloalkyl;

each $R^a$ is independently selected from the group consisting of halogen, cyano, OH, $C_{1-4}$ alkyl, $C_{1-4}$ alkoxy, $C_{1-4}$ haloalkyl, $C_{1-4}$ haloalkoxy, $C_{1-4}$ hydroxyalkyl, —$NH_2$, —NH($C_{1-4}$ alkyl), —N($C_{1-4}$ alkyl)$_2$, —$CO_2H$, —$CO_2C_{1-4}$ alkyl, and $C_{3-6}$ cycloalkyl;

each $R^b$ and $R^c$ is independently selected from the group consisting of hydrogen, $C_{1-4}$ alkyl, $C_{1-4}$ haloalkyl, $C_{1-4}$ hydroxyalkyl, and $C_{3-6}$ cycloalkyl; and each $R^d$ is independently selected from the group consisting of hydroxyl, oxo, halogen, cyano, $C_{1-4}$ alkyl, $C_{1-4}$ haloalkyl, $C_{1-4}$ alkoxy, $C_{1-4}$ haloalkoxy, $C_{1-4}$ hydroxyalkyl, $C_{1-4}$ alkoxy$C_{1-4}$ alkyl, —$NH_2$, —NH($C_{1-4}$ alkyl), —N($C_{1-4}$ alkyl)$_2$, —$CO_2H$, —$CO_2C_{1-4}$ alkyl, —$COC_{1-4}$ alkyl, —$NHCO_2C_{1-4}$ alkyl, and $C_{3-6}$ cycloalkyl.

In one group of embodiments, compounds of formula (I) are provided, as well as their pharmaceutically acceptable salts, wherein R is $C_{1-4}$ alkyl which is unsubstituted or substituted with $R^5$, $R^6$ and/or $R^7$. In another group of embodiments, compounds of formula (I) are provided, as well as their pharmaceutically acceptable salts, wherein R is $C_{3-7}$ cycloalkyl, having 0, 1 or 2 double bonds between ring vertices and which is substituted with 0 to 4 $R^d$. In still other embodiments, compounds of formula (I) are provided, as well as their pharmaceutically acceptable salts, wherein R is a 4- to 7-membered monocyclic heterocyclic ring having 1 or 2 heteroatoms as ring vertices selected from N, O, S and $S(O)_2$, having 0, 1 or 2 double bonds between ring vertices and which is substituted with 0 to 4 $R^d$. In some selected embodiments, compounds of formula (I) are provided, as well as their pharmaceutically acceptable salts, wherein R is pyrrolidinyl, piperidinyl, tetrahydropyranyl, morpholinyl, and tetrahydrofuranyl, each of which is substituted with 0 to 4 $R^d$. In another group of embodiments, compounds of formula (I) are provided, as well as their pharmaceutically acceptable salts, wherein R is phenyl or —CO-phenyl, each of which is substituted with 0 to 4 $R^a$. In yet another group of embodiments, compounds of formula (I) are provided, as well as their pharmaceutically acceptable salts, wherein R is a 5- or 6-membered heteroaryl ring, substituted with 0 to 3 $R^a$. In some selected embodiments, compounds of formula (I) are provided, as well as their pharmaceutically acceptable salts, wherein R is selected from the group consisting of pyrrolyl, furanyl, thienyl, pyrazolyl, imidazolyl, triazolyl, 1,2-oxazolyl, 1,3-oxazolyl, 1,2-thiazolyl, 1,3-thiazolyl, 1,3-thiazolyl, pyridyl, pyrimidinyl, and pyrazinyl, each of which is substituted with 0 to 3 $R^a$.

In some embodiments, compounds of formula (I) are provided, as well as their pharmaceutically acceptable salts, wherein $R^3$ and $R^4$ are independently selected from the group consisting of halogen, CN, $C_{1-4}$ alkyl, $C_{1-4}$ haloalkyl, $C_{1-4}$ hydroxyalkyl, $C_{3-6}$ cycloalkyl, $C_{1-4}$ alkoxy, and $C_{1-4}$ haloalkoxy.

In some embodiments, compounds of formula (I) are provided, and are represented by formula (Ia):

(Ia)

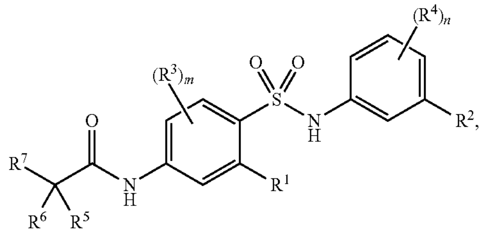

or a pharmaceutically acceptable salt thereof, wherein m is 0 or 1; and n is 0 or 1. In further embodiments, m is 0, and n is 0 or 1. In other embodiments of formula (Ia), $R^5$, $R^6$ and $R^7$ are each independently selected from the group consisting of OH, $C_{1-6}$ alkyl, $C_{1-6}$ haloalkyl, $C_{1-6}$ hydroxyalkyl, $C_{1-6}$ alkoxy, —X—$CO_2R^b$, —X—$NR^bR^c$, —X—$NR^b$-$COR^c$, —X—$NR^bCO_2R^c$, —X—$NR^bS(O)_2R^c$, —X—$NR^b$-$CONR^bR^c$, and —X—$CONR^bR^c$, wherein each X is a bond or $C_{1-4}$ alkylene.

In some embodiments, compounds of formula (I) are provided, and are represented by formula (Ia1):

(Ia1)

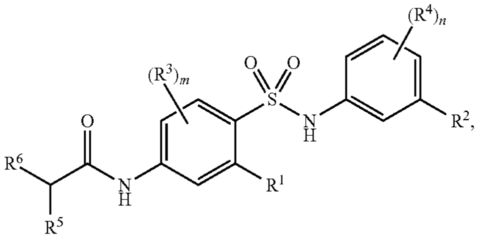

or a pharmaceutically acceptable salt thereof, wherein m is 0 or 1; and n is 0 or 1. In some embodiments of formula (Ia1), $R^1$ is —$OR^{1a}$ wherein $R^{1a}$ is methyl, ethyl or propyl; $R^2$ is $CF_3$, $OCF_3$, or cyclopropyl; the subscript m is 0; the subscript n is 0 or 1; $R^4$ is halogen, $C_{1-4}$ alkyl or $C_{1-4}$ haloalkyl; and $R^5$ is OH or $CH_2OH$. In other embodiments of formula (Ia1), $R^1$ is —$OR^{1a}$ wherein $R^{1a}$ is methyl, ethyl or propyl; $R^2$ is $CF_3$, $OCF_3$, or cyclopropyl; the subscript m is 0; the subscript n is 0 or 1; $R^4$ is halogen, $C_{1-4}$ alkyl or $C_{1-4}$ haloalkyl; and $R^5$ is $C_{1-4}$ alkyl; and $R^6$ is NHCO—$C_{1-4}$ alkyl.

In some embodiments, compounds of formula (I) are provided, and are represented by formula (Ia2):

(Ia2)

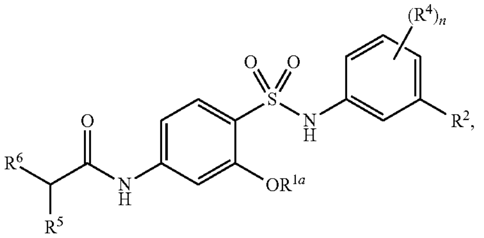

or a pharmaceutically acceptable salt thereof. In some embodiments of formula (Ia2), $R^{1a}$ is methyl, ethyl or propyl; $R^2$ is $CF_3$, $OCF_3$, or cyclopropyl; the subscript n is 0 or 1; $R^4$ is halogen, $C_{1-4}$ alkyl or $C_{1-4}$ haloalkyl; and $R^5$ is OH or $CH_2OH$. In other embodiments of formula (Ia2), $R^{1a}$ is methyl, ethyl or propyl; $R^2$ is $CF_3$, $OCF_3$, or cyclopropyl; the subscript n is 0 or 1; $R^4$ is halogen, $C_{1-4}$ alkyl or $C_{1-4}$ haloalkyl; $R^5$ is $C_{1-4}$ alkyl; and $R^6$ is NHCO—$C_{1-4}$ alkyl.

In some embodiments, compounds of formula (I) are provided, and are represented by formula (Ia3):

(Ia3)

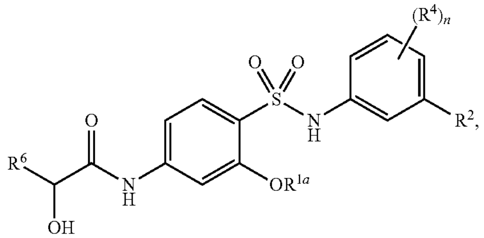

or a pharmaceutically acceptable salt thereof. In some embodiments of formula (Ia2), compounds are provided wherein $R^6$ is selected from the group consisting of $C_{1-6}$ alkyl, $C_{1-6}$ haloalkyl, $C_{1-6}$ hydroxyalkyl, $C_{2-8}$ alkenyl, —X—Y, —X—$CO_2R^b$, —X—$NR^bR^c$, —X—$NR^bCOR^c$, —X—$NR^bCO_2R^c$, —X—$NR^bS(O)_2R^c$, —X—$NR^bCONR^b$ $R^c$, and —X—$CONR^bOR^c$. In further selected embodiments, $R^{1a}$ is methyl, ethyl or propyl; $R^2$ is $CF_3$, $OCF_3$, or cyclopropyl; the subscript n is 0 or 1; and $R^4$ is halogen, $C_{1-4}$ alkyl or $C_{1-4}$ haloalkyl. In still other embodiments, $R^{1a}$ is methyl, ethyl or propyl; $R^2$ is $CF_3$, $OCF_3$, or cyclopropyl; the subscript n is 0 or 1; $R^4$ is halogen, $C_{1-4}$ alkyl or $C_{1-4}$ haloalkyl; and $R^6$ is selected from the group consisting of $C_{1-6}$ alkyl, $C_{1-6}$ haloalkyl, $C_{1-6}$ hydroxyalkyl, and —X—Y.

In some embodiments, compounds of formula (I) are provided, and are represented by formula (Ia4):

(Ia4)

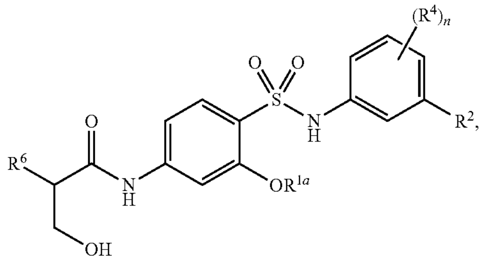

or a pharmaceutically acceptable salt thereof, wherein $R^6$ is selected from the group consisting of $C_{1-6}$ alkyl, $C_{1-6}$ haloalkyl, $C_{1-6}$ hydroxyalkyl, $C_{2-g}$ alkenyl, —X—Y, —X—$CO_2R^b$, —X—$NR^bR^c$, —X—$NR^bCOR^c$, —X—$NR^bCO_2R^c$, —X—$NR^bS(O)_2R^c$, —X—$NR^bCONR^b$ $R^c$, and —X—$CONR^bR^c$. In some embodiments of formula (Ia4), $R^6$ is selected from the group consisting of $C_{1-6}$ alkyl, $C_{1-6}$ haloalkyl, $C_{1-6}$ hydroxyalkyl, $C_{2-8}$ alkenyl, and —X—Y. In other embodiments, $R^{1a}$ is methyl, ethyl or propyl; $R^2$ is $CF_3$, $OCF_3$, or cyclopropyl; the subscript n is 0 or 1; $R^4$ is halogen, $C_{1-4}$ alkyl or $C_{1-4}$ haloalkyl; and $R^6$ is selected from the group consisting of $C_{1-6}$ alkyl, $C_{1-6}$ haloalkyl, $C_{1-6}$ hydroxyalkyl, $C_{2-g}$ alkenyl, and —X—Y.

In other embodiments, compounds of formula (I) or their pharmaceutically acceptable salts are provided, wherein $R^1$ is methoxy or ethoxy; $R^2$ is cyclopropyl, $OCF_3$, or $CF_3$; and R is selected from the group consisting of

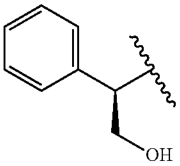
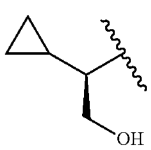
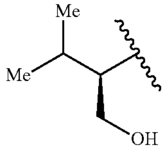
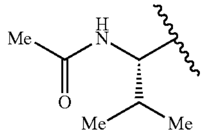
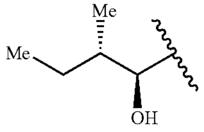
and
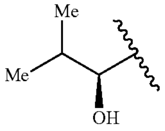

wherein the wavy line indicates the position of attachment to the remainder of the compound.

In some selected embodiments, compounds are provided which are selected from the group consisting of:

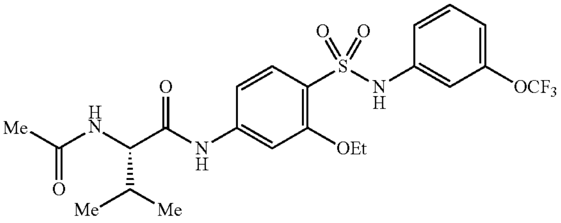

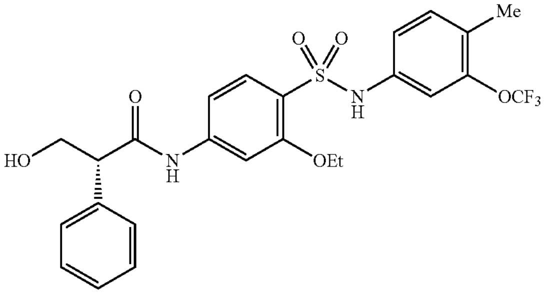

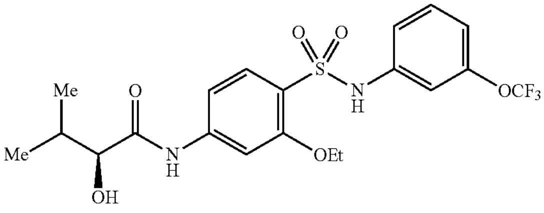

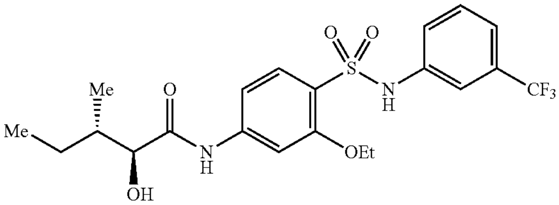

-continued

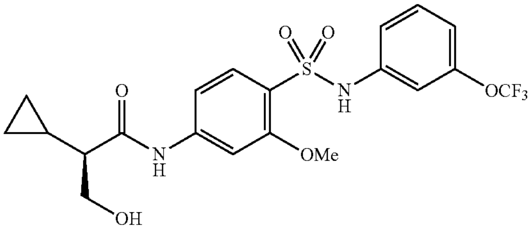

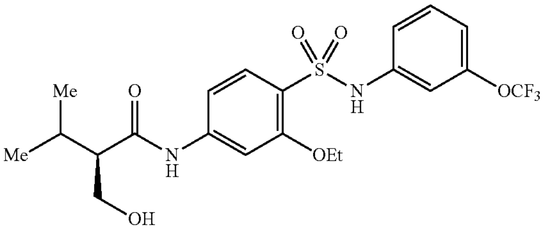

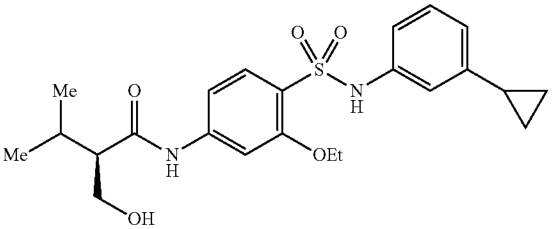

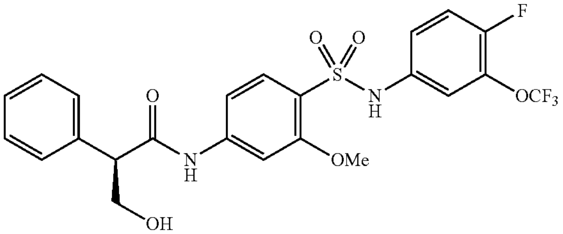

or a pharmaceutically acceptable salt thereof

Preparation of Compounds of the Claims

Those skilled in the art will recognize that there are a variety of methods available to synthesize molecules represented in the claims. In general, useful methods for synthesizing compounds represented in the claims consist of three parts, which may be done in any order: Formation of the sulfonamide, formation of the amide bond, and installation and/or modification of functional groups on the various substituents.

Several methods for the preparation of claimed compounds are illustrated below (eq. 1-6). Equations 1-3 demonstrate some methods of sulfonamide formation. Equations 4-6 demonstrate methods for the formation of the amide bond, which result in the compounds of the invention.

A variety of methods described above have been used to prepare compounds of the invention, some of which are described in the examples.

eq. 1

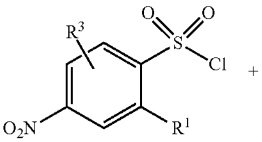

-continued

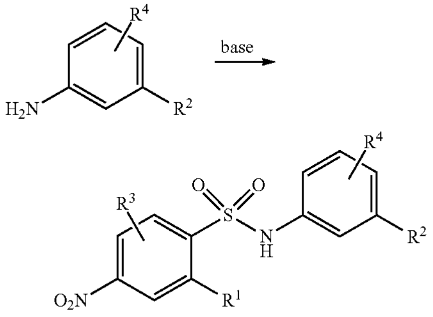

eq. 2

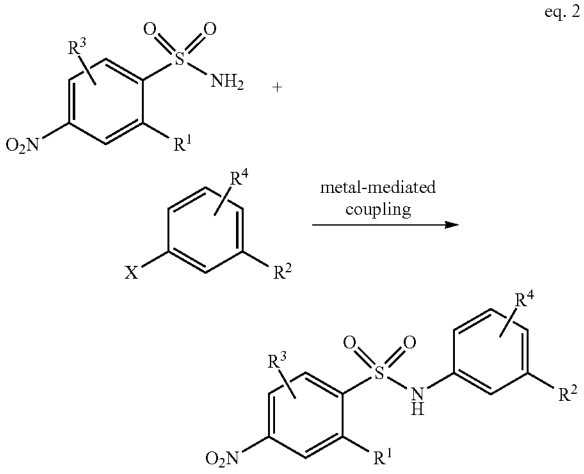

eq. 3

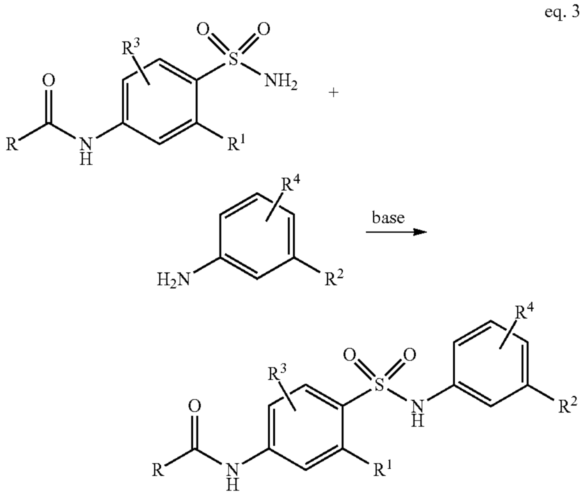

eq. 4

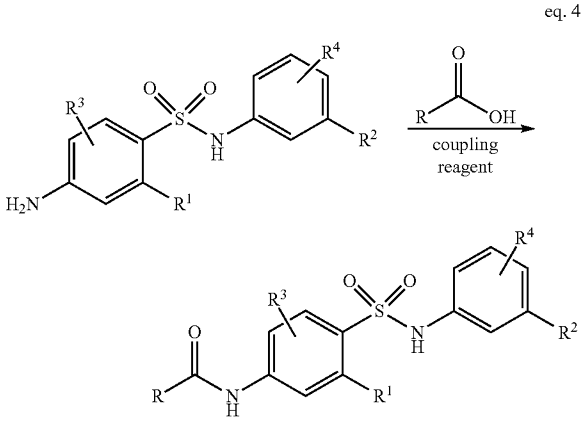

-continued eq. 5

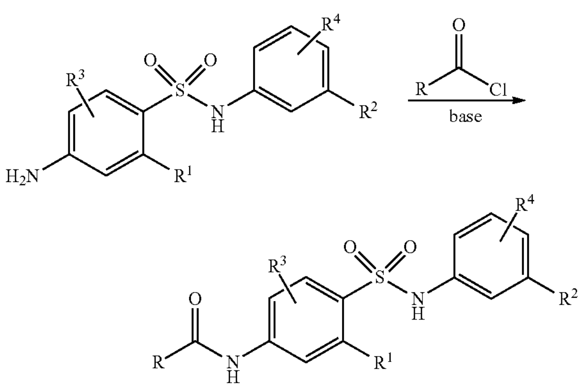

eq. 6

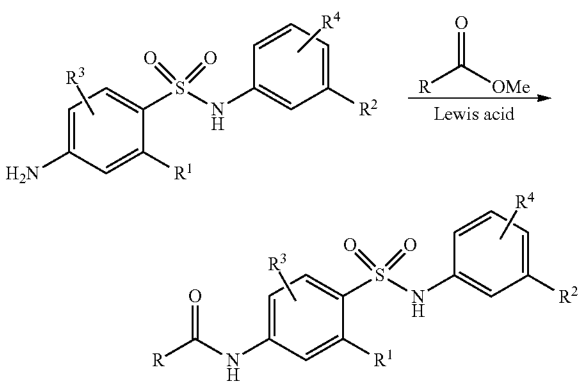

IV. Pharmaceutical Compositions

In addition the compounds provided above, the compositions for modulating CXCR6, activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), 4,800,882 (Gianturco), or 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

V. Methods of Treating Diseases Modulated by CXCR6

In one aspect, the present invention provides methods of treating or preventing a CXCR6-mediated condition or disease by administering to a subject having such a condition or disease, a therapeutically effective amount of any compound of the invention. Preferred compounds for use in the present methods are those compounds specifically exemplified in the Examples below, and provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CXCR6-mediated condition or disease" and related phrases and terms refer to a condition or disease characterized by inappropriate, e.g., less than or greater than normal, CXCR6 functional activity. Inappropriate CXCR6 functional activity might arise as the result of CXCR6 expression in cells which normally do not express CXCR6, increased CXCR6 expression (leading to, e.g., inflammatory and immunoregulatory disorders and diseases) or decreased CXCR6 expression. Inappropriate CXCR6 functional activity might also arise as the result of CCL20 secretion by cells which normally do not secrete CCL20, increased CCL20 expression (leading to, e.g., inflammatory and immunoregulatory disorders and diseases) or decreased CCL20 expression. A CXCR6-mediated condition or disease may be completely or partially mediated by inappropriate CXCR6 functional activity. However, a CXCR6-mediated condition or disease is one in which modulation of CXCR6 results in some effect on the underlying condition or disease (e.g., a CXCR6 antagonist results in some improvement in patient well-being in at least some patients). In some embodiments, described herein are methods of treating cancer in a subject in need thereof comprising administering to the subject in need thereof a therapeutically effective amount of a compound of formula (I), (Ia), (Ia1), (Ia2), (Ia3), or (Ia4).

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection, Th17-mediated autoimmunity and cancer can be treated or prevented with the present compounds and compositions. In one group of embodiments, diseases or conditions, including chronic diseases, of humans or other species can be treated with inhibitors of CXCR6 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, Vitiligo (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic) as well as for instance Hashimoto's thyroiditis and Grave's disease, multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

Preferably, the present methods are directed to the treatment of diseases or conditions selected from cancer, allergic diseases, psoriasis, skin conditions such as atopic dermatitis and asthma and scleroderma.

Beginning with methods or uses involving cancer, in some embodiments, the cancer is adrenal cortical cancer, anal cancer, aplastic anemia, bile duct cancer, bladder cancer, bone cancer, bone metastasis, Adult CNS brain tumors, Children CNS brain tumors, breast cancer, Castleman Disease, cervical cancer, Childhood Non-Hodgkin's lymphoma, colon and rectum (colorectal) cancer, endometrial cancer, esophagus cancer, Ewing's family of tumors, eye cancer, gallbladder cancer, gastrointestinal carcinoid tumors, gastrointestinal stromal tumors, gestational trophoblastic disease, glioblastoma multiforme, Hodgkin's disease, Kaposi's sarcoma, kidney cancer, laryngeal and hypopharyageal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, thyroid cancer, uterine sarcoma, vaginal cancer, vulvar cancer, Waldenstrom's macroglobulinemia, cancers of viral origin and virus-associated cancers. In some embodiments, the cancer is selected from the group consisting of breast cancer, colon cancer, glioblastoma multiforme, lung cancer, melanoma, ovarian cancer, prostate cancer, and transformed stem cells cancer. In some embodiments, the cancer is breast cancer. In some embodiments, the cancer is triple-negative breast cancer. In some embodiments, the cancer is ovarian cancer.

Diseases and conditions associated with inflammation, immune disorder, and infection can be treated or prevented with the present compounds, compositions, and methods.

Hepatitis is an inflammatory process in the liver which can be caused by a variety of etiologies, including viruses and drugs. When a patient is suffering from a chronic hepatitis, but the cause of the disease is not known (i.e., following exclusion of other causes), and is associated with abnormalities in immunoregulation, the patient is said to have “autoimmune hepatitis”. Untreated, autoimmune hepatitis is progressive, and can result in liver failure and death.

Autoimmune hepatitis can further be classified as follows.

Type 1, or “classic” autoimmune hepatitis, is characterized in patients by the presence of antinuclear antibodies (ANA) in approximately 70% of such patients, the presence of anti-smooth muscle (anti-actin) antibodies (SMA) in more than 30% of such patients, and sensitivity to corticosteroids.

Type 2 autoimmune hepatitis is characterized by the presence of anti-liver-kidney-microsomal antibodies (ANTI-LKM-1), absence of ANA and SMA, and sensitivity to corticosteroids.

Type 3 autoimmune hepatitis patients are characterized by the presence by liver-pancreas antigen antibody (ANTI-LP) or anti-soluble liver antigen antibodies (ANTI-SLA), absence of ANA and ANTI-LKM-1, presence of SMA in 30% of such patients, and sensitivity to corticosteroids.

Type 4 autoimmune hepatitis patients are characterized as cryptogenic (tentative), and are characterized by the absence of ANA, SMA, ANTI-LKM-1, ANTI-SLA and ANTI-LP, and sensitivity to corticosteroids.

In some embodiments, described herein is a method of treating autoimmune hepatitis in a subject in need thereof comprising administering to the subject in need thereof a therapeutically effective amount of a compound of formula (I), (Ia), (Ia1), (Ia2), (Ia3), or (Ia4).

Non-Alcoholic Fatty Liver Disease (NAFLD)

NAFLD is a disorder affecting as many as 1 in 3-5 adults and 1 in 10 children in the United States, and refers to conditions where there is an accumulation of excess fat in the liver of people who drink little or no alcohol. The most common form of NAFLD is a non-serious condition called hepatic steatosis (fatty liver), in which fat accumulates in the liver cells: although this is not normal, by itself it probably does not damage the liver. NAFLD most often presents itself in individuals with a constellation of risk factors called the metabolic syndrome, which is characterized by elevated fasting plasma glucose (FPG) with or without intolerance to post-prandial glucose, being overweight or obese, high blood lipids such as cholesterol and triglycerides (TGs) and low high-density lipoprotein cholesterol (HDL-C) levels, and high blood pressure; but not all patients have all the manifestations of the metabolic syndrome. Obesity is thought to be the most common cause of NAFLD; and some experts estimate that about two-thirds of obese adults and one-half of obese children may have fatty liver. The majority of individuals with NAFLD have no symptoms and a normal physical examination (although the liver may be slightly enlarged); children may exhibit symptoms such as abdominal pain and fatigue, and may show patchy dark skin discoloration (acanthosis nigricans). The diagnosis of NAFLD is usually first suspected in an overweight or obese person who is found to have mild elevations in their liver blood tests during routine testing, though NAFLD can be present with normal liver blood tests, or incidentally detected on imaging investigations such as abdominal ultrasound or CT scan. It is confirmed by imaging studies, most commonly a liver ultrasound or magnetic resonance imaging (MRI), and exclusion of other causes.

In some embodiments, described herein is a method of treating non-alcoholic fatty liver disease (NAFLD) in a subject in need thereof comprising administering to the subject in need thereof a therapeutically effective amount of a compound of formula (I), (Ia), (Ia1), (Ia2), (Ia3), or (Ia4).

Kidney Injury and Lung Injury

Kidney injury takes many forms and can be life-threatening. Renal fibrosis is a direct consequence of the kidney’s limited capacity to regenerate after injury. Renal scarring results in a progressive loss of renal function, ultimately leading to end-stage renal failure and a requirement for dialysis or kidney transplantation Mesangial cell hyperplasia is often a key feature of kidney or renal diseases and disorders. Such diseases and disorders may be caused by immunological or other mechanisms of injury, including IgAN, membranoproliferative glomerulonephritis or lupus nephritis. Imbalances in the control of mesangial cell replication also appear to play a key role in the pathogenesis of progressive renal failure. Renal fibrosis is the principal process underlying the progression of chronic kidney disease (CKD) to end-stage renal disease (ESRD).

Lung injury is a class of respiratory diseases in which scars are formed in the lung tissues, leading to serious breathing problems. Scar formation, the accumulation of excess fibrous connective tissue (the process called fibrosis), leads to thickening of the walls, and causes reduced oxygen supply in the blood. As a consequence patients suffer from perpetual shortness of breath. These diseases and disorders include but are not limited to idiopathic pulmonary fibrosis (IPF), secondary pulmonary hypertension (SPH), chronic thromboembolic pulmonary hypertension, lymphangioleiomyomatosis, and chronic obstructive pulmonary disease (COPD).

In some embodiments, described herein is a method of treating kidney injury or lung injury in a subject in need thereof comprising administering to the subject in need thereof a therapeutically effective amount of a compound of formula (I), (Ia), (Ia1), (Ia2), (Ia3), or (Ia4). In some embodiments, the kidney injury is acute kidney injury.

Myocardial Ischemia or Reperfusion Injury

Myocardial ischemic injury results from severe impairment of coronary blood supply and produces a spectrum of clinical syndromes. As a result of intensive investigation over decades, a detailed understanding is now available of the complexity of the response of the myocardium to an ischemic insult. Myocardial ischemia results in a characteristic pattern of metabolic and ultrastructural changes that lead to irreversible injury. Recent studies have explored the relationship of myocardial ischemic injury to the major modes of cell death, namely, oncosis and apoptosis. The evidence indicates that apoptotic and oncotic mechanisms can proceed together in ischemic myocytes with oncotic mechanisms and morphology dominating the end stage of irreversible injury. Myocardial infarcts evolve as a wavefront of necrosis, extending from subendocardium to subepicardium over a 3- to 4-hour period. A number of processes can profoundly influence the evolution of myocardial ischemic injury. Timely reperfusion produces major effects on ischemic myocardium, including a component of reperfusion injury and a greater amount of salvage of myocardium. Preconditioning by several short bouts of coronary occlusion and reperfusion can temporarily salvage significant amounts of myocardium and extend the window of myocardial viability.

In some embodiments, described herein is a method of treating myocardial ischemia or reperfusion injury in a subject in need thereof comprising administering to the subject in need thereof a therapeutically effective amount of a compound of formula (I), (Ia), (Ia1), (Ia2), (Ia3), or (Ia4).

Inflammation

Inflammation is a non-specific first reaction mounted by the immune system in response to a perceived injury or threat. It is an innate defensive response, distinguished from the more precisely tailored adaptive responses of the immune system. Inflammation may work cooperatively with adaptive responses of the immune system, which develop more slowly but are more precisely targeted to a harmful agent such as a chemical or pathogen that may be causing localized injury.

Inflammation may be associated with infections, but it occurs in response to virtually any type of injury or threat, including physical trauma, cold, burns from radiation, heat or corrosive materials, chemical irritants, bacterial or viral pathogens, localized oxygen deprivation (ischemia) or reperfusion (sudden reinfusion of oxygen to ischemic tissue), and others. It includes the classic symptoms of redness, heat, swelling, and pain, and may be accompanied by decreased function of the inflamed organ or tissue. It is a generalized reaction involving several effects that may tend to combat an injurious agent that may be present at the site where an injury or threat was detected, or it may tend to contain the injury or threat to its initial location, to keep it from spreading rapidly.

Adaptive immune responses, on the other hand, develop when the body is exposed to a particular harmful agent: the cellular immune system 'learns' to recognize and attack the particular harmful agent by developing cell-mediated responses. Then, if that harmful agent persists long enough or returns later, the adaptive system recognizes the harmful agent and attacks it with a very specific response directed at the harmful agent itself. Such adaptive responses take time to develop, but are usually extremely specific, while the innate responses like inflammation involve more general changes in the affected tissue, and are not specifically targeted at an agent that is causing injury. These innate reactions involve recruitment of protective cells and substances to the area of the injury, and, unlike the adaptive responses, they typically occur rapidly.

In some embodiments, described herein is a method of treating myocardial ischemia or reperfusion injury in a subject in need thereof comprising administering to the subject in need thereof a therapeutically effective amount of a compound of formula (I), (Ia), (Ia1), (Ia2), (Ia3), or (Ia4).

In another group of embodiments, modulation of CXCR6 dependent regulatory T cell trafficking may be modulated to treat diseases or conditions including cancers, infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation.

Those of skill in the art will understand that agents that modulate CXCR6 activity can be combined in treatment regimens with other therapeutic agents and/or with chemotherapeutic agents or radiation. In some cases, the amount of chemotherapeutic agent or radiation is an amount which would be sub-therapeutic if provided without combination with a composition of the invention. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

The compounds of the present invention are accordingly useful in the prevention and treatment of a wide variety of inflammatory and immunoregulatory disorders and diseases.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®), Tofacitinib (Xeljanz®) and other FK-506 type immunosuppressants, and rycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106, 203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, niroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), adalimumab (Humira®), golimumab (Simponi@), rituximab (Rituxan®), tocilizumab (Actemra®), (1) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate and leflunomide (u) other compounds such as 5-aminosalicylic acid and prodrugs thereof, hydroxychloroquine; D-penicillamine; antimetabolites such as azathioprine, 6-mercaptopurine and methotrexate; DNA synthesis inhibitors such as hydroxyurea and microtubule disrupters such as colchicine and proteasome inhibitors such as bortezomib (Velcade®). The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

VI. EXAMPLES

The following examples are offered to illustrate, but not to limit the claimed invention.

Reagents and solvents used below can be obtained from commercial sources such as Aldrich Chemical Co. (Milwaukee, Wisconsin, USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

The following abbreviations are used in the Examples and throughout the description of the invention:

HPLC, High Pressure Liquid Chromatography; DMF, dimethyl formamide; TFA, trifluoroacetic acid; THF, tetrahydrofuran; EtOAc, ethyl acetate; $Boc_2O$, di-tertbutyl dicarbonate or Boc anhydride; DIPEA, diisopropyl ethylamine; HBTU, O-(benzotriazol-1-yl)-N,N,N',N'-tetramethyluronium hexafluorophosphate; dppf, 1,1'-Bis(diphenylphosphino)ferrocene; $Pd_2(dba)_3$, tris(dibenzylideneacetone)dipalladium(0); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of (S)-N-(3-ethoxy-4-(N-(3-(trifluoromethoxy)phenyl)sulfamoyl)phenyl)-2-hydroxy-2-phenylacetamide

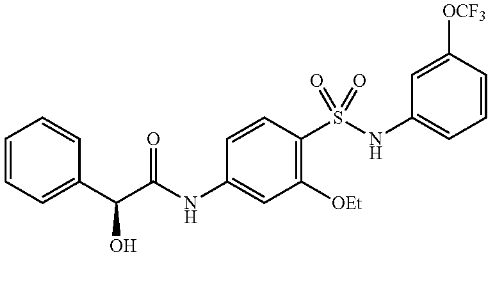 [SMILES: CCOc1cc(NC(=O)[C@@H](O)c2ccccc2)ccc1S(=O)(=O)Nc1cccc(OC(F)(F)F)c1]

a) To a solution of 2-chloro-5-nitrophenol (10.0 g, 57.8 mmol) in acetone (48 mL) was added solid potassium carbonate (9.5 g, 69.4 mmol) and ethyl iodide (10.8 g, 69.4 mmol). The mixture was refluxed for 4 h and the solid was filtered off. The resulting filtrate was concentrated in vacuo and dried under vacuum for 2 h to provide 1-chloro-2-ethoxy-4-nitrobenzene.

b) To a mixture of the crude 1-chloro-2-ethoxy-4-nitrobenzene and solid potassium thioacetate (8.6 g, 75.1 mmol) was added 25 mL of 1-methyl-2-pyrrolidinone. The reaction was stirred at 45° C. for 50 min, then added over 1 h to a solution containing 1,3-dichloro-5,5-dimethyl-2,4-imidazolidinedione (29.7 g, 150.3 mmol) in acetonitrile (50 mL), acetic acid (15 mL), and water (30 mL) cooled in a water bath. Upon completion of the reaction, the mixture was concentrated in vacuo to half of the volume, then diluted with water, and extracted with diethyl ether. The combined organic layers were dried with $Na_2SO_4$, and concentrated in vacuo to provide 2-ethoxy-4-nitrobenzenesulfonyl chloride.

c) To a solution of the crude 2-ethoxy-4-nitrobenzenesulfonyl chloride in dichloromethane (60 mL) and pyridine (7 mL, 87 mmol) was added 3-(trifluoromethoxy)aniline (7.6 mL, 57.8 mmol) dropwise. The mixture was stirred at room temperature for 4 h, and then quenched with aqueous 1 N hydrochloric acid. The aqueous layer was extracted with dichloromethane. The combined organic layers were dried with $Na_2SO_4$ and concentrated in vacuo. The crude oil was purified by silica gel column chromatography to give 4-nitro-2-ethoxy-N-(3-(trifluoromethoxy)phenyl)benzenesulfonamide.

d) Iron powder (3.0 g, 54.6 mmol) was added slowly to a solution of 4-nitro-2-ethoxy-N-(3-(trifluoromethoxy)phenyl)benzenesulfonamide (11.1 g, 27.3 mmol) in ethanol (27 mL) and concentrated hydrochloric acid (7 mL). The reaction was stirred at room temperature for 1 h, then at 60° C. for 1 h. The mixture was cooled to room temperature and the remaining ethanol was removed in vacuo. The slurry was then adjusted to pH~5 with aqueous saturated sodium bicarbonate solution. The mixture was extracted with ethyl acetate and the combined organic layers were filtered through Celite. The resulting filtrate was washed with brine, dried with $Na_2SO_4$, and concentrated in vacuo. The crude oil was then triturated with dichloromethane to give 4-amino-2-ethoxy-N-(3-(trifluoromethoxy)phenyl)benzenesulfonamide. MS: (ES) m/z calculated for $C_{15}H_{16}F_3N_2O_4S$ $[M+H]^+$ 377.3, found 377.0.

e) To a solution of (S)-(+)-mandelic acid (0.046 g, 0.3 mmol) in dichloromethane (1 mL) was added N,N-diisopropylethylamine (0.12 mL, 0.66 mmol), trimethylsilyl chloride (0.077 mL, 0.61 mmol), methanesulfonyl chloride (0.023 mL, 0.3 mmol), 4-amino-2-ethoxy-N-(3-(trifluoromethoxy)phenyl)benzenesulfonamide (0.038 g, 0.095 mmol), and solid sodium bicarbonate (0.008 g, 0.095 mmol). The reaction was stirred at room temperature for 15 h and the dichloromethane was removed. The mixture was diluted with water and the aqueous layer was extracted with ethyl acetate. The combined organic layers were dried with $Na_2SO_4$, and concentrated in vacuo. The resulting crude oil was purified by silica gel column chromatography to give (S)-N-(3-ethoxy-4-(N-(3-(trifluoromethoxy)phenyl)sulfamoyl)phenyl)-2-hydroxy-2-phenylacetamide. $^1H$ NMR (400 MHz, DMSO-$d_6$) δ 10.13 (s, 2H), 7.65 (d, J=8.8 Hz, 1H), 7.52 (d, J=1.6 Hz, 1H), 7.40-7.37 (m, 3H), 7.28-7.19 (m, 4H), 6.99-6.95 (m, 2H), 6.81 (d, J=6.8 Hz, 1H), 6.46 (d, J=4.4 Hz, 1H), 5.02 (d, J=4.4 Hz, 1H), 4.02 (q, J=7.2 Hz, 2H), 1.22 (t, J=6.8 Hz, 3H); MS: (ES) m/z calculated for $C_{23}H_{22}F_3N_2O_6S$ $[M+H]^+$ 511.5, found 511.3.

Example 2: Synthesis of (R)-N-(3-ethoxy-4-(N-(3-(trifluoromethoxy)phenyl)sulfamoyl)phenyl)-2-(hydroxymethyl)-3-methylbutanamide

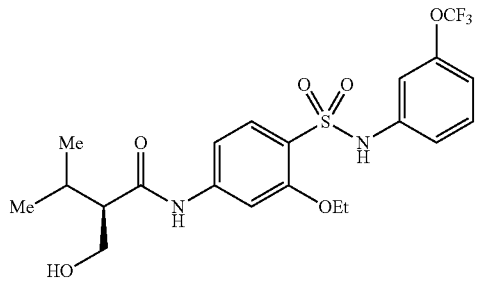 [SMILES: CCOc1cc(NC(=O)[C@@H](CO)C(C)C)ccc1S(=O)(=O)Nc1cccc(OC(F)(F)F)c1]

a) Acetyl chloride (3 mL) was added dropwise to (R)-2-(hydroxymethyl)-3-methylbutanoic acid (0.30 g, 2.3 mmol) at 0° C. The solution was stirred at room temperature for 1 h, then at 50° C. for 1 h. The mixture was diluted with benzene and then concentrated. The crude oil was then dissolved in thionyl chloride (2 mL) and heated at 60° C. for 1 h. The solution was diluted with benzene and then concentrated to provide (R)-2-(acetoxymethyl)-3-methylbutanoic acid chloride.

b) Pyridine (0.3 mL, 3.7 mmol) was added to a solution of 4-amino-2-ethoxy-N-(3-(trifluoromethoxy)phenyl)benzenesulfonamide (1.0 g, 2.7 mmol) and (R)-2-(acetoxymethyl)-3-methylbutanoic acid chloride (0.62 g, 3.2 mmol) at 0° C. The mixture was stirred at 0° C. for 30 min and then quenched with aqueous 1 N hydrochloric acid. The aqueous layer was extracted with dichloromethane, dried with $Na_2SO_4$, and concentrated in vacuo. The crude oil was purified by silica gel column chromatography. The resulting material was cooled to 0° C. and treated with a prepared solution of methanol (25 mL) containing acetyl chloride (5 mL). The reaction was stirred at 0° C. for 2 h and then concentrated in vacuo. The resulting crude oil was dissolved in ethyl acetate and neutralized with a solution of aqueous saturated sodium bicarbonate. The phases were separated and the aqueous layer was further extracted with ethyl acetate. The combined organic layers were washed with brine, dried with $Na_2SO_4$, and concentrated in vacuo. The crude oil was purified by silica gel column chromatography then dissolved in acetonitrile and treated with aqueous 1 N sodium hydroxide solution to give (R)-N-(3-ethoxy-4-(N-(3-(trifluoromethoxy)phenyl)sulfamoyl)phenyl)-2-(hydroxymethyl)-3-methylbutanamide. $^1H$ NMR (400 MHz, DMSO-$d_6$) δ 9.79 (s, 1H), 7.56 (d, J=8.4 Hz, 1H), 7.37 (d, J=2.0 Hz, 1H), 7.03 (dd, J=1.6, 8.4 Hz, 1H), 6.87 (dd, J=6.8, 9.2 Hz, 1H), 6.68 (s, 1H), 6.61 (d, J=8.4 Hz, 1H), 6.23 (d, J=8.0 Hz, 1H), 4.60 (s, 1H), 3.91 (q, J=6.8 Hz, 2H), 3.64-3.59 (m, 1H), 3.54-3.50 (m, 1H), 2.26 (ddd, J=4.8, 8.4, 8.4 Hz, 1H), 1.76 (ddd, J=7.6, 14.4, 14.4 Hz, 1H), 1.20 (t, J=6.8 Hz, 3H), 0.90 (d, J=7.2 Hz, 3H), 0.85 (d, J=6.8 Hz, 3H); MS: (ES) m/z calculated for $C_{21}H_{27}F_3N_2O_6S$ $[M+H]^+$ 491.5, found 491.0.

Example 3: Synthesis of (R)-2-cyclopropyl-N-(3-ethoxy-4-(N-(3-(trifluoromethoxy)phenyl)sulfamoyl)phenyl)-3-hydroxypropanamide

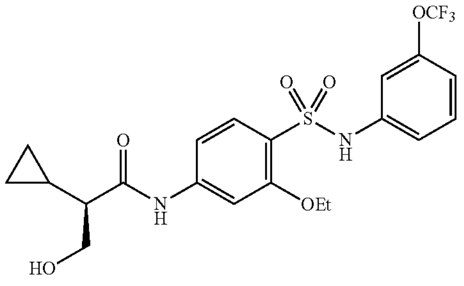 [SMILES: CCOc1cc(NC(=O)[C@@H](CO)C2CC2)ccc1S(=O)(=O)Nc1cccc(OC(F)(F)F)c1]

a) To a solution of (4S)-4-benzyl-3-(2-cyclopropylacetyl)oxazolidin-2-one (10 g, 39 mmol) in dichloromethane (150 mL) at 0° C. was added a solution of titanium tetrachloride (1 N solution in dichloromethane, 41 mL, 41 mmol). Dropwise addition of $iPr_2NEt$ (5.8 mL, 42 mmol) was followed and the reaction was stirred at 0° C. for 75 min. The reaction was then treated with a solution of trioxane (3.8 g, 42.4 mmol) in dichloromethane (22 mL). The contents were stirred at 0° C. for 10 min and additional titanium tetrachloride (1 M solution, 41 mL, 41 mmol) was added. The mixture was stirred at 0° C. for another 2.5 hand then quenched with aqueous saturated ammonium chloride solution and diluted with deionized water. The aqueous layer was extracted with dichloromethane. The combined organic layers were dried with $Na_2SO_4$, and concentrated. The crude oil was purified by silica gel column chromatography to give (R)-2-cyclopropyl-N-(3-ethoxy-4-(N-(3-(trifluoromethoxy)phenyl)sulfamoyl)phenyl)-3-hydroxypropanamide. $^1H$ NMR (400 MHz, $CDCl_3$) δ 7.34-7.22 (m, 5H), 4.77-4.72 (m, 1H), 4.25-4.17 (m, 2H), 4.01-3.94 (m, 2H), 3.38 (ddd, J=4.8, 5.2, 10.0 Hz, 1H), 3.31 (dd, J=3.2, 13.6 Hz, 1H), 2.83 (dd, J=9.2, 13.2 Hz, 1H), 2.16 (dd, J=4.4, 7.6 Hz, 1H), 1.16-110 (m, 1H), 0.60 (ddd, J=4.4, 9.2, 9.2 Hz, 1H), 0.52 (ddd, J=4.4, 8.4, 8.4 Hz, 1H), 0.35-0.26 (m, 2H).

b) 30% Hydrogen peroxide (2.6 mL, 26 mmol) was added dropwise over 10 min to a solution of (S)-4-benzyl-3-((R)-2-cyclopropyl-3-hydroxypropanoyl)oxazolidin-2-one (1.8 g, 6.4 mmol) in 4:1 tetrahydrofuran/$H_2O$ (32 mL) at 0° C. Aqueous lithium hydroxide (0.4 g, 10 mmol) was added and the reaction was maintained at 0° C. Upon completion, the reaction was quenched with a solution of aqueous sodium sulfite and then concentrated in vacuo to remove THF. The aqueous layer was washed with dichloromethane then cooled in an ice bath and acidified with aqueous 6 M hydrochloric acid until pH~3. The aqueous layer was extracted with ethyl acetate. The combined organic layers were dried with $Na_2SO_4$, and concentrated in vacuo to give (R)-3-hydroxymethyl-2-cyclopropylpropanoic acid. $^1H$ NMR (400 MHz, $CDCl_3$) δ 3.97-3.87 (m, 2H), 1.86 (ddd, J=2.8, 4.8, 7.2 Hz, 1H), 1.00-0.95 (m, 1H), 0.65-0.59 (m, 2H), 0.47-0.43 (m, 1H), 0.27-0.23 (m, 1H).

c) Acetyl chloride (3 mL) was added dropwise to (R)-3-hydroxymethyl-2-cyclopropylpropanoic acid (0.6 g, 4.5 mmol) at 0° C. The solution was stirred at room temperature for 1 h, then at 50° C. for 1 h. The solution was diluted with benzene and then concentrated. The crude oil was dissolved in thionyl chloride (6 mL) at room temperature and stirred at 60° C. for 1 h. The solution was diluted with benzene and concentrated to give 4-amino-2-ethoxy-N-(3-(trifluoromethoxy)phenyl)benzenesulfonamide.

d) Pyridine (0.28 mL, 3.5 mmol) was added to a solution of 4-amino-2-ethoxy-N-(3-(trifluoromethoxy)phenyl)benzenesulfonamide (0.7 g, 1.9 mmol) and (R)-3-acetoxy-2-cyclopropylpropanoic acid chloride (0.5 g, 2.6 mmol) at 0° C. The mixture was stirred at 0° C. for 2 h and was then quenched with aqueous 1 M hydrochloric acid. The aqueous layer was extracted with ethyl acetate and the combined organic layers were dried with $Na_2SO_4$, and concentrated in vacuo. The crude oil was purified by silica gel column chromatography. The resulting material was cooled to 0° C. and treated with a prepared solution of methanol (25 mL) containing acetyl chloride (5 mL). The contents were stirred at 0° C. for 4 h and then concentrated in vacuo. The crude material was purified by silica gel column chromatography to give (R)-2-cyclopropyl-N-(3-ethoxy-4-(N-(3-(trifluoromethoxy)phenyl)sulfamoyl)phenyl)-3-hydroxypropanamide. $^1$H NMR (400 MHz, DMSO-$d_6$) δ 9.77 (s, 1H), 7.58 (d, J=8.4 Hz, 1H), 7.39 (d, J=1.6 Hz, 1H), 7.03 (dd, J=1.6, 8.4 Hz, 1H), 6.88 (t, J=8.0 Hz, 1H), 6.69 (s, 1H), 6.62 (dd, J=0.8, 7.2 Hz, 1H), 6.25 (dd, J=1.2, 8.0 Hz, 1H), 4.71 (bs, 1H), 3.93 (q, J=6.8 Hz, 2H), 3.73 (t, J=9.8 Hz, 1H), 3.50 (dd, J=4.8, 10.2 Hz, 1H), 1.78 (ddd, J=4.4, 9.6, 9.6 Hz, 1H), 1.20 (t, J=6.8 Hz, 2H), 0.83-0.74 (m, 1H), 0.47 (dddd, J=4.4, 4.4, 9.2, 9.2 Hz, 1H), 0.35 (dddd, J=4.4, 4.4, 9.6, 9.6 Hz, 1H), 0.29 (ddd, J=4.8, 5.2, 9.6 Hz, 1H), 0.13 (ddd, J=4.4, 5.2, 9.6 Hz, 1H); MS: (ES) m/z calculated for $C_{21}H_{24}F_3N_2O_6S$ $[M+H]^+$ 489.5, found 489.3.

Example 4: Synthesis of (R)-2-cyclopropyl-3-hydroxy-N-(3-methoxy-4-(N-(3-(trifluoromethoxy)phenyl)sulfamoyl)phenyl)propanamide

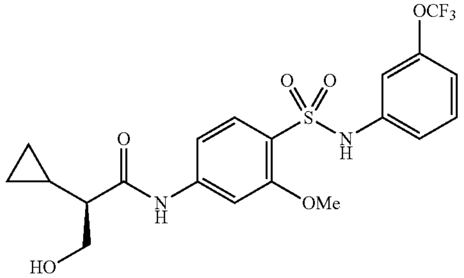 [SMILES: COc1cc(NC(=O)[C@@H](CO)C2CC2)ccc1S(=O)(=O)Nc1cccc(OC(F)(F)F)c1]

a) A mixture of 3-(trifluoromethoxy)aniline (7.8 g, 44.0 mmol) in pyridine (40 mL) was added to 2-methoxy-4-nitrobenzene-1-sulfonyl chloride (10.0 g, 40.0 mmol). The reaction was heated at 65° C. for 2 h and the mixture was then cooled to room temperature. The contents were concentrated in vacuo, diluted with ethyl acetate, and extracted with aqueous 1 N hydrochloric acid. The organic layer was separated, dried with $Na_2SO_4$, and concentrated in vacuo. The crude material was recrystallized from hot ethanol, and the solid was collected by filtration to give the desired compound 4-nitro-2-methoxy-N-(3-(trifluoromethoxy)phenyl)benzenesulfonamide. MS: (ES) m/z calculated for $C_{14}H_{12}F_3N_2O_6S$ $[M+H]^+$ 393.3, found 339.4.

b) Cyclohexene (70 mL, 671 mmol) was added to a solution containing 4-nitro-2-methoxy-N-(3-(trifluoromethoxy)phenyl)benzenesulfonamide (13.8 g, 35.0 mmol), and 10% Pd/C (3.7 g, 3.5 mmol) in ethanol (70 mL) at 80° C. The mixture was heated at 80° C. for 1 h and the reaction was then diluted with ethyl acetate. The solution was filtered through Celite and the filtrate was concentrated in vacuo to give 4-amino-2-methoxy-N-(3-(trifluoromethoxy)phenyl)benzenesulfonamide. MS: (ES) m/z calculated for $C_{14}H_{14}F_3N_2O_4S$ $[M+H]^+$ 363.3, found 363.2.

c) Pyridine (0.026 mL, 0.32 mmol) was added to a solution of 4-amino-2-methoxy-N-(3-(trifluoromethoxy)phenyl)benzenesulfonamide (0.072 g, 0.2 mmol) and (R)-3-acetoxy-2-cyclopropylpropanoic acid chloride (0.053 g, 2.6 mmol) in 1.2 mL of dichloromethane at 0° C. The mixture was stirred at 0° C. for 2 h and quenched with aqueous 1 N hydrochloric acid. The aqueous layer was extracted with ethyl acetate. The combined organic layers were dried with $Na_2SO_4$, and concentrated in vacuo. The resulting crude oil was then cooled to 0° C., and treated with a solution of methanol (10 mL) containing acetyl chloride (2 mL). The reaction was stirred at 0° C. for 1 h and was then concentrated in vacuo. The crude material was purified by reverse phase HPLC to give (R)-2-cyclopropyl-3-hydroxy-N-(3-methoxy-4-(N-(3-(trifluoromethoxy)phenyl)sulfamoyl)phenyl)propanamide. $^1$H NMR (400 MHz, DMSO-$d_6$) δ 10.27 (s, 1H), 10.09 (s, 1H), 7.69 (d, J=8.8 Hz, 1H), 7.58 (d, J=2.0 Hz, 1H), 7.28 (t, J=8.0 Hz, 1H), 7.19 (dd, J=2.0, 8.8 Hz, 1H), 7.06-7.02 (m, 2H), 6.89 (dd, 1.2, 8.0 Hz, 1H), 3.79 (s, 3H), 3.76-3.69 (m, 1H), 3.51 (ddd, J=4.4, 5.2, 8.8 Hz, 1H), 1.80 (ddd, J=4.4, 9.6, 9.6 Hz, 1H), 0.76 (dddd, J=4.8, 5.2, 8.0, 8.0 Hz, 1H), 0.48 (dddd, J=4.4, 4.4, 9.2, 9.2 Hz, 1H), 0.34 (dddd, J=4.4, 5.2, 8.8, 8.8 Hz, 1H), 0.27 (ddd, J=4.4, 9.2, 9.2 Hz, 1H), 0.13 (ddd, J=4.8, 9.2, 9.2 Hz, 1H); MS: (ES) m/z calculated for $C_{20}H_{21}F_3N_2O_6S$ $[M+H]^+$ 475.5, found 475.2.

Example 5: Synthesis of (R)-N-(3-ethoxy-4-(N-(4-methyl-3-(trifluoromethoxy)phenyl)sulfamoyl)phenyl)-3-hydroxy-2-phenylpropanamide

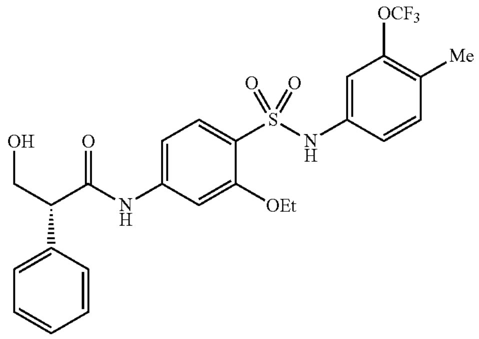 [SMILES: CCOc1cc(NC(=O)[C@@H](CO)c2ccccc2)ccc1S(=O)(=O)Nc1ccc(C)c(OC(F)(F)F)c1]

a) A mixture of tropic acid (30 g, 180.5 mmol) and (1S,2S)-1-(p-nitrophenyl)-2-amino-1,3-propanediol (38.31 g, 180.5 mmol) in water (350 mL) was heated to 70° C. The solution was allowed to stand at room temperature overnight. The resulting crystals were collected by filtration, washed with water, and dried in air. The resulting solid (46 g) was dissolved in hot water (300 mL) and was allowed to stand at room temperature overnight. The resulting crystals were collected by filtration and washed with water, and dried in air. The resulting solid (16.5 g) was dissolved in hot water (80 mL) and charged with ammonium hydroxide (37%, 35 mL) to form a suspension (pH~12). The solid was filtered off, and washed with water. The filtrate was cooled in an ice bath and the pH was adjusted to 1 with concentrated aqueous hydrochloric acid and extracted with ethyl acetate. The organic layer was dried over anhydrous $Na_2SO_4$, filtered, and then concentrated in vacuo to give (R)-tropic acid.

b) Acetyl chloride (2.40 g, 30.9 mmol) was added dropwise to (R)-tropic acid (0.30 g, 1.81 mmol) at 0° C. The mixture was stirred at room temperature for 1 h, then at 50° C. for 1 h. The solvent was evaporated, and benzene (5 mL) was added and then concentrated in vacuo. Benzene (3 mL) and thionyl chloride (3 mL) were added to the residue and the mixture was stirred at 60° C. for 2 h. The solvent was removed in vacuo and benzene (5 mL) was added and concentrated again in vacuo to give the O-acetyl-tropic acid chloride.

c) The O-acetyl-tropic acid chloride (0.060 g, 0.23 mmol) was added to a solution of 4-amino-2-ethoxy-N-(4-methyl-3-(trifluoromethoxy)phenyl)benzenesulfonamide (0.060 g, 0.15 mmol) in dichloromethane (4 mL) and pyridine (0.2 mL, 2.47 mmol) at 0° C. The mixture was stirred at 0° C. for 1 h, diluted with ethyl acetate and washed with a solution of aqueous 1 N hydrochloric acid, followed by brine. The organic layer was concentrated in vacuo.

In a separate flask, acetyl chloride (2.40 g, 30.9 mmol) was added dropwise to 10 mL of methanol at 0° C. and stirred for 10 min. The resulting solution was poured into the residue prepared above, and the mixture was stirred at 0° C. for 2 h. The reaction mixture was diluted with ethyl acetate and washed with aqueous saturated sodium bicarbonate solution, followed by brine. The organic layer was concentrated in vacuo and the residue was purified by reverse phase HPLC to give (R)-N-(3-ethoxy-4-(N-(4-methyl-3-(trifluoromethoxy)phenyl)sulfamoyl)phenyl)-3-hydroxy-2-phenylpropanamide. $^1$H NMR (400 MHz, $CD_3OD$) δ 7.68 (d, J=8.8 Hz, 1H), 7.61 (d, J=2.0 Hz, 1H), 7.38-7.22 (m, 5H), 7.07-6.90 (m, 3H), 6.92 (dd, J=2.0, 8.4 Hz, 1H), 4.88 (br s, 3H), 4.22-4.14 (m, 3H), 3.83 (dd, J=4.8, 9.6 Hz, 1H), 3.68 (dd, J=4.8, 10.0 Hz, 1H), 2.14 (s, 3H), 1.44 (t, J=7.2 Hz, 3H); MS: (ES) m/z calculated for $C_{25}H_{26}F_3N_2O_6S$ [M+H]+ 539.2, found 539.1.

Example 6: Synthesis of (S)-N-(3-ethoxy-4-(N-(3-(trifluoromethoxy)phenyl)sulfamoyl)phenyl)-2-hydroxy-3-methylbutanamide

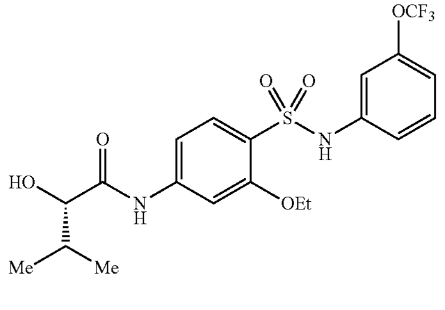 [SMILES: CCOc1cc(NC(=O)[C@@H](O)C(C)C)ccc1S(=O)(=O)Nc1cccc(OC(F)(F)F)c1]

a) Acetyl chloride (4.80 g, 61.8 mmol) was added dropwise to (S)-2-hydroxy-3-methylbutanoic acid (0.90 g, 7.62 mmol) at 0° C. The mixture was stirred at room temperature for 1 h, then at 50° C. for 1 h. The solvent was evaporated and benzene (5 mL) was added and the contents were concentrated in vacuo. Benzene (4 mL) and thionyl chloride (4 mL) were added to the residue and the mixture was stirred at 60° C. for 2 h. The solvent was evaporated, and benzene (5 mL) was added and the contents were concentrated in vacuo to give (S)-2-acetoxyl-3-methylbutanoic chloride.

b) (S)-2-acetoxyl-3-methylbutanoic chloride (0.15 g, 0.84 mmol) was added to a solution of 4-amino-2-ethoxy-N-(3-(trifluoromethoxy)phenyl)benzenesulfonamide (0.24 g, 0.63 mmol) in dichloromethane (8 mL) and pyridine (0.2 mL, 2.47 mmol) at 0° C. The mixture was stirred at 0° C. for 1 h, diluted with ethyl acetate and washed with aqueous 1 N hydrochloric acid, followed by brine. The organic layer was concentrated in vacuo.

In a separate flask, acetyl chloride (4.80 g, 61.8 mmol) was added dropwise to 20 mL of methanol at 0° C. and stirred for 10 min. The resulting solution was poured into the residue prepared above and the mixture stirred at 0° C. for 3 h. The contents were diluted with ethyl acetate and washed with aqueous saturated sodium bicarbonate solution, followed by brine. The organic layer was concentrated in vacuo and the residue purified by reverse phase HPLC to give (S)-N-(3-ethoxy-4-(N-(3-(trifluoromethoxy)phenyl)sulfamoyl)phenyl)-2-hydroxy-3-methylbutanamide. $^1$H NMR (400 MHz, $CD_3OD$) δ 7.77 (d, J=8.4 Hz, 1H), 7.63 (d, J=2.0 Hz, 1H), 7.26-7.16 (m, 2H), 7.06-7.02 (m, 2H), 6.85 (dt, J=0.8, 8.4 Hz, 1H), 4.87 (bs, 3H), 4.19 (q, J=7.2 Hz, 2H), 3.94 (d, J=3.6 Hz, 1H), 2.12 (m, 1H), 1.44 (t, J=7.2 Hz, 3H), 1.02 (d, J=7.2 Hz, 3H), 0.89 (d, J=7.2 Hz, 3H). MS: (ES) m/z calculated for $C_{20}H_{24}F_3N_2O_6S$ $[M+H]^+$ 477.5, found 477.0.

Example 7: Synthesis of (2S,3S)-N-(3-ethoxy-4-(N-(3-(trifluoromethoxy)phenyl)sulfamoyl)phenyl)-2-hydroxy-3-methylpentanamide

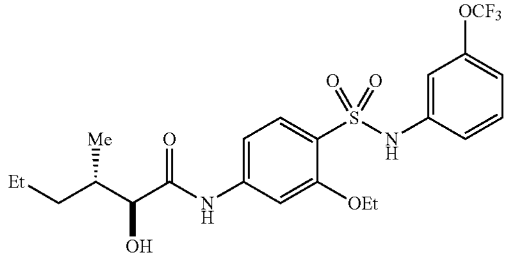 [SMILES: CCC[C@H](C)[C@H](O)C(=O)Nc1ccc(S(=O)(=O)Nc2cccc(OC(F)(F)F)c2)c(OCC)c1]

a) Sodium nitrite (25 g, 0.36 mol) in water (100 mL) was added dropwise over 30 min to a solution of (2S,3S)-2-amino-3-methylpentanoic acid (9.2 g, 0.07 mol) in aqueous 2.5 M sulfuric acid (200 mL). The solution was stirred at 0° C. for 1 h, and then at room temperature overnight. The mixture was extracted with ethyl acetate and the combined organic layers were washed with brine, and concentrated in vacuo. The crude material was purified by silica gel column chromatography to give (2S,3S)-2-hydroxy-3-methylpentanoic acid. $^1$H NMR (400 MHz, $CDCl_3$) δ 6.20 (bs, 2H), 4.19 (d, J=4.0 Hz, 1H), 1.90 (m, 1H), 1.45 (m, 1H), 1.30 (m, 1H), 1.04 (d, J=6.8 Hz, 3H), 0.94 (t, J=7.6 Hz, 3H). MS: (ES) m/z calculated for $C_6H_{13}O_3[M+H]^+$ 133.2, found 133.1.

b) Acetyl chloride (4.80 g, 61.8 mmol) was added dropwise to (2S,3S)-2-hydroxy-3-methylpentanoic acid (0.65 g, 4.92 mmol) at 0° C. The mixture was stirred at room temperature for 1 h, then at 50° C. for 1 h. The solvent was evaporated, and benzene (5 mL) was added and the contents were concentrated in vacuo. Benzene (4 mL) and thionyl chloride (4 mL) were added to the residue and the mixture was stirred at 60° C. for 2 h. The solvent was evaporated, benzene (5 mL) was added and the mixture was concentrated in vacuo to give (2S,3S)-2-acetoxyl-3-methylpentanoic acid chloride.

c) (2S,3S)-2-acetoxyl-3-methylpentanoic acid chloride (0.060 g, 0.31 mmol) was added to a solution of 4-amino-2-ethoxy-N-(3-(trifluoromethoxy)phenyl)benzenesulfonamide (0.065 g, 0.17 mmol) in dichloromethane (4 mL) and pyridine (0.1 mL, 1.24 mmol) at 0° C. The mixture was stirred at 0° C. for 1 h, diluted with ethyl acetate and washed with aqueous 1 N hydrochloric acid, followed by brine. The organic layer was concentrated in vacuo.

In a separate flask, acetyl chloride (2.40 g, 30.9 mmol) was added dropwise to 10 mL of methanol at 0° C. and stirred for 10 min. The resulting solution was poured into the residue prepared above and the mixture was stirred at 0° C. for 3 h. The reaction mixture was diluted with ethyl acetate and washed with aqueous saturated sodium bicarbonate solution, followed by brine. The organic layer was concentrated in vacuo and the residue purified by reverse phase HPLC to give (2S,3S)-N-(3-ethoxy-4-(N-(3-(trifluoromethoxy)phenyl)sulfamoyl)phenyl)-2-hydroxy-3-methylpentanamide. $^1$H NMR (400 MHz, $CD_3OD$) δ 7.77 (d, J=8.8 Hz, 1H), 7.63 (d, J=1.6 Hz, 1H), 7.26-7.16 (m, 2H), 7.06-7.03 (m, 2H), 6.85 (dt, J=0.8, 8.4 Hz, 1H), 4.87 (bs, 3H), 4.19 (q, J=7.2 Hz, 2H), 3.98 (d, J=4.4 Hz, 1H), 1.90 (m, 1H), 1.49 (m, 1H), 1.44 (t, J=7.2 Hz, 3H), 1.27 (m, 1H), 0.99 (d, J=6.8 Hz, 3H), 0.90 (t, J=7.6 Hz, 3H); MS: (ES) m/z calculated for $C_{21}H_{26}F_3N_2O_6S$ $[M+H]^+$ 491.5, found 491.0.

Example 8: Synthesis of (2S,3S)-N-(3-ethoxy-4-(N-(3-(trifluoromethyl)phenyl)sulfamoyl)phenyl)-2-hydroxy-3-methylpentanamide

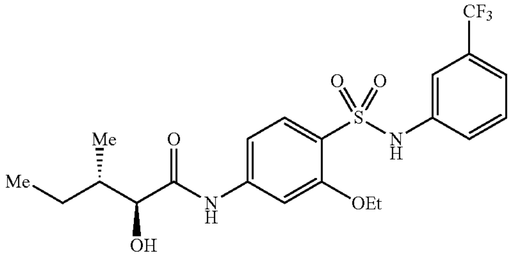 [SMILES: CCOc1cc(NC(=O)[C@@H](O)[C@@H](C)CC)ccc1S(=O)(=O)Nc1cccc(C(F)(F)F)c1]

(2S,3S)-2-Acetoxy-3-methylpentanoic acid chloride (0.040 g, 0.21 mmol) was added to a solution of 4-amino-2-ethoxy-N-(3-(trifluoromethyl)phenyl)benzenesulfonamide (0.045 g, 0.12 mmol) in dichloromethane (4 mL) and pyridine (0.1 mL, 1.24 mmol) at 0° C. The mixture was stirred at 0° C. for 1 h, diluted with ethyl acetate, and washed with aqueous 1 N hydrochloric acid, followed by brine. The organic layer was concentrated in vacuo.

In a separate flask, acetyl chloride (2.40 g, 30.9 mmol) was added dropwise to 10 mL of methanol at 0° C. and stirred for 10 min. The resulting solution was poured into the residue prepared above and the mixture was stirred at 0° C. for 3 h. The reaction mixture was diluted with ethyl acetate and washed with aqueous saturated sodium bicarbonate solution, followed by brine. The organic layer was concentrated in vacuo and the residue was purified by reverse phase HPLC to give (2S,3S)-N-(3-ethoxy-4-(N-(3-(trifluoromethyl)phenyl)sulfamoyl)phenyl)-2-hydroxy-3-methylpentanamide. $^1$H NMR (400 MHz, $CD_3OD$) S 7.77 (d, J=8.4 Hz, 1H), 7.62 (d, J=2.0 Hz, 1H), 7.39-7.23 (m, 4H), 7.19 (dd, J=2.0, 8.4 Hz, 1H), 4.87 (br s, 3H), 4.19 (q, J=7.2 Hz, 2H), 3.97 (d, J=4.4 Hz, 1H), 1.88 (m, 1H), 1.47 (m, 1H), 1.43 (t, J=7.2 Hz, 3H), 1.27 (m, 1H), 0.99 (d, J=6.8 Hz, 3H), 0.89 (t, J=7.6 Hz, 3H); MS: (ES) m/z calculated for $C_{21}H_{26}F_3N_2O_5S$ $[M+H]^+$ 475.5, found 475.0.

Example 9: Synthesis of (R)-N-(3-ethoxy-4-(N-(4-fluoro-3-(trifluoromethoxy)phenyl)sulfamoyl)phenyl)-2-(hydroxymethyl)-3-methylbutanamide

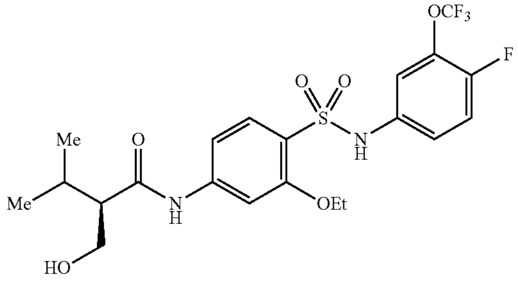 [SMILES: CCOc1cc(NC(=O)[C@@H](CO)C(C)C)ccc1S(=O)(=O)Nc1ccc(F)c(OC(F)(F)F)c1]

a) A mixture of 4-fluoro-3-(trifluoromethoxy)aniline (0.32 g, 1.65 mmol), 2-ethoxy-4-nitrobenzene-1-sulfonyl chloride (0.40 g, 1.5 mmol), and pyridine (0.30 mL, 3.75 mmol) in dichloromethane (6 mL) was stirred at room temperature overnight. The solution was then poured into 5% aqueous solution of hydrochloric acid and extracted with ethyl acetate. The organic layer was separated, dried with $Na_2SO_4$, and concentrated in vacuo to give the desired product 2-ethoxy-N-(4-fluoro-3-(trifluoromethoxy)phenyl)-4-nitrobenzenesulfonamide. MS: (ES) m/z calculated for $C_{15}H_{13}F_4N_2O_6S$ $[M+H]^+$ 425.3, found 425.

b) A mixture of 2-ethoxy-N-(4-fluoro-3-(trifluoromethoxy)phenyl)-4-nitrobenzenesulfonamide (0.6 g, 1.41 mmol) and tin(II) chloride ($SnCl_2 \cdot 2H_2O$) (1.27 g, 5.64 mmol) in ethyl acetate (10 mL) was refluxed for 1.5 h. The mixture was cooled to room temperature, neutralized with ammonium hydroxide, and extracted with ethyl acetate. The organic layer was separated, dried with $Na_2SO_4$, concentrated in vacuo, and purified by silica gel column chromatography to give 4-amino-2-ethoxy-N-(4-fluoro-3-(trifluoromethoxy)phenyl)benzenesulfonamide. MS: (ES) m/z calculated for $C_{15}H_{15}F_4N_2O_4S$ $[M+H]^+$ 395.4, found 395.

c) A mixture of 4-amino-2-ethoxy-N-(4-fluoro-3-(trifluoromethoxy)phenyl)benzenesulfonamide (0.45 g, 1.14 mmol), (R)-2-(acetoxymethyl)-3-methylbutanoic acid chloride (0.26 g, 1.37 mmol) and pyridine (0.18 mL, 2.28 mmol) in dichloromethane (7 mL) was stirred at 0° C. for 45 min. The contents were then poured into 5% aqueous hydrochloric acid and extracted with ethyl acetate. The organic layer was separated, dried with $Na_2SO_4$, and concentrated in vacuo to give the desired product (R)-2-((3-ethoxy-4-(N-(4-fluoro-3-(trifluoromethoxy)phenyl)sulfamoyl)phenyl)carbamoyl)-3-methylbutyl acetate. MS: (ES) m/z calculated for $C_{23}H_{27}F_4N_2O_7S$ $[M+H]^+$ 551.5, found 551.

d) Acetyl chloride (2 mL) and methanol (10 mL) was stirred for 5 min at 0° C. The solution was then poured into (R)-2-((3-ethoxy-4-(N-(4-fluoro-3-(trifluoromethoxy)phenyl)sulfamoyl)phenyl)carbamoyl)-3-methylbutyl acetate (0.62 g, 1.14 mmol). The mixture was stirred for 4 h at 0° C., then poured into water and extracted with ethyl acetate. The organic layer was separated, dried with $Na_2SO_4$, concentrated in vacuo and purified by silica gel column chromatography to give (R)-N-(3-ethoxy-4-(N-(4-fluoro-3-(trifluoromethoxy)phenyl)sulfamoyl)phenyl)-2-(hydroxymethyl)-3-methylbutanamide. $^1$H NMR (400 MHz, $CD_3OD$) δ 7.70 (d, J=10.4 Hz, 1H), 7.69 (s, 1H), 7.06 (m, 2H), 7.14 (m, 2H), 4.21 (q, J=7.2 Hz, 2H), 3.81 (dd, J=9.2, 10.8 Hz, 1H), 3.74 (dd, J=4.4, 10.4 Hz, 1H), 2.33 (ddd, J=4.4, 8.8, 8.8 Hz, 1H), 1.89 (ddd, J=6.8, 6.8, 7.0 Hz, 1H), 1.46 (t, J=6.8 Hz, 3H), 0.99 (d, J=6.8 Hz, 3H), 0.96 (t, J=6.8 Hz, 3H); MS: (ES) m/z calculated for $C_{21}H_{25}F_4N_2O_6S$ $[M+H]^+$ 509.1, found 509.

Example 10: Synthesis of (R)-N-(3-ethoxy-4-(N-(4-fluoro-3-(trifluoromethoxy)phenyl)sulfamoyl)phenyl)-3-hydroxy-2-phenylpropanamide

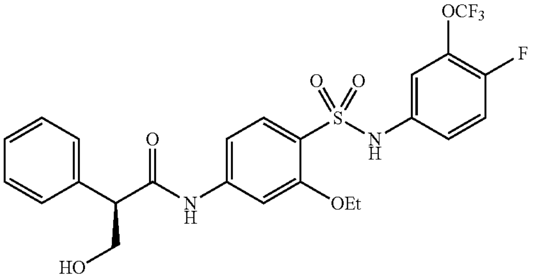 [SMILES: CCOc1cc(NC(=O)[C@@H](CO)c2ccccc2)ccc1S(=O)(=O)Nc1ccc(F)c(OC(F)(F)F)c1]

To a mixture of (R)-tropic acid (0.050 g, 0.3 mmol), trimethylsilyl chloride (0.038 mL, 0.3 mmol), and methanesulfonyl chloride (0.023 mL, 0.3 mmol) in dichloromethane (1.2 ml) was added N-methylmorpholine (0.76 ml, 0.7 mmol), 4-amino-2-ethoxy-N-(4-fluoro-3 (trifluoromethoxy) phenyl)benzenesulfonamide (0.040 g, 0.10 mmol) and solid sodium bicarbonate (0.080 g, 0.95 mmol). The mixture was stirred overnight at room temperature. The reaction was then quenched with water and extracted with ethyl acetate. The organic layer was separated, dried with $Na_2SO_4$, concentrated in vacuo and purified by reverse phase HPLC to yield (R)-N-(3-ethoxy-4-(N-(4-fluoro-3-(trifluoromethoxy)phenyl)sulfamoyl)phenyl)-3-hydroxy-2-phenylpropanamide. $^1H$ NMR (400 MHz, $CD_3OD$) S 7.67 (d, J=8.4 Hz, 1H), 7.65 (d, J=1.6 Hz, 1H), 7.36 (m, 2H), 7.30 (2H), 7.24 (m, 1H), 7.12 (dd, J=9.4, 9.4 Hz, 2H), 7.04 (m, 2H), 4.19 (q, J=7.2 Hz, 2H), 4.18 (dd, J=1.6, 11.2 Hz, 1H), 3.84 (dd, J=9.2, 9.6 Hz, 1H), 3.68 (dd, J=9.6, 10.0 Hz, 1H), 1.44 (t, J=7.2 Hz, 3H). MS: (ES) m/z calculated for $C_{24}H_{23}F_4N_2O_6S$ $[M+H]^+$ 543.5, found 543.

Example 11: Synthesis of (S)-2-acetamido-N-(3-ethoxy-4-(N-(3-(trifluoromethoxy)phenyl)sulfamoyl)phenyl)-3-methylbutanamide

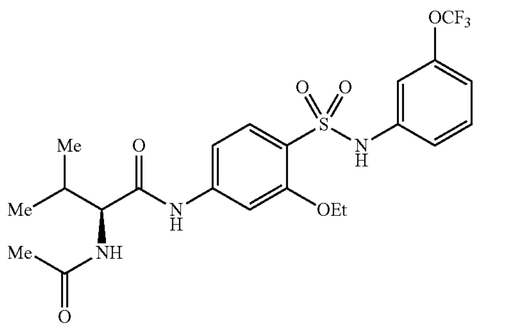 [SMILES: CCOc1cc(NC(=O)[C@@H](NC(C)=O)C(C)C)ccc1S(=O)(=O)Nc1cccc(OC(F)(F)F)c1]

A mixture of methyl acetyl-L-valinate (0.37 g, 2.12 mmol), 4-amino-2-ethoxy-N-(3-(trifluoromethoxy)phenyl)benzenesulfonamide (0.50 g, 1.32 mmol) and trimethylaluminum (2 M in heptane, 1.98 mL, 3.96 mmol) in 10 mL of dichloroethane was refluxed for 3.5 h. The solution was then cooled to room temperature, poured into aqueous 1 N hydrochloric acid and extracted with ethyl acetate. The organic layer was separated, dried with $Na_2SO_4$, and concentrated in vacuo. The crude material was purified by silica gel column chromatography followed by reverse phase HPLC to give (S)-2-acetamido-N-(3-ethoxy-4-(N-(3-(trifluoromethoxy)phenyl)sulfamoyl)phenyl)-3-methylbutanamide. $^1H$ NMR (400 MHz, $CD_3OD$) δ 7.76 (d, J=8.4 Hz, 1H), 7.57 (d, J=2.0 Hz, 1H), 7.23 (dd, J=8.4, 8.4 Hz, 1H), 7.04 (m, 1H), 7.03 (s, 1H), 7.09 (dd, J=2.0, 8.4 Hz, 1H), 6.85 (d, J=8.4 Hz, 1H), 4.22 (m, 1H), 4.18 (q, J=6.8 Hz, 2H), 2.08 (ddd, J=6.9, 7.0, 7.2 Hz, 1H), 2.00 (s, 3H), 1.44 (t, J=7.2 Hz, 3H), 0.99 (d, J=6.8 Hz, 3H), 0.98 (d, J=6.8 Hz, 3H); MS: (ES) m/z calculated for $C_{22}H_{26}F_3N_3O_6S$ $[M+H]^+$ 518.5, found 518.

Example 12: Synthesis of (2R)-N-[4-[(3-cyclopropylphenyl)sulfamoyl]-3-ethoxy-phenyl]-2-(hydroxymethyl)-3-methyl-butanamide

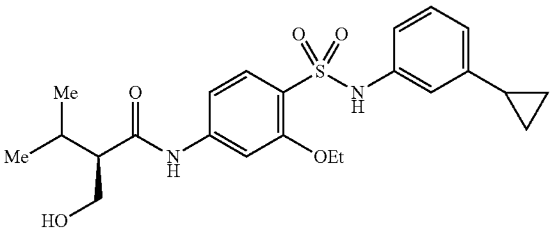 [SMILES: CCOc1cc(NC(=O)[C@@H](CO)C(C)C)ccc1S(=O)(=O)Nc1cccc(C2CC2)c1]

a) To a mixture of 2-ethoxy-4-nitrobenzene-1-sulfonyl chloride (0.27 g, 1.0 mmol) and 3-cyclopropylaniline (0.014 g, 1.06 mmol) in dichloromethane (6 mL) was slowly added pyridine (0.12 mL, 1.5 mmol) at room temperature. After stirring for 1 h, the reaction mixture was concentrated in vacuo. The residue was redissolved in dichloromethane (50 mL) and washed with brine (50 mL). The organic layer was dried over $MgSO_4$, filtered, and concentrated in vacuo to produce N-(3-cyclopropylphenyl)-2-ethoxy-4-nitrobenzenesulfonamide. MS: (ES) m/z calculated for $C_{17}H_{18}N_2NaO_5S$ $[M+Na]^+$ 385.4, found 385.

b) To the crude residue N-(3-cyclopropylphenyl)-2-ethoxy-4-nitrobenzenesulfonamide in ethanol (5 mL) was added concentrated hydrochloric acid (0.35 mL, 4.0 mmol). Iron powder (0.14 g, 2.5 mmol) was added slowly and the reaction mixture was allowed to gradually cool to room temperature for 30 min. Ethanol was removed in vacuo and the crude mixture was re-suspended in ethyl acetate and washed with water. The organic layer was dried over $MgSO_4$, filtered, and concentrated. The crude oil was purified by silica gel column chromatography to give the desired compound 4-amino-N-(3-cyclopropylphenyl)-2-ethoxybenzenesulfonamide. MS: (ES) m/z calculated for $C_{17}H_{21}N_2NaO_3S$ $[M+H]^+$ 333.4, found 333.

c) Pyridine (0.2 mL, 2.6 mmol) was slowly added to a cooled, 0° C. solution of 4-amino-N-(3-cyclopropylphenyl)-2-ethoxybenzenesulfonamide (0.28 g, 0.85 mmol) and (R)-2-(acetoxymethyl)-3-methylbutanoic acid chloride (0.21 g, 1.1 mmol) in dichloromethane (5 mL). After stirring for 1.5 h at 0° C., the reaction mixture was diluted with dichloromethane (20 mL) and washed with aqueous saturated sodium bicarbonate solution. The aqueous layer was re-extracted with dichloromethane. The combined organic layers were dried over $MgSO_4$, filtered, and concentrated in vacuo. The crude residue was poured a pre-cooled, 0° C. solution of 1:5 acetyl chloride in methanol (12 mL). The mixture was maintained at 0° C. while stirring for 1.5 h. The solvent was removed in vacuo and the crude residue was purified by silica gel column chromatography to provide (2R)-N-[4-[(3-cyclopropylphenyl)sulfamoyl]-3-ethoxy-phenyl]-2-(hydroxymethyl)-3-methyl-butanamide. $^1H$ NMR (400 MHz, DMSO-$d_6$) δ 9.80 (s, 1H), 7.56 (dd, J=2.4, 8.0 Hz, 1H), 7.37 (s, 1H), 7.03 (d, J=8.4 Hz, 1H), 6.69 (t, J=6.4 Hz, 1H), 6.43 (s, 1H), 6.11 (s, 1H), 4.61 (s, 1H), 3.95 (q, J=7.0 Hz, 2H), 3.34-3.24 (m, 1H), 3.24-3.18 (m, 1H), 2.30-2.21 (m, 1H), 1.66-1.56 (m, 1H), 1.27 (t, J=6.8 Hz, 3H), 0.91 (d, J=6.4 Hz, 3H), 0.87 (d, J=6.4 Hz, 3H), 0.80-0.72 (m, 2H), 0.50-0.40 (m, 2H); MS: (ES) m/z calculated for $C_{23}H_{31}N_2O_5S$ [M+H]$^+$ 447.6, found 447.

Example 13: Synthesis of (2R)-2-(hydroxymethyl)-N-[3-methoxy-4-[[3-(trifluoromethyl)phenyl]sulfamoyl]phenyl]-3-methyl-butanamide

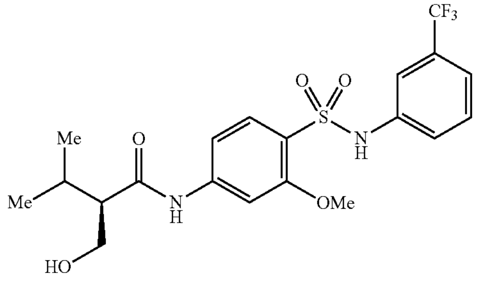 [SMILES: COc1cc(NC(=O)[C@@H](CO)C(C)C)ccc1S(=O)(=O)Nc1cccc(C(F)(F)F)c1]

a) To a cooled, 0° C. solution of 2-methoxy-4-nitrobenzene-1-sulfonyl chloride (3.9 g, 15.4 mmol) and 3-trifluoromethylaniline (2.0 mL, 16.2 mmol) in dichloromethane (10 mL) was slowly added pyridine (1.9 mL, 23.1 mmol). The mixture was allowed to warm to room temperature. After stirring for 1 h, the solvent was removed in vacuo to provide the crude residue 2-methoxy-4-nitro-N-(3-(trifluoromethyl)phenyl)benzenesulfonamide. MS: (ES) m/z calculated for $C_{14}H_{12}F_3N_2O_5S$ [M+H]$^+$ 377.3, found 377.

b) To the crude residue 2-methoxy-4-nitro-N-(3-(trifluoromethyl)phenyl)benzenesulfonamide in ethanol (30 mL) was added concentrated hydrochloric acid (6.5 mL, 75 mmol) at room temperature. Iron powder (2.3 g, 41.2 mmol) was added to the solution slowly portionwise. The reaction mixture was stirred for 30 min at room temperature and then heated to 70° C. for 15 min. After cooling to room temperature, the mixture was washed with deionized water. The aqueous layer was extracted with ethyl acetate. The combined organic layers were dried over $MgSO_4$, filtered, and concentrated in vacuo. The crude material was purified by silica gel column chromatography to give the desired compound (2R)-2-(hydroxymethyl)-N-[3-methoxy-4-[[3-(trifluoromethyl)phenyl]sulfamoyl]phenyl]-3-methyl-butanamide. MS: (ES) m/z calculated for $C_{14}H_{14}F_3N_2O_3S$ [M+H]$^+$ 347.3, found 347.

c) Pyridine (0.35 mL, 4.3 mmol) was slowly added to a cooled, 0° C. solution of 4-amino-2-methoxy-N-(3-(trifluoromethyl)phenyl)benzenesulfonamide (0.54 g, 1.44 mmol) and (R)-2-(acetoxymethyl)-3-methylbutanoic acid chloride (0.36 g, 1.88 mmol) in dichloromethane (7 mL). After stirring for 1.5 h at 0° C., the reaction mixture was diluted with dichloromethane (30 mL) and washed with aqueous saturated sodium bicarbonate solution. The aqueous layer was re-extracted with dichloromethane. The combined organic layers were dried over $MgSO_4$, filtered, and concentrated. The crude residue was poured into a pre-cooled, 0° C. solution of 1:5 AcCl in MeOH (12 mL). The mixture was stirred at 0° C. for 1.5 h and the solvent was removed in vacuo. The crude residue was purified by silica gel column chromatography to provide (2R)-2-(hydroxymethyl)-N-[3-methoxy-4-[[3-(trifluoromethyl)phenyl]sulfamoyl]phenyl]-3-methyl-butanamide. $^1H$ NMR (400 MHz, DMSO-$d_6$) δ 9.85 (s, 1H), 7.58 (d, J=8.4 Hz, 1H), 7.39 (s, 1H), 7.07 (dd, J=2.0, 8.4 Hz, 1H), 7.04 (d, J=8.0 Hz, 1H), 7.00 (d, J=7.6 Hz, 1H), 6.87 (d, J=8.4 Hz, 1H), 6.62 (d, J=8.0 Hz, 1H), 4.62 (s, 1H), 3.65 (s, 3H), 3.64-3.58 (m, 1H), 3.58-3.50 (m, 1H), 2.28 (ddd, J=4.0, 8.0, 8.0 Hz, 1H), 1.77 (ddq, J=6.8, 14.0, 14.0 Hz, 1H), 0.91 (d, J=6.8 Hz, 3H), 0.87 (d, J=6.8 Hz, 3H); MS: (ES) m/z calculated for $C_{20}H_{24}F_3N_2O_5S$ [M+H]$^+$ 461.5, found 461.

Example 14: Synthesis of (2R)-2-hydroxy-N-[3-methoxy-4-[[3-(trifluoromethyl)phenyl]sulfamoyl]phenyl]-3-methyl-butanamide

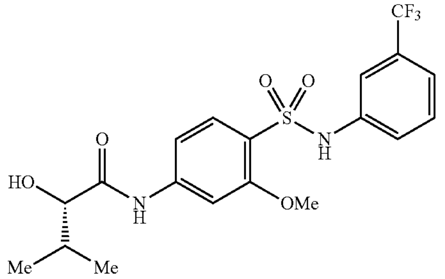 [SMILES: COc1cc(NC(=O)[C@@H](O)C(C)C)ccc1S(=O)(=O)Nc1cccc(C(F)(F)F)c1]

Pyridine (0.35 mL, 4.3 mmol) was slowly added to a cooled, 0° C. solution of 4-amino-2-methoxy-N-(3-(trifluoromethyl)phenyl)benzenesulfonamide (0.50 mg, 1.44 mmol) and (S)-2-acetoxy-3-methylbutanoic acid chloride (0.34 mg, 1.88 mmol) in dichloromethane (10 mL). After stirring for 2 h at 0° C., the reaction mixture was diluted with dichloromethane and washed with aqueous saturated sodium bicarbonate solution. The aqueous layer was re-extracted with dichloromethane. The combined organic layers were dried over $MgSO_4$, filtered, and concentrated. The crude residue was poured into a pre-cooled, 0° C. solution of 1:5 AcCl in MeOH (12 mL). The mixture was stirred at 0° C. for 1.5 h, and the solvent was removed in vacuo. The crude residue was purified by silica gel column chromatography to provide (2R)-2-hydroxy-N-[3-methoxy-4-[[3-(trifluoromethyl)phenyl]sulfamoyl]phenyl]-3-methyl-butanamide. $^1H$ NMR (400 MHz, DMSO-$d_6$) δ 9.61 (s, 1H), 7.56 (d, J=8.8 Hz, 1H), 7.40 (s, 1H), 7.22 (d, J=8.4 Hz, 1H), 7.04 (s, 1H), 7.00 (dd, J=7.2, 8.8 Hz, 1H), 6.85 (d, J=8.4 Hz, 1H), 6.60 (d, J=7.6 Hz, 1H), 5.67 (br s, 1H), 3.78 (d, J=4.4 Hz, 1H), 3.62 (s, 3H), 2.09-1.95 (m, 1H), 0.91 (d, J=6.8 Hz, 3H), 0.81 (d, J=6.4 Hz, 3H); MS: (ES) m/z calculated for $C_{19}H_{22}F_3N_2O_5S$ [M+H]$^+$ 447.5, found 447.

Biological Examples

Radioligand Binding Assay

L1.2 cells stably transfected with human CXCR6 cDNA (~105 cell/well) were incubated at 4° C. in HBSS containing 0.1% BSA and 0.1 nM of $^{125}$I-CXCL16 plus various concentrations of Compound. Following a three-hour incubation period, cells were aspirated onto polyethyleneimine-treated GF/B glass fiber filters (PerkinElmer, Waltham, MA) with a cell harvester (Tomtec, Hamden, CT) and washed twice with washing buffer (25 mM Hepes, 500 mM NaCl, 1 mM $CaCl_2$), 5 mM $MgCl_2$, pH 7.1). Fifty μl of MicroScint-20 (PerkinElmer, Waltham, MA) was added to each well of the filters, and radioactive emissions (cpm) were measured on a Packard TopCount Scintillation counter (PerkinElmer, Waltham, MA). IC50 values were calculated with GraphPad Prism using 3 parameter nonlinear regression.

The compounds in the Table below were prepared according to synthetic methodology as described above (and in the specific examples). Evaluation in the Radioligand Binding Assay produced the results shown:

| Compound ID | Structure | Potency |
|---|---|---|
| 1.001 | 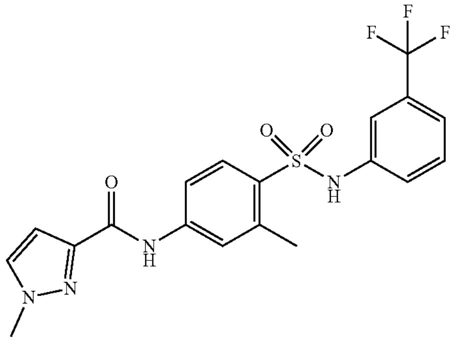 [SMILES: Cc1cc(NC(=O)c2ccn(C)n2)ccc1S(=O)(=O)Nc1cccc(C(F)(F)F)c1] | + |
| 1.002 | 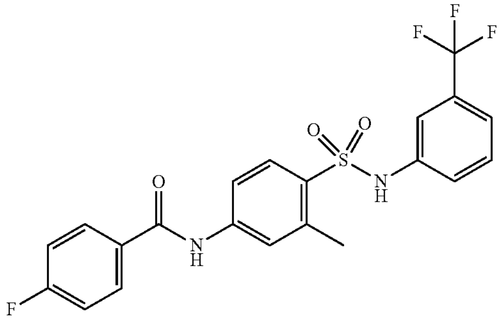 [SMILES: Cc1cc(NC(=O)c2ccc(F)cc2)ccc1S(=O)(=O)Nc1cccc(C(F)(F)F)c1] | +++ |
| 1.003 | 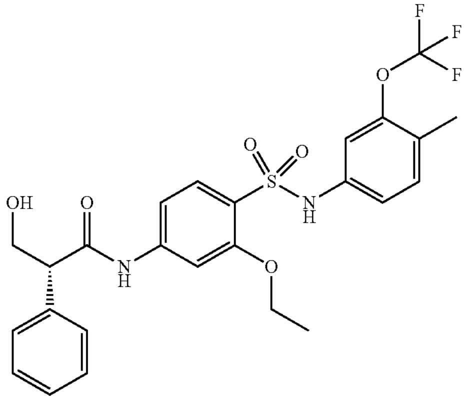 [SMILES: CCOc1cc(NC(=O)[C@@H](CO)c2ccccc2)ccc1S(=O)(=O)Nc1ccc(C)c(OC(F)(F)F)c1] | ++++ |
| 1.004 | 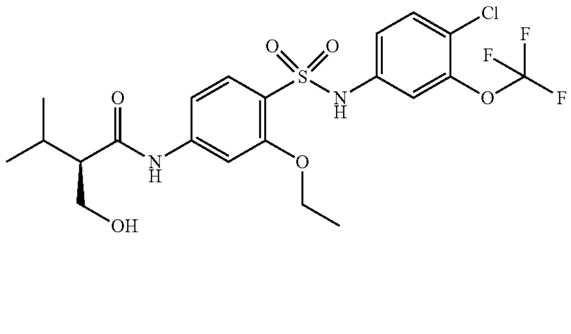 | ++++ |

-continued
| Compound ID | Structure | Potency |
| --- | --- | --- |
| 1.005 | 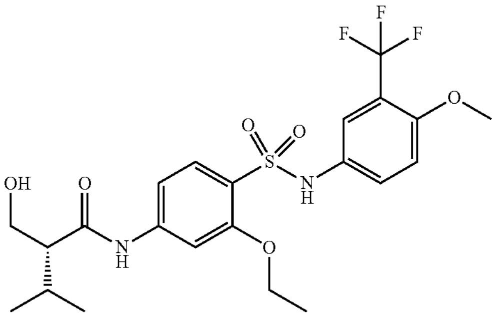 [SMILES: CCOc1cc(NC(=O)[C@@H](CO)C(C)C)ccc1S(=O)(=O)Nc1ccc(OC)c(C(F)(F)F)c1] | ++++ |
| 1.006 | 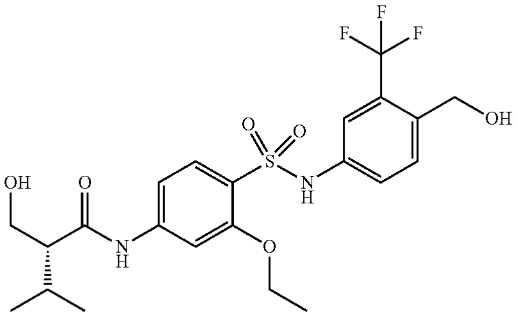 [SMILES: CCOc1cc(NC(=O)[C@@H](CO)C(C)C)ccc1S(=O)(=O)Nc1ccc(CO)c(C(F)(F)F)c1] | + |
| 1.007 | AND Enantiomer 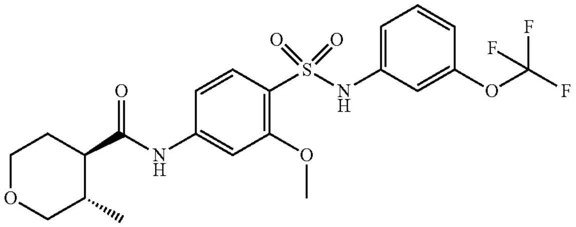 | +++ |
| 1.008 | 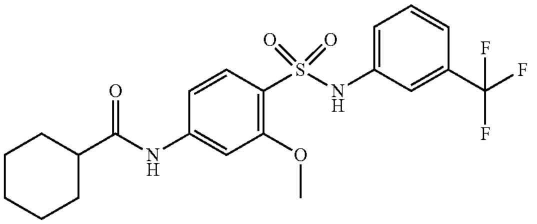 [SMILES: COc1cc(NC(=O)C2CCCCC2)ccc1S(=O)(=O)Nc1cccc(C(F)(F)F)c1] | + |
| 1.009 | 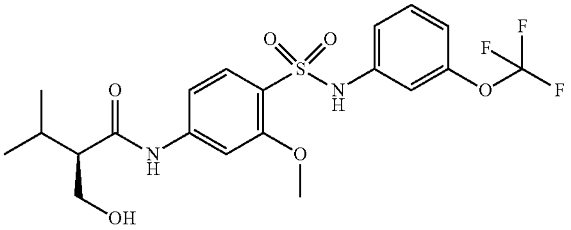 [SMILES: COc1cc(NC(=O)[C@@H](CO)C(C)C)ccc1S(=O)(=O)Nc1cccc(OC(F)(F)F)c1] | ++++ |

-continued
| Compound ID | Structure | Potency |
|---|---|---|
| 1.010 | AND Enantiomer 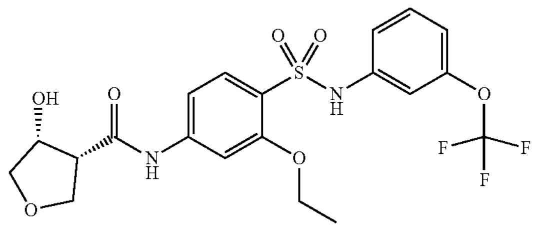 | +++ |
| 1.011 | 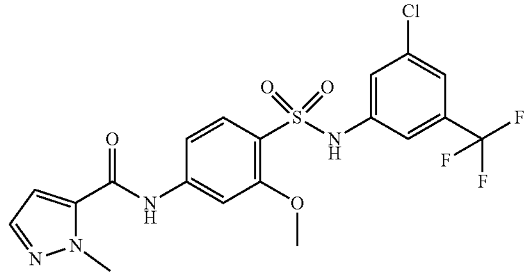 [SMILES: COc1cc(NC(=O)c2ccnn2C)ccc1S(=O)(=O)Nc1cc(Cl)cc(C(F)(F)F)c1] | ++ |
| 1.012 | 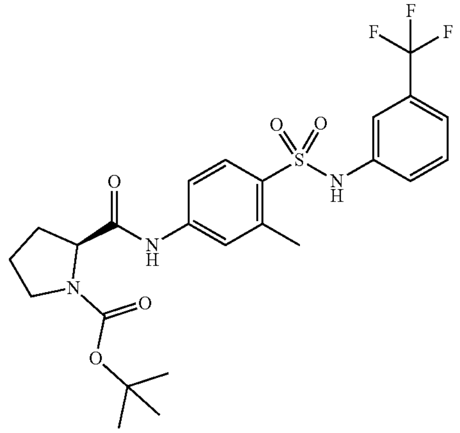 [SMILES: Cc1cc(NC(=O)[C@@H]2CCCN2C(=O)OC(C)(C)C)ccc1S(=O)(=O)Nc1cccc(C(F)(F)F)c1] | + |
| 1.013 | 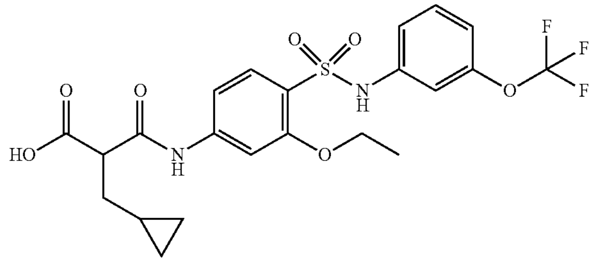 [SMILES: CCOc1cc(NC(=O)C(CC2CC2)C(=O)O)ccc1S(=O)(=O)Nc1cccc(OC(F)(F)F)c1] | ++++ |
| 1.014 | 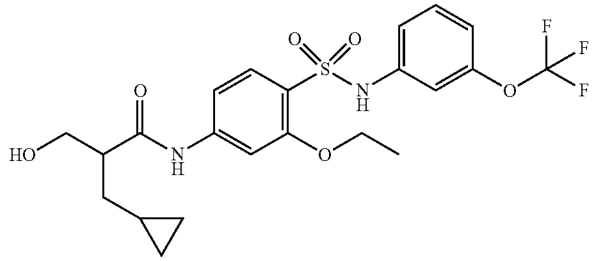 [SMILES: CCOc1cc(NC(=O)C(CO)CC2CC2)ccc1S(=O)(=O)Nc1cccc(OC(F)(F)F)c1] | ++++ |

-continued
| Compound ID | Structure | Potency |
|---|---|---|
| 1.015 | 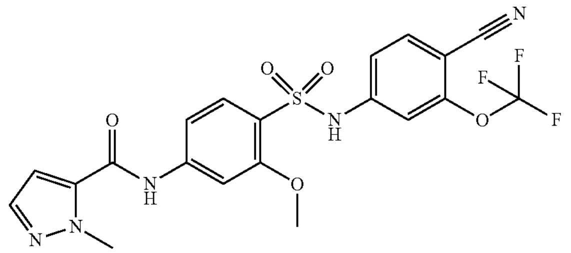 [SMILES: COc1cc(NC(=O)c2ccnn2C)ccc1S(=O)(=O)Nc1ccc(C#N)c(OC(F)(F)F)c1] | ++ |
| 1.016 | 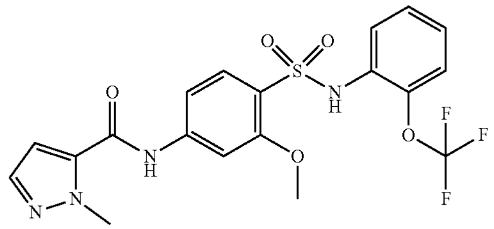 [SMILES: COc1cc(NC(=O)c2ccnn2C)ccc1S(=O)(=O)Nc1ccccc1OC(F)(F)F] | + |
| 1.017 | 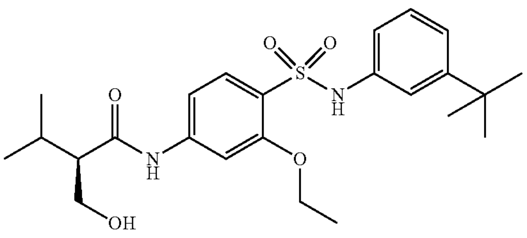 [SMILES: CCOc1cc(NC(=O)[C@@H](CO)C(C)C)ccc1S(=O)(=O)Nc1cccc(C(C)(C)C)c1] | ++++ |
| 1.018 | 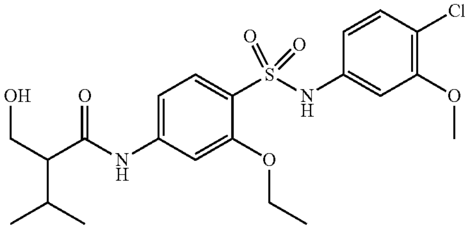 [SMILES: CCOc1cc(NC(=O)C(CO)C(C)C)ccc1S(=O)(=O)Nc1ccc(Cl)c(OC)c1] | ++++ |
| 1.019 | 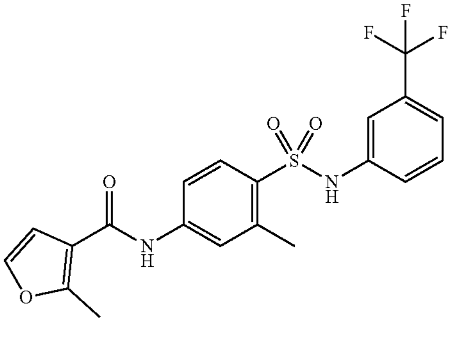 [SMILES: Cc1cc(NC(=O)c2ccoc2C)ccc1S(=O)(=O)Nc1cccc(C(F)(F)F)c1] | +++ |

-continued
| Compound ID | Structure | Potency |
| --- | --- | --- |
| 1.020 | 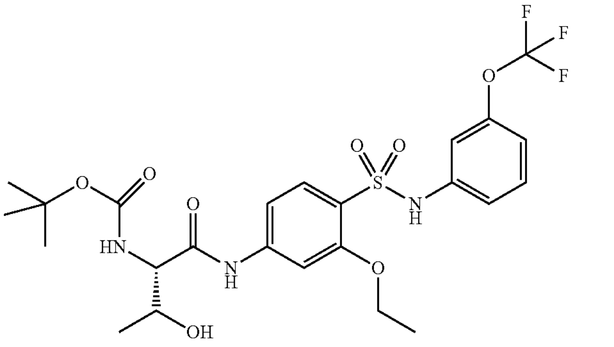 [SMILES: CCOc1cc(NC(=O)[C@@H](NC(=O)OC(C)(C)C)C(C)O)ccc1S(=O)(=O)Nc1cccc(OC(F)(F)F)c1] | ++ |
| 1.021 | 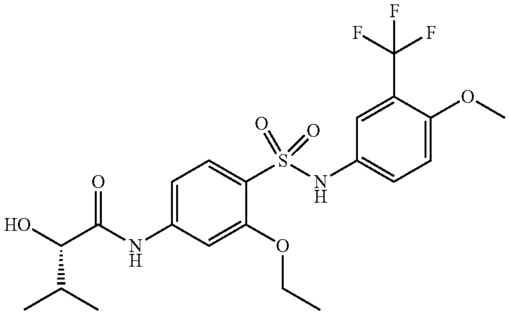 [SMILES: CCOc1cc(NC(=O)[C@@H](O)C(C)C)ccc1S(=O)(=O)Nc1ccc(OC)c(C(F)(F)F)c1] | ++++ |
| 1.022 | 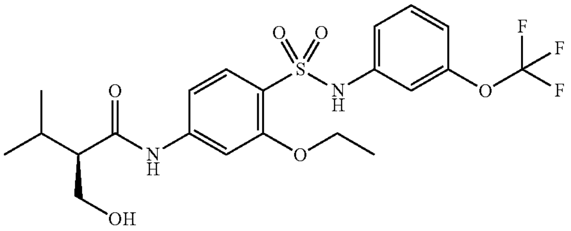 [SMILES: CCOc1cc(NC(=O)[C@@H](CO)C(C)C)ccc1S(=O)(=O)Nc1cccc(OC(F)(F)F)c1] | ++++ |
| 1.023 | 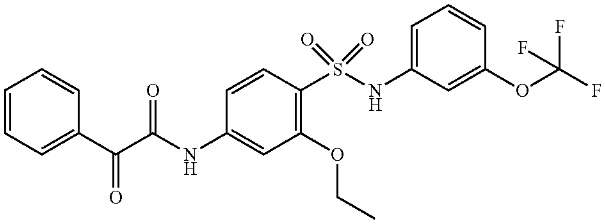 [SMILES: CCOc1cc(NC(=O)C(=O)c2ccccc2)ccc1S(=O)(=O)Nc1cccc(OC(F)(F)F)c1] | +++ |
| 1.024 | 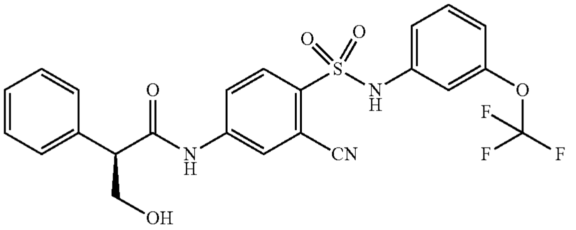 [SMILES: N#Cc1cc(NC(=O)[C@@H](CO)c2ccccc2)ccc1S(=O)(=O)Nc1cccc(OC(F)(F)F)c1] | ++++ |

-continued
| Compound ID | Structure | Potency |
|---|---|---|
| 1.025 | 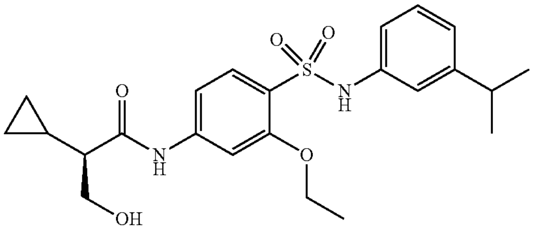 [SMILES: CCOc1cc(NC(=O)[C@@H](CO)C2CC2)ccc1S(=O)(=O)Nc1cccc(C(C)C)c1] | ++++ |
| 1.026 | AND Enantiomer 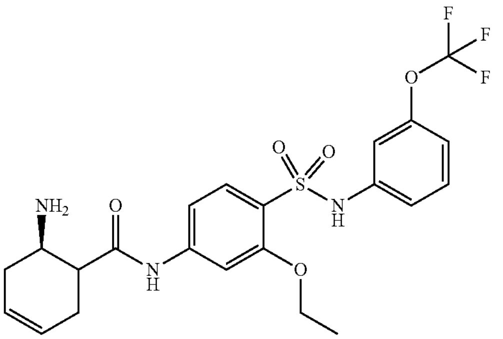 | ++ |
| 1.027 | 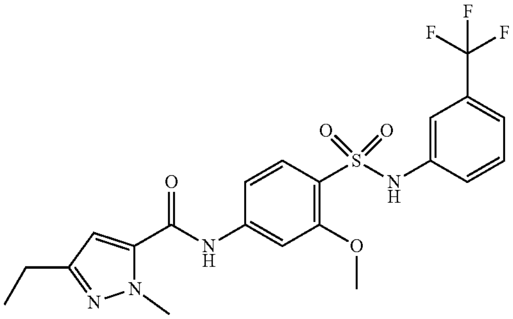 [SMILES: CCc1cc(C(=O)Nc2ccc(S(=O)(=O)Nc3cccc(C(F)(F)F)c3)c(OC)c2)n(C)n1] | ++ |
| 1.028 | 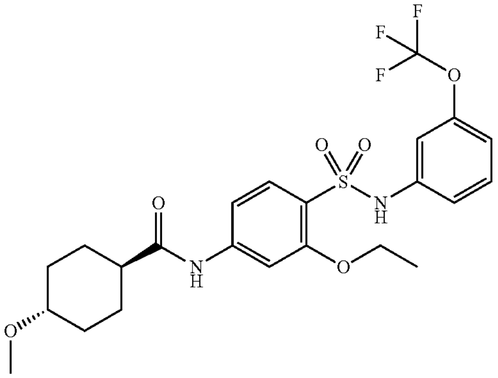 [SMILES: CCOc1cc(NC(=O)[C@H]2CC[C@H](OC)CC2)ccc1S(=O)(=O)Nc1cccc(OC(F)(F)F)c1] | ++ |

-continued
| Compound ID | Structure | Potency |
| --- | --- | --- |
| 1.029 | 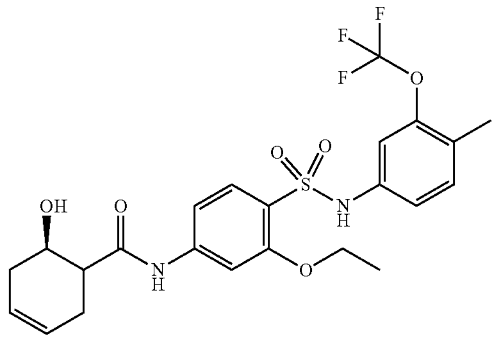 [SMILES: CCOc1cc(NC(=O)C2CC=CC[C@H]2O)ccc1S(=O)(=O)Nc1ccc(C)c(OC(F)(F)F)c1] | ++++ |
| 1.030 | 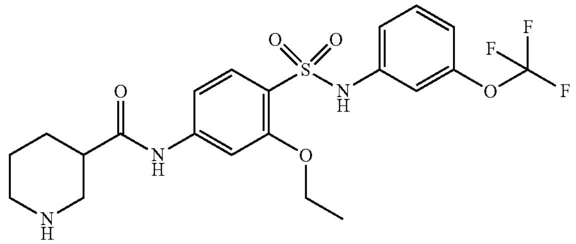 [SMILES: CCOc1cc(NC(=O)C2CCCNC2)ccc1S(=O)(=O)Nc1cccc(OC(F)(F)F)c1] | + |
| 1.031 | 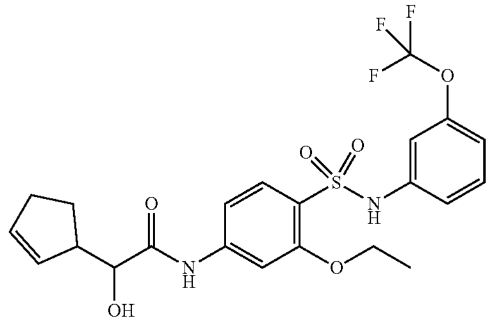 [SMILES: CCOc1cc(NC(=O)C(O)C2C=CCC2)ccc1S(=O)(=O)Nc1cccc(OC(F)(F)F)c1] | ++++ |
| 1.032 | 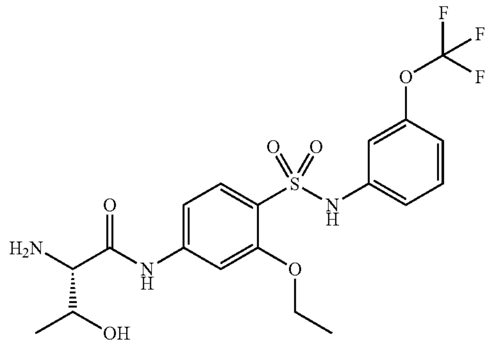 [SMILES: CCOc1cc(NC(=O)[C@@H](N)C(C)O)ccc1S(=O)(=O)Nc1cccc(OC(F)(F)F)c1] | ++++ |

-continued
| Compound ID | Structure | Potency |
|---|---|---|
| 1.033 | 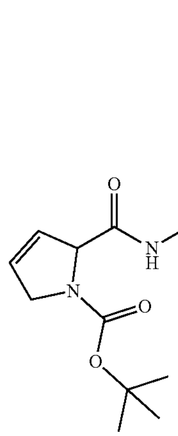 | + |
| 1.034 | 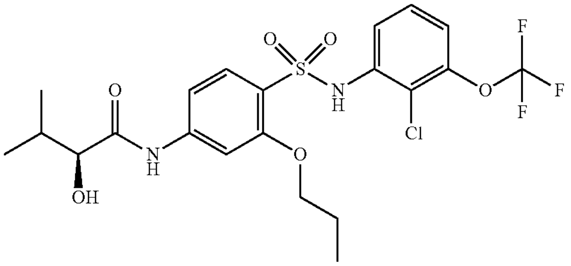 [SMILES: CCCOc1cc(NC(=O)[C@@H](O)C(C)C)ccc1S(=O)(=O)Nc1cccc(OC(F)(F)F)c1Cl] | ++++ |
| 1.035 | 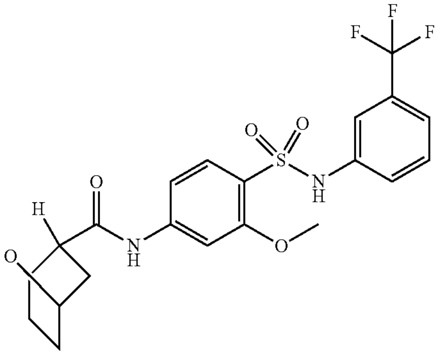 [SMILES: COc1cc(NC(=O)C2CC3CCC2O3)ccc1S(=O)(=O)Nc1cccc(C(F)(F)F)c1] | +++ |
| 1.036 | 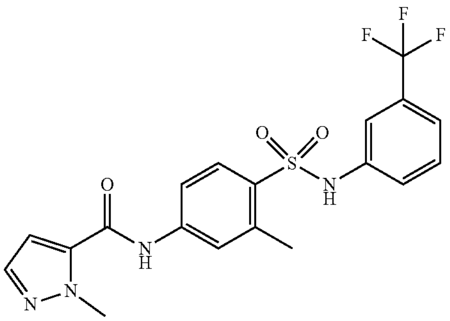 [SMILES: Cc1cc(NC(=O)c2ccnn2C)ccc1S(=O)(=O)Nc1cccc(C(F)(F)F)c1] | ++++ |

-continued
| Compound ID | Structure | Potency |
| --- | --- | --- |
| 1.037 | 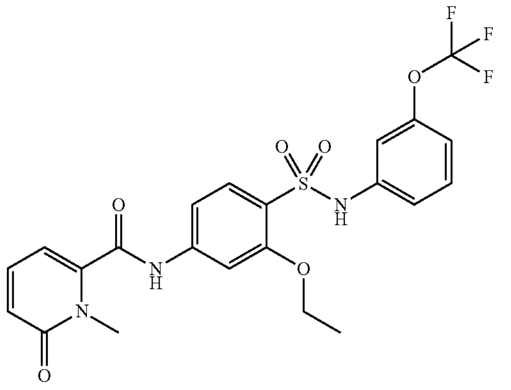 [SMILES: CCOc1cc(NC(=O)c2cccc(=O)n2C)ccc1S(=O)(=O)Nc1cccc(OC(F)(F)F)c1] | +++ |
| 1.038 | 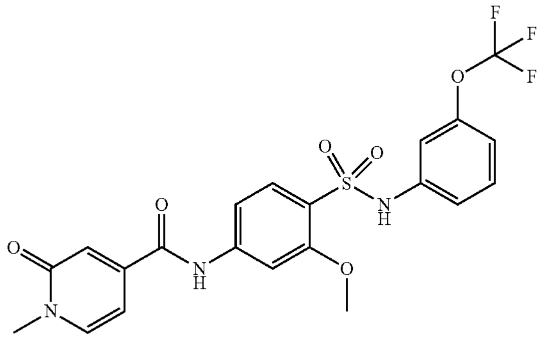 [SMILES: COc1cc(NC(=O)c2ccn(C)c(=O)c2)ccc1S(=O)(=O)Nc1cccc(OC(F)(F)F)c1] | +++ |
| 1.039 | 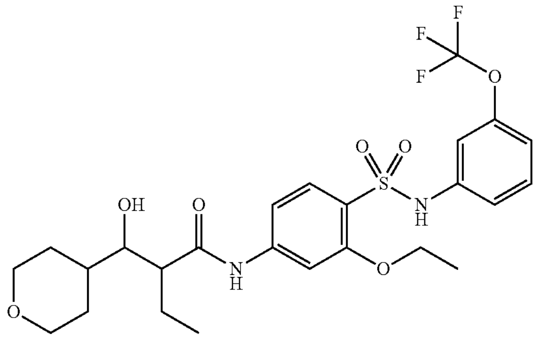 [SMILES: CCOc1cc(NC(=O)C(CC)C(O)C2CCOCC2)ccc1S(=O)(=O)Nc1cccc(OC(F)(F)F)c1] | ++++ |
| 1.040 | 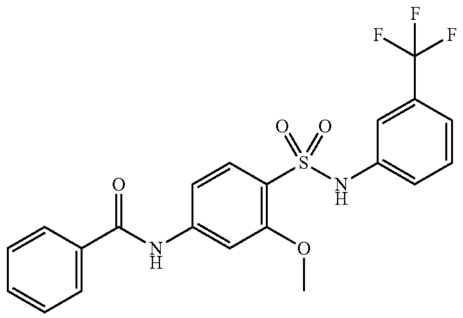 [SMILES: COc1cc(NC(=O)c2ccccc2)ccc1S(=O)(=O)Nc1cccc(C(F)(F)F)c1] | +++ |

-continued
| Compound ID | Structure | Potency |
|---|---|---|
| 1.041 | 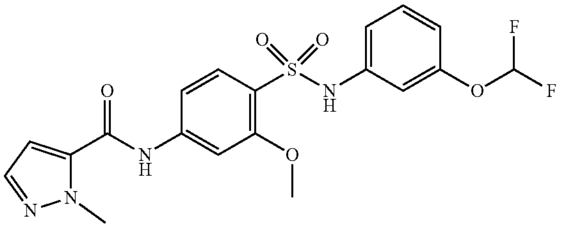 [SMILES: COc1cc(NC(=O)c2ccnn2C)ccc1S(=O)(=O)Nc1cccc(OC(F)F)c1] | +++ |
| 1.042 | 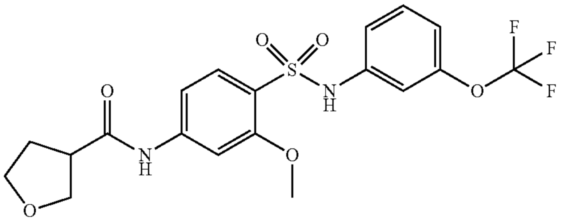 [SMILES: COc1cc(NC(=O)C2CCOC2)ccc1S(=O)(=O)Nc1cccc(OC(F)(F)F)c1] | ++ |
| 1.043 | AND Enantiomer 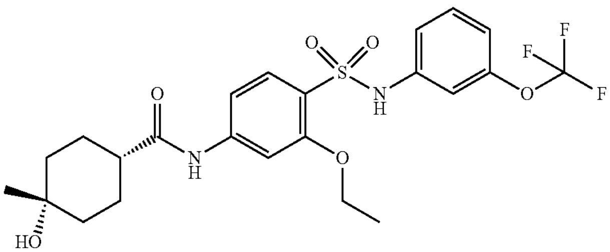 | + |
| 1.044 | 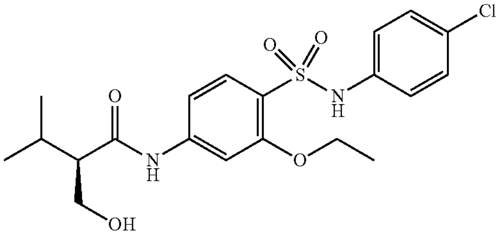 [SMILES: CCOc1cc(NC(=O)[C@@H](CO)C(C)C)ccc1S(=O)(=O)Nc1ccc(Cl)cc1] | +++ |
| 1.045 | 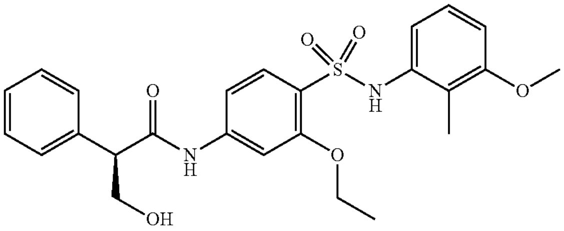 [SMILES: CCOc1cc(NC(=O)[C@@H](CO)c2ccccc2)ccc1S(=O)(=O)Nc1cccc(OC)c1C] | + |
| 1.046 | 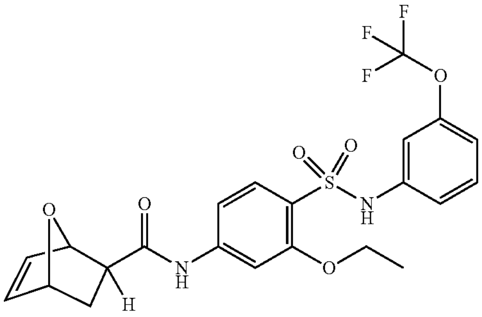 [SMILES: CCOc1cc(NC(=O)C2CC3C=CC2O3)ccc1S(=O)(=O)Nc1cccc(OC(F)(F)F)c1] | +++ |

-continued
| Compound ID | Structure | Potency |
| --- | --- | --- |
| 1.047 | 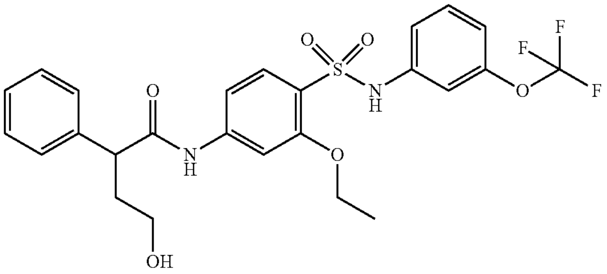 [SMILES: CCOc1cc(NC(=O)C(CCO)c2ccccc2)ccc1S(=O)(=O)Nc1cccc(OC(F)(F)F)c1] | ++++ |
| 1.048 | 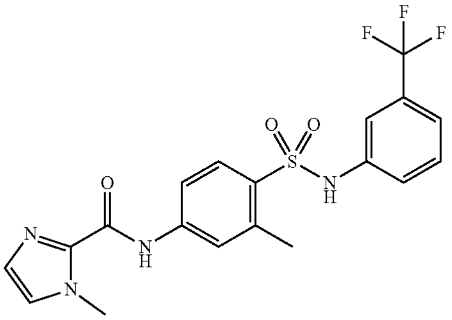 [SMILES: Cc1cc(NC(=O)c2nccn2C)ccc1S(=O)(=O)Nc1cccc(C(F)(F)F)c1] | + |
| 1.049 | 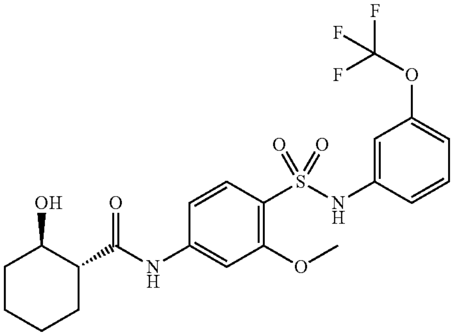 [SMILES: COc1cc(NC(=O)[C@@H]2CCCC[C@H]2O)ccc1S(=O)(=O)Nc1cccc(OC(F)(F)F)c1] | ++ |
| 1.050 | 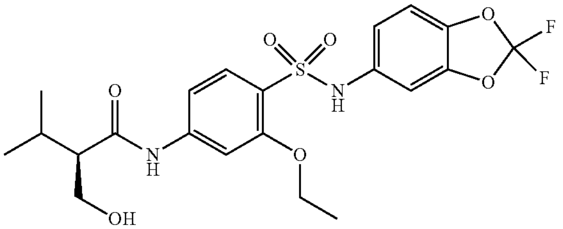 [SMILES: CCOc1cc(NC(=O)[C@@H](CO)C(C)C)ccc1S(=O)(=O)Nc1ccc2c(c1)OC(F)(F)O2] | +++ |
| 1.051 | AND Enantiomer 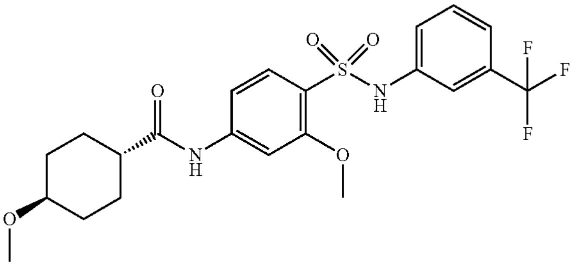 | + |

-continued
| Compound ID | Structure | Potency |
| --- | --- | --- |
| 1.052 | 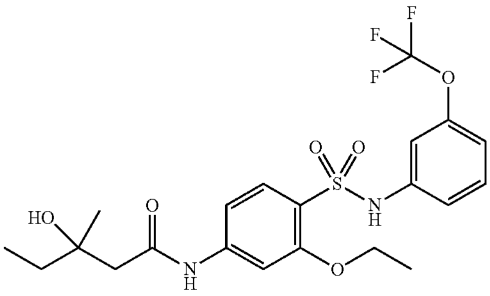 [SMILES: CCOc1cc(NC(=O)CC(C)(O)CC)ccc1S(=O)(=O)Nc1cccc(OC(F)(F)F)c1] | +++ |
| 1.053 | 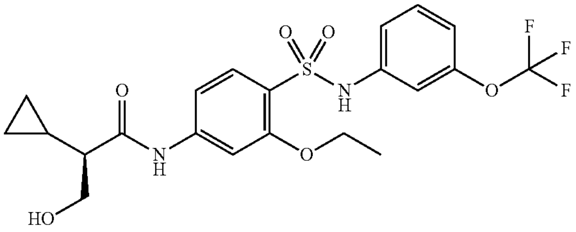 [SMILES: CCOc1cc(NC(=O)[C@@H](CO)C2CC2)ccc1S(=O)(=O)Nc1cccc(OC(F)(F)F)c1] | ++++ |
| 1.054 | 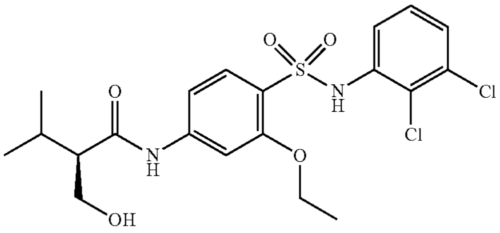 [SMILES: CCOc1cc(NC(=O)[C@@H](CO)C(C)C)ccc1S(=O)(=O)Nc1cccc(Cl)c1Cl] | +++ |
| 1.055 | 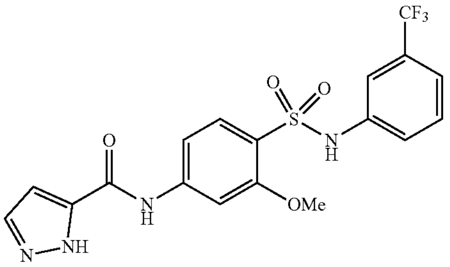 [SMILES: COc1cc(NC(=O)c2ccn[nH]2)ccc1S(=O)(=O)Nc1cccc(C(F)(F)F)c1] | ++ |
| 1.056 | 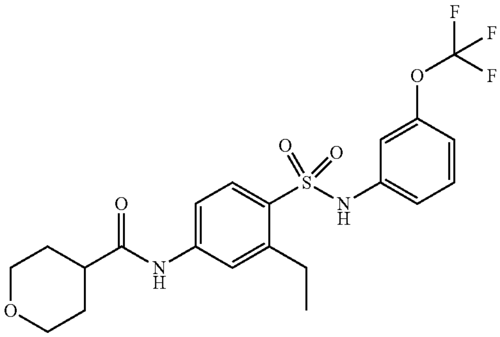 [SMILES: CCc1cc(NC(=O)C2CCOCC2)ccc1S(=O)(=O)Nc1cccc(OC(F)(F)F)c1] | ++++ |

-continued
| Compound ID | Structure | Potency |
|---|---|---|
| 1.057 | 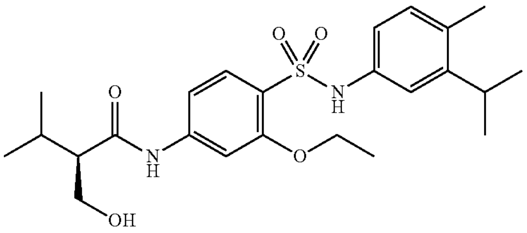 [SMILES: CCOc1cc(NC(=O)[C@@H](CO)C(C)C)ccc1S(=O)(=O)Nc1ccc(C)c(C(C)C)c1] | ++++ |
| 1.058 | 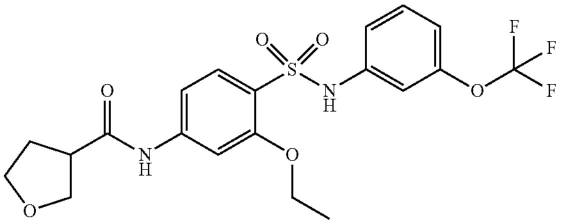 [SMILES: CCOc1cc(NC(=O)C2CCOC2)ccc1S(=O)(=O)Nc1cccc(OC(F)(F)F)c1] | +++ |
| 1.059 | 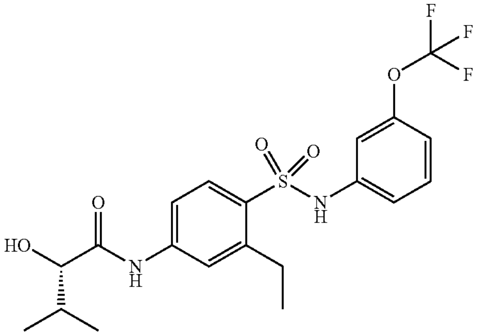 [SMILES: CCc1cc(NC(=O)[C@@H](O)C(C)C)ccc1S(=O)(=O)Nc1cccc(OC(F)(F)F)c1] | ++++ |
| 1.060 | 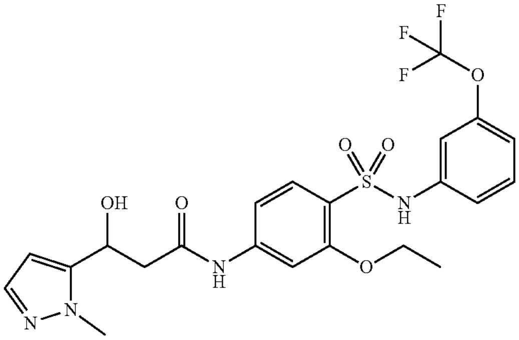 [SMILES: CCOc1cc(NC(=O)CC(O)c2ccnn2C)ccc1S(=O)(=O)Nc1cccc(OC(F)(F)F)c1] | ++ |
| 1.061 | 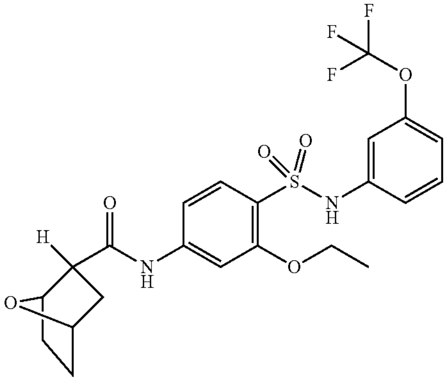 [SMILES: CCOc1cc(NC(=O)C2CC3CCC2O3)ccc1S(=O)(=O)Nc1cccc(OC(F)(F)F)c1] | ++++ |

-continued
| Compound ID | Structure | Potency |
|---|---|---|
| 1.062 | 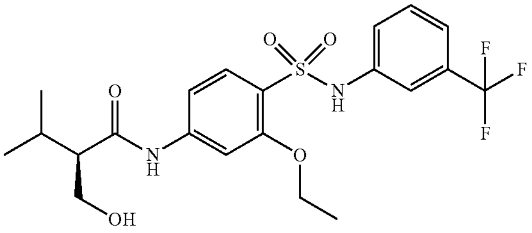 [SMILES: CCOc1cc(NC(=O)[C@@H](CO)C(C)C)ccc1S(=O)(=O)Nc1cccc(C(F)(F)F)c1] | ++++ |
| 1.063 | 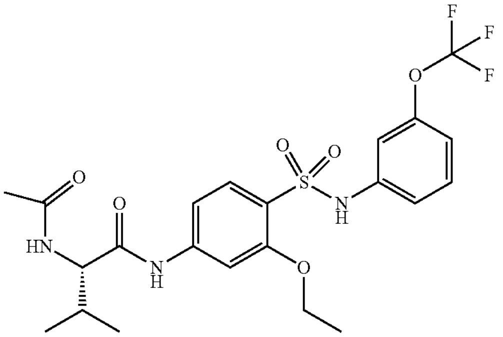 [SMILES: CCOc1cc(NC(=O)[C@@H](NC(C)=O)C(C)C)ccc1S(=O)(=O)Nc1cccc(OC(F)(F)F)c1] | ++++ |
| 1.064 | 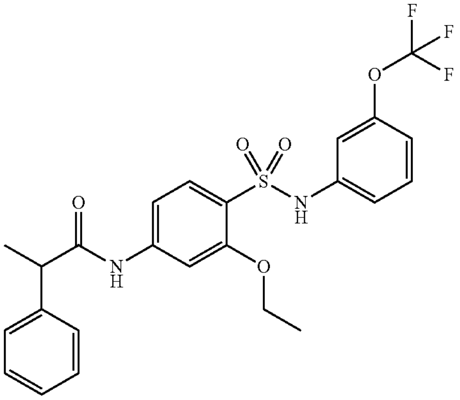 [SMILES: CCOc1cc(NC(=O)C(C)c2ccccc2)ccc1S(=O)(=O)Nc1cccc(OC(F)(F)F)c1] | ++++ |
| 1.065 | 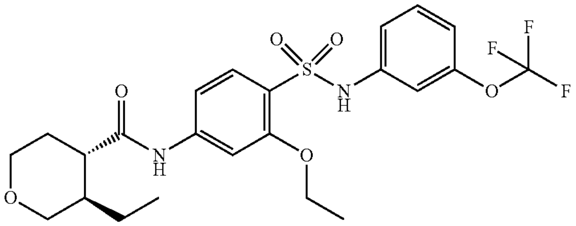 [SMILES: CCOc1cc(NC(=O)[C@H]2CCOC[C@@H]2CC)ccc1S(=O)(=O)Nc1cccc(OC(F)(F)F)c1] | ++++ |
| 1.066 | 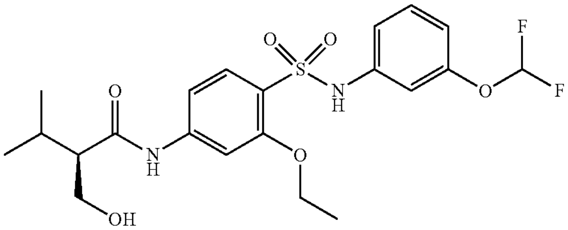 [SMILES: CCOc1cc(NC(=O)[C@@H](CO)C(C)C)ccc1S(=O)(=O)Nc1cccc(OC(F)F)c1] | ++++ |

-continued
| Compound ID | Structure | Potency |
|---|---|---|
| 1.067 | 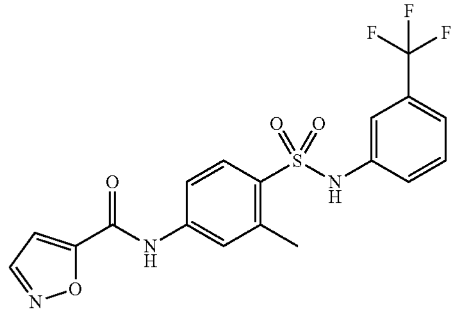 [SMILES: Cc1cc(NC(=O)c2ccno2)ccc1S(=O)(=O)Nc1cccc(C(F)(F)F)c1] | +++ |
| 1.068 | 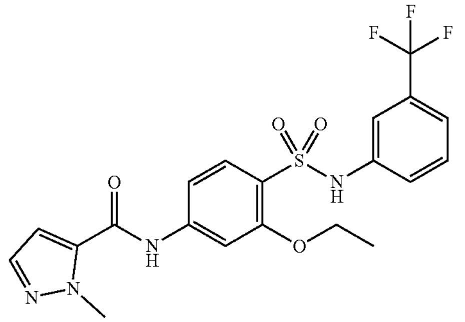 [SMILES: CCOc1cc(NC(=O)c2ccnn2C)ccc1S(=O)(=O)Nc1cccc(C(F)(F)F)c1] | ++++ |
| 1.069 | 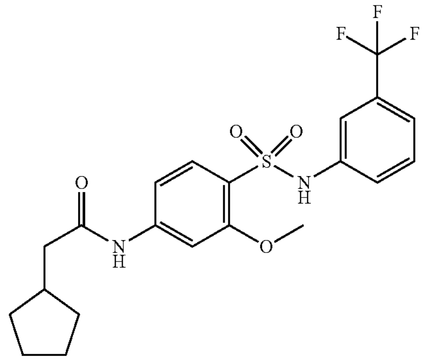 [SMILES: COc1cc(NC(=O)CC2CCCC2)ccc1S(=O)(=O)Nc1cccc(C(F)(F)F)c1] | +++ |
| 1.070 | 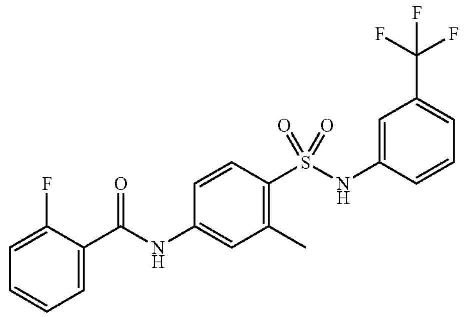 [SMILES: Cc1cc(NC(=O)c2ccccc2F)ccc1S(=O)(=O)Nc1cccc(C(F)(F)F)c1] | + |
| 1.071 | 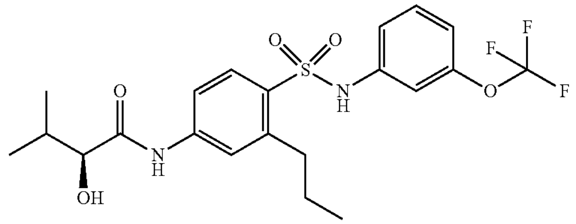 | ++++ |

-continued
| Compound ID | Structure | Potency |
|---|---|---|
| 1.072 | 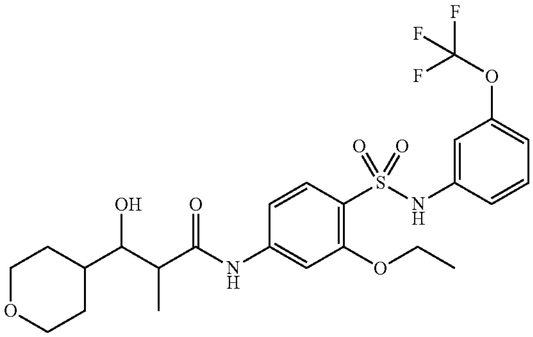 [SMILES: CCOc1cc(NC(=O)C(C)C(O)C2CCOCC2)ccc1S(=O)(=O)Nc1cccc(OC(F)(F)F)c1] | +++ |
| 1.073 | 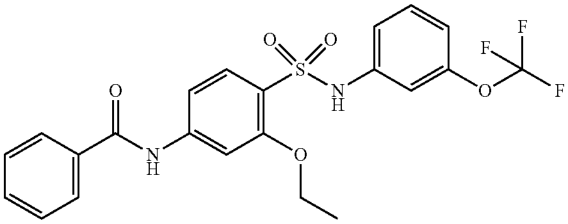 [SMILES: CCOc1cc(NC(=O)c2ccccc2)ccc1S(=O)(=O)Nc1cccc(OC(F)(F)F)c1] | ++++ |
| 1.074 | 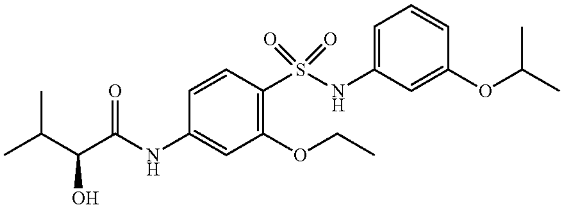 [SMILES: CCOc1cc(NC(=O)[C@@H](O)C(C)C)ccc1S(=O)(=O)Nc1cccc(OC(C)C)c1] | +++ |
| 1.075 | 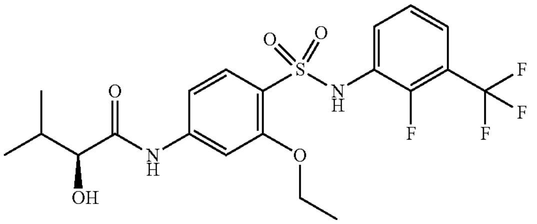 [SMILES: CCOc1cc(NC(=O)[C@@H](O)C(C)C)ccc1S(=O)(=O)Nc1cccc(C(F)(F)F)c1F] | + |
| 1.076 | 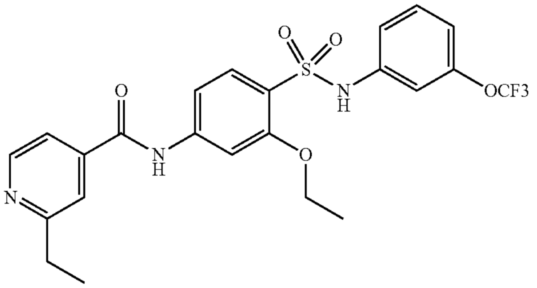 [SMILES: CCOc1cc(NC(=O)c2ccnc(CC)c2)ccc1S(=O)(=O)Nc1cccc(OC(F)(F)F)c1] | +++ |

-continued
| Compound ID | Structure | Potency |
|---|---|---|
| 1.077 | 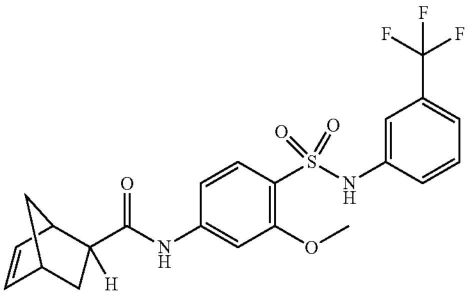 [SMILES: COc1cc(NC(=O)C2CC3C=CC2C3)ccc1S(=O)(=O)Nc1cccc(C(F)(F)F)c1] | + |
| 1.078 | 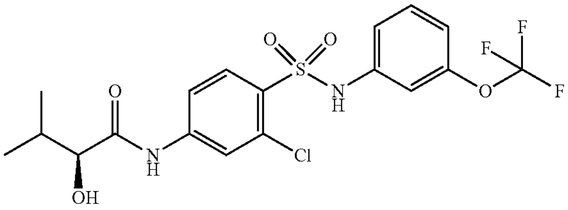 [SMILES: CC(C)[C@H](O)C(=O)Nc1ccc(S(=O)(=O)Nc2cccc(OC(F)(F)F)c2)c(Cl)c1] | ++++ |
| 1.079 | 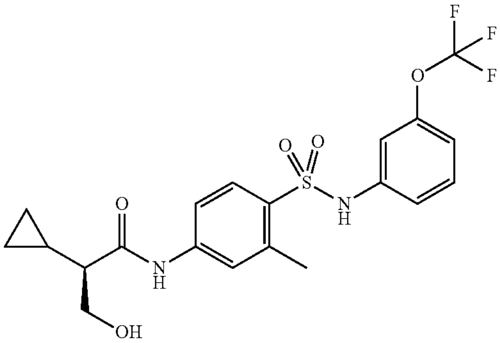 [SMILES: Cc1cc(NC(=O)[C@@H](CO)C2CC2)ccc1S(=O)(=O)Nc1cccc(OC(F)(F)F)c1] | ++++ |
| 1.080 | 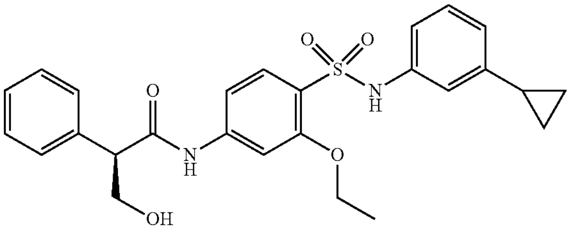 [SMILES: CCOc1cc(NC(=O)[C@@H](CO)c2ccccc2)ccc1S(=O)(=O)Nc1cccc(C2CC2)c1] | ++++ |
| 1.081 | 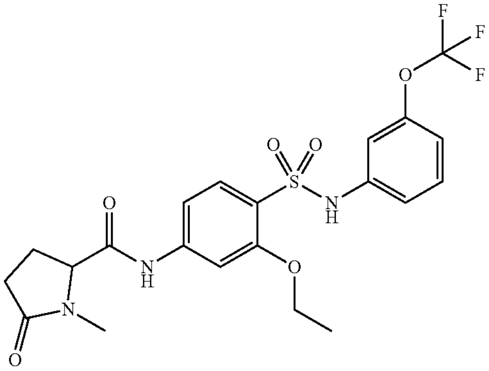 [SMILES: CCOc1cc(NC(=O)C2CCC(=O)N2C)ccc1S(=O)(=O)Nc1cccc(OC(F)(F)F)c1] | ++ |

-continued
| Compound ID | Structure | Potency |
|---|---|---|
| 1.082 | 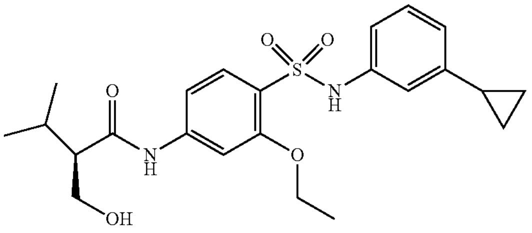 [SMILES: CCOc1cc(NC(=O)[C@@H](CO)C(C)C)ccc1S(=O)(=O)Nc1cccc(C2CC2)c1] | ++++ |
| 1.083 | 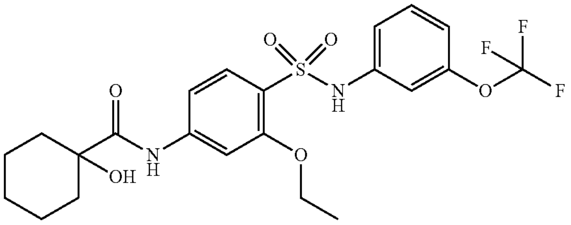 [SMILES: CCOc1cc(NC(=O)C2(O)CCCCC2)ccc1S(=O)(=O)Nc1cccc(OC(F)(F)F)c1] | ++ |
| 1.084 | 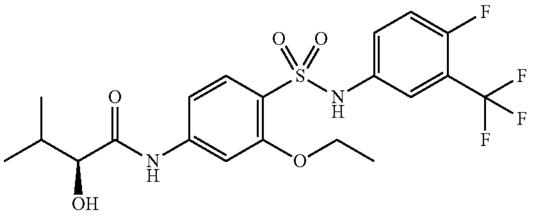 [SMILES: CCOc1cc(NC(=O)[C@@H](O)C(C)C)ccc1S(=O)(=O)Nc1ccc(F)c(C(F)(F)F)c1] | ++++ |
| 1.085 | 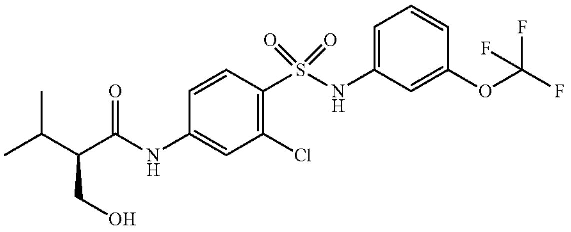 | ++++ |
| 1.086 | 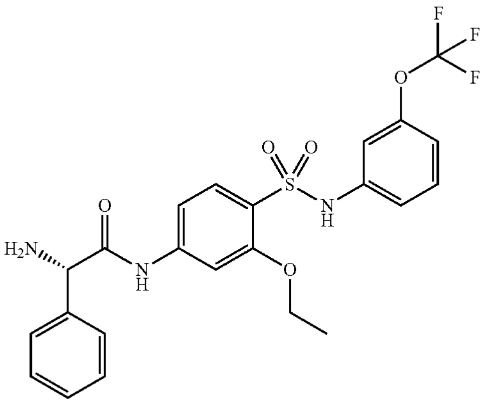 [SMILES: CCOc1cc(NC(=O)[C@@H](N)c2ccccc2)ccc1S(=O)(=O)Nc1cccc(OC(F)(F)F)c1] | ++++ |

-continued
| Compound ID | Structure | Potency |
| --- | --- | --- |
| 1.087 | 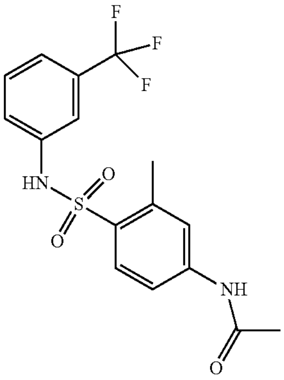 [SMILES: CC(=O)Nc1ccc(S(=O)(=O)Nc2cccc(C(F)(F)F)c2)c(C)c1] | + |
| 1.088 | 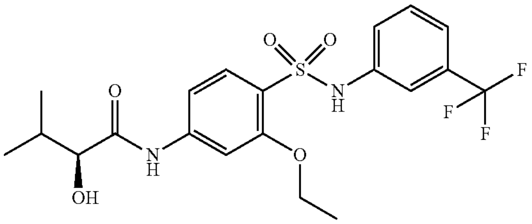 [SMILES: CCOc1cc(NC(=O)[C@@H](O)C(C)C)ccc1S(=O)(=O)Nc1cccc(C(F)(F)F)c1] | ++++ |
| 1.089 | 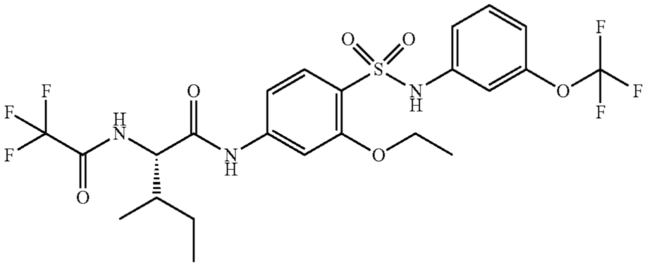 [SMILES: CCOc1cc(NC(=O)[C@@H](NC(=O)C(F)(F)F)C(C)CC)ccc1S(=O)(=O)Nc1cccc(OC(F)(F)F)c1] | ++++ |
| 1.090 | 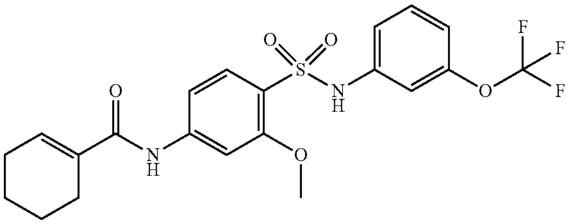 [SMILES: COc1cc(NC(=O)C2=CCCCC2)ccc1S(=O)(=O)Nc1cccc(OC(F)(F)F)c1] | ++ |
| 1.091 | 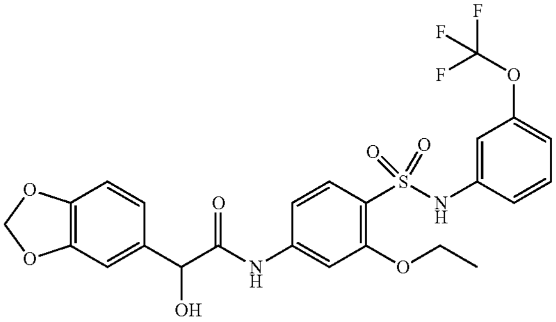 [SMILES: CCOc1cc(NC(=O)C(O)c2ccc3c(c2)OCO3)ccc1S(=O)(=O)Nc1cccc(OC(F)(F)F)c1] | +++ |

-continued
| Compound ID | Structure | Potency |
|---|---|---|
| 1.092 | 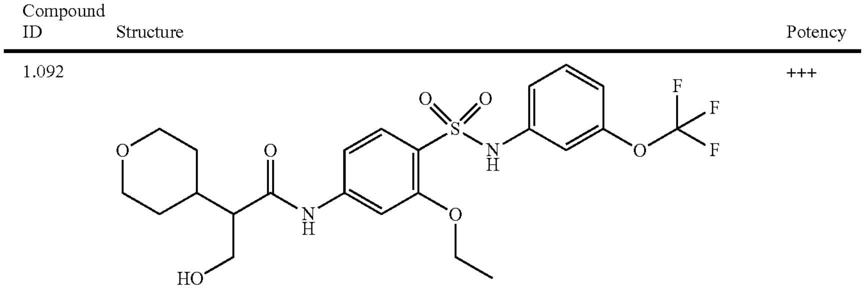 | +++ |
| 1.093 | 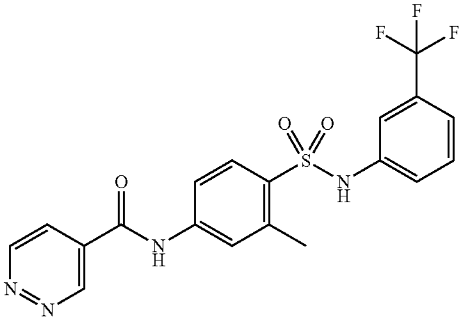 [SMILES: Cc1cc(NC(=O)c2ccnnc2)ccc1S(=O)(=O)Nc1cccc(C(F)(F)F)c1] | ++ |
| 1.094 | 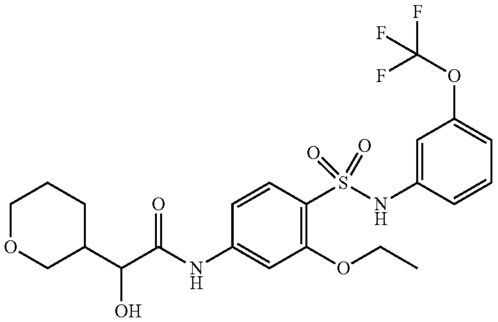 [SMILES: CCOc1cc(NC(=O)C(O)C2CCCOC2)ccc1S(=O)(=O)Nc1cccc(OC(F)(F)F)c1] | ++++ |
| 1.095 | 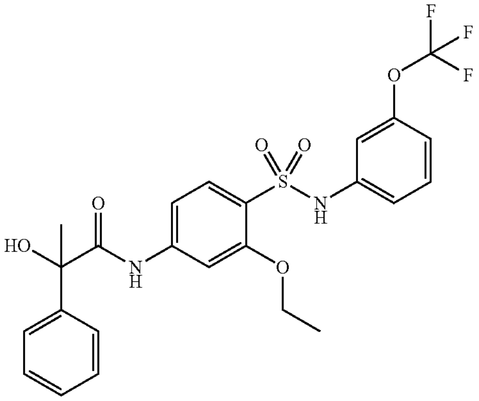 [SMILES: CCOc1cc(NC(=O)C(C)(O)c2ccccc2)ccc1S(=O)(=O)Nc1cccc(OC(F)(F)F)c1] | ++++ |
| 1.096 | 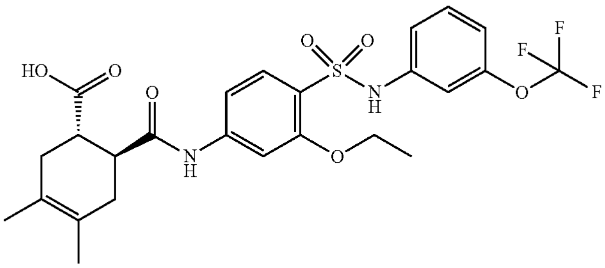 [SMILES: CCOc1cc(NC(=O)[C@H]2CC(C)=C(C)C[C@@H]2C(=O)O)ccc1S(=O)(=O)Nc1cccc(OC(F)(F)F)c1] | ++++ |

-continued
| Compound ID | Structure | Potency |
|---|---|---|
| 1.097 | 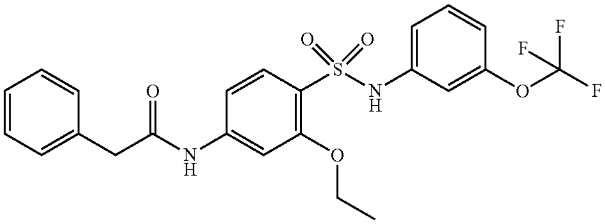 [SMILES: CCOc1cc(NC(=O)Cc2ccccc2)ccc1S(=O)(=O)Nc1cccc(OC(F)(F)F)c1] | ++++ |
| 1.098 | 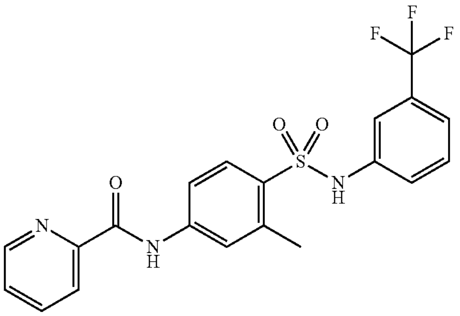 [SMILES: Cc1cc(NC(=O)c2ccccn2)ccc1S(=O)(=O)Nc1cccc(C(F)(F)F)c1] | + |
| 1.099 | 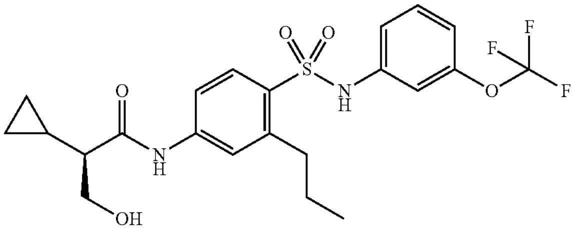 [SMILES: CCCc1cc(NC(=O)[C@@H](CO)C2CC2)ccc1S(=O)(=O)Nc1cccc(OC(F)(F)F)c1] | ++++ |
| 1.100 | 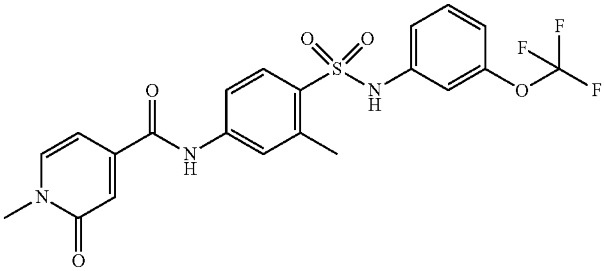 [SMILES: Cc1cc(NC(=O)c2ccn(C)c(=O)c2)ccc1S(=O)(=O)Nc1cccc(OC(F)(F)F)c1] | +++ |
| 1.101 | 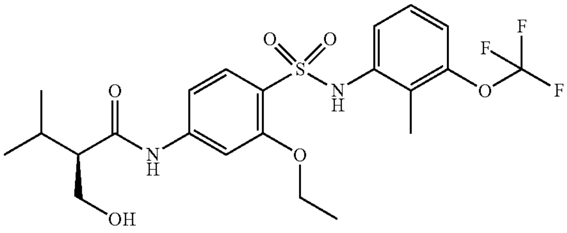 [SMILES: CCOc1cc(NC(=O)[C@@H](CO)C(C)C)ccc1S(=O)(=O)Nc1cccc(OC(F)(F)F)c1C] | + |

-continued
| Compound ID | Structure | Potency |
| --- | --- | --- |
| 1.102 | 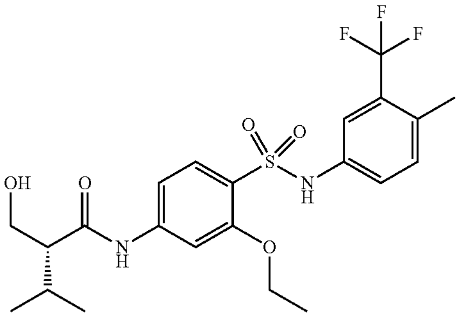 [SMILES: CCOc1cc(NC(=O)[C@@H](CO)C(C)C)ccc1S(=O)(=O)Nc1ccc(C)c(C(F)(F)F)c1] | ++++ |
| 1.103 | 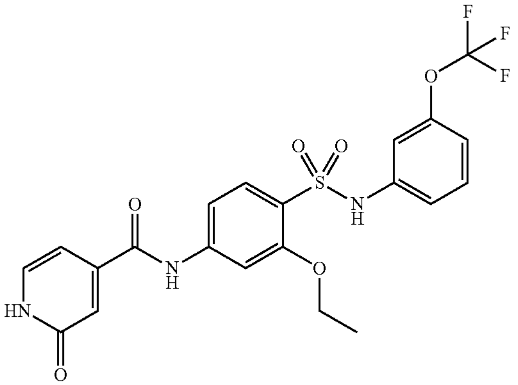 [SMILES: CCOc1cc(NC(=O)c2cc[nH]c(=O)c2)ccc1S(=O)(=O)Nc1cccc(OC(F)(F)F)c1] | ++++ |
| 1.104 | 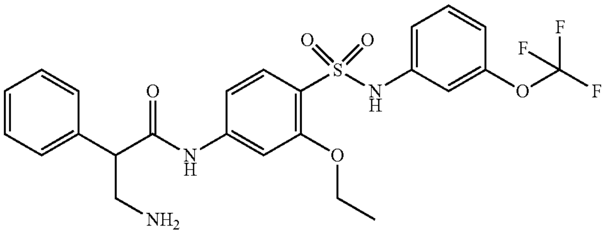 [SMILES: CCOc1cc(NC(=O)C(CN)c2ccccc2)ccc1S(=O)(=O)Nc1cccc(OC(F)(F)F)c1] | ++++ |
| 1.105 | 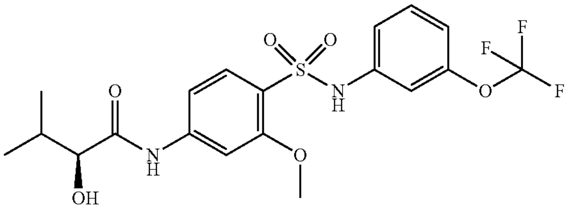 [SMILES: COc1cc(NC(=O)[C@@H](O)C(C)C)ccc1S(=O)(=O)Nc1cccc(OC(F)(F)F)c1] | ++++ |
| 1.106 | 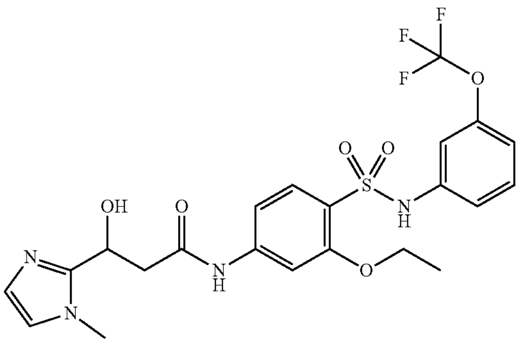 [SMILES: CCOc1cc(NC(=O)CC(O)c2nccn2C)ccc1S(=O)(=O)Nc1cccc(OC(F)(F)F)c1] | + |

-continued
| Compound ID | Structure | Potency |
|---|---|---|
| 1.107 | AND Enantiomer 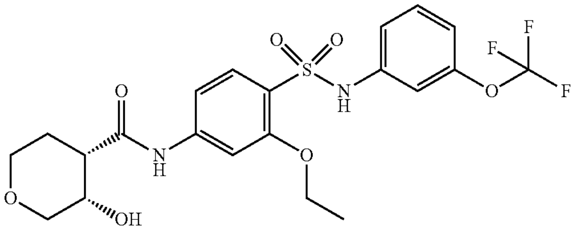 | +++ |
| 1.108 | 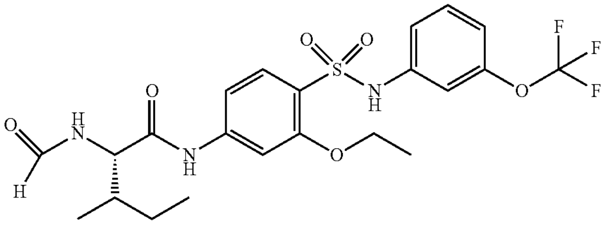 [SMILES: CCOc1cc(NC(=O)[C@@H](NC=O)C(C)CC)ccc1S(=O)(=O)Nc1cccc(OC(F)(F)F)c1] | ++++ |
| 1.109 | 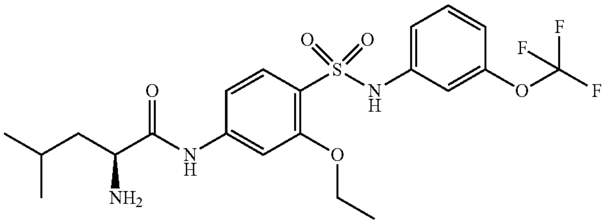 [SMILES: CCOc1cc(NC(=O)[C@@H](N)CC(C)C)ccc1S(=O)(=O)Nc1cccc(OC(F)(F)F)c1] | ++++ |
| 1.110 | 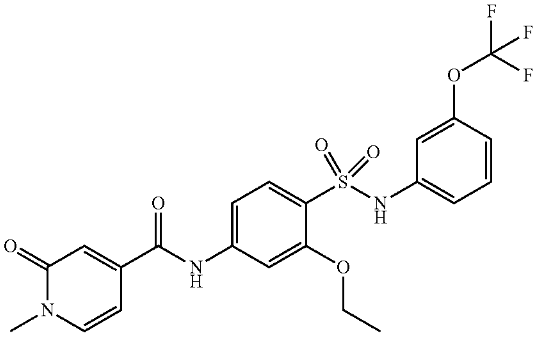 [SMILES: CCOc1cc(NC(=O)c2ccn(C)c(=O)c2)ccc1S(=O)(=O)Nc1cccc(OC(F)(F)F)c1] | ++++ |
| 1.111 | 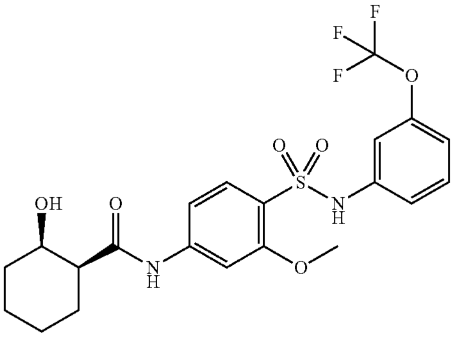 [SMILES: COc1cc(NC(=O)[C@H]2CCCC[C@H]2O)ccc1S(=O)(=O)Nc1cccc(OC(F)(F)F)c1] | +++ |

-continued
| Compound ID | Structure | Potency |
|---|---|---|
| 1.112 | 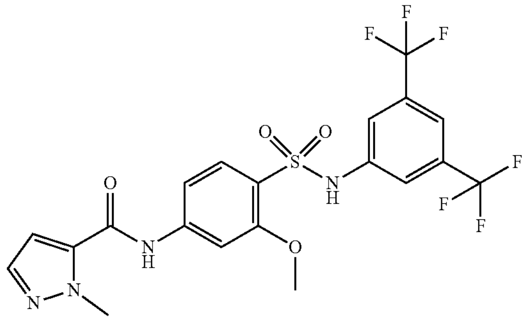 [SMILES: COc1cc(NC(=O)c2ccnn2C)ccc1S(=O)(=O)Nc1cc(C(F)(F)F)cc(C(F)(F)F)c1] | + |
| 1.113 | 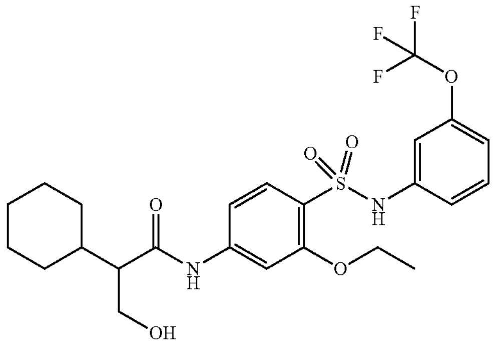 [SMILES: CCOc1cc(NC(=O)C(CO)C2CCCCC2)ccc1S(=O)(=O)Nc1cccc(OC(F)(F)F)c1] | ++++ |
| 1.114 | 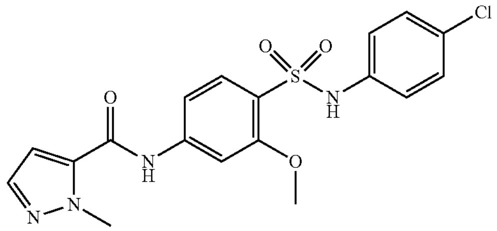 [SMILES: COc1cc(NC(=O)c2ccnn2C)ccc1S(=O)(=O)Nc1ccc(Cl)cc1] | +++ |
| 1.115 | 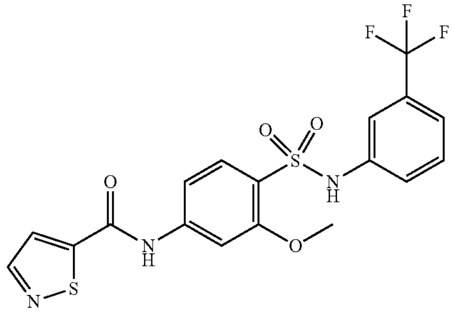 [SMILES: COc1cc(NC(=O)c2ccns2)ccc1S(=O)(=O)Nc1cccc(C(F)(F)F)c1] | ++++ |
| 1.116 | 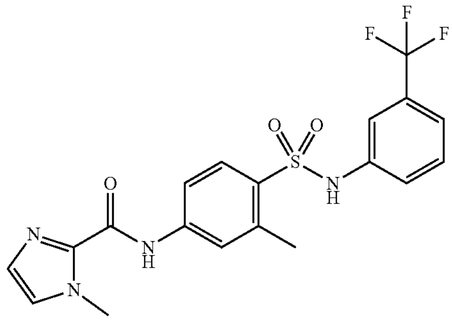 [SMILES: Cc1cc(NC(=O)c2nccn2C)ccc1S(=O)(=O)Nc1cccc(C(F)(F)F)c1] | + |

-continued
| Compound ID | Structure | Potency |
|---|---|---|
| 1.117 | 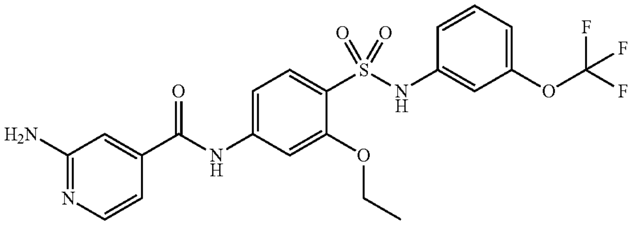 [SMILES: CCOc1cc(NC(=O)c2ccnc(N)c2)ccc1S(=O)(=O)Nc1cccc(OC(F)(F)F)c1] | ++++ |
| 1.118 | 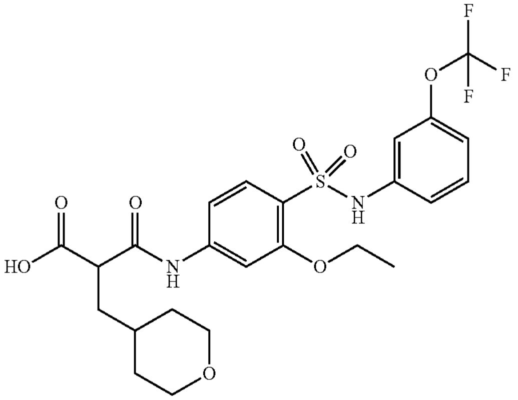 [SMILES: CCOc1cc(NC(=O)C(CC2CCOCC2)C(=O)O)ccc1S(=O)(=O)Nc1cccc(OC(F)(F)F)c1] | ++++ |
| 1.119 | 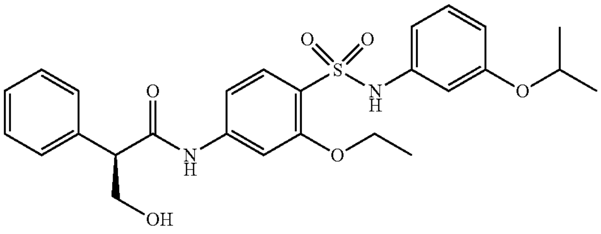 [SMILES: CCOc1cc(NC(=O)[C@@H](CO)c2ccccc2)ccc1S(=O)(=O)Nc1cccc(OC(C)C)c1] | +++ |
| 1.120 | 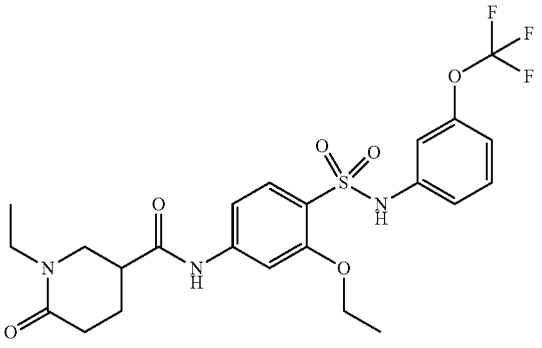 [SMILES: CCOc1cc(NC(=O)C2CCC(=O)N(CC)C2)ccc1S(=O)(=O)Nc1cccc(OC(F)(F)F)c1] | + |
| 1.121 | 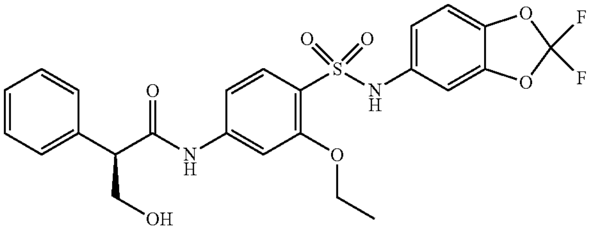 [SMILES: CCOc1cc(NC(=O)[C@@H](CO)c2ccccc2)ccc1S(=O)(=O)Nc1ccc2c(c1)OC(F)(F)O2] | + |

-continued
| Compound ID | Structure | Potency |
| --- | --- | --- |
| 1.122 | 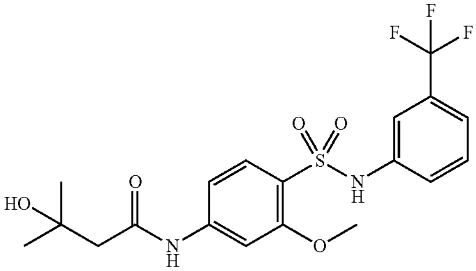 [SMILES: COc1cc(NC(=O)CC(C)(C)O)ccc1S(=O)(=O)Nc1cccc(C(F)(F)F)c1] | + |
| 1.123 | 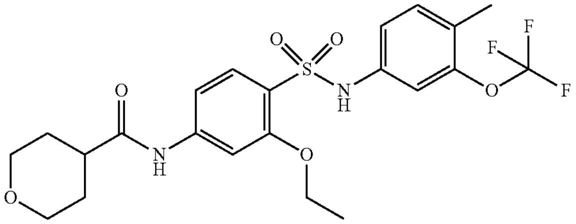 [SMILES: CCOc1cc(NC(=O)C2CCOCC2)ccc1S(=O)(=O)Nc1ccc(C)c(OC(F)(F)F)c1] | ++++ |
| 1.124 | 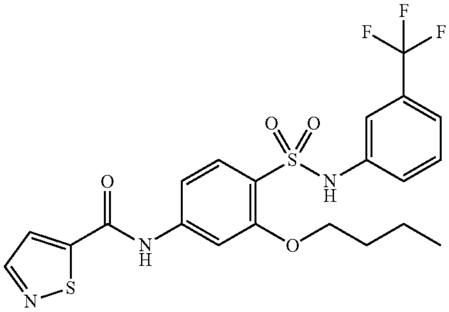 [SMILES: CCCCOc1cc(NC(=O)c2ccns2)ccc1S(=O)(=O)Nc1cccc(C(F)(F)F)c1] | + |
| 1.125 | 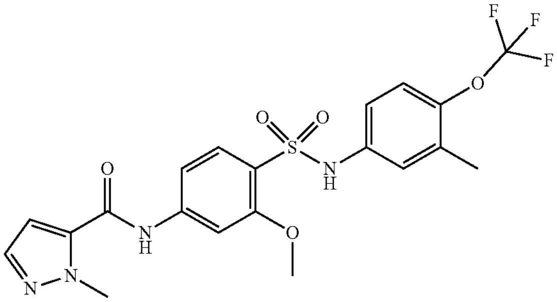 [SMILES: COc1cc(NC(=O)c2ccnn2C)ccc1S(=O)(=O)Nc1ccc(OC(F)(F)F)c(C)c1] | ++ |
| 1.126 | 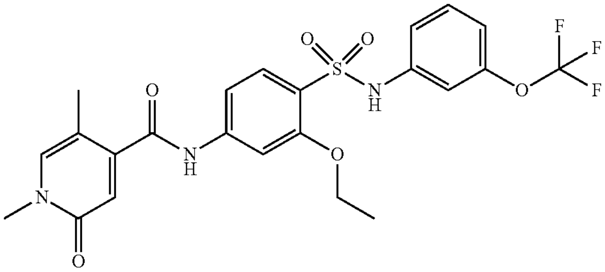 [SMILES: CCOc1cc(NC(=O)c2cc(=O)n(C)cc2C)ccc1S(=O)(=O)Nc1cccc(OC(F)(F)F)c1] | ++++ |

-continued
| Compound ID | Structure | Potency |
|---|---|---|
| 1.127 | 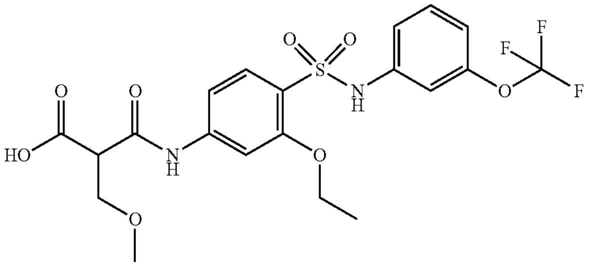 [SMILES: CCOc1cc(NC(=O)C(COC)C(=O)O)ccc1S(=O)(=O)Nc1cccc(OC(F)(F)F)c1] | +++ |
| 1.128 | 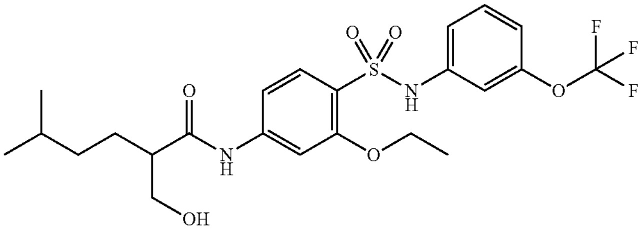 [SMILES: CCOc1cc(NC(=O)C(CO)CCC(C)C)ccc1S(=O)(=O)Nc1cccc(OC(F)(F)F)c1] | ++++ |
| 1.129 | 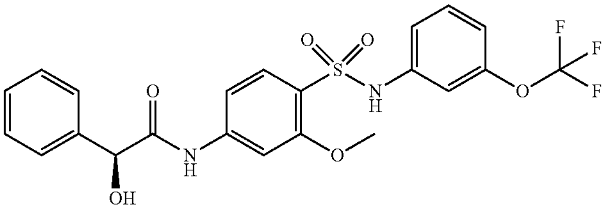 [SMILES: COc1cc(NC(=O)[C@@H](O)c2ccccc2)ccc1S(=O)(=O)Nc1cccc(OC(F)(F)F)c1] | ++++ |
| 1.130 | 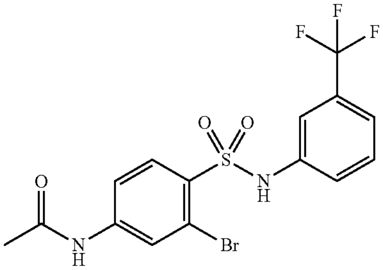 | + |
| 1.131 | 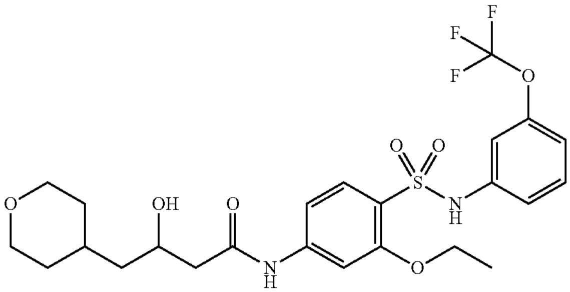 [SMILES: CCOc1cc(NC(=O)CC(O)CC2CCOCC2)ccc1S(=O)(=O)Nc1cccc(OC(F)(F)F)c1] | + |

-continued
| Compound ID | Structure | Potency |
|---|---|---|
| 1.132 | 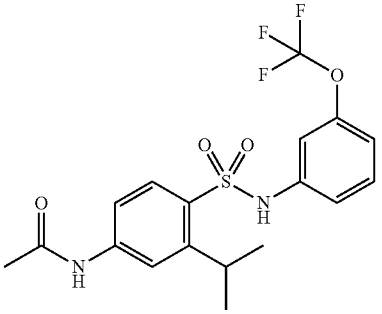 [SMILES: CC(=O)Nc1ccc(S(=O)(=O)Nc2cccc(OC(F)(F)F)c2)c(C(C)C)c1] | + |
| 1.133 | 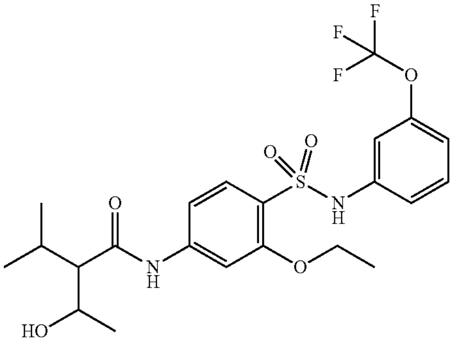 [SMILES: CCOc1cc(NC(=O)C(C(C)C)C(C)O)ccc1S(=O)(=O)Nc1cccc(OC(F)(F)F)c1] | ++++ |
| 1.134 | 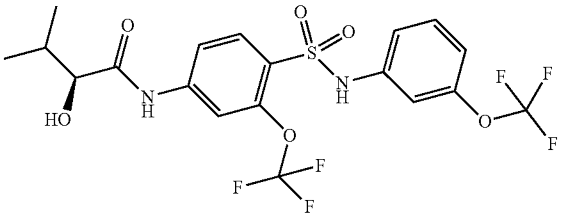 [SMILES: CC(C)[C@H](O)C(=O)Nc1ccc(S(=O)(=O)Nc2cccc(OC(F)(F)F)c2)c(OC(F)(F)F)c1] | +++ |
| 1.135 | 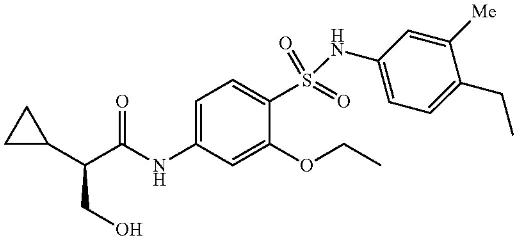 [SMILES: CCOc1cc(NC(=O)[C@@H](CO)C2CC2)ccc1S(=O)(=O)Nc1ccc(CC)c(C)c1] | ++++ |
| 1.136 | 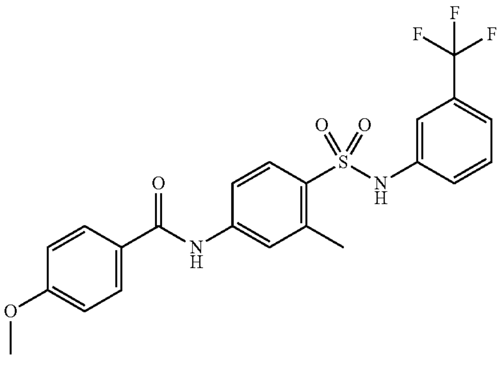 [SMILES: COc1ccc(C(=O)Nc2ccc(S(=O)(=O)Nc3cccc(C(F)(F)F)c3)c(C)c2)cc1] | ++ |

-continued
| Compound ID | Structure | Potency |
|---|---|---|
| 1.137 | 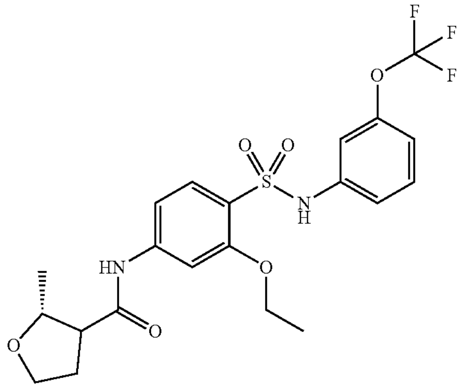 [SMILES: CCOc1cc(NC(=O)C2CCO[C@@H]2C)ccc1S(=O)(=O)Nc1cccc(OC(F)(F)F)c1] | +++ |
| 1.138 | 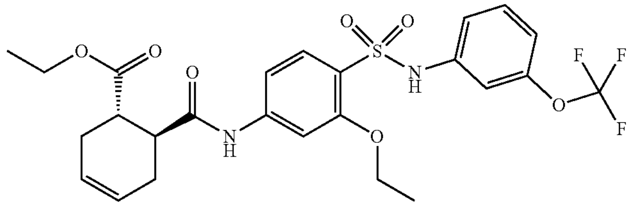 [SMILES: CCOC(=O)[C@H]1CC=CC[C@@H]1C(=O)Nc1ccc(S(=O)(=O)Nc2cccc(OC(F)(F)F)c2)c(OCC)c1] | ++++ |
| 1.139 | 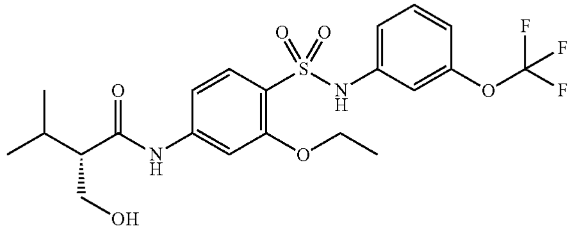 [SMILES: CCOc1cc(NC(=O)[C@H](CO)C(C)C)ccc1S(=O)(=O)Nc1cccc(OC(F)(F)F)c1] | ++++ |
| 1.140 | 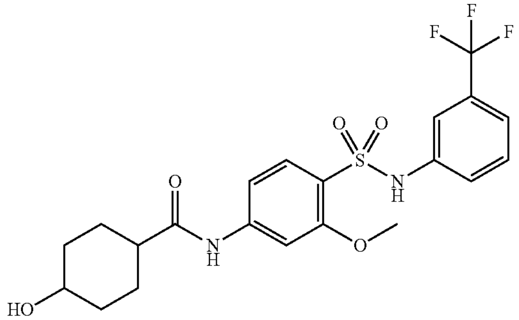 [SMILES: COc1cc(NC(=O)C2CCC(O)CC2)ccc1S(=O)(=O)Nc1cccc(C(F)(F)F)c1] | + |
| 1.141 | 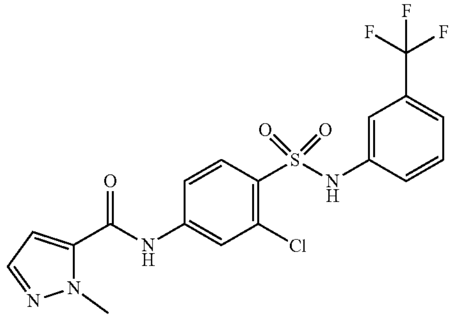 | +++ |

-continued
| Compound ID | Structure | Potency |
|---|---|---|
| 1.142 | 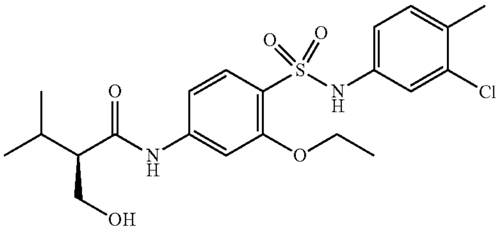 [SMILES: CCOc1cc(NC(=O)[C@@H](CO)C(C)C)ccc1S(=O)(=O)Nc1ccc(C)c(Cl)c1] | ++++ |
| 1.143 | 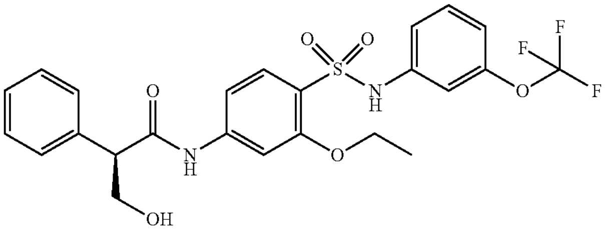 [SMILES: CCOc1cc(NC(=O)[C@@H](CO)c2ccccc2)ccc1S(=O)(=O)Nc1cccc(OC(F)(F)F)c1] | ++++ |
| 1.144 | 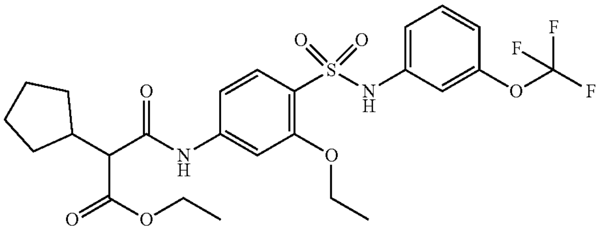 [SMILES: CCOC(=O)C(C(=O)Nc1ccc(S(=O)(=O)Nc2cccc(OC(F)(F)F)c2)c(OCC)c1)C1CCCC1] | ++++ |
| 1.145 | 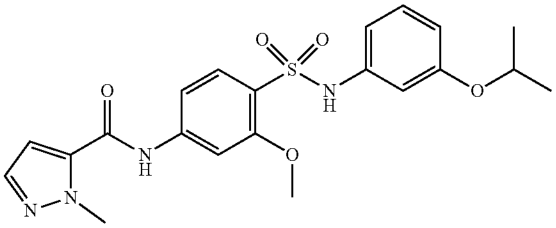 [SMILES: COc1cc(NC(=O)c2ccnn2C)ccc1S(=O)(=O)Nc1cccc(OC(C)C)c1] | ++ |
| 1.146 | 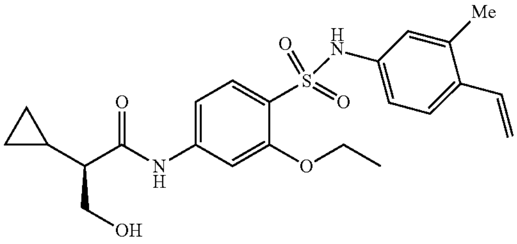 [SMILES: C=Cc1ccc(NS(=O)(=O)c2ccc(NC(=O)[C@@H](CO)C3CC3)cc2OCC)cc1C] | ++++ |
| 1.147 | 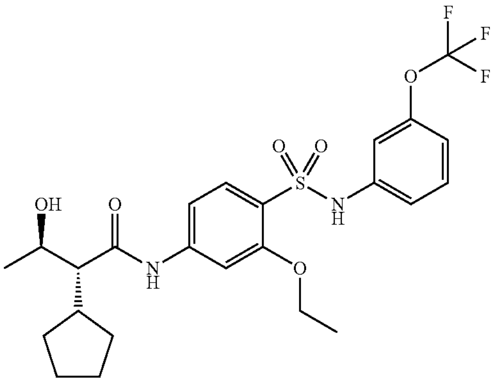 [SMILES: CCOc1cc(NC(=O)[C@H](C2CCCC2)[C@@H](C)O)ccc1S(=O)(=O)Nc1cccc(OC(F)(F)F)c1] | ++++ |

-continued
| Compound ID | Structure | Potency |
| --- | --- | --- |
| 1.148 | 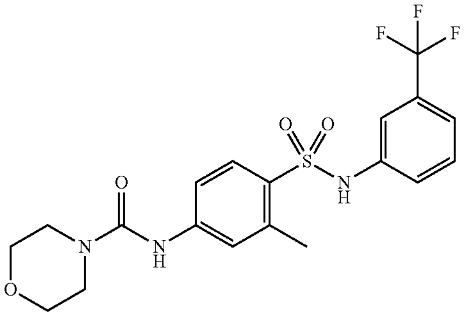 [SMILES: Cc1cc(NC(=O)N2CCOCC2)ccc1S(=O)(=O)Nc1cccc(C(F)(F)F)c1] | + |
| 1.149 | 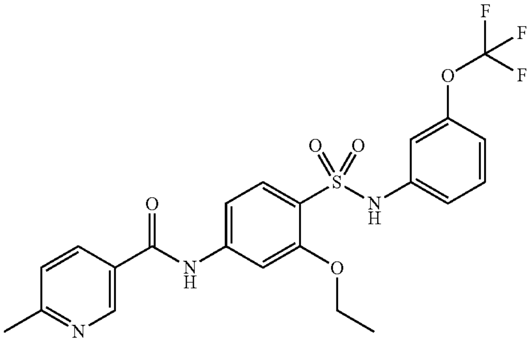 [SMILES: CCOc1cc(NC(=O)c2ccc(C)nc2)ccc1S(=O)(=O)Nc1cccc(OC(F)(F)F)c1] | ++++ |
| 1.150 | 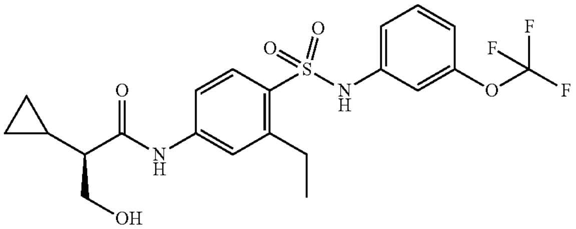 [SMILES: CCc1cc(NC(=O)[C@@H](CO)C2CC2)ccc1S(=O)(=O)Nc1cccc(OC(F)(F)F)c1] | ++++ |
| 1.151 | 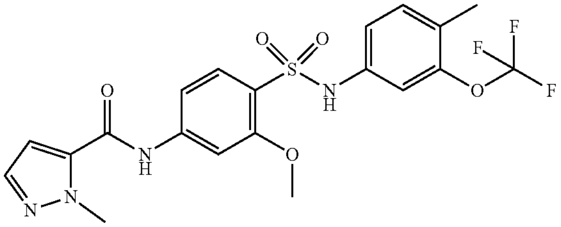 [SMILES: COc1cc(NC(=O)c2ccnn2C)ccc1S(=O)(=O)Nc1ccc(C)c(OC(F)(F)F)c1] | ++++ |
| 1.152 | 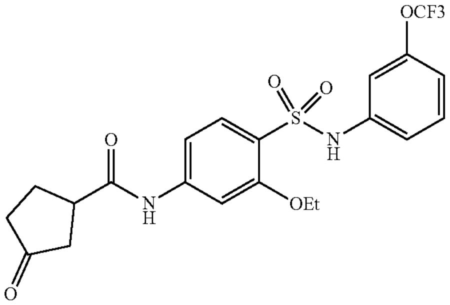 [SMILES: CCOc1cc(NC(=O)C2CCC(=O)C2)ccc1S(=O)(=O)Nc1cccc(OC(F)(F)F)c1] | +++ |

-continued
| Compound ID | Structure | Potency |
|---|---|---|
| 1.153 | 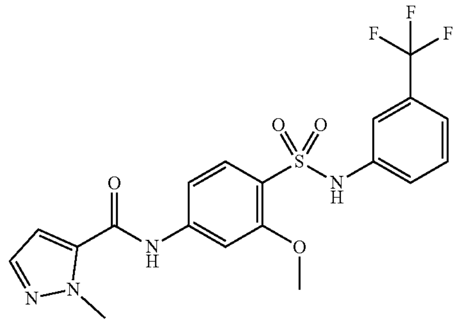 [SMILES: COc1cc(NC(=O)c2ccnn2C)ccc1S(=O)(=O)Nc1cccc(C(F)(F)F)c1] | +++ |
| 1.154 | 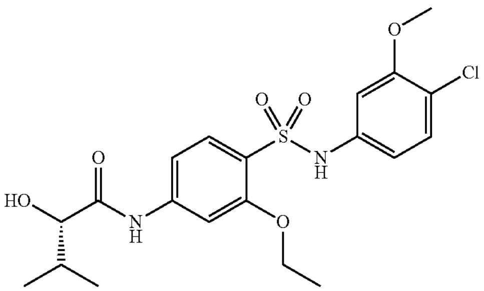 [SMILES: CCOc1cc(NC(=O)[C@@H](O)C(C)C)ccc1S(=O)(=O)Nc1ccc(Cl)c(OC)c1] | +++ |
| 1.155 | 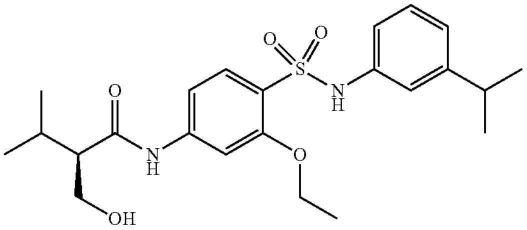 [SMILES: CCOc1cc(NC(=O)[C@@H](CO)C(C)C)ccc1S(=O)(=O)Nc1cccc(C(C)C)c1] | ++++ |
| 1.156 | 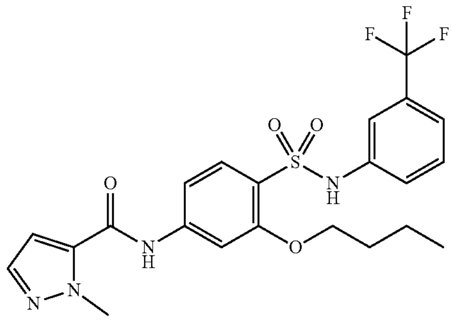 [SMILES: CCCCOc1cc(NC(=O)c2ccnn2C)ccc1S(=O)(=O)Nc1cccc(C(F)(F)F)c1] | + |
| 1.157 | 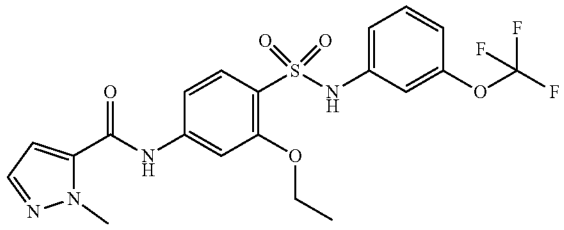 [SMILES: CCOc1cc(NC(=O)c2ccnn2C)ccc1S(=O)(=O)Nc1cccc(OC(F)(F)F)c1] | ++++ |

-continued
| Compound ID | Structure | Potency |
|---|---|---|
| 1.158 | 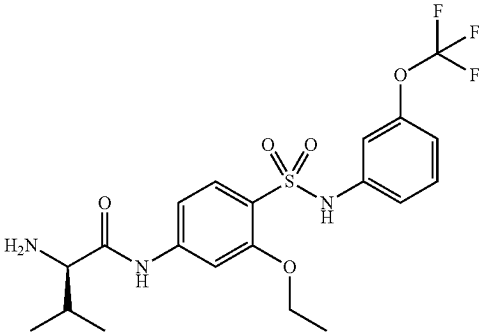 [SMILES: CCOc1cc(NC(=O)[C@H](N)C(C)C)ccc1S(=O)(=O)Nc1cccc(OC(F)(F)F)c1] | ++++ |
| 1.159 | 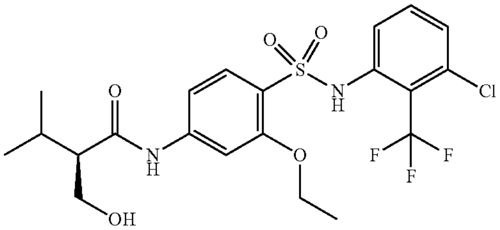 [SMILES: CCOc1cc(NC(=O)[C@@H](CO)C(C)C)ccc1S(=O)(=O)Nc1cccc(Cl)c1C(F)(F)F] | + |
| 1.160 | 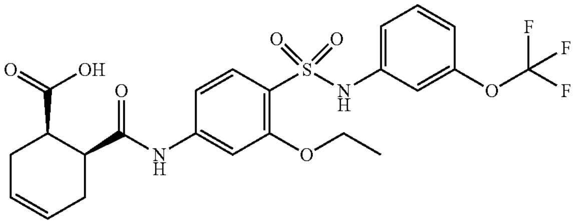 [SMILES: CCOc1cc(NC(=O)[C@H]2CC=CC[C@H]2C(=O)O)ccc1S(=O)(=O)Nc1cccc(OC(F)(F)F)c1] | ++++ |
| 1.161 | 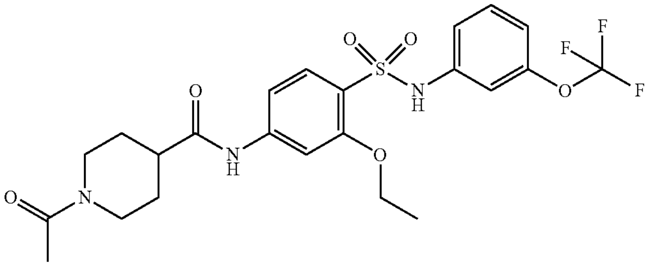 [SMILES: CCOc1cc(NC(=O)C2CCN(C(C)=O)CC2)ccc1S(=O)(=O)Nc1cccc(OC(F)(F)F)c1] | + |
| 1.162 | 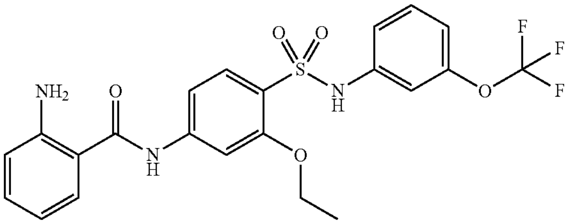 [SMILES: CCOc1cc(NC(=O)c2ccccc2N)ccc1S(=O)(=O)Nc1cccc(OC(F)(F)F)c1] | ++++ |

-continued
| Compound ID | Structure | Potency |
|---|---|---|
| 1.163 | 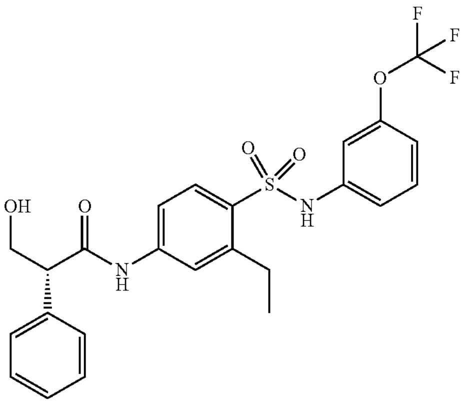 [SMILES: CCc1cc(NC(=O)[C@@H](CO)c2ccccc2)ccc1S(=O)(=O)Nc1cccc(OC(F)(F)F)c1] | ++++ |
| 1.164 | 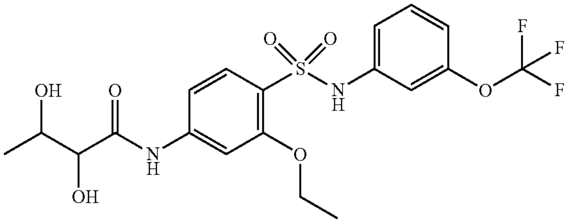 [SMILES: CCOc1cc(NC(=O)C(O)C(C)O)ccc1S(=O)(=O)Nc1cccc(OC(F)(F)F)c1] | ++ |
| 1.165 | 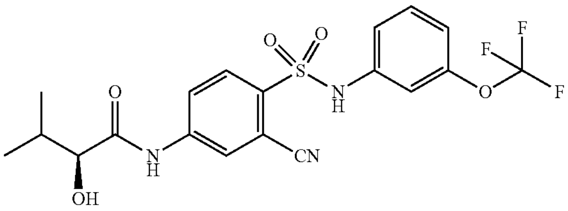 [SMILES: CC(C)[C@H](O)C(=O)Nc1ccc(S(=O)(=O)Nc2cccc(OC(F)(F)F)c2)c(C#N)c1] | +++ |
| 1.166 | 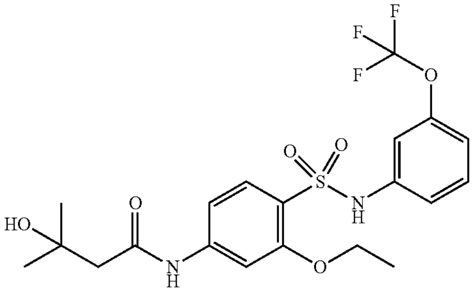 [SMILES: CCOc1cc(NC(=O)CC(C)(C)O)ccc1S(=O)(=O)Nc1cccc(OC(F)(F)F)c1] | ++ |
| 1.167 | AND Enantiomer 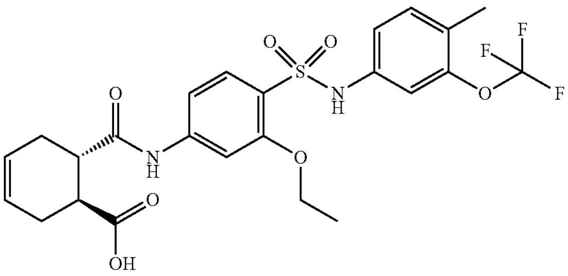 | + |

-continued
| Compound ID | Structure | Potency |
|---|---|---|
| 1.168 | 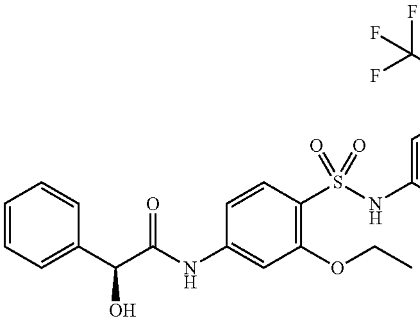 | ++++ |
| 1.169 | 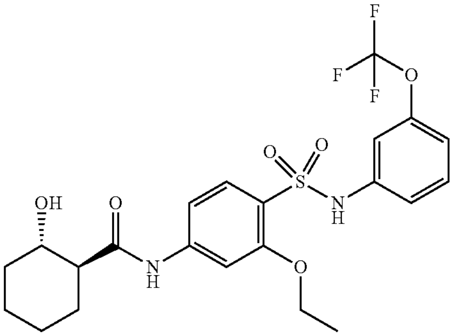 [SMILES: CCOc1cc(NC(=O)[C@H]2CCCC[C@@H]2O)ccc1S(=O)(=O)Nc1cccc(OC(F)(F)F)c1] | ++ |
| 1.170 | 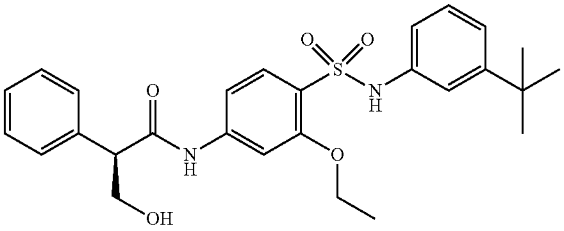 [SMILES: CCOc1cc(NC(=O)[C@@H](CO)c2ccccc2)ccc1S(=O)(=O)Nc1cccc(C(C)(C)C)c1] | ++++ |
| 1.171 | 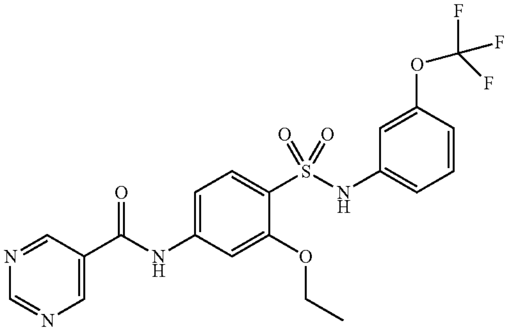 [SMILES: CCOc1cc(NC(=O)c2cncnc2)ccc1S(=O)(=O)Nc1cccc(OC(F)(F)F)c1] | ++++ |
| 1.172 | 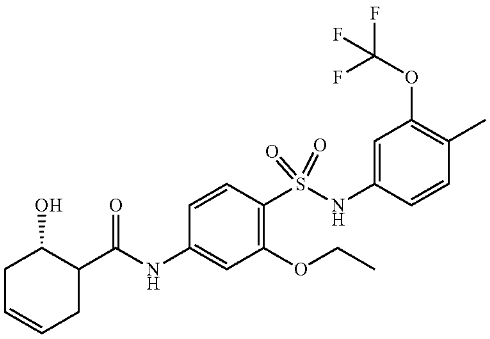 [SMILES: CCOc1cc(NC(=O)C2CC=CC[C@@H]2O)ccc1S(=O)(=O)Nc1ccc(C)c(OC(F)(F)F)c1] | ++++ |

-continued
| Compound ID | Structure | Potency |
|---|---|---|
| 1.173 | 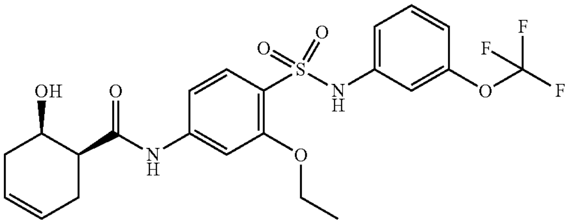 [SMILES: CCOc1cc(NC(=O)[C@H]2CC=CC[C@H]2O)ccc1S(=O)(=O)Nc1cccc(OC(F)(F)F)c1] | +++ |
| 1.174 | 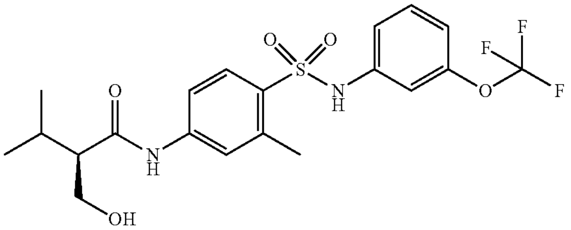 [SMILES: Cc1cc(NC(=O)[C@@H](CO)C(C)C)ccc1S(=O)(=O)Nc1cccc(OC(F)(F)F)c1] | ++++ |
| 1.175 | 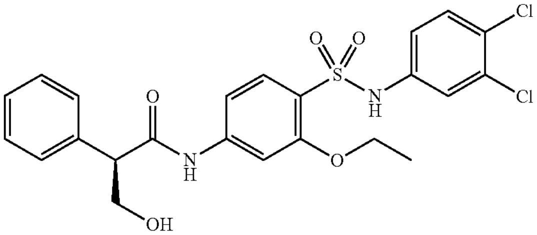 [SMILES: CCOc1cc(NC(=O)[C@@H](CO)c2ccccc2)ccc1S(=O)(=O)Nc1ccc(Cl)c(Cl)c1] | +++ |
| 1.176 | 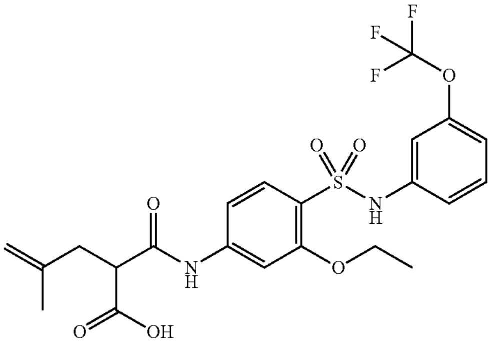 [SMILES: C=C(C)CC(C(=O)O)C(=O)Nc1ccc(S(=O)(=O)Nc2cccc(OC(F)(F)F)c2)c(OCC)c1] | ++++ |
| 1.177 | 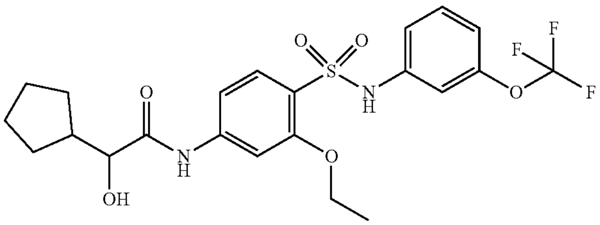 [SMILES: CCOc1cc(NC(=O)C(O)C2CCCC2)ccc1S(=O)(=O)Nc1cccc(OC(F)(F)F)c1] | ++++ |
| 1.178 | 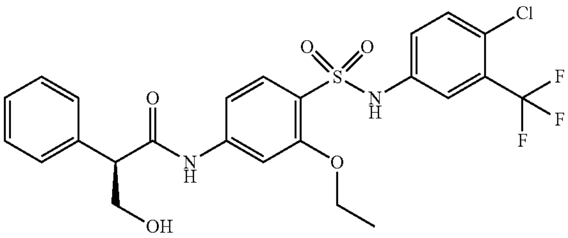 [SMILES: CCOc1cc(NC(=O)[C@@H](CO)c2ccccc2)ccc1S(=O)(=O)Nc1ccc(Cl)c(C(F)(F)F)c1] | +++ |

-continued
| Compound ID | Structure | Potency |
|---|---|---|
| 1.179 | 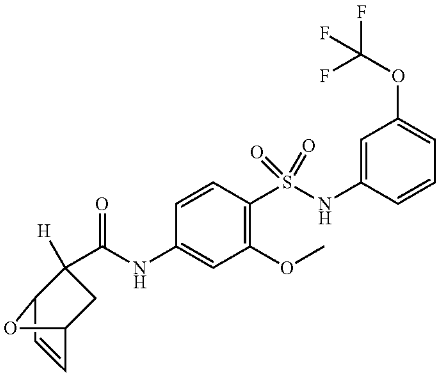 [SMILES: COc1cc(NC(=O)C2CC3C=CC2O3)ccc1S(=O)(=O)Nc1cccc(OC(F)(F)F)c1] | +++ |
| 1.180 | 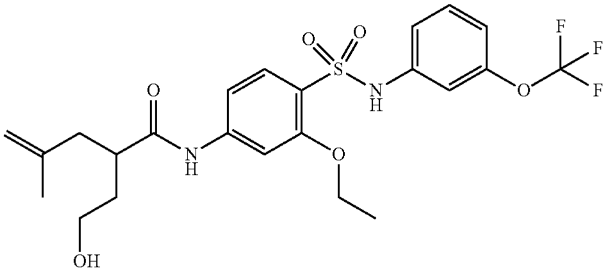 [SMILES: C=C(C)CC(CCO)C(=O)Nc1ccc(S(=O)(=O)Nc2cccc(OC(F)(F)F)c2)c(OCC)c1] | ++++ |
| 1.181 | 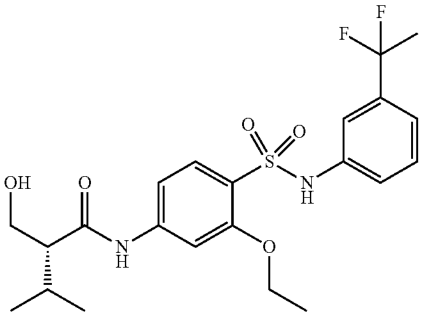 [SMILES: CCOc1cc(NC(=O)[C@@H](CO)C(C)C)ccc1S(=O)(=O)Nc1cccc(C(C)(F)F)c1] | ++++ |
| 1.182 | 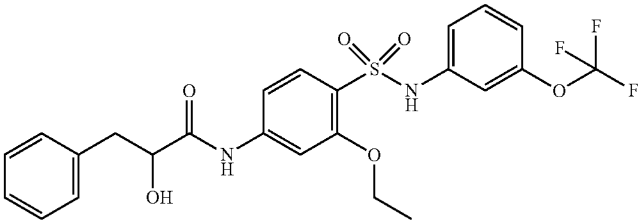 [SMILES: CCOc1cc(NC(=O)C(O)Cc2ccccc2)ccc1S(=O)(=O)Nc1cccc(OC(F)(F)F)c1] | ++++ |
| 1.183 | 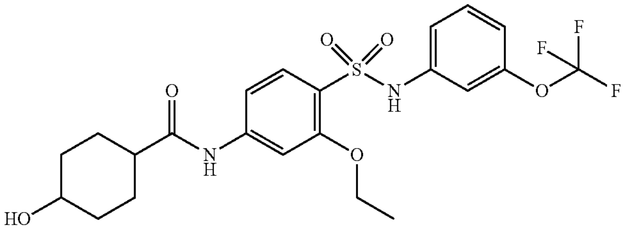 [SMILES: CCOc1cc(NC(=O)C2CCC(O)CC2)ccc1S(=O)(=O)Nc1cccc(OC(F)(F)F)c1] | +++ |

-continued
| Compound ID | Structure | Potency |
| --- | --- | --- |
| 1.184 | 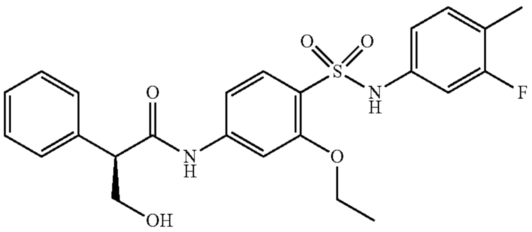 [SMILES: CCOc1cc(NC(=O)[C@@H](CO)c2ccccc2)ccc1S(=O)(=O)Nc1ccc(C)c(F)c1] | ++ |
| 1.185 | 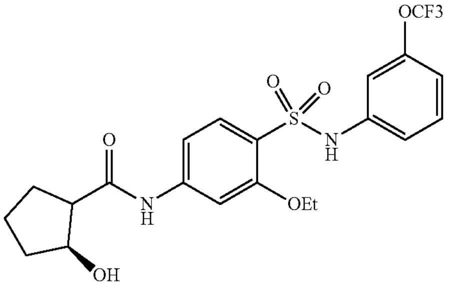 [SMILES: CCOc1cc(NC(=O)C2CCC[C@@H]2O)ccc1S(=O)(=O)Nc1cccc(OC(F)(F)F)c1] | +++ |
| 1.186 | 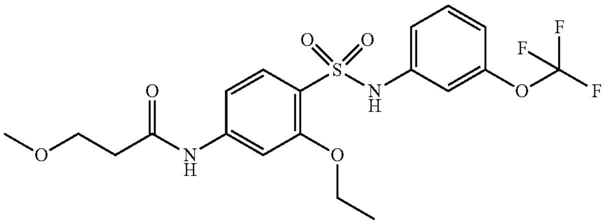 [SMILES: CCOc1cc(NC(=O)CCOC)ccc1S(=O)(=O)Nc1cccc(OC(F)(F)F)c1] | ++ |
| 1.187 | 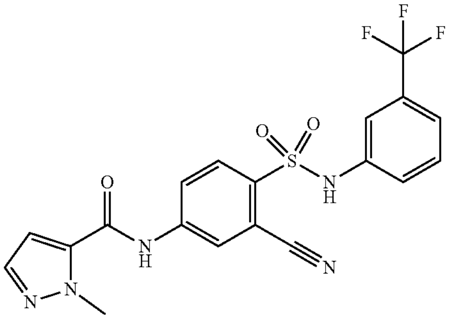 [SMILES: Cn1nccc1C(=O)Nc1ccc(S(=O)(=O)Nc2cccc(C(F)(F)F)c2)c(C#N)c1] | + |
| 1.188 | 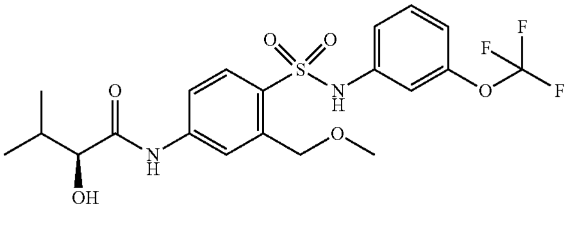 [SMILES: COCc1cc(NC(=O)[C@@H](O)C(C)C)ccc1S(=O)(=O)Nc1cccc(OC(F)(F)F)c1] | ++++ |
| 1.189 | 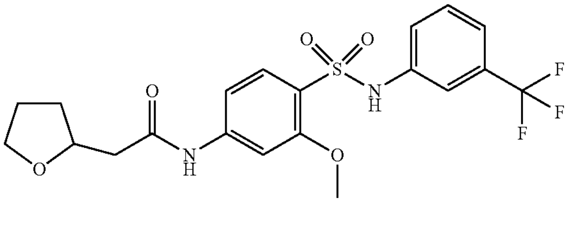 [SMILES: COc1cc(NC(=O)CC2CCCO2)ccc1S(=O)(=O)Nc1cccc(C(F)(F)F)c1] | + |

-continued
| Compound ID | Structure | Potency |
| --- | --- | --- |
| 1.190 | 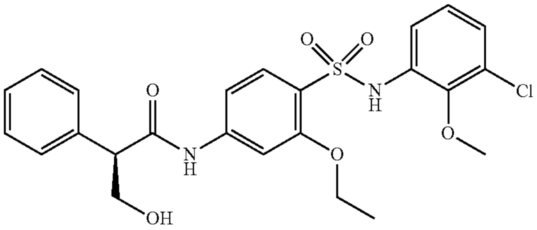 [SMILES: CCOc1cc(NC(=O)[C@@H](CO)c2ccccc2)ccc1S(=O)(=O)Nc1cccc(Cl)c1OC] | + |
| 1.191 | 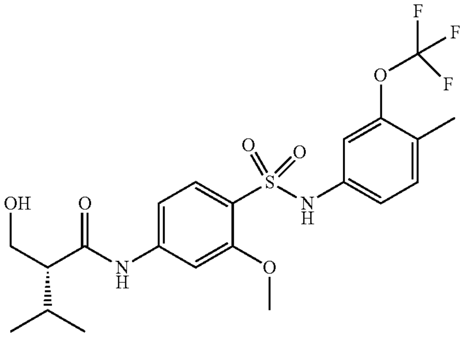 [SMILES: COc1cc(NC(=O)[C@@H](CO)C(C)C)ccc1S(=O)(=O)Nc1ccc(C)c(OC(F)(F)F)c1] | ++++ |
| 1.192 | 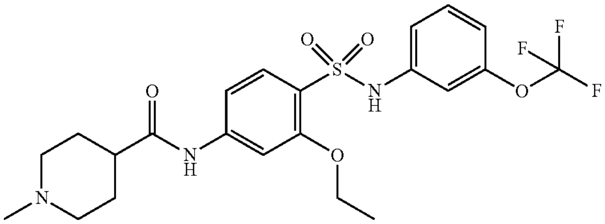 [SMILES: CCOc1cc(NC(=O)C2CCN(C)CC2)ccc1S(=O)(=O)Nc1cccc(OC(F)(F)F)c1] | + |
| 1.193 | 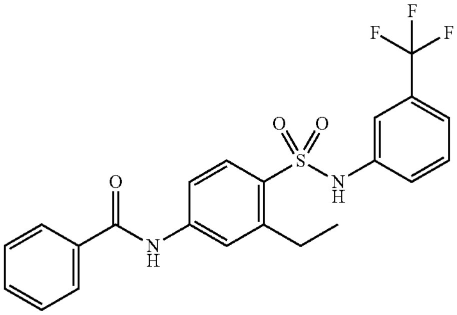 [SMILES: CCc1cc(NC(=O)c2ccccc2)ccc1S(=O)(=O)Nc1cccc(C(F)(F)F)c1] | +++ |
| 1.194 | 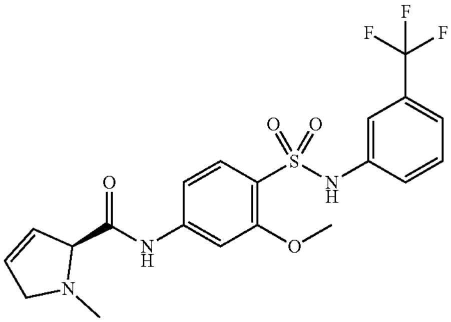 [SMILES: COc1cc(NC(=O)[C@@H]2C=CCN2C)ccc1S(=O)(=O)Nc1cccc(C(F)(F)F)c1] | + |

-continued
| Compound ID | Structure | Potency |
| --- | --- | --- |
| 1.195 | 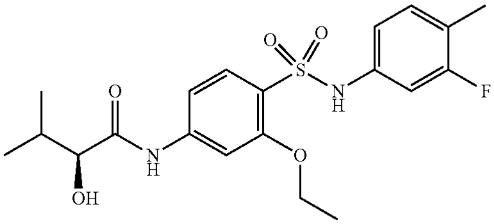 [SMILES: CCOc1cc(NC(=O)[C@@H](O)C(C)C)ccc1S(=O)(=O)Nc1ccc(C)c(F)c1] | +++ |
| 1.196 | 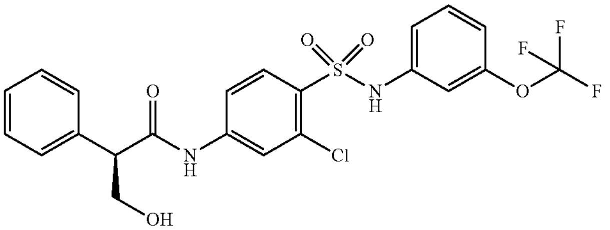 [SMILES: O=C(Nc1ccc(S(=O)(=O)Nc2cccc(OC(F)(F)F)c2)c(Cl)c1)[C@@H](CO)c1ccccc1] | ++++ |
| 1.197 | 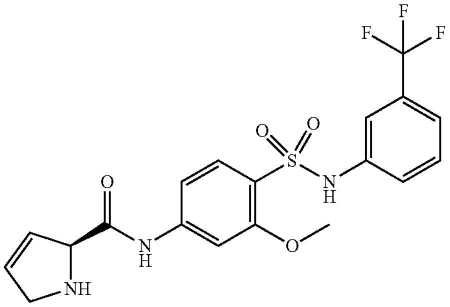 [SMILES: COc1cc(NC(=O)[C@@H]2C=CCN2)ccc1S(=O)(=O)Nc1cccc(C(F)(F)F)c1] | ++ |
| 1.198 | 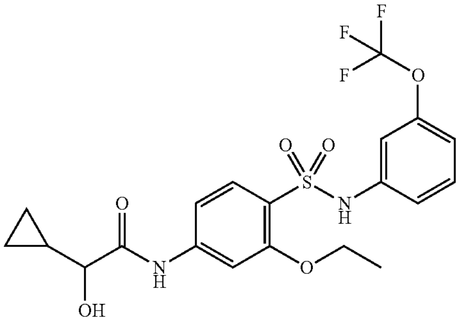 [SMILES: CCOc1cc(NC(=O)C(O)C2CC2)ccc1S(=O)(=O)Nc1cccc(OC(F)(F)F)c1] | ++++ |
| 1.199 | 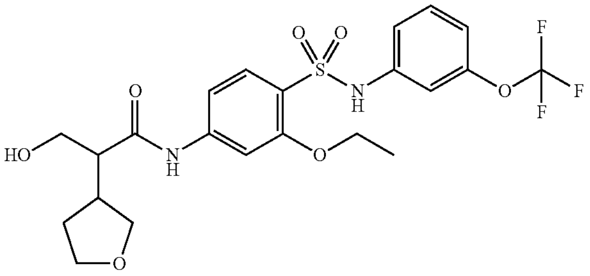 [SMILES: CCOc1cc(NC(=O)C(CO)C2CCOC2)ccc1S(=O)(=O)Nc1cccc(OC(F)(F)F)c1] | ++++ |

-continued
| Compound ID | Structure | Potency |
|---|---|---|
| 1.200 | 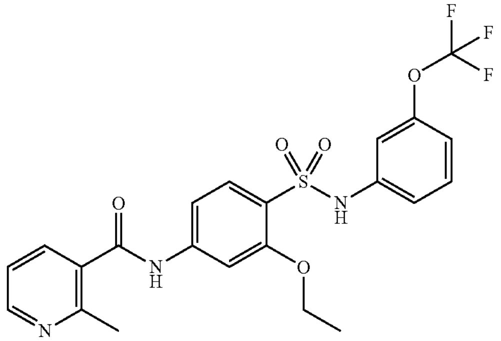 [SMILES: CCOc1cc(NC(=O)c2cccnc2C)ccc1S(=O)(=O)Nc1cccc(OC(F)(F)F)c1] | ++++ |
| 1.201 | 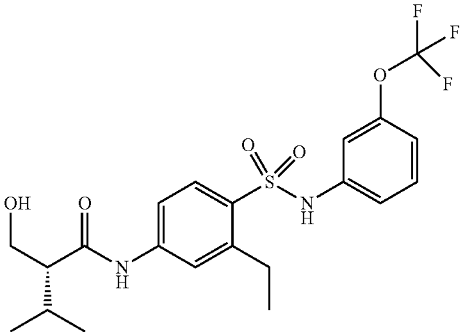 [SMILES: CCc1cc(NC(=O)[C@@H](CO)C(C)C)ccc1S(=O)(=O)Nc1cccc(OC(F)(F)F)c1] | ++++ |
| 1.202 | 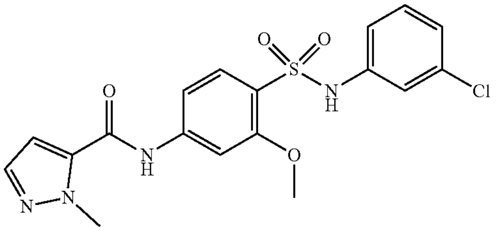 [SMILES: COc1cc(NC(=O)c2ccnn2C)ccc1S(=O)(=O)Nc1cccc(Cl)c1] | + |
| 1.203 | 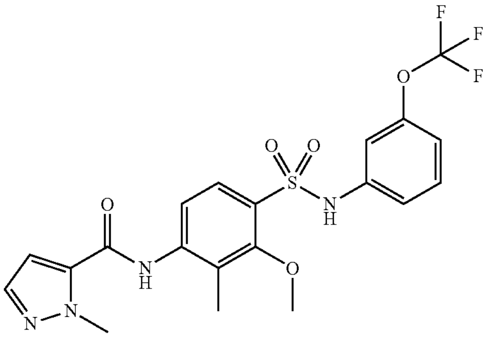 [SMILES: COc1c(S(=O)(=O)Nc2cccc(OC(F)(F)F)c2)ccc(NC(=O)c2ccnn2C)c1C] | + |
| 1.204 | 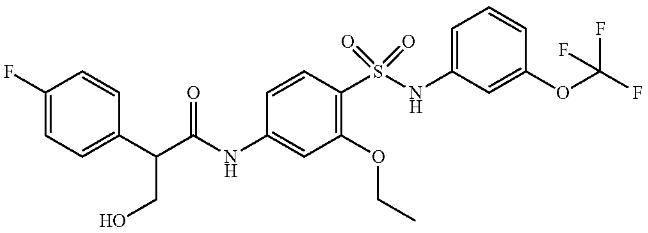 [SMILES: CCOc1cc(NC(=O)C(CO)c2ccc(F)cc2)ccc1S(=O)(=O)Nc1cccc(OC(F)(F)F)c1] | ++++ |

-continued
| Compound ID | Structure | Potency |
|---|---|---|
| 1.205 | 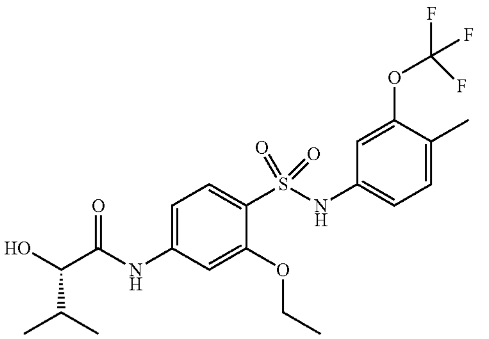 [SMILES: CCOc1cc(NC(=O)[C@@H](O)C(C)C)ccc1S(=O)(=O)Nc1ccc(C)c(OC(F)(F)F)c1] | ++++ |
| 1.206 | 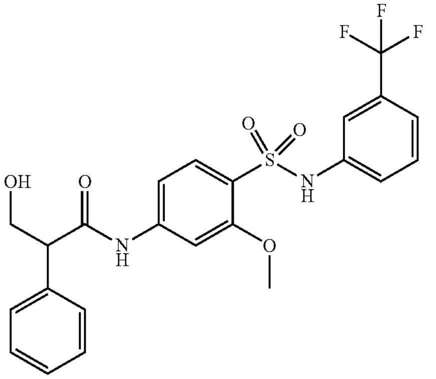 [SMILES: COc1cc(NC(=O)C(CO)c2ccccc2)ccc1S(=O)(=O)Nc1cccc(C(F)(F)F)c1] | +++ |
| 1.207 | 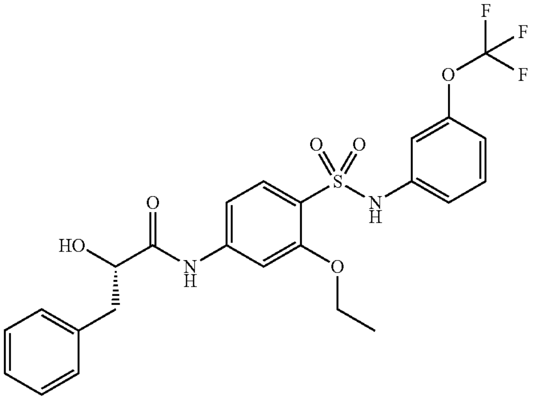 [SMILES: CCOc1cc(NC(=O)[C@@H](O)Cc2ccccc2)ccc1S(=O)(=O)Nc1cccc(OC(F)(F)F)c1] | ++++ |
| 1.208 | 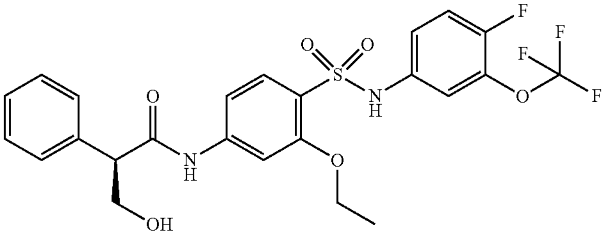 [SMILES: CCOc1cc(NC(=O)[C@@H](CO)c2ccccc2)ccc1S(=O)(=O)Nc1ccc(F)c(OC(F)(F)F)c1] | ++++ |

-continued
| Compound ID | Structure | Potency |
|---|---|---|
| 1.209 | 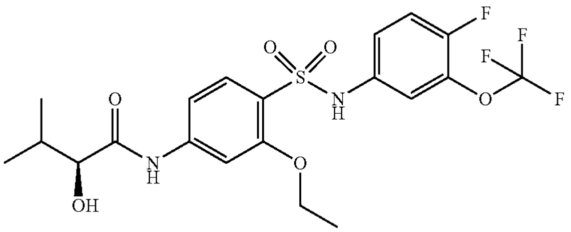 [SMILES: CCOc1cc(NC(=O)[C@@H](O)C(C)C)ccc1S(=O)(=O)Nc1ccc(F)c(OC(F)(F)F)c1] | ++++ |
| 1.210 | 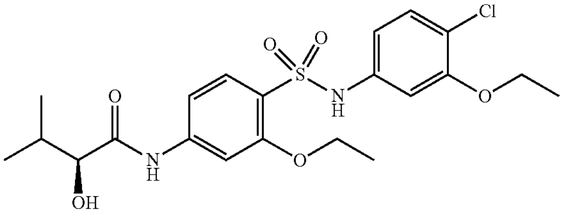 [SMILES: CCOc1cc(NS(=O)(=O)c2ccc(NC(=O)[C@@H](O)C(C)C)cc2OCC)ccc1Cl] | +++ |
| 1.211 | 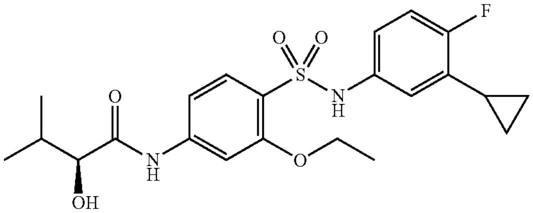 [SMILES: CCOc1cc(NC(=O)[C@@H](O)C(C)C)ccc1S(=O)(=O)Nc1ccc(F)c(C2CC2)c1] | ++++ |
| 1.212 | 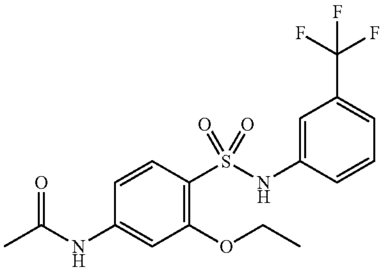 [SMILES: CCOc1cc(NC(C)=O)ccc1S(=O)(=O)Nc1cccc(C(F)(F)F)c1] | + |
| 1.213 | 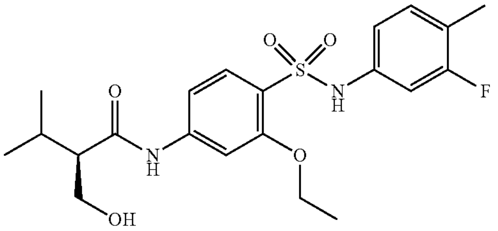 [SMILES: CCOc1cc(NC(=O)[C@@H](CO)C(C)C)ccc1S(=O)(=O)Nc1ccc(C)c(F)c1] | +++ |
| 1.214 | 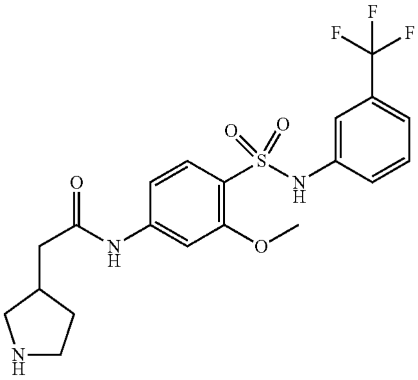 [SMILES: COc1cc(NC(=O)CC2CCNC2)ccc1S(=O)(=O)Nc1cccc(C(F)(F)F)c1] | + |

-continued
| Compound ID | Structure | Potency |
|---|---|---|
| 1.215 | 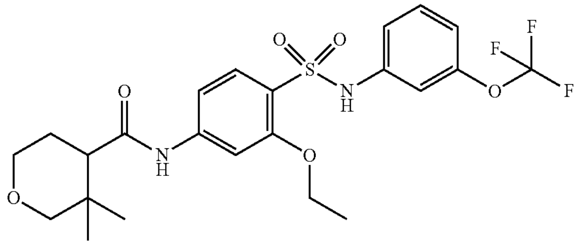 [SMILES: CCOc1cc(NC(=O)C2CCOCC2(C)C)ccc1S(=O)(=O)Nc1cccc(OC(F)(F)F)c1] | +++ |
| 1.216 | 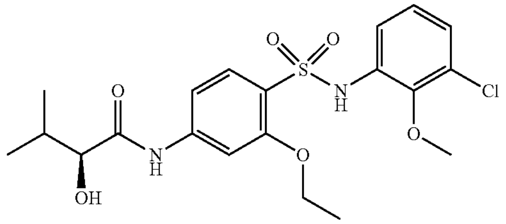 [SMILES: CCOc1cc(NC(=O)[C@@H](O)C(C)C)ccc1S(=O)(=O)Nc1cccc(Cl)c1OC] | + |
| 1.217 | 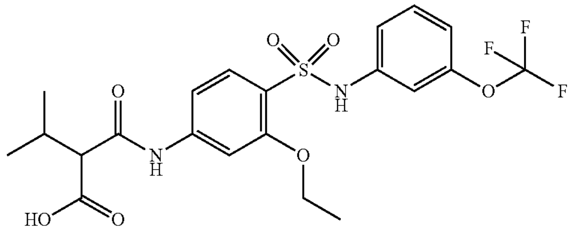 [SMILES: CCOc1cc(NC(=O)C(C(=O)O)C(C)C)ccc1S(=O)(=O)Nc1cccc(OC(F)(F)F)c1] | ++++ |
| 1.218 | 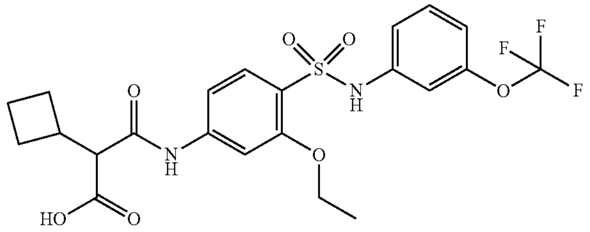 [SMILES: CCOc1cc(NC(=O)C(C(=O)O)C2CCC2)ccc1S(=O)(=O)Nc1cccc(OC(F)(F)F)c1] | ++++ |
| 1.219 | AND Enantiomer 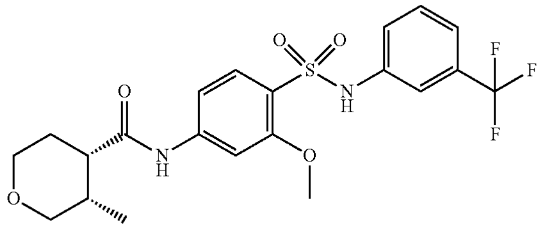 | +++ |
| 1.220 | 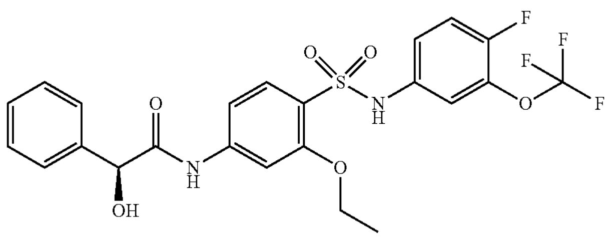 | + .++ |

-continued
| Compound ID | Structure | Potency |
|---|---|---|
| 1.221 | 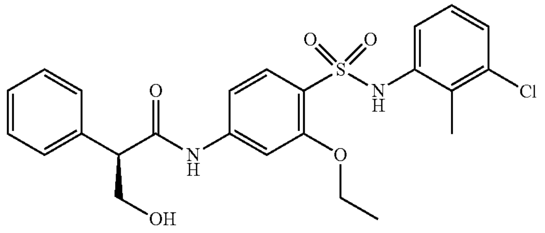 [SMILES: CCOc1cc(NC(=O)[C@@H](CO)c2ccccc2)ccc1S(=O)(=O)Nc1cccc(Cl)c1C] | + |
| 1.222 | 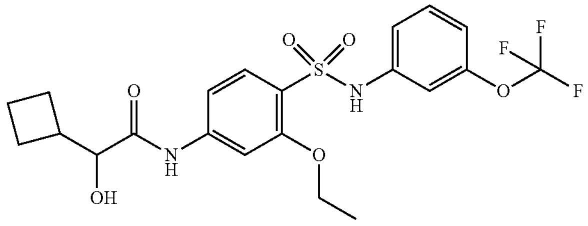 [SMILES: CCOc1cc(NC(=O)C(O)C2CCC2)ccc1S(=O)(=O)Nc1cccc(OC(F)(F)F)c1] | ++++ |
| 1.223 | 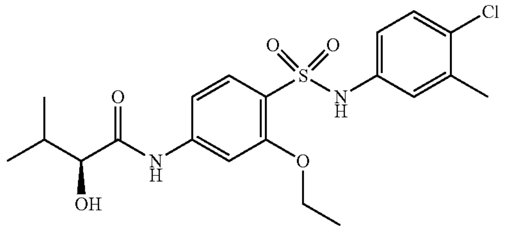 [SMILES: CCOc1cc(NC(=O)[C@@H](O)C(C)C)ccc1S(=O)(=O)Nc1ccc(Cl)c(C)c1] | ++++ |
| 1.224 | 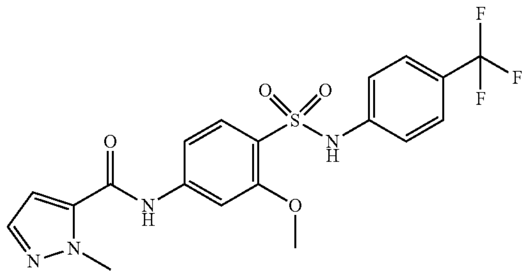 [SMILES: COc1cc(NC(=O)c2ccnn2C)ccc1S(=O)(=O)Nc1ccc(C(F)(F)F)cc1] | +++ |
| 1.225 | 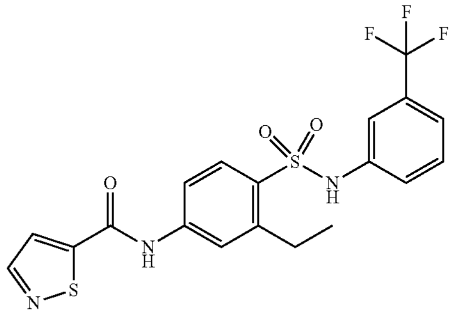 | +++ |
| 1.226 | 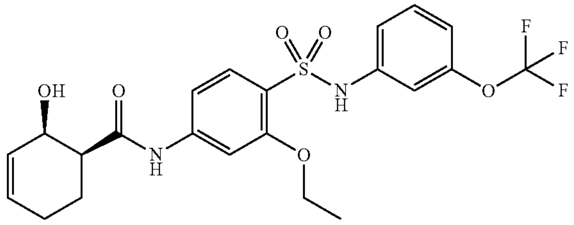 [SMILES: CCOc1cc(NC(=O)[C@H]2CCC=C[C@H]2O)ccc1S(=O)(=O)Nc1cccc(OC(F)(F)F)c1] | +++ |

-continued
| Compound ID | Structure | Potency |
|---|---|---|
| 1.227 | AND Enantiomer 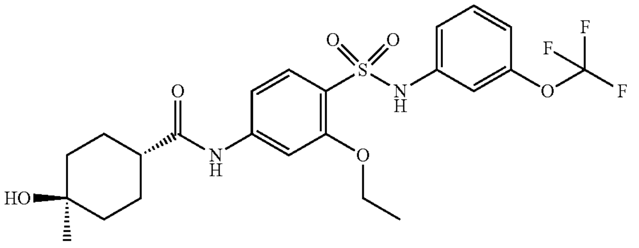 | ++ |
| 1.228 | 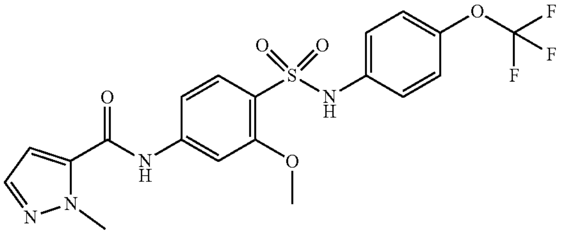 [SMILES: COc1cc(NC(=O)c2ccnn2C)ccc1S(=O)(=O)Nc1ccc(OC(F)(F)F)cc1] | +++ |
| 1.229 | 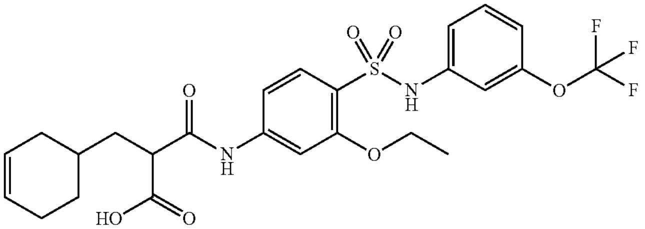 [SMILES: CCOc1cc(NC(=O)C(CC2CC=CCC2)C(=O)O)ccc1S(=O)(=O)Nc1cccc(OC(F)(F)F)c1] | ++++ |
| 1.230 | 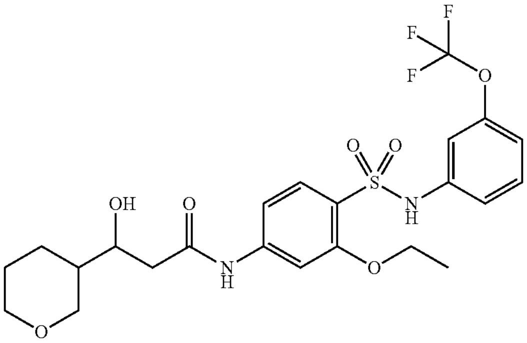 [SMILES: CCOc1cc(NC(=O)CC(O)C2CCCOC2)ccc1S(=O)(=O)Nc1cccc(OC(F)(F)F)c1] | ++ |
| 1.231 | 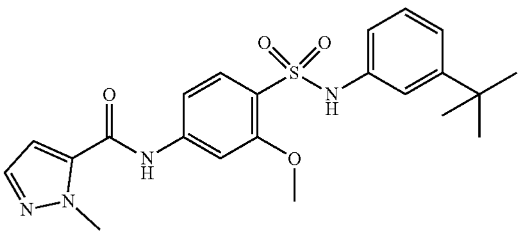 [SMILES: COc1cc(NC(=O)c2ccnn2C)ccc1S(=O)(=O)Nc1cccc(C(C)(C)C)c1] | +++ |

-continued
| Compound ID | Structure | Potency |
|---|---|---|
| 1.232 | 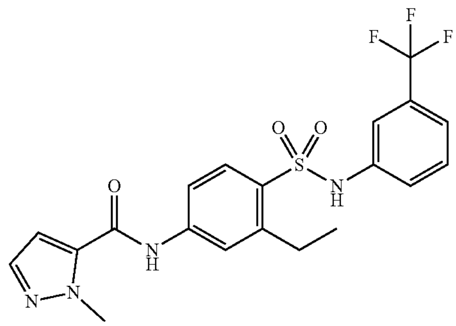 [SMILES: CCc1cc(NC(=O)c2ccnn2C)ccc1S(=O)(=O)Nc1cccc(C(F)(F)F)c1] | ++++ |
| 1.233 | AND Enantiomer 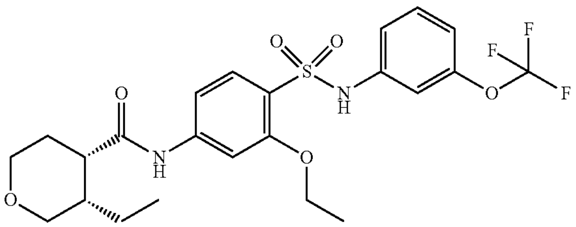 | ++++ |
| 1.234 | 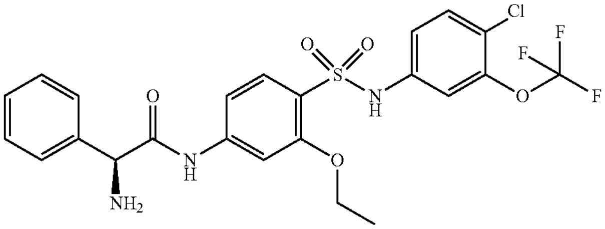 | ++++ |
| 1.235 | 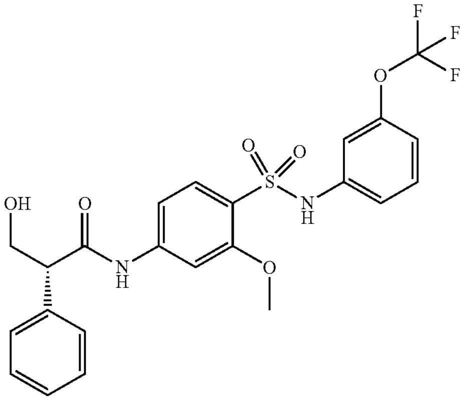 [SMILES: COc1cc(NC(=O)[C@@H](CO)c2ccccc2)ccc1S(=O)(=O)Nc1cccc(OC(F)(F)F)c1] | +++ |
| 1.236 | 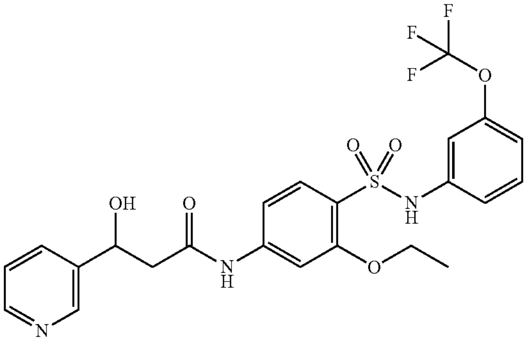 [SMILES: CCOc1cc(NC(=O)CC(O)c2cccnc2)ccc1S(=O)(=O)Nc1cccc(OC(F)(F)F)c1] | ++ |

-continued
| Compound ID | Structure | Potency |
| --- | --- | --- |
| 1.237 | AND Enantiomer 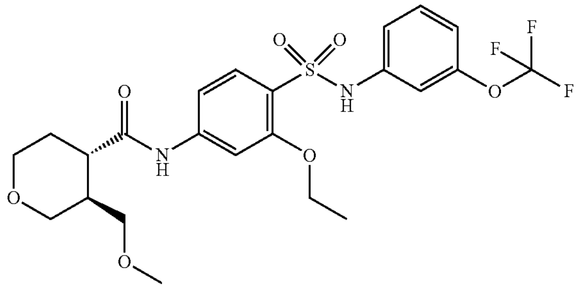 | +++ |
| 1.238 | 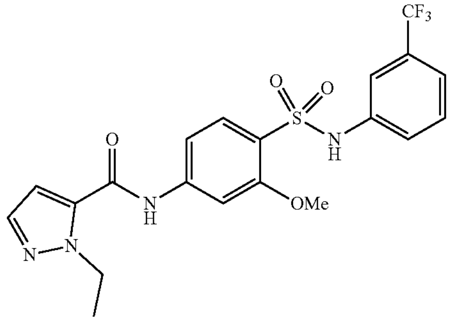 [SMILES: CCn1nccc1C(=O)Nc1ccc(S(=O)(=O)Nc2cccc(C(F)(F)F)c2)c(OC)c1] | +++ |
| 1.239 | 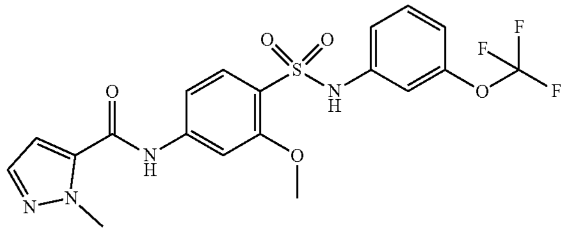 [SMILES: COc1cc(NC(=O)c2ccnn2C)ccc1S(=O)(=O)Nc1cccc(OC(F)(F)F)c1] | ++++ |
| 1.240 | 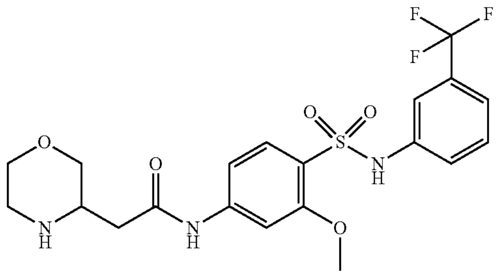 [SMILES: COc1cc(NC(=O)CC2COCCN2)ccc1S(=O)(=O)Nc1cccc(C(F)(F)F)c1] | + |
| 1.241 | 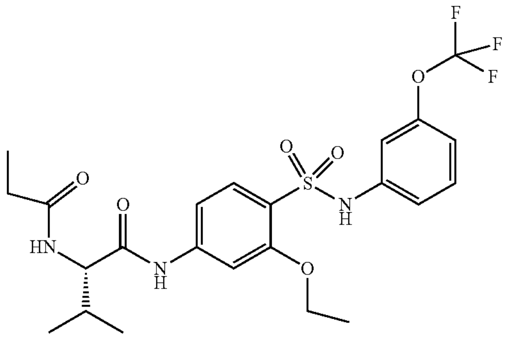 [SMILES: CCOc1cc(NC(=O)[C@@H](NC(=O)CC)C(C)C)ccc1S(=O)(=O)Nc1cccc(OC(F)(F)F)c1] | ++++ |

-continued
| Compound ID | Structure | Potency |
|---|---|---|
| 1.242 | 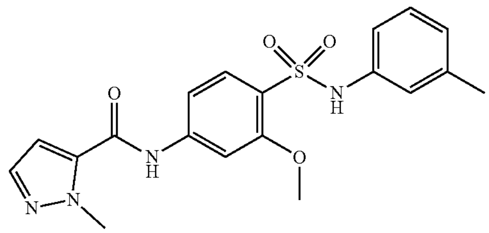 [SMILES: COc1cc(NC(=O)c2ccnn2C)ccc1S(=O)(=O)Nc1cccc(C)c1] | + |
| 1.243 | 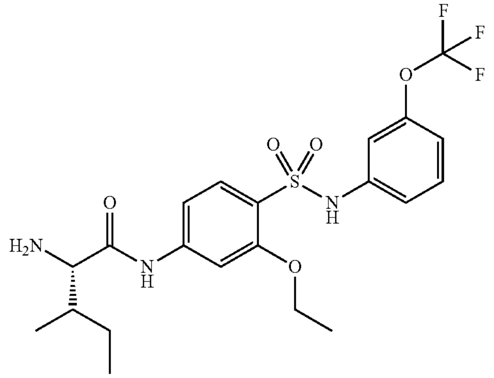 [SMILES: CCOc1cc(NC(=O)[C@@H](N)C(C)CC)ccc1S(=O)(=O)Nc1cccc(OC(F)(F)F)c1] | ++++ |
| 1.244 | 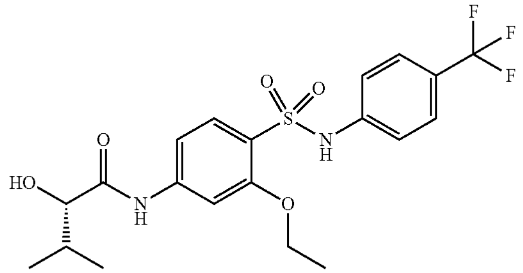 [SMILES: CCOc1cc(NC(=O)[C@@H](O)C(C)C)ccc1S(=O)(=O)Nc1ccc(C(F)(F)F)cc1] | +++ |
| 1.245 | 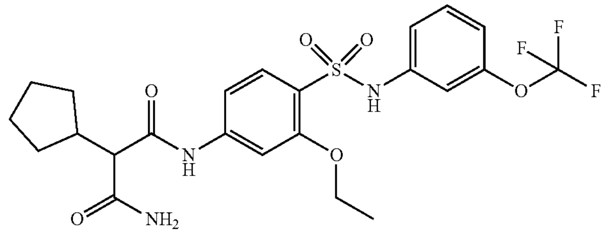 [SMILES: CCOc1cc(NC(=O)C(C(N)=O)C2CCCC2)ccc1S(=O)(=O)Nc1cccc(OC(F)(F)F)c1] | ++++ |
| 1.246 | 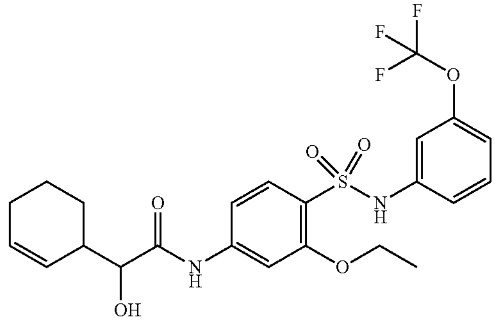 [SMILES: CCOc1cc(NC(=O)C(O)C2C=CCCC2)ccc1S(=O)(=O)Nc1cccc(OC(F)(F)F)c1] | ++++ |

-continued
| Compound ID | Structure | Potency |
|---|---|---|
| 1.247 | 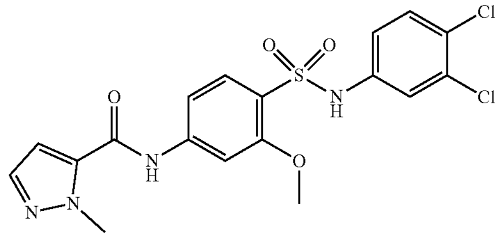 [SMILES: COc1cc(NC(=O)c2ccnn2C)ccc1S(=O)(=O)Nc1ccc(Cl)c(Cl)c1] | ++ |
| 1.248 | 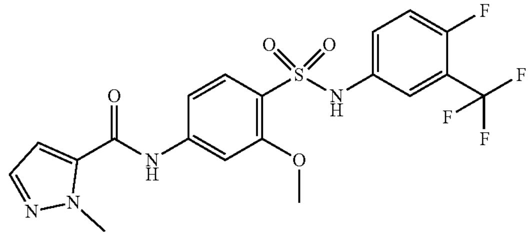 [SMILES: COc1cc(NC(=O)c2ccnn2C)ccc1S(=O)(=O)Nc1ccc(F)c(C(F)(F)F)c1] | ++ |
| 1.249 | 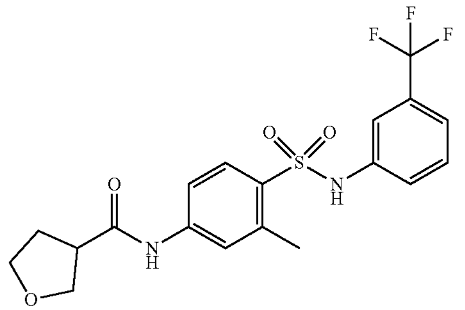 [SMILES: Cc1cc(NC(=O)C2CCOC2)ccc1S(=O)(=O)Nc1cccc(C(F)(F)F)c1] | + |
| 1.250 | 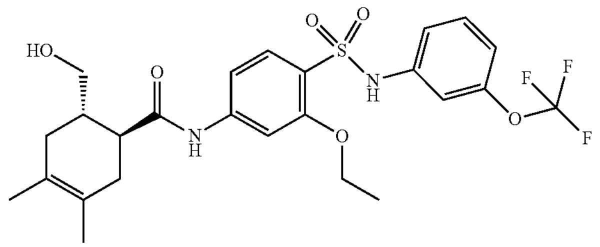 [SMILES: CCOc1cc(NC(=O)[C@H]2CC(C)=C(C)C[C@@H]2CO)ccc1S(=O)(=O)Nc1cccc(OC(F)(F)F)c1] | ++++ |
| 1.251 | 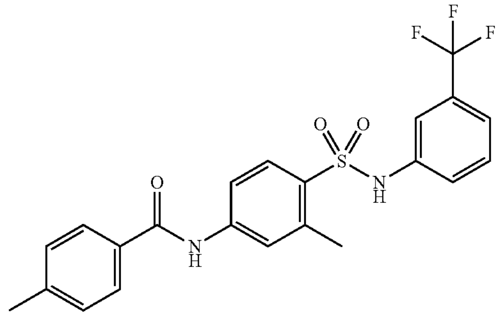 [SMILES: Cc1ccc(C(=O)Nc2ccc(S(=O)(=O)Nc3cccc(C(F)(F)F)c3)c(C)c2)cc1] | ++ |

-continued
| Compound ID | Structure | Potency |
|---|---|---|
| 1.252 | 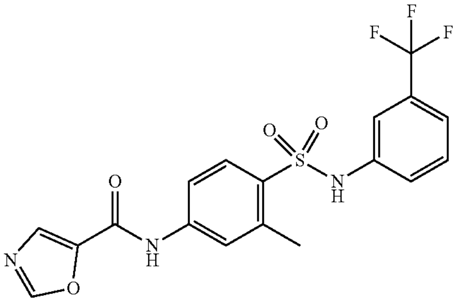 [SMILES: Cc1cc(NC(=O)c2cnco2)ccc1S(=O)(=O)Nc1cccc(C(F)(F)F)c1] | ++ |
| 1.253 | 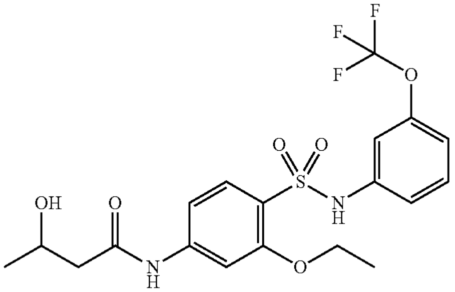 [SMILES: CCOc1cc(NC(=O)CC(C)O)ccc1S(=O)(=O)Nc1cccc(OC(F)(F)F)c1] | +++ |
| 1.254 | 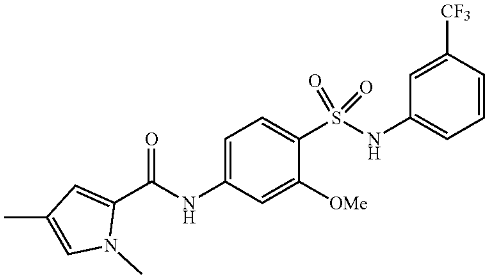 [SMILES: COc1cc(NC(=O)c2cc(C)cn2C)ccc1S(=O)(=O)Nc1cccc(C(F)(F)F)c1] | +++ |
| 1.255 | 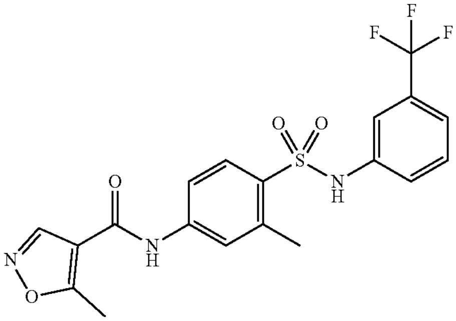 [SMILES: Cc1cc(NC(=O)c2cnoc2C)ccc1S(=O)(=O)Nc1cccc(C(F)(F)F)c1] | +++ |
| 1.256 | 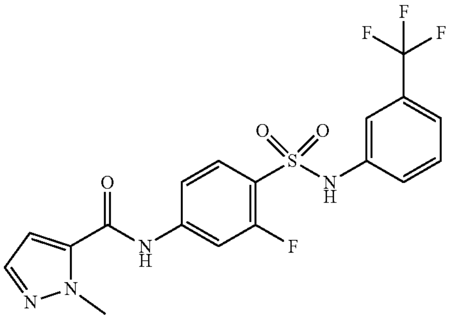 [SMILES: Cn1nccc1C(=O)Nc1ccc(S(=O)(=O)Nc2cccc(C(F)(F)F)c2)c(F)c1] | + |

-continued
| Compound ID | Structure | Potency |
|---|---|---|
| 1.257 | 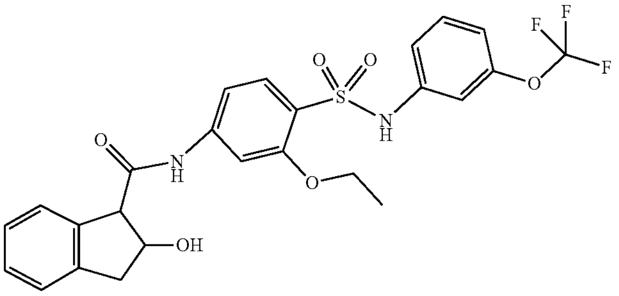 [SMILES: CCOc1cc(NC(=O)C2c3ccccc3CC2O)ccc1S(=O)(=O)Nc1cccc(OC(F)(F)F)c1] | ++++ |
| 1.258 | 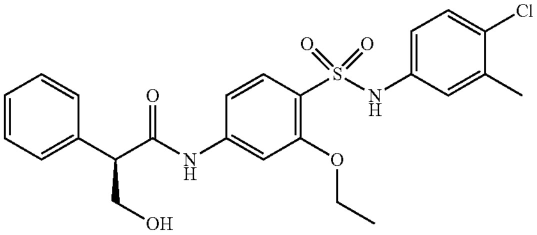 [SMILES: CCOc1cc(NC(=O)[C@@H](CO)c2ccccc2)ccc1S(=O)(=O)Nc1ccc(Cl)c(C)c1] | +++ |
| 1.259 | 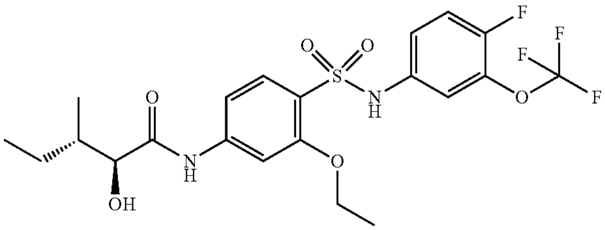 [SMILES: CCOc1cc(NC(=O)[C@@H](O)[C@@H](C)CC)ccc1S(=O)(=O)Nc1ccc(F)c(OC(F)(F)F)c1] | ++++ |
| 1.260 | 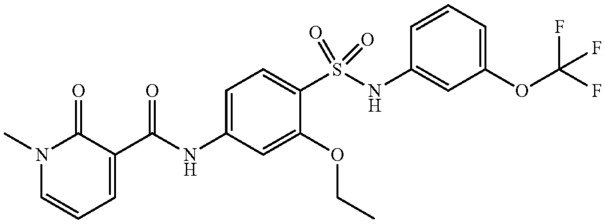 [SMILES: CCOc1cc(NC(=O)c2cccn(C)c2=O)ccc1S(=O)(=O)Nc1cccc(OC(F)(F)F)c1] | + |
| 1.261 | 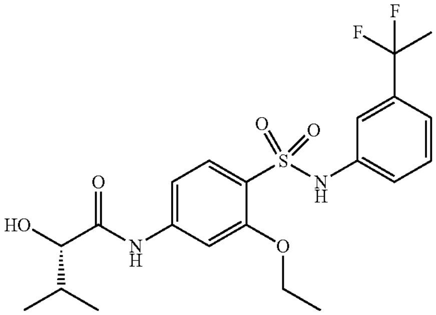 [SMILES: CCOc1cc(NC(=O)[C@@H](O)C(C)C)ccc1S(=O)(=O)Nc1cccc(C(C)(F)F)c1] | ++++ |
| 1.262 | 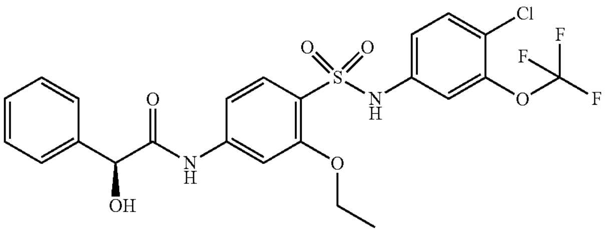 [SMILES: CCOc1cc(NC(=O)[C@@H](O)c2ccccc2)ccc1S(=O)(=O)Nc1ccc(Cl)c(OC(F)(F)F)c1] | ++++ |

-continued
| Compound ID | Structure | Potency |
|---|---|---|
| 1.263 | 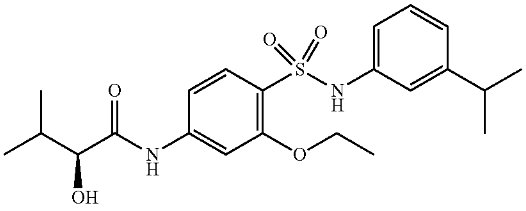 [SMILES: CCOc1cc(NC(=O)[C@@H](O)C(C)C)ccc1S(=O)(=O)Nc1cccc(C(C)C)c1] | ++++ |
| 1.264 | 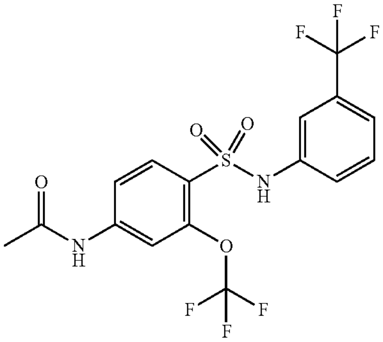 [SMILES: CC(=O)Nc1ccc(S(=O)(=O)Nc2cccc(C(F)(F)F)c2)c(OC(F)(F)F)c1] | + |
| 1.265 | 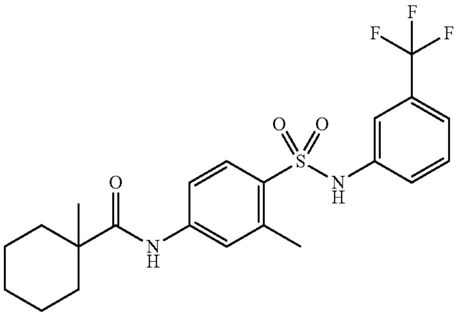 [SMILES: Cc1cc(NC(=O)C2(C)CCCCC2)ccc1S(=O)(=O)Nc1cccc(C(F)(F)F)c1] | + |
| 1.266 | 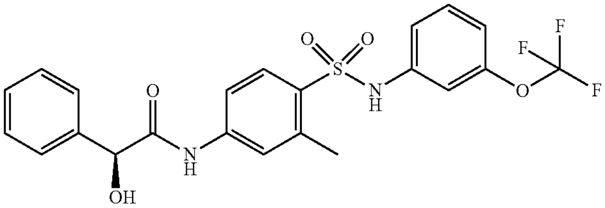 [SMILES: Cc1cc(NC(=O)[C@@H](O)c2ccccc2)ccc1S(=O)(=O)Nc1cccc(OC(F)(F)F)c1] | +++ |
| 1.267 | 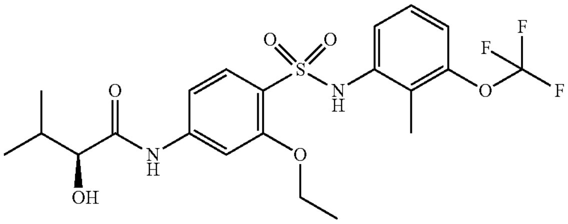 [SMILES: CCOc1cc(NC(=O)[C@@H](O)C(C)C)ccc1S(=O)(=O)Nc1cccc(OC(F)(F)F)c1C] | + |

-continued
| Compound ID | Structure | Potency |
|---|---|---|
| 1.268 | 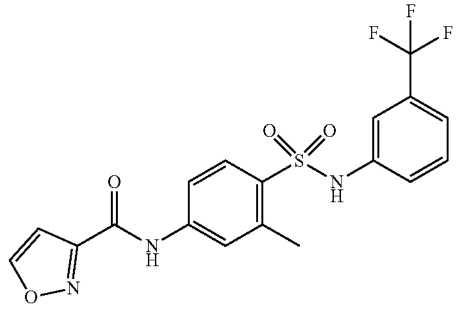 [SMILES: Cc1cc(NC(=O)c2ccon2)ccc1S(=O)(=O)Nc1cccc(C(F)(F)F)c1] | ++ |
| 1.269 | 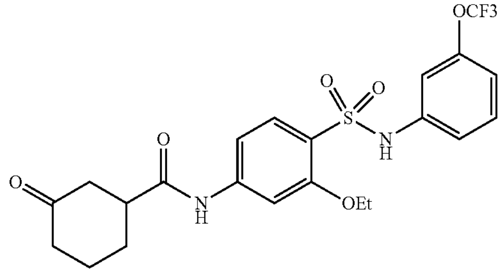 [SMILES: CCOc1cc(NC(=O)C2CCCC(=O)C2)ccc1S(=O)(=O)Nc1cccc(OC(F)(F)F)c1] | +++ |
| 1.270 | 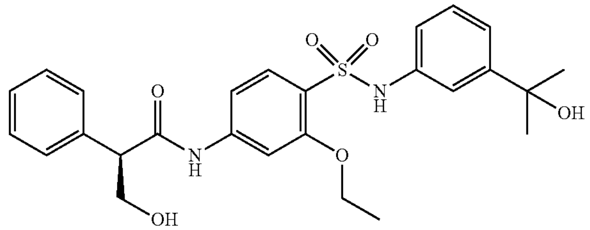 [SMILES: CCOc1cc(NC(=O)[C@@H](CO)c2ccccc2)ccc1S(=O)(=O)Nc1cccc(C(C)(C)O)c1] | + |
| 1.271 | 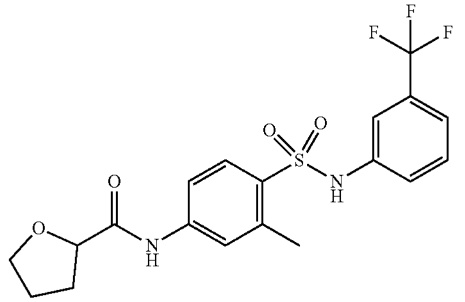 [SMILES: Cc1cc(NC(=O)C2CCCO2)ccc1S(=O)(=O)Nc1cccc(C(F)(F)F)c1] | + |
| 1.272 | 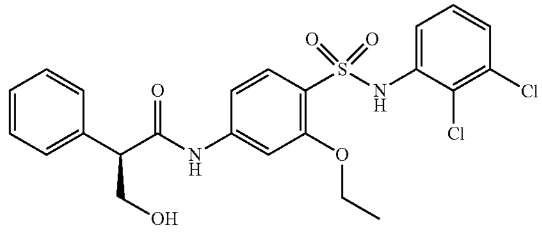 [SMILES: CCOc1cc(NC(=O)[C@@H](CO)c2ccccc2)ccc1S(=O)(=O)Nc1cccc(Cl)c1Cl] | ++ |

-continued
| Compound ID | Structure | Potency |
| --- | --- | --- |
| 1.273 | 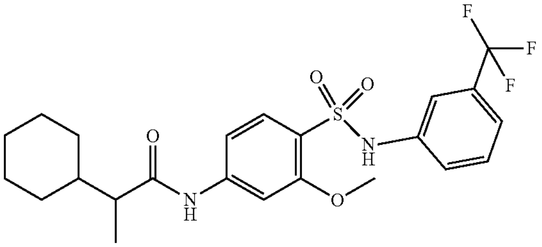 [SMILES: COc1cc(NC(=O)C(C)C2CCCCC2)ccc1S(=O)(=O)Nc1cccc(C(F)(F)F)c1] | ++ |
| 1.274 | 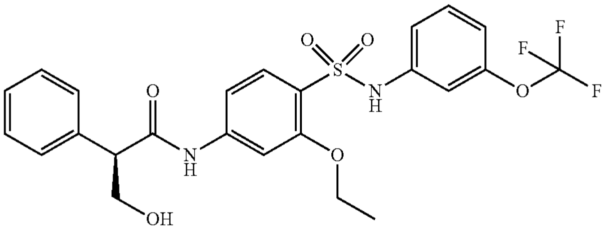 [SMILES: CCOc1cc(NC(=O)[C@@H](CO)c2ccccc2)ccc1S(=O)(=O)Nc1cccc(OC(F)(F)F)c1] | + |
| 1.275 | 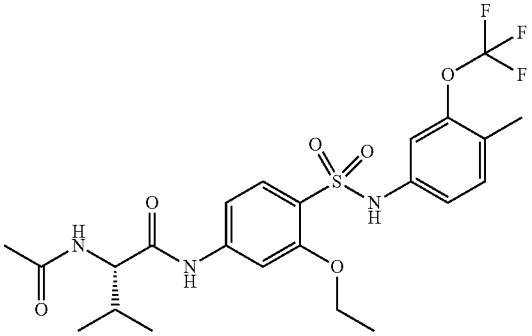 [SMILES: CCOc1cc(NC(=O)[C@@H](NC(C)=O)C(C)C)ccc1S(=O)(=O)Nc1ccc(C)c(OC(F)(F)F)c1] | ++++ |
| 1.276 | 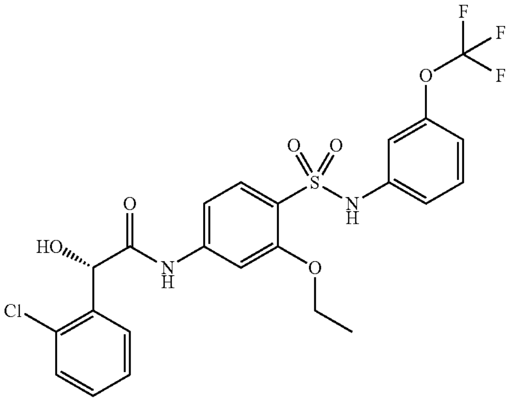 [SMILES: CCOc1cc(NC(=O)[C@@H](O)c2ccccc2Cl)ccc1S(=O)(=O)Nc1cccc(OC(F)(F)F)c1] | ++++ |
| 1.277 | 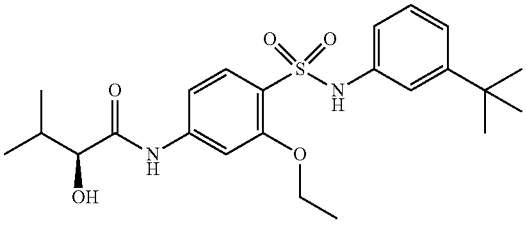 [SMILES: CCOc1cc(NC(=O)[C@@H](O)C(C)C)ccc1S(=O)(=O)Nc1cccc(C(C)(C)C)c1] | +++ |

-continued
| Compound ID | Structure | Potency |
| --- | --- | --- |
| 1.278 | 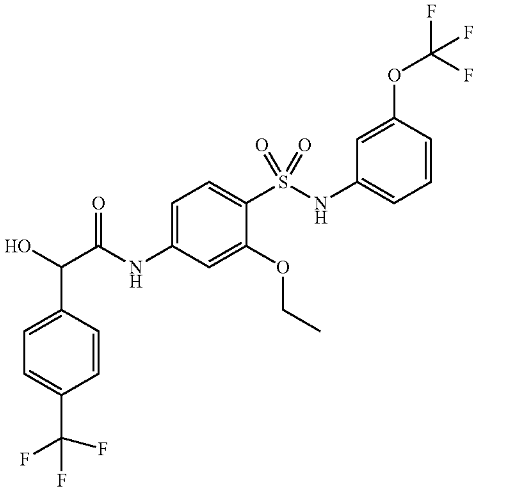 [SMILES: CCOc1cc(NC(=O)C(O)c2ccc(C(F)(F)F)cc2)ccc1S(=O)(=O)Nc1cccc(OC(F)(F)F)c1] | +++ |
| 1.279 | 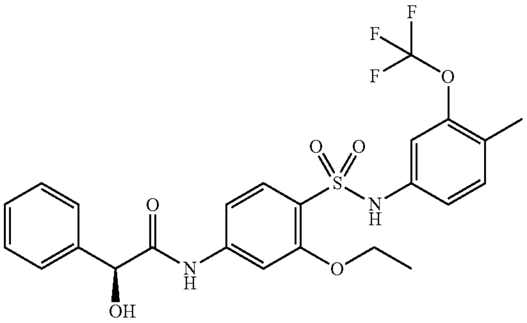 [SMILES: CCOc1cc(NC(=O)[C@@H](O)c2ccccc2)ccc1S(=O)(=O)Nc1ccc(C)c(OC(F)(F)F)c1] | ++++ |
| 1.280 | 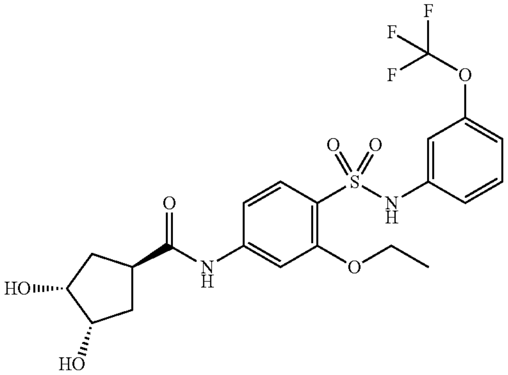 [SMILES: CCOc1cc(NC(=O)[C@@H]2C[C@@H](O)[C@@H](O)C2)ccc1S(=O)(=O)Nc1cccc(OC(F)(F)F)c1] | + |
| 1.281 | 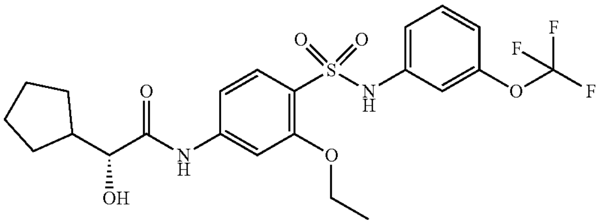 [SMILES: CCOc1cc(NC(=O)[C@H](O)C2CCCC2)ccc1S(=O)(=O)Nc1cccc(OC(F)(F)F)c1] | ++++ |

-continued
| Compound ID | Structure | Potency |
|---|---|---|
| 1.282 | 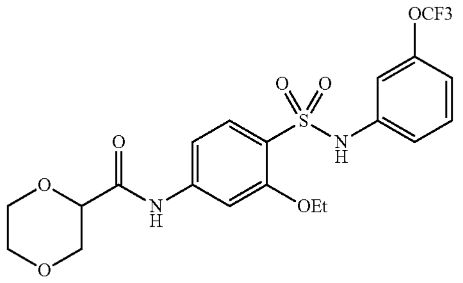 [SMILES: CCOc1cc(NC(=O)C2COCCO2)ccc1S(=O)(=O)Nc1cccc(OC(F)(F)F)c1] | ++ |
| 1.283 | 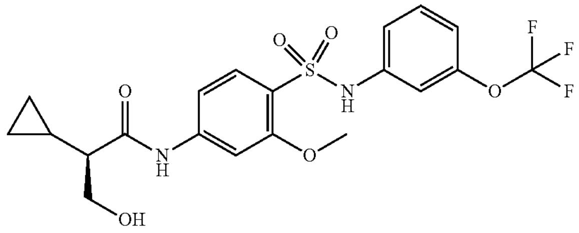 [SMILES: COc1cc(NC(=O)[C@@H](CO)C2CC2)ccc1S(=O)(=O)Nc1cccc(OC(F)(F)F)c1] | ++++ |
| 1.284 | 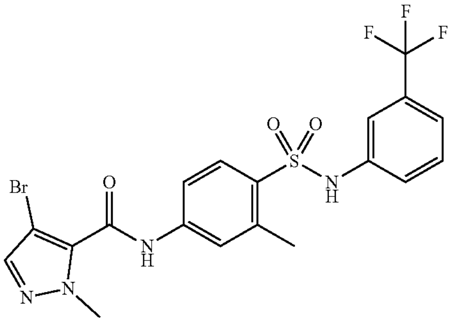 [SMILES: Cc1cc(NC(=O)c2c(Br)cnn2C)ccc1S(=O)(=O)Nc1cccc(C(F)(F)F)c1] | + |
| 1.285 | 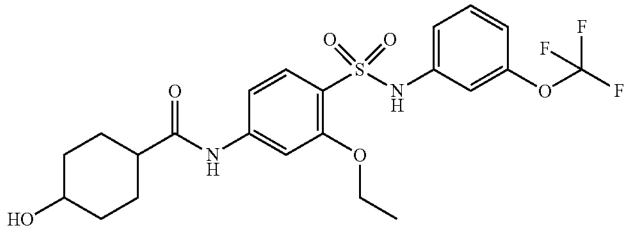 [SMILES: CCOc1cc(NC(=O)C2CCC(O)CC2)ccc1S(=O)(=O)Nc1cccc(OC(F)(F)F)c1] | + |
| 1.286 | 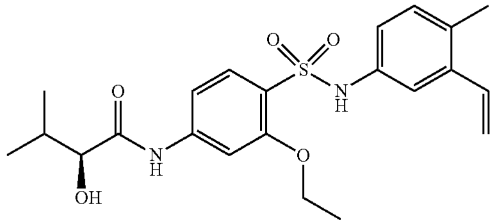 [SMILES: C=Cc1cc(NS(=O)(=O)c2ccc(NC(=O)[C@@H](O)C(C)C)cc2OCC)ccc1C] | ++++ |

-continued
| Compound ID | Structure | Potency |
| --- | --- | --- |
| 1.287 | 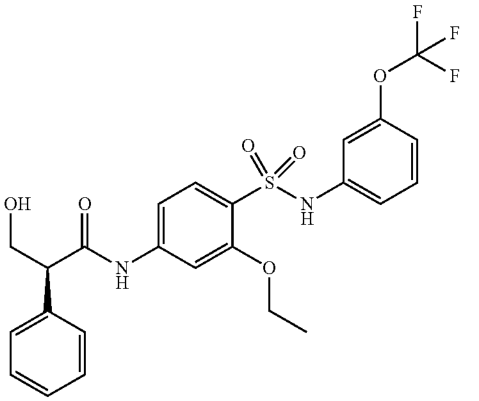 [SMILES: CCOc1cc(NC(=O)[C@H](CO)c2ccccc2)ccc1S(=O)(=O)Nc1cccc(OC(F)(F)F)c1] | +++ |
| 1.288 | 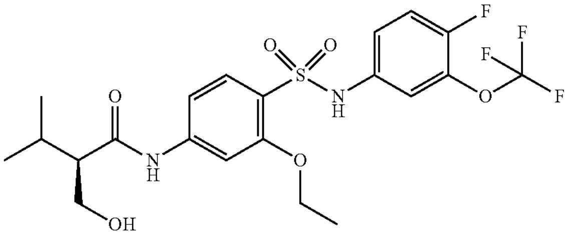 [SMILES: CCOc1cc(NC(=O)[C@@H](CO)C(C)C)ccc1S(=O)(=O)Nc1ccc(F)c(OC(F)(F)F)c1] | ++++ |
| 1.289 | 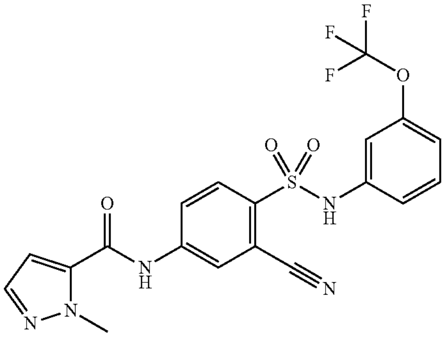 [SMILES: Cn1nccc1C(=O)Nc1ccc(S(=O)(=O)Nc2cccc(OC(F)(F)F)c2)c(C#N)c1] | ++ |
| 1.290 | 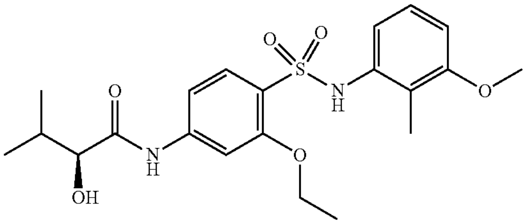 [SMILES: CCOc1cc(NC(=O)[C@@H](O)C(C)C)ccc1S(=O)(=O)Nc1cccc(OC)c1C] | ++ |
| 1.291 | 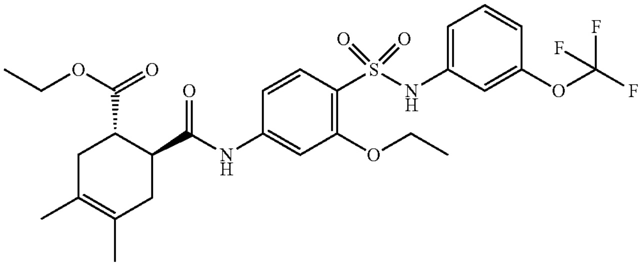 [SMILES: CCOC(=O)[C@H]1CC(C)=C(C)C[C@@H]1C(=O)Nc1ccc(S(=O)(=O)Nc2cccc(OC(F)(F)F)c2)c(OCC)c1] | +++ |

-continued
| Compound ID | Structure | Potency |
|---|---|---|
| 1.292 | 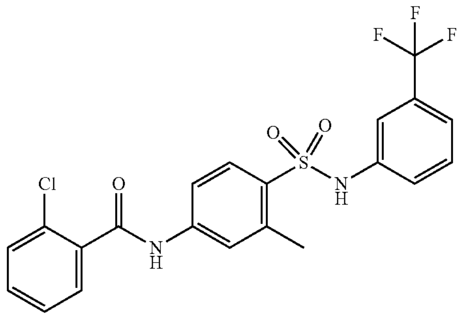 [SMILES: Cc1cc(NC(=O)c2ccccc2Cl)ccc1S(=O)(=O)Nc1cccc(C(F)(F)F)c1] | +++ |
| 1.293 | 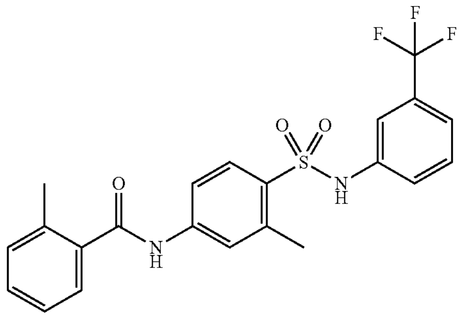 | +++ |
| 1.294 | 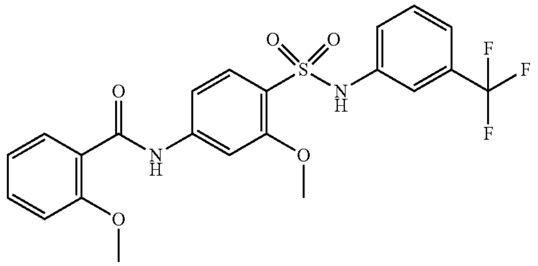 [SMILES: COc1ccccc1C(=O)Nc1ccc(S(=O)(=O)Nc2cccc(C(F)(F)F)c2)c(OC)c1] | + |
| 1.295 | 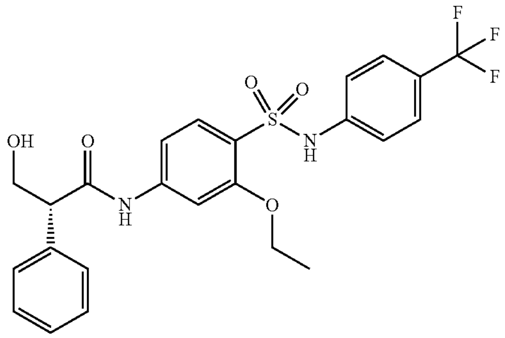 [SMILES: CCOc1cc(NC(=O)[C@@H](CO)c2ccccc2)ccc1S(=O)(=O)Nc1ccc(C(F)(F)F)cc1] | ++ |

-continued
| Compound ID | Structure | Potency |
|---|---|---|
| 1.296 | 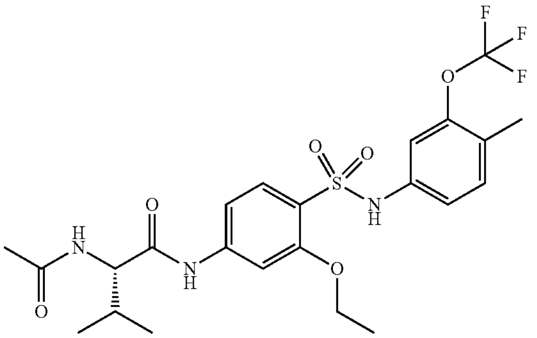 [SMILES: CCOc1cc(NC(=O)[C@@H](NC(C)=O)C(C)C)ccc1S(=O)(=O)Nc1ccc(C)c(OC(F)(F)F)c1] | ++++ |
| 1.297 | 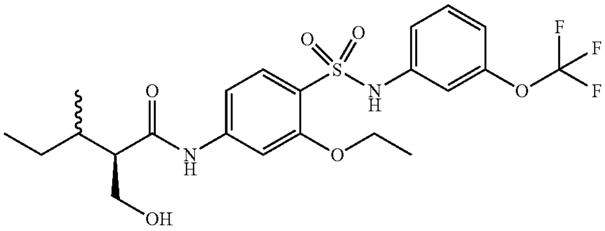 [SMILES: CCOc1cc(NC(=O)[C@@H](CO)C(C)CC)ccc1S(=O)(=O)Nc1cccc(OC(F)(F)F)c1] | ++++ |
| 1.298 | 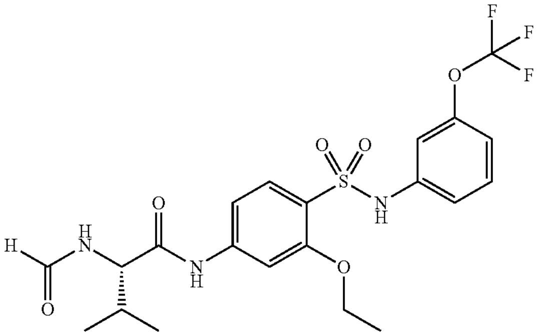 [SMILES: CCOc1cc(NC(=O)[C@@H](NC=O)C(C)C)ccc1S(=O)(=O)Nc1cccc(OC(F)(F)F)c1] | ++++ |
| 1.299 | 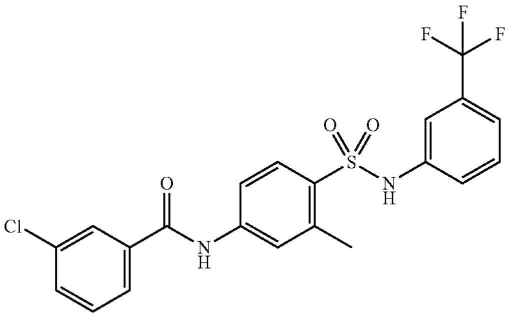 [SMILES: Cc1cc(NC(=O)c2cccc(Cl)c2)ccc1S(=O)(=O)Nc1cccc(C(F)(F)F)c1] | +++ |
| 1.300 | 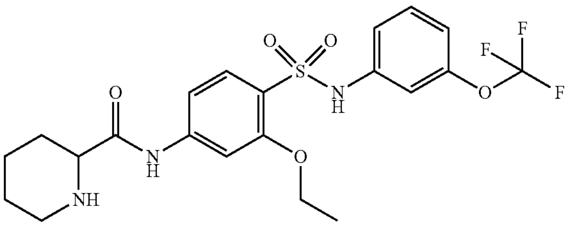 [SMILES: CCOc1cc(NC(=O)C2CCCCN2)ccc1S(=O)(=O)Nc1cccc(OC(F)(F)F)c1] | +++ |

-continued
| Compound ID | Structure | Potency |
|---|---|---|
| 1.301 | 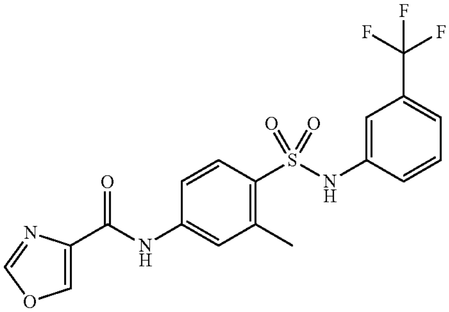 [SMILES: Cc1cc(NC(=O)c2cocn2)ccc1S(=O)(=O)Nc1cccc(C(F)(F)F)c1] | + |
| 1.302 | 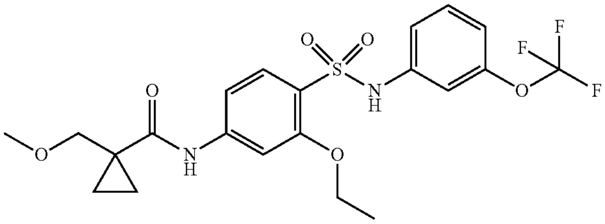 [SMILES: CCOc1cc(NC(=O)C2(COC)CC2)ccc1S(=O)(=O)Nc1cccc(OC(F)(F)F)c1] | ++ |
| 1.303 | 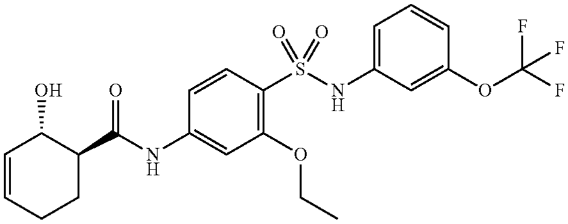 [SMILES: CCOc1cc(NC(=O)[C@H]2CCC=C[C@@H]2O)ccc1S(=O)(=O)Nc1cccc(OC(F)(F)F)c1] | ++++ |
| 1.304 | 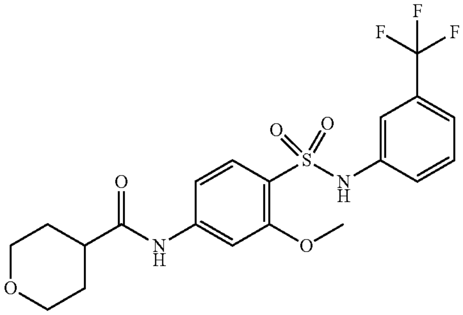 [SMILES: COc1cc(NC(=O)C2CCOCC2)ccc1S(=O)(=O)Nc1cccc(C(F)(F)F)c1] | ++ |
| 1.305 | AND Enantiomer 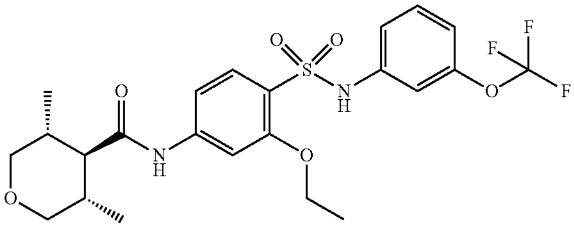 | ++++ |

-continued
| Compound ID | Structure | Potency |
|---|---|---|
| 1.306 | 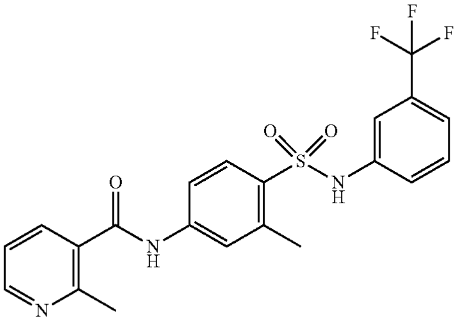 [SMILES: Cc1cc(NC(=O)c2cccnc2C)ccc1S(=O)(=O)Nc1cccc(C(F)(F)F)c1] | ++ |
| 1.307 | 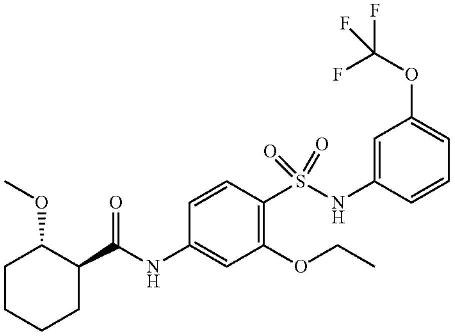 [SMILES: CCOc1cc(NC(=O)[C@H]2CCCC[C@@H]2OC)ccc1S(=O)(=O)Nc1cccc(OC(F)(F)F)c1] | +++ |
| 1.308 | 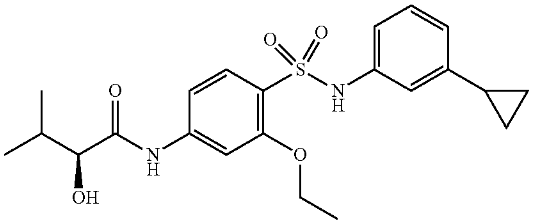 [SMILES: CCOc1cc(NC(=O)[C@@H](O)C(C)C)ccc1S(=O)(=O)Nc1cccc(C2CC2)c1] | ++++ |
| 1.309 | 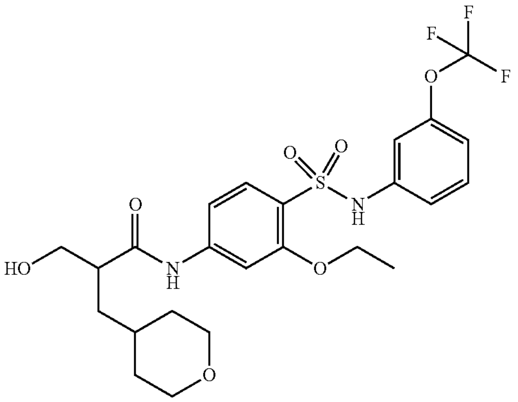 [SMILES: CCOc1cc(NC(=O)C(CO)CC2CCOCC2)ccc1S(=O)(=O)Nc1cccc(OC(F)(F)F)c1] | +++ |
| 1.311 | 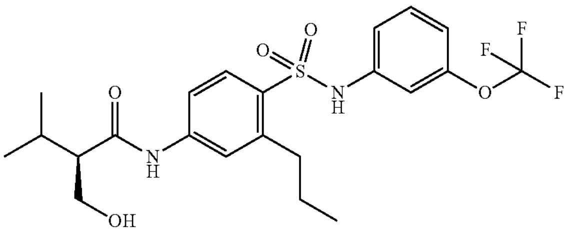 [SMILES: CCCc1cc(NC(=O)[C@@H](CO)C(C)C)ccc1S(=O)(=O)Nc1cccc(OC(F)(F)F)c1] | ++++ |

-continued
| Compound ID | Structure | Potency |
|---|---|---|
| 1.312 | 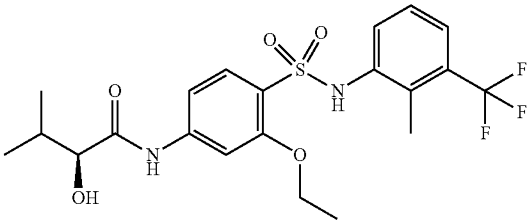 [SMILES: CCOc1cc(NC(=O)[C@@H](O)C(C)C)ccc1S(=O)(=O)Nc1cccc(C(F)(F)F)c1C] | + |
| 1.313 | 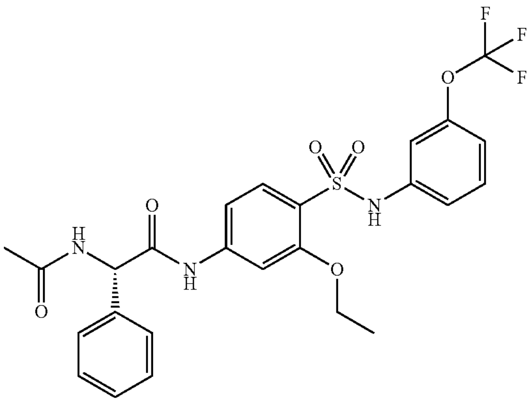 [SMILES: CCOc1cc(NC(=O)[C@@H](NC(C)=O)c2ccccc2)ccc1S(=O)(=O)Nc1cccc(OC(F)(F)F)c1] | ++++ |
| 1.314 | AND Enantiomer<br>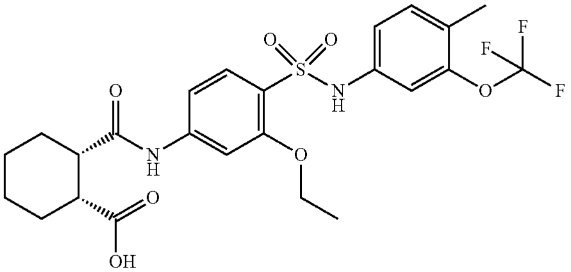 | ++ |
| 1.315 | 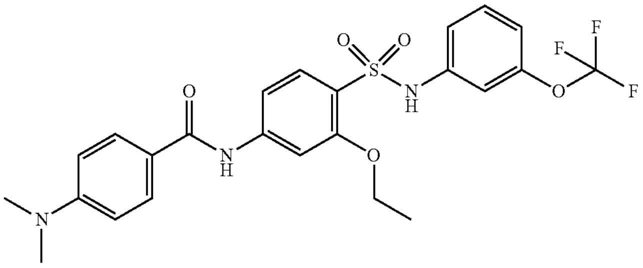 [SMILES: CCOc1cc(NC(=O)c2ccc(N(C)C)cc2)ccc1S(=O)(=O)Nc1cccc(OC(F)(F)F)c1] | ++ |

-continued
| Compound ID | Structure | Potency |
|---|---|---|
| 1.316 | 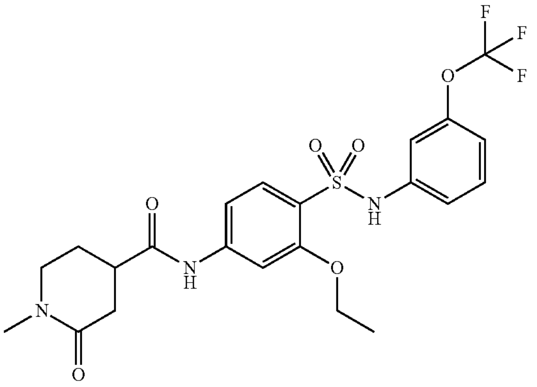 [SMILES: CCOc1cc(NC(=O)C2CCN(C)C(=O)C2)ccc1S(=O)(=O)Nc1cccc(OC(F)(F)F)c1] | ++ |
| 1.317 | 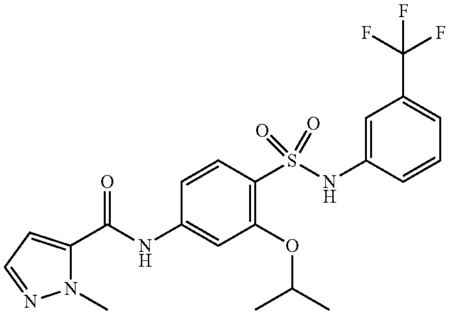 [SMILES: CC(C)Oc1cc(NC(=O)c2ccnn2C)ccc1S(=O)(=O)Nc1cccc(C(F)(F)F)c1] | + |
| 1.318 | 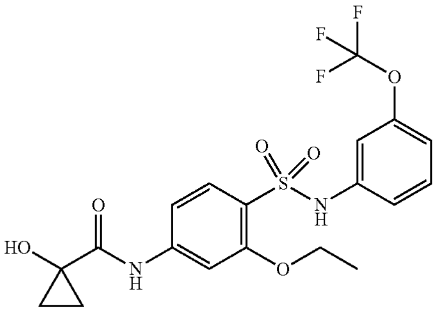 [SMILES: CCOc1cc(NC(=O)C2(O)CC2)ccc1S(=O)(=O)Nc1cccc(OC(F)(F)F)c1] | ++ |
| 1.319 | 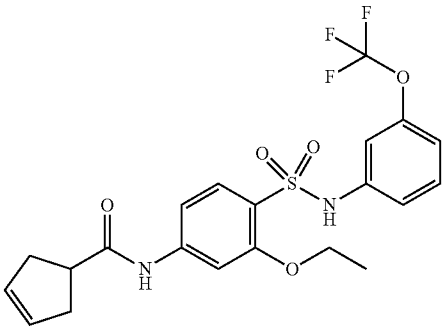 [SMILES: CCOc1cc(NC(=O)C2CC=CC2)ccc1S(=O)(=O)Nc1cccc(OC(F)(F)F)c1] | ++ |
| 1.320 | 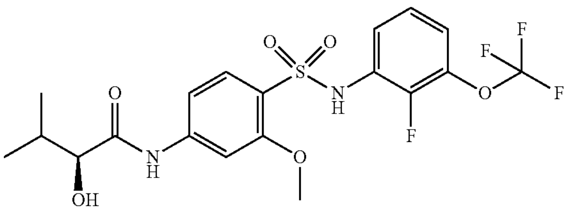 [SMILES: COc1cc(NC(=O)[C@@H](O)C(C)C)ccc1S(=O)(=O)Nc1cccc(OC(F)(F)F)c1F] | +++ |

-continued
| Compound ID | Structure | Potency |
|---|---|---|
| 1.321 | 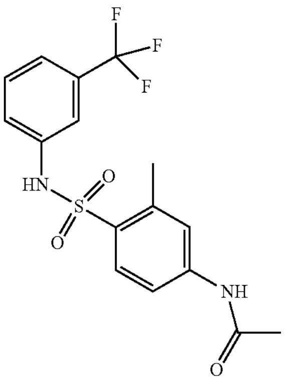 [SMILES: CC(=O)Nc1ccc(S(=O)(=O)Nc2cccc(C(F)(F)F)c2)c(C)c1] | + |
| 1.322 | 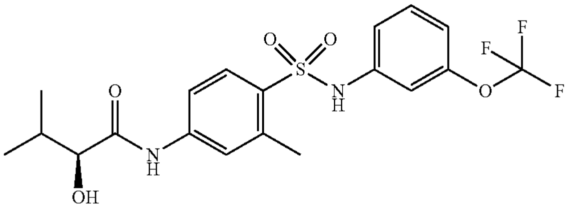 [SMILES: Cc1cc(NC(=O)[C@@H](O)C(C)C)ccc1S(=O)(=O)Nc1cccc(OC(F)(F)F)c1] | ++++ |
| 1.323 | 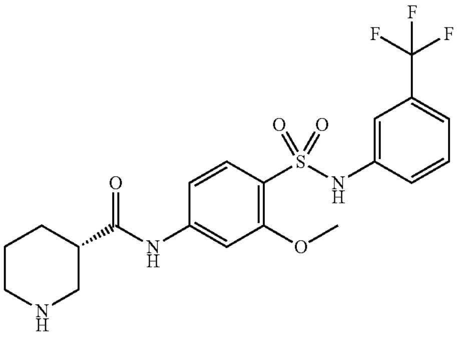 [SMILES: COc1cc(NC(=O)[C@H]2CCCNC2)ccc1S(=O)(=O)Nc1cccc(C(F)(F)F)c1] | + |
| 1.324 | 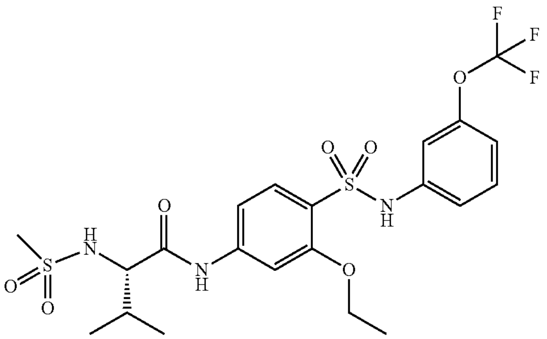 [SMILES: CCOc1cc(NC(=O)[C@@H](NS(C)(=O)=O)C(C)C)ccc1S(=O)(=O)Nc1cccc(OC(F)(F)F)c1] | ++++ |

-continued
| Compound ID | Structure | Potency |
|---|---|---|
| 1.325 | 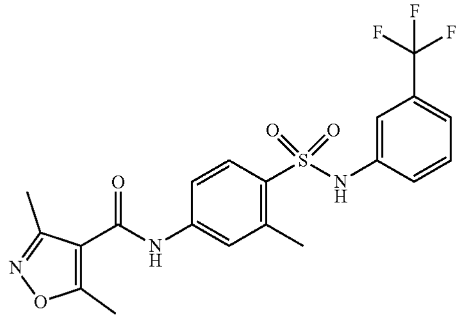 [SMILES: Cc1cc(NC(=O)c2c(C)noc2C)ccc1S(=O)(=O)Nc1cccc(C(F)(F)F)c1] | + |
| 1.326 | 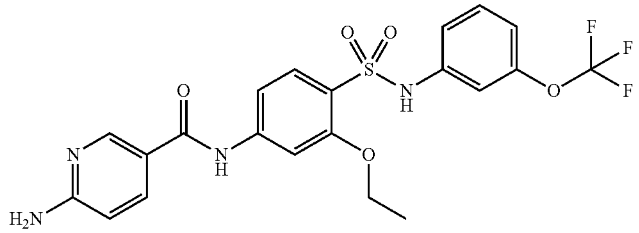 [SMILES: CCOc1cc(NC(=O)c2ccc(N)nc2)ccc1S(=O)(=O)Nc1cccc(OC(F)(F)F)c1] | ++++ |
| 1.327 | 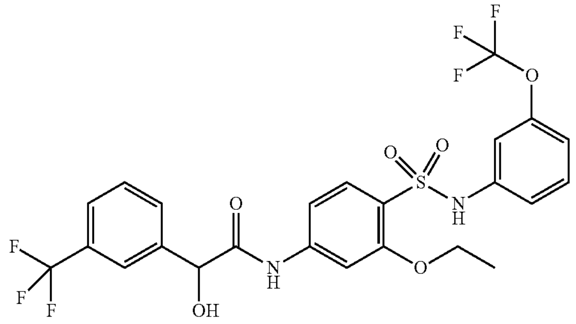 [SMILES: CCOc1cc(NC(=O)C(O)c2cccc(C(F)(F)F)c2)ccc1S(=O)(=O)Nc1cccc(OC(F)(F)F)c1] | ++++ |
| 1.328 | 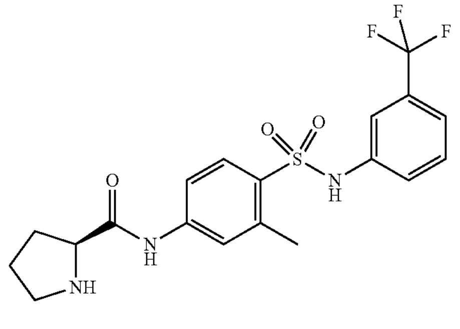 [SMILES: Cc1cc(NC(=O)[C@@H]2CCCN2)ccc1S(=O)(=O)Nc1cccc(C(F)(F)F)c1] | ++ |
| 1.329 | 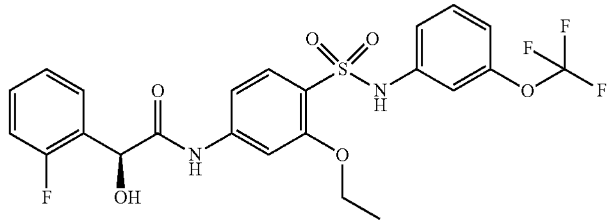 [SMILES: CCOc1cc(NC(=O)[C@@H](O)c2ccccc2F)ccc1S(=O)(=O)Nc1cccc(OC(F)(F)F)c1] | ++++ |

-continued
| Compound ID | Structure | Potency |
| --- | --- | --- |
| 1.330 | 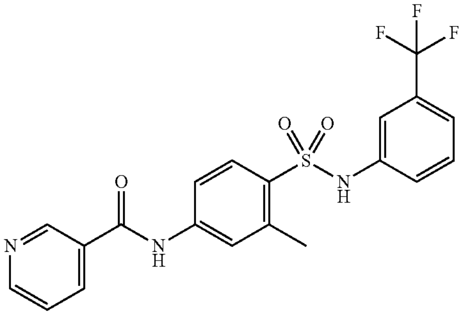 [SMILES: Cc1cc(NC(=O)c2cccnc2)ccc1S(=O)(=O)Nc1cccc(C(F)(F)F)c1] | +++ |
| 1.331 | 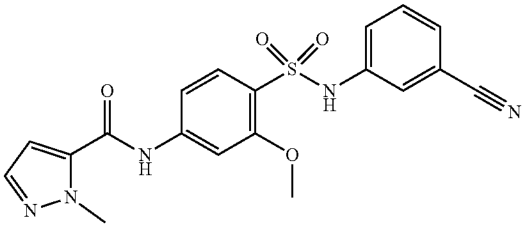 [SMILES: COc1cc(NC(=O)c2ccnn2C)ccc1S(=O)(=O)Nc1cccc(C#N)c1] | + |
| 1.332 | 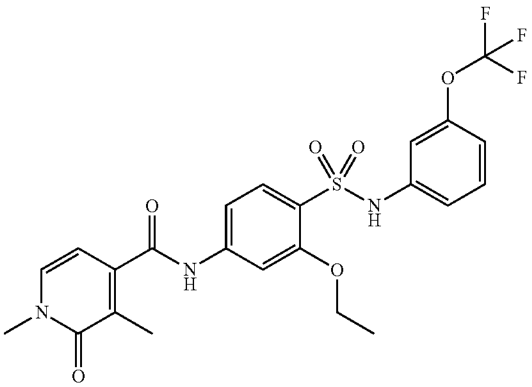 [SMILES: CCOc1cc(NC(=O)c2ccn(C)c(=O)c2C)ccc1S(=O)(=O)Nc1cccc(OC(F)(F)F)c1] | ++++ |
| 1.333 | AND Enantiomer 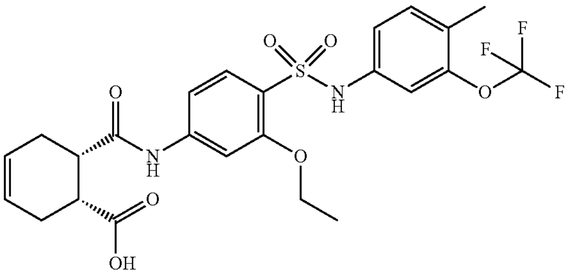 | ++ |

-continued
| Compound ID | Structure | Potency |
|---|---|---|
| 1.334 | 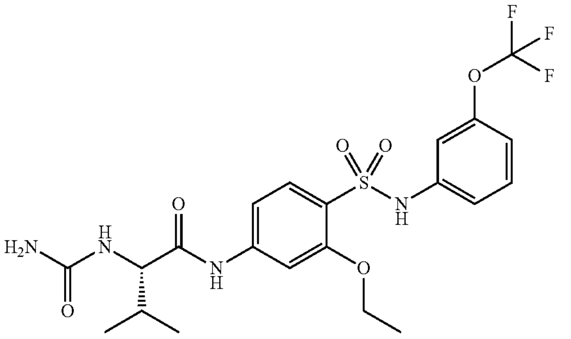 [SMILES: CCOc1cc(NC(=O)[C@@H](NC(N)=O)C(C)C)ccc1S(=O)(=O)Nc1cccc(OC(F)(F)F)c1] | ++++ |
| 1.335 | 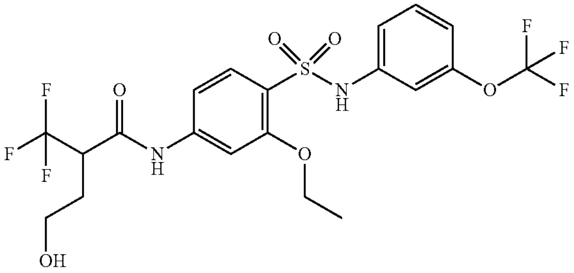 [SMILES: CCOc1cc(NC(=O)C(CCO)C(F)(F)F)ccc1S(=O)(=O)Nc1cccc(OC(F)(F)F)c1] | ++++ |
| 1.336 | 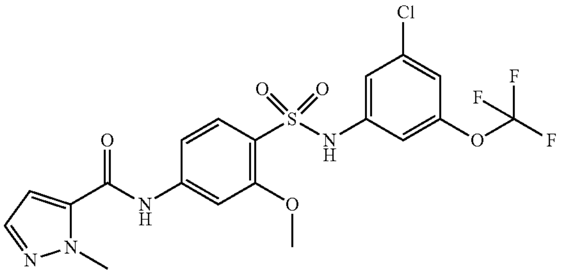 [SMILES: COc1cc(NC(=O)c2ccnn2C)ccc1S(=O)(=O)Nc1cc(Cl)cc(OC(F)(F)F)c1] | +++ |
| 1.337 | 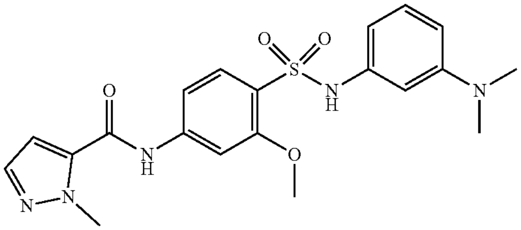 [SMILES: COc1cc(NC(=O)c2ccnn2C)ccc1S(=O)(=O)Nc1cccc(N(C)C)c1] | ++ |
| 1.338 | 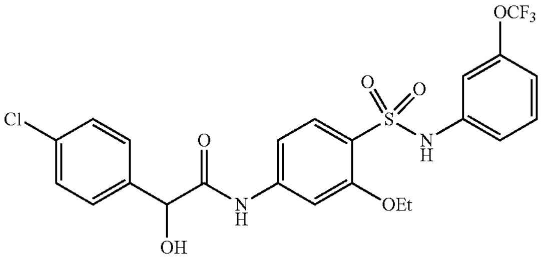 [SMILES: CCOc1cc(NC(=O)C(O)c2ccc(Cl)cc2)ccc1S(=O)(=O)Nc1cccc(OC(F)(F)F)c1] | ++++ |

-continued
| Compound ID | Structure | Potency |
|---|---|---|
| 1.339 | 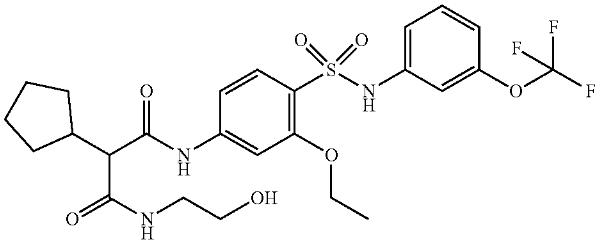 [SMILES: CCOc1cc(NC(=O)C(C(=O)NCCO)C2CCCC2)ccc1S(=O)(=O)Nc1cccc(OC(F)(F)F)c1] | ++++ |
| 1.340 | 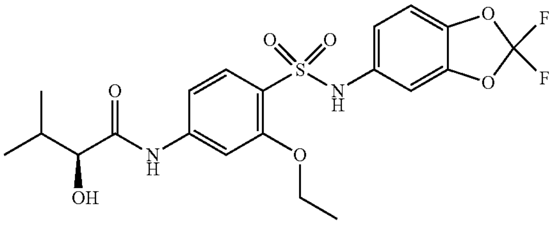 [SMILES: CCOc1cc(NC(=O)[C@@H](O)C(C)C)ccc1S(=O)(=O)Nc1ccc2c(c1)OC(F)(F)O2] | ++ |
| 1.341 | AND Enantiomer 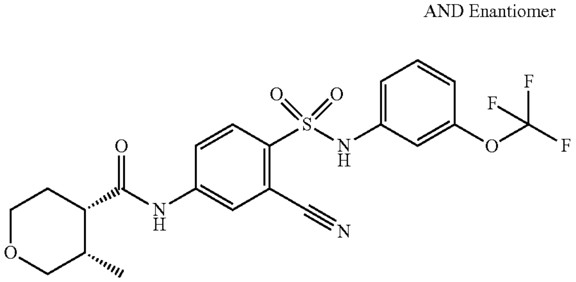 [SMILES: C[C@@H]1COCC[C@@H]1C(=O)Nc1ccc(S(=O)(=O)Nc2cccc(OC(F)(F)F)c2)c(C#N)c1] | + |
| 1.342 | 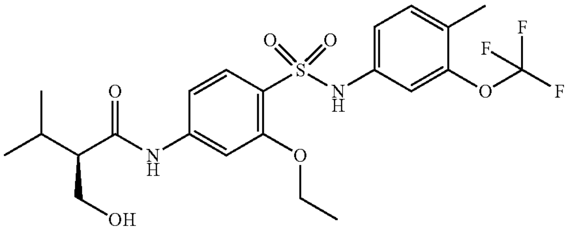 [SMILES: CCOc1cc(NC(=O)[C@@H](CO)C(C)C)ccc1S(=O)(=O)Nc1ccc(C)c(OC(F)(F)F)c1] | ++++ |
| 1.343 | 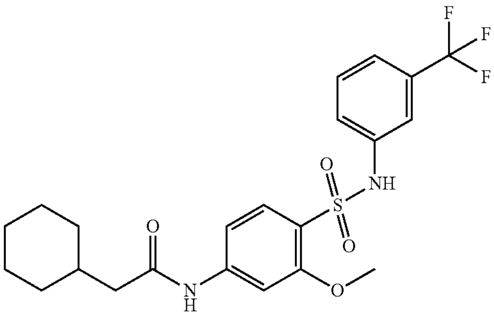 [SMILES: COc1cc(NC(=O)CC2CCCCC2)ccc1S(=O)(=O)Nc1cccc(C(F)(F)F)c1] | ++ |

-continued
| Compound ID | Structure | Potency |
|---|---|---|
| 1.344 | 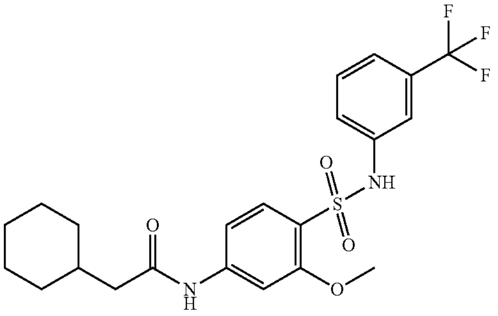 [SMILES: COc1cc(NC(=O)CC2CCCCC2)ccc1S(=O)(=O)Nc1cccc(C(F)(F)F)c1] | ++++ |
| 1.345 | 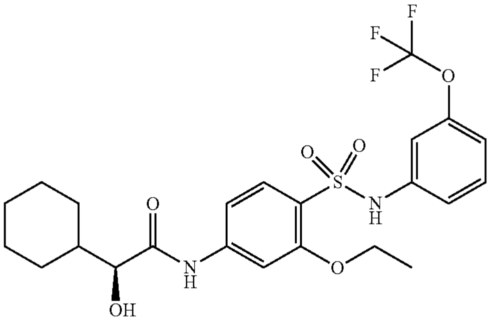 [SMILES: CCOc1cc(NC(=O)[C@@H](O)C2CCCCC2)ccc1S(=O)(=O)Nc1cccc(OC(F)(F)F)c1] | ++++ |
| 1.346 | 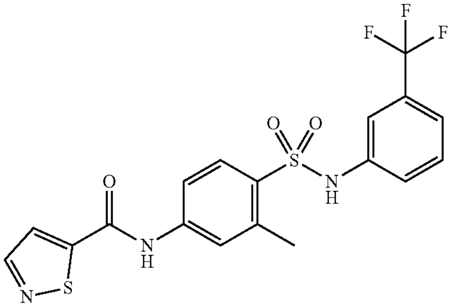 [SMILES: Cc1cc(NC(=O)c2ccns2)ccc1S(=O)(=O)Nc1cccc(C(F)(F)F)c1] | ++++ |
| 1.347 | 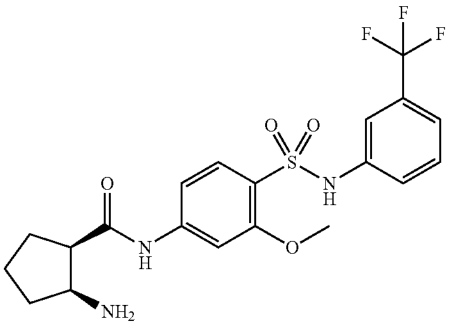 [SMILES: COc1cc(NC(=O)[C@@H]2CCC[C@@H]2N)ccc1S(=O)(=O)Nc1cccc(C(F)(F)F)c1] | + |
| 1.348 | 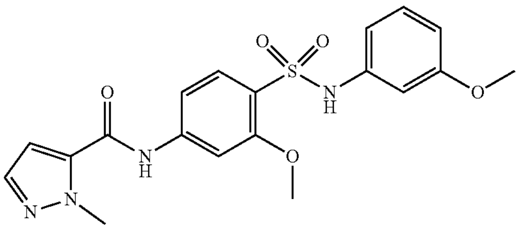 [SMILES: COc1cccc(NS(=O)(=O)c2ccc(NC(=O)c3ccnn3C)cc2OC)c1] | ++ |

-continued
| Compound ID | Structure | Potency |
|---|---|---|
| 1.349 | 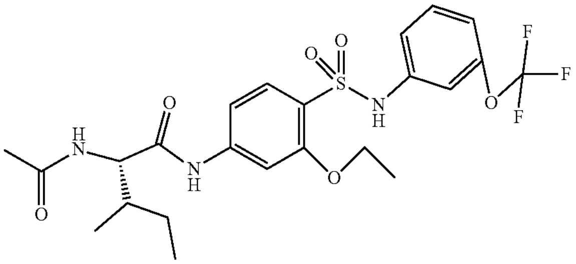 [SMILES: CCOc1cc(NC(=O)[C@@H](NC(C)=O)C(C)CC)ccc1S(=O)(=O)Nc1cccc(OC(F)(F)F)c1] | ++++ |
| 1.350 | 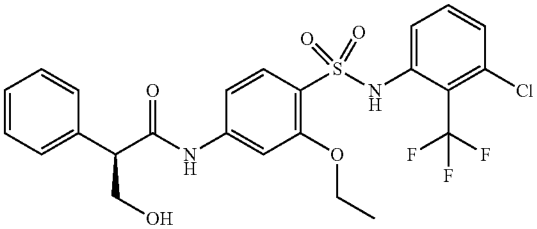 [SMILES: CCOc1cc(NC(=O)[C@@H](CO)c2ccccc2)ccc1S(=O)(=O)Nc1cccc(Cl)c1C(F)(F)F] | + |
| 1.351 | 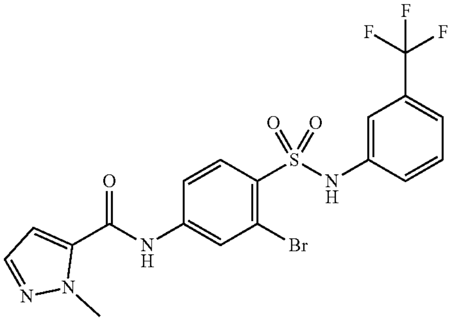 | +++ |
| 1.352 | 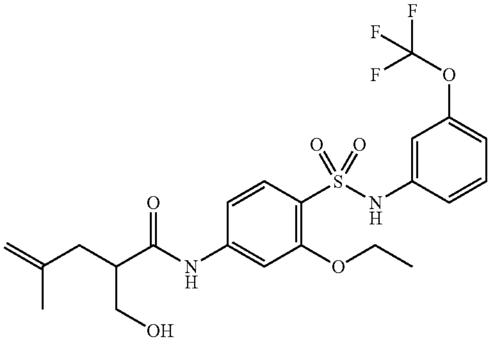 [SMILES: C=C(C)CC(CO)C(=O)Nc1ccc(S(=O)(=O)Nc2cccc(OC(F)(F)F)c2)c(OCC)c1] | ++++ |
| 1.353 | 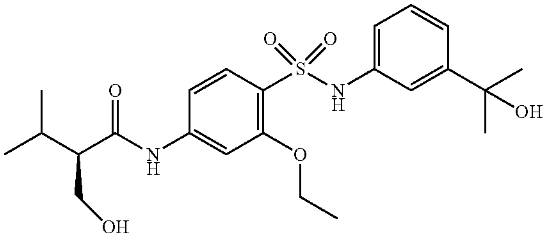 [SMILES: CCOc1cc(NC(=O)[C@@H](CO)C(C)C)ccc1S(=O)(=O)Nc1cccc(C(C)(C)O)c1] | + |

-continued
| Compound ID | Structure | Potency |
| --- | --- | --- |
| 1.354 | 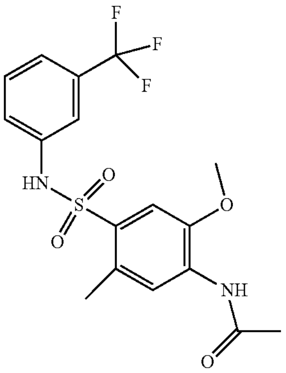 [SMILES: COc1cc(S(=O)(=O)Nc2cccc(C(F)(F)F)c2)c(C)cc1NC(C)=O] | + |
| 1.355 | 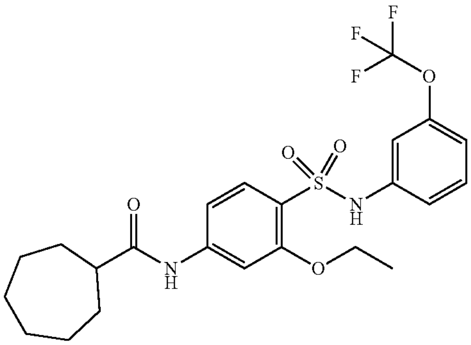 [SMILES: CCOc1cc(NC(=O)C2CCCCCC2)ccc1S(=O)(=O)Nc1cccc(OC(F)(F)F)c1] | ++ |
| 1.356 | 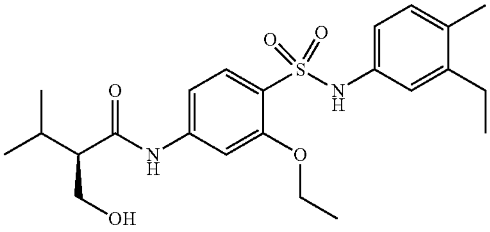 [SMILES: CCOc1cc(NC(=O)[C@@H](CO)C(C)C)ccc1S(=O)(=O)Nc1ccc(C)c(CC)c1] | ++++ |
| 1.357 | 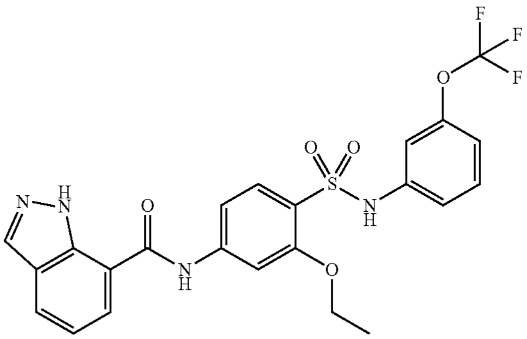 [SMILES: CCOc1cc(NC(=O)c2cccc3cn[nH]c23)ccc1S(=O)(=O)Nc1cccc(OC(F)(F)F)c1] | +++ |
| 1.358 | 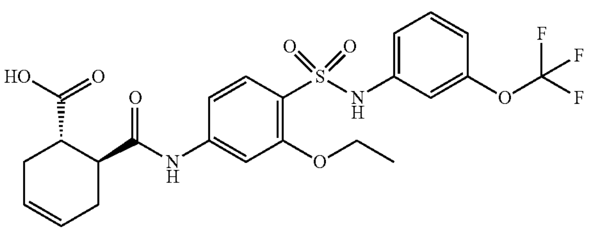 [SMILES: CCOc1cc(NC(=O)[C@H]2CC=CC[C@@H]2C(=O)O)ccc1S(=O)(=O)Nc1cccc(OC(F)(F)F)c1] | ++++ |

-continued
| Compound ID | Structure | Potency |
| --- | --- | --- |
| 1.359 | 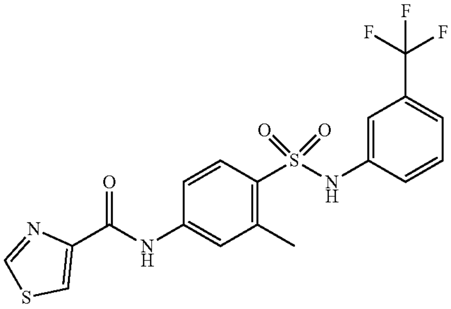 [SMILES: Cc1cc(NC(=O)c2cscn2)ccc1S(=O)(=O)Nc1cccc(C(F)(F)F)c1] | + |
| 1.360 | 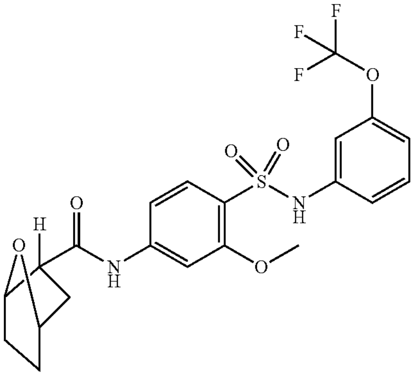 [SMILES: COc1cc(NC(=O)C2CC3CCC2O3)ccc1S(=O)(=O)Nc1cccc(OC(F)(F)F)c1] | +++ |
| 1.361 | 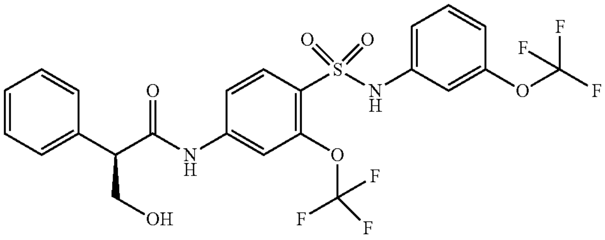 [SMILES: O=C(Nc1ccc(S(=O)(=O)Nc2cccc(OC(F)(F)F)c2)c(OC(F)(F)F)c1)[C@@H](CO)c1ccccc1] | ++++ |
| 1.362 | 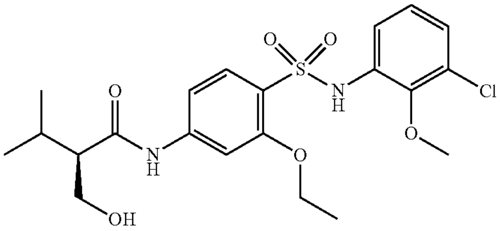 [SMILES: CCOc1cc(NC(=O)[C@@H](CO)C(C)C)ccc1S(=O)(=O)Nc1cccc(Cl)c1OC] | ++ |
| 1.363 | 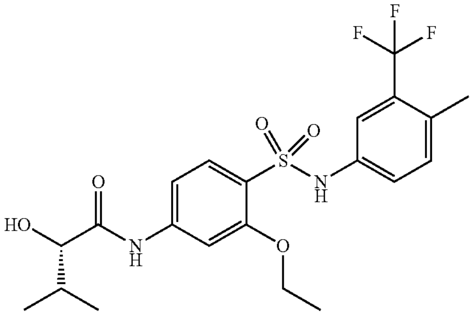 [SMILES: CCOc1cc(NC(=O)[C@@H](O)C(C)C)ccc1S(=O)(=O)Nc1ccc(C)c(C(F)(F)F)c1] | ++++ |

-continued
| Compound ID | Structure | Potency |
|---|---|---|
| 1.364 | 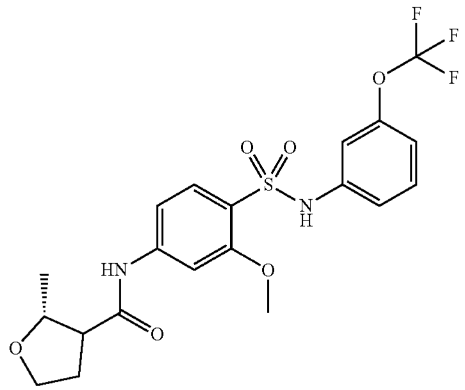 [SMILES: COc1cc(NC(=O)C2CCO[C@@H]2C)ccc1S(=O)(=O)Nc1cccc(OC(F)(F)F)c1] | ++ |
| 1.365 | 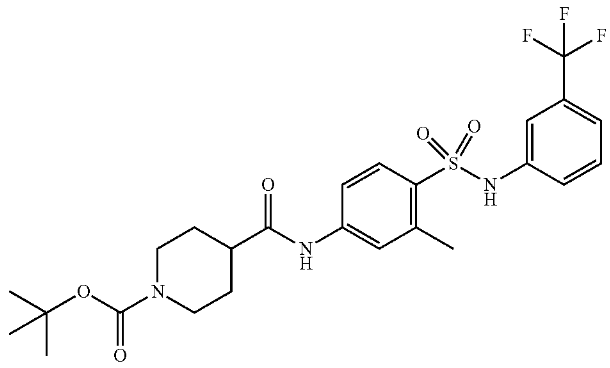 [SMILES: Cc1cc(NC(=O)C2CCN(C(=O)OC(C)(C)C)CC2)ccc1S(=O)(=O)Nc1cccc(C(F)(F)F)c1] | + |
| 1.366 | 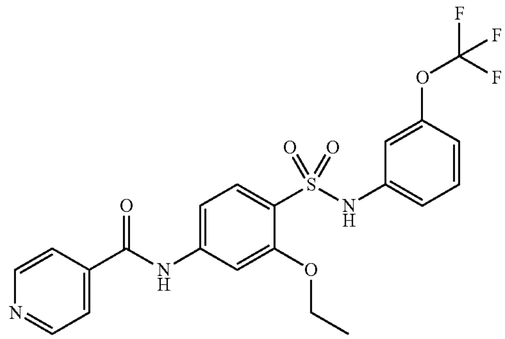 [SMILES: CCOc1cc(NC(=O)c2ccncc2)ccc1S(=O)(=O)Nc1cccc(OC(F)(F)F)c1] | ++++ |
| 1.367 | 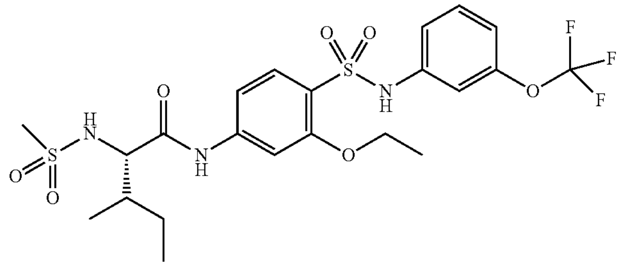 [SMILES: CCOc1cc(NC(=O)[C@@H](NS(C)(=O)=O)C(C)CC)ccc1S(=O)(=O)Nc1cccc(OC(F)(F)F)c1] | + |
| 1.368 | 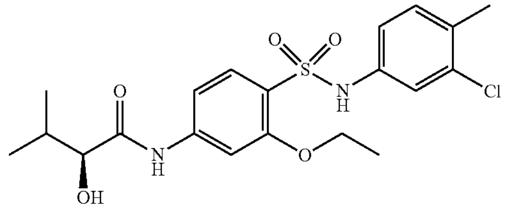 [SMILES: CCOc1cc(NC(=O)[C@@H](O)C(C)C)ccc1S(=O)(=O)Nc1ccc(C)c(Cl)c1] | ++++ |

-continued
| Compound ID | Structure | Potency |
|---|---|---|
| 1.369 | 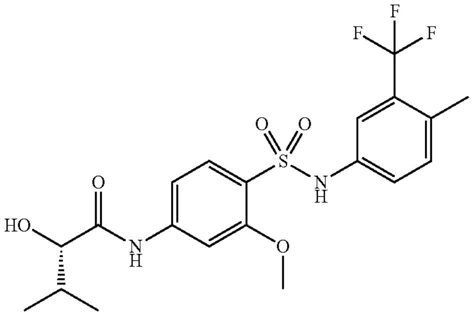 [SMILES: COc1cc(NC(=O)[C@@H](O)C(C)C)ccc1S(=O)(=O)Nc1ccc(C)c(C(F)(F)F)c1] | +++ |
| 1.370 | 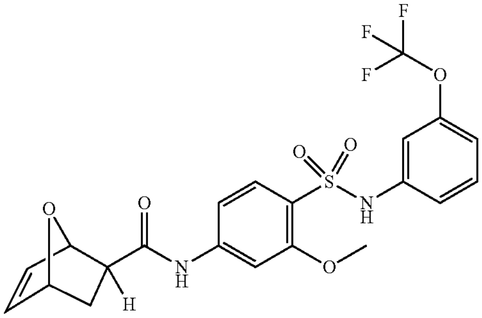 [SMILES: COc1cc(NC(=O)C2CC3C=CC2O3)ccc1S(=O)(=O)Nc1cccc(OC(F)(F)F)c1] | ++ |
| 1.371 | 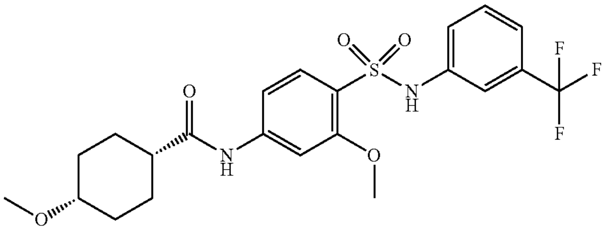 [SMILES: COc1cc(NC(=O)[C@H]2CC[C@@H](OC)CC2)ccc1S(=O)(=O)Nc1cccc(C(F)(F)F)c1] | + |
| 1.372 | 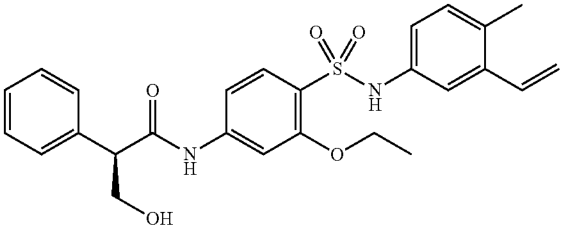 [SMILES: C=Cc1cc(NS(=O)(=O)c2ccc(NC(=O)[C@@H](CO)c3ccccc3)cc2OCC)ccc1C] | ++++ |
| 1.373 | 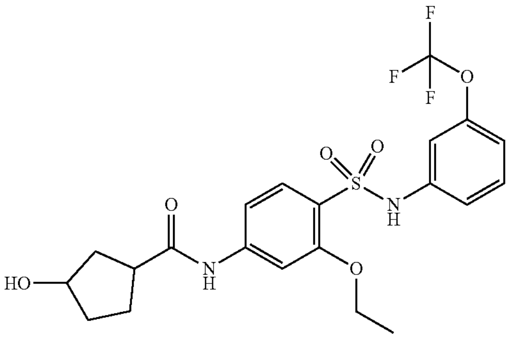 [SMILES: CCOc1cc(NC(=O)C2CCC(O)C2)ccc1S(=O)(=O)Nc1cccc(OC(F)(F)F)c1] | ++ |

-continued
| Compound ID | Structure | Potency |
|---|---|---|
| 1.374 | 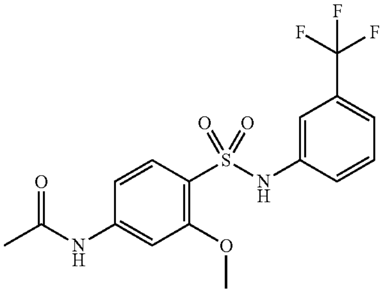 [SMILES: COc1cc(NC(C)=O)ccc1S(=O)(=O)Nc1cccc(C(F)(F)F)c1] | + |
| 1.375 | 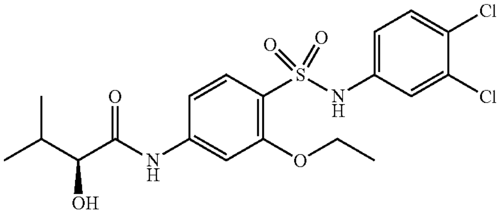 [SMILES: CCOc1cc(NC(=O)[C@@H](O)C(C)C)ccc1S(=O)(=O)Nc1ccc(Cl)c(Cl)c1] | ++++ |
| 1.376 | 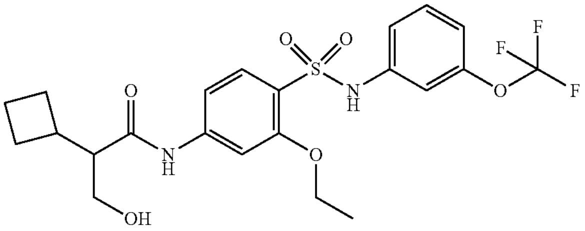 [SMILES: CCOc1cc(NC(=O)C(CO)C2CCC2)ccc1S(=O)(=O)Nc1cccc(OC(F)(F)F)c1] | ++++ |
| 1.377 | 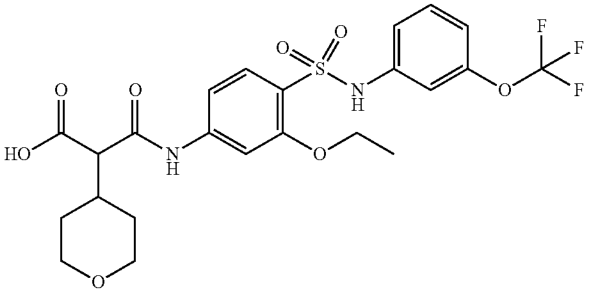 [SMILES: CCOc1cc(NC(=O)C(C(=O)O)C2CCOCC2)ccc1S(=O)(=O)Nc1cccc(OC(F)(F)F)c1] | ++++ |
| 1.378 | 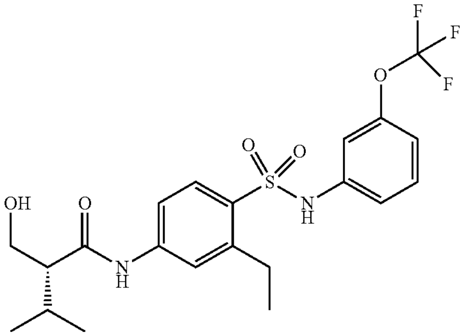 [SMILES: CCc1cc(NC(=O)[C@@H](CO)C(C)C)ccc1S(=O)(=O)Nc1cccc(OC(F)(F)F)c1] | ++++ |

-continued
| Compound ID | Structure | Potency |
|---|---|---|
| 1.379 | 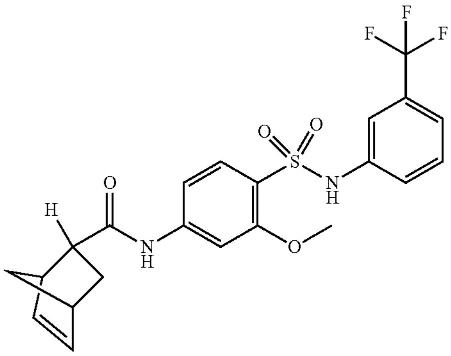 [SMILES: COc1cc(NC(=O)C2CC3C=CC2C3)ccc1S(=O)(=O)Nc1cccc(C(F)(F)F)c1] | +++ |
| 1.380 | 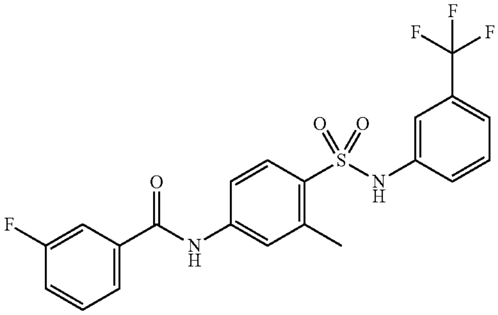 [SMILES: Cc1cc(NC(=O)c2cccc(F)c2)ccc1S(=O)(=O)Nc1cccc(C(F)(F)F)c1] | +++ |
| 1.381 | 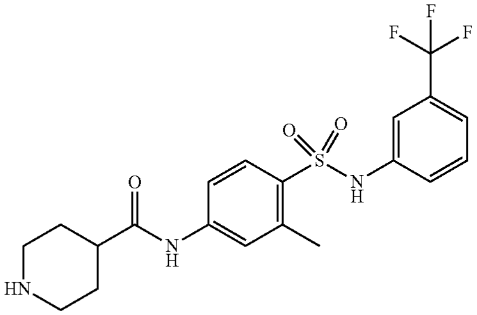 [SMILES: Cc1cc(NC(=O)C2CCNCC2)ccc1S(=O)(=O)Nc1cccc(C(F)(F)F)c1] | + |
| 1.382 | 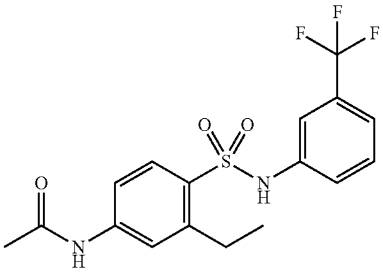 [SMILES: CCc1cc(NC(C)=O)ccc1S(=O)(=O)Nc1cccc(C(F)(F)F)c1] | ++ |
| 1.383 | 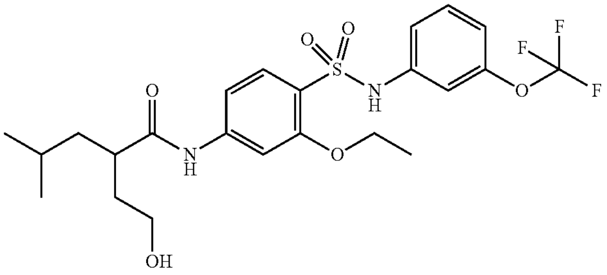 [SMILES: CCOc1cc(NC(=O)C(CCO)CC(C)C)ccc1S(=O)(=O)Nc1cccc(OC(F)(F)F)c1] | ++++ |

-continued
| Compound ID | Structure | Potency |
| --- | --- | --- |
| 1.384 | 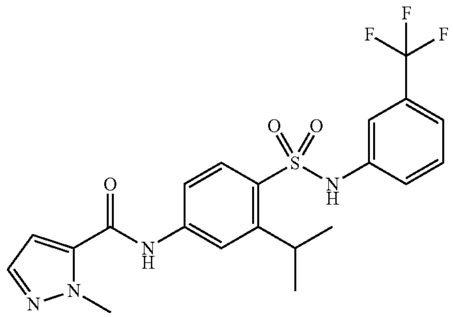 [SMILES: CC(C)c1cc(NC(=O)c2ccnn2C)ccc1S(=O)(=O)Nc1cccc(C(F)(F)F)c1] | +++ |
| 1.385 | 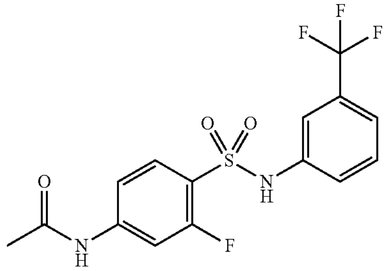 [SMILES: CC(=O)Nc1ccc(S(=O)(=O)Nc2cccc(C(F)(F)F)c2)c(F)c1] | + |
| 1.386 | 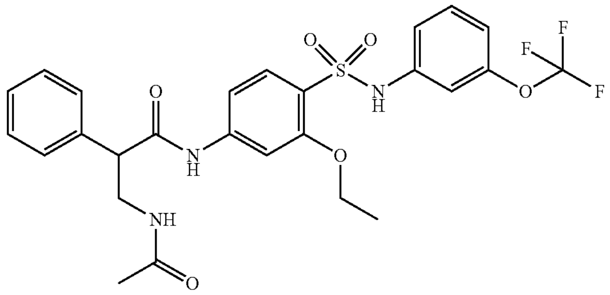 [SMILES: CCOc1cc(NC(=O)C(CNC(C)=O)c2ccccc2)ccc1S(=O)(=O)Nc1cccc(OC(F)(F)F)c1] | ++++ |
| 1.387 | 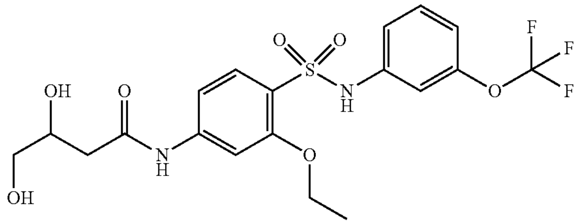 [SMILES: CCOc1cc(NC(=O)CC(O)CO)ccc1S(=O)(=O)Nc1cccc(OC(F)(F)F)c1] | ++ |
| 1.388 | 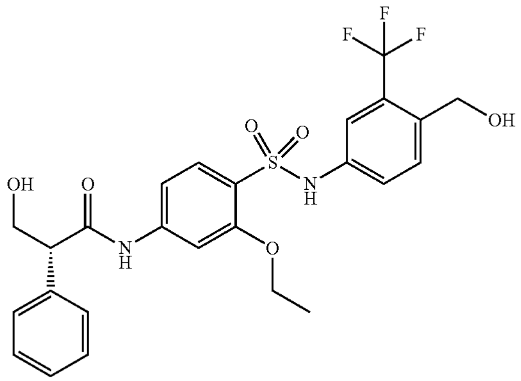 [SMILES: CCOc1cc(NC(=O)[C@@H](CO)c2ccccc2)ccc1S(=O)(=O)Nc1ccc(CO)c(C(F)(F)F)c1] | + |

-continued
| Compound ID | Structure | Potency |
|---|---|---|
| 1.389 | 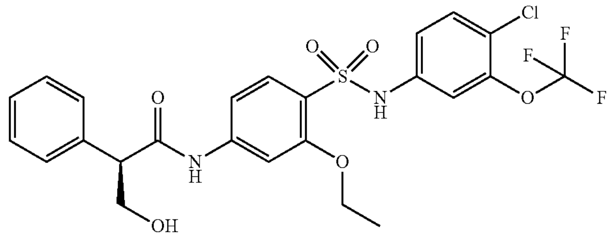 [SMILES: CCOc1cc(NC(=O)[C@@H](CO)c2ccccc2)ccc1S(=O)(=O)Nc1ccc(Cl)c(OC(F)(F)F)c1] | ++++ |
| 1.390 | 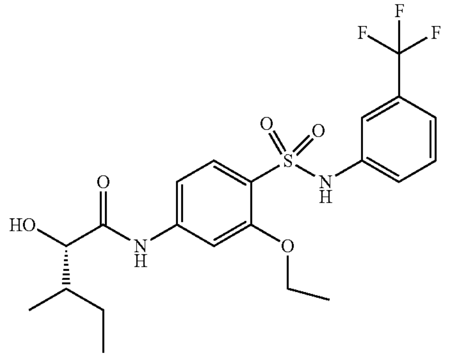 [SMILES: CCOc1cc(NC(=O)[C@@H](O)C(C)CC)ccc1S(=O)(=O)Nc1cccc(C(F)(F)F)c1] | ++++ |
| 1.391 | 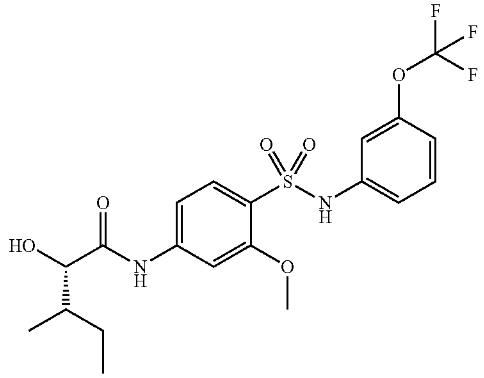 [SMILES: CCC(C)[C@H](O)C(=O)Nc1ccc(S(=O)(=O)Nc2cccc(OC(F)(F)F)c2)c(OC)c1] | ++++ |
| 1.392 | 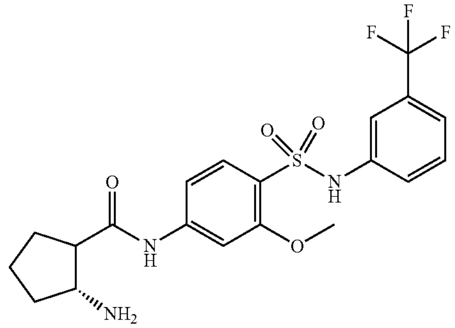 [SMILES: COc1cc(NC(=O)C2CCC[C@H]2N)ccc1S(=O)(=O)Nc1cccc(C(F)(F)F)c1] | + |
| 1.393 | 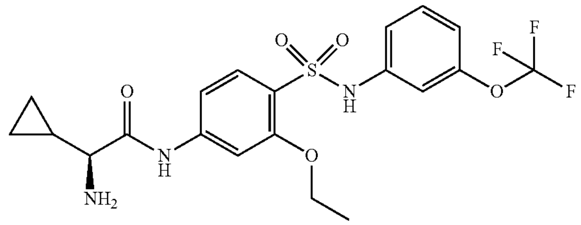 [SMILES: CCOc1cc(NC(=O)[C@@H](N)C2CC2)ccc1S(=O)(=O)Nc1cccc(OC(F)(F)F)c1] | ++++ |

-continued
| Compound ID | Structure | Potency |
|---|---|---|
| 1.394 | 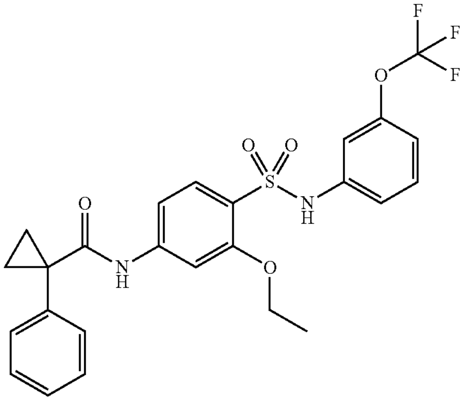 [SMILES: CCOc1cc(NC(=O)C2(c3ccccc3)CC2)ccc1S(=O)(=O)Nc1cccc(OC(F)(F)F)c1] | ++ |
| 1.395 | 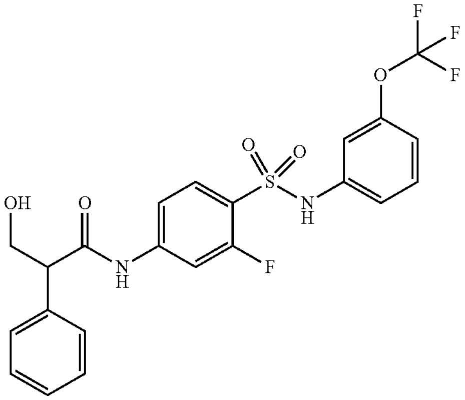 [SMILES: O=C(Nc1ccc(S(=O)(=O)Nc2cccc(OC(F)(F)F)c2)c(F)c1)C(CO)c1ccccc1] | ++ |
| 1.396 | 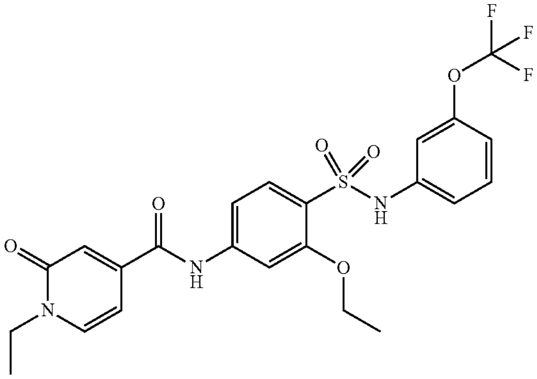 [SMILES: CCOc1cc(NC(=O)c2ccn(CC)c(=O)c2)ccc1S(=O)(=O)Nc1cccc(OC(F)(F)F)c1] | ++++ |
| 1.397 | 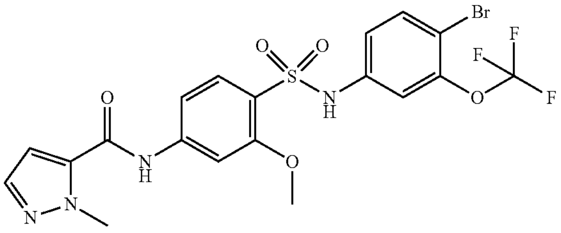 | ++++ |

-continued
| Compound ID | Structure | Potency |
| --- | --- | --- |
| 1.398 | 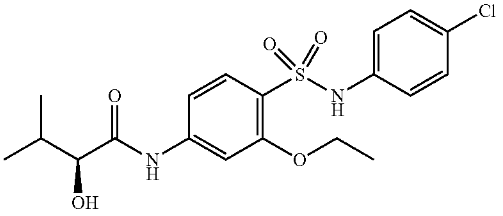 [SMILES: CCOc1cc(NC(=O)[C@@H](O)C(C)C)ccc1S(=O)(=O)Nc1ccc(Cl)cc1] | +++ |
| 1.399 | 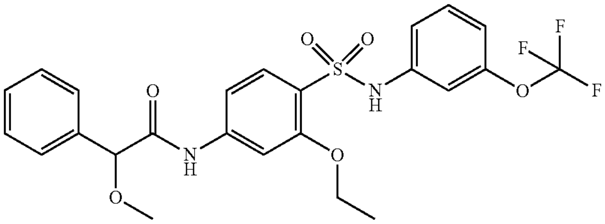 [SMILES: CCOc1cc(NC(=O)C(OC)c2ccccc2)ccc1S(=O)(=O)Nc1cccc(OC(F)(F)F)c1] | ++++ |
| 1.400 | 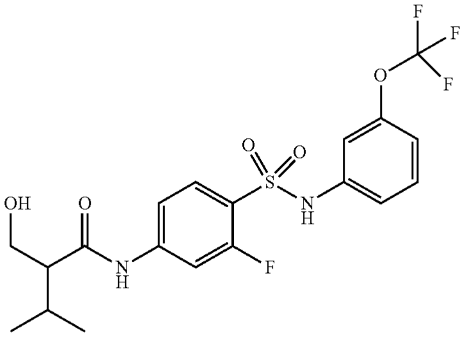 [SMILES: CC(C)C(CO)C(=O)Nc1ccc(S(=O)(=O)Nc2cccc(OC(F)(F)F)c2)c(F)c1] | +++ |
| 1.401 | 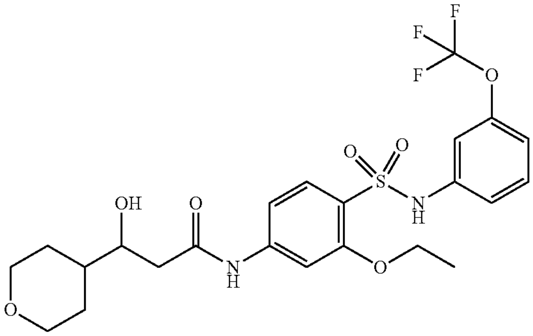 [SMILES: CCOc1cc(NC(=O)CC(O)C2CCOCC2)ccc1S(=O)(=O)Nc1cccc(OC(F)(F)F)c1] | +++ |
| 1.402 | 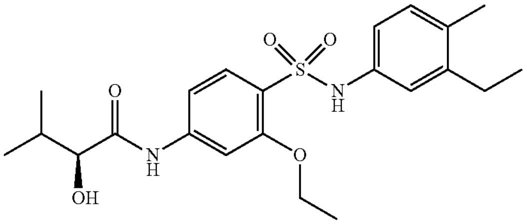 [SMILES: CCOc1cc(NC(=O)[C@@H](O)C(C)C)ccc1S(=O)(=O)Nc1ccc(C)c(CC)c1] | ++++ |

-continued
| Compound ID | Structure | Potency |
|---|---|---|
| 1.403 | 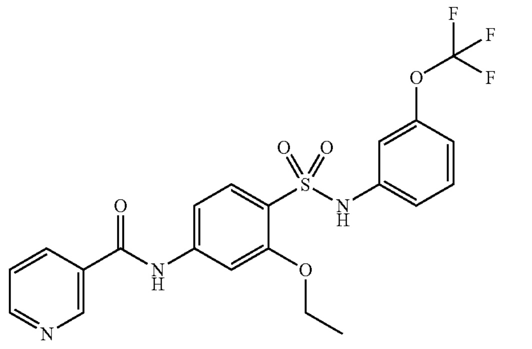 [SMILES: CCOc1cc(NC(=O)c2cccnc2)ccc1S(=O)(=O)Nc1cccc(OC(F)(F)F)c1] | ++++ |
| 1.404 | 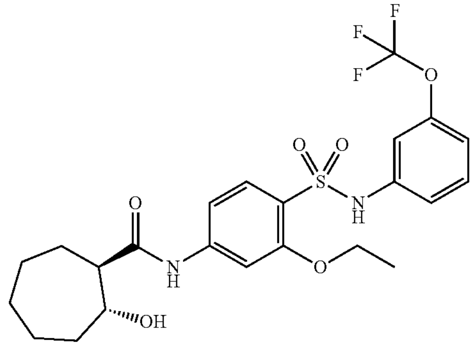 [SMILES: CCOc1cc(NC(=O)[C@@H]2CCCCC[C@H]2O)ccc1S(=O)(=O)Nc1cccc(OC(F)(F)F)c1] | ++++ |
| 1.405 | 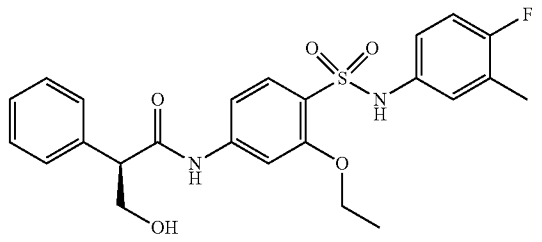 [SMILES: CCOc1cc(NC(=O)[C@@H](CO)c2ccccc2)ccc1S(=O)(=O)Nc1ccc(F)c(C)c1] | +++ |
| 1.406 | 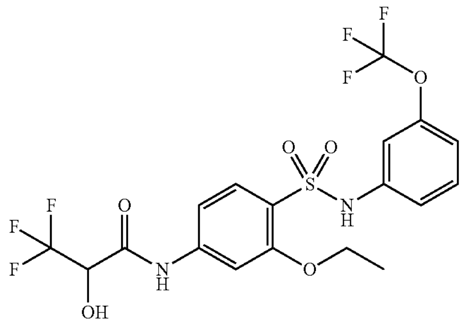 [SMILES: CCOc1cc(NC(=O)C(O)C(F)(F)F)ccc1S(=O)(=O)Nc1cccc(OC(F)(F)F)c1] | ++++ |

-continued
| Compound ID | Structure | Potency |
|---|---|---|
| 1.407 | 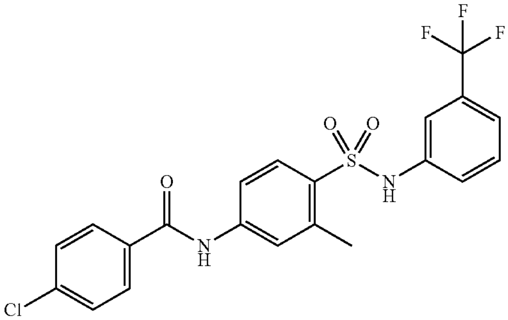 [SMILES: Cc1cc(NC(=O)c2ccc(Cl)cc2)ccc1S(=O)(=O)Nc1cccc(C(F)(F)F)c1] | ++ |
| 1.408 | 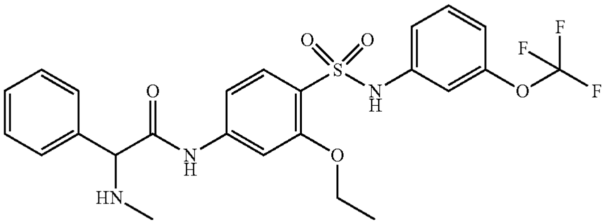 [SMILES: CCOc1cc(NC(=O)C(NC)c2ccccc2)ccc1S(=O)(=O)Nc1cccc(OC(F)(F)F)c1] | ++++ |
| 1.409 | 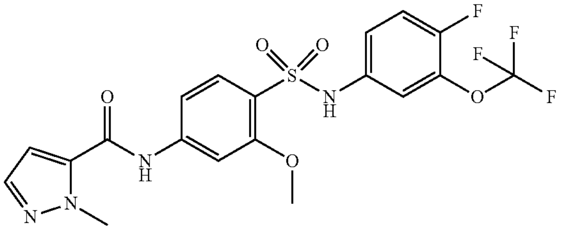 | ++++ |
| 1.410 | 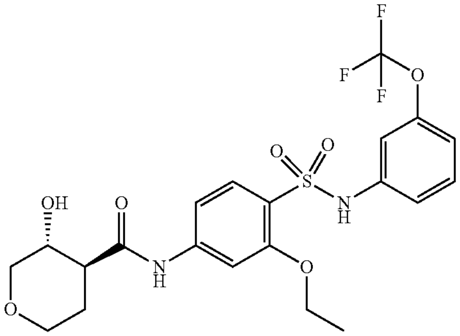 [SMILES: CCOc1cc(NC(=O)[C@H]2CCOC[C@@H]2O)ccc1S(=O)(=O)Nc1cccc(OC(F)(F)F)c1] | +++ |
| 1.411 | 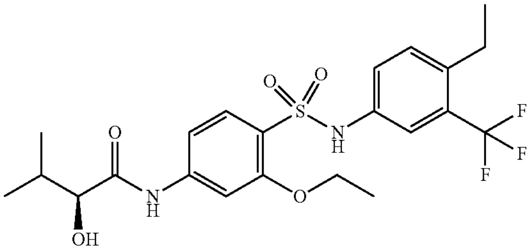 [SMILES: CCOc1cc(NC(=O)[C@@H](O)C(C)C)ccc1S(=O)(=O)Nc1ccc(CC)c(C(F)(F)F)c1] | ++++ |

-continued
| Compound ID | Structure | Potency |
|---|---|---|
| 1.412 | 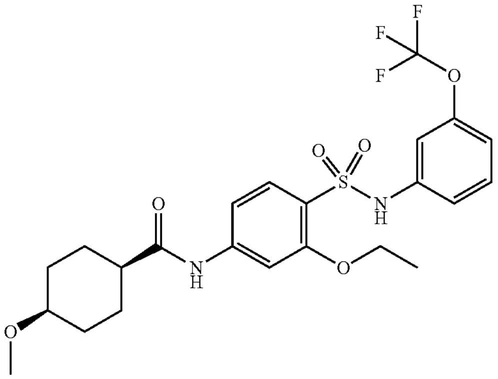 [SMILES: CCOc1cc(NC(=O)[C@H]2CC[C@@H](OC)CC2)ccc1S(=O)(=O)Nc1cccc(OC(F)(F)F)c1] | ++ |
| 1.413 | 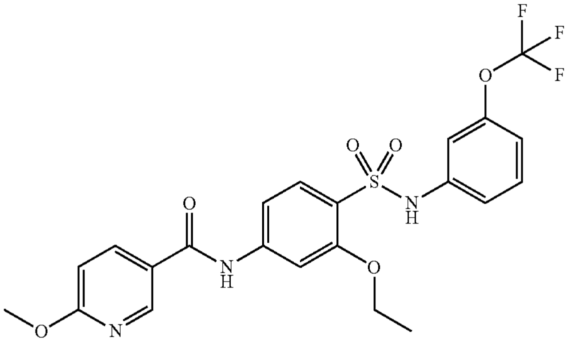 [SMILES: CCOc1cc(NC(=O)c2ccc(OC)nc2)ccc1S(=O)(=O)Nc1cccc(OC(F)(F)F)c1] | ++++ |
| 1.414 | 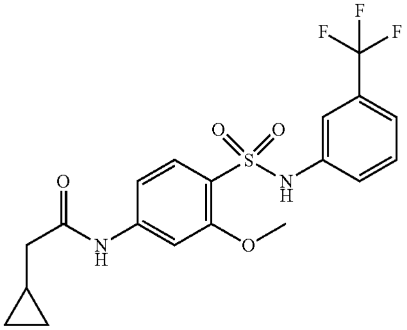 [SMILES: COc1cc(NC(=O)CC2CC2)ccc1S(=O)(=O)Nc1cccc(C(F)(F)F)c1] | + |
| 1.415 | 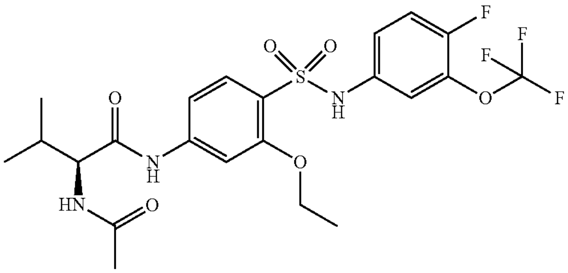 | ++++ |
| 1.416 | 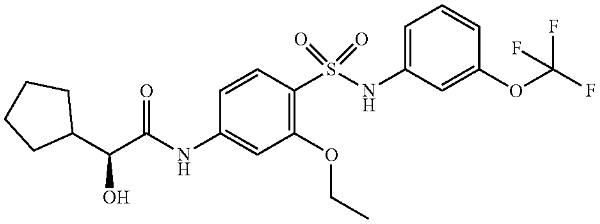 [SMILES: CCOc1cc(NC(=O)[C@@H](O)C2CCCC2)ccc1S(=O)(=O)Nc1cccc(OC(F)(F)F)c1] | ++++ |

-continued
| Compound ID | Structure | Potency |
|---|---|---|
| 1.417 | 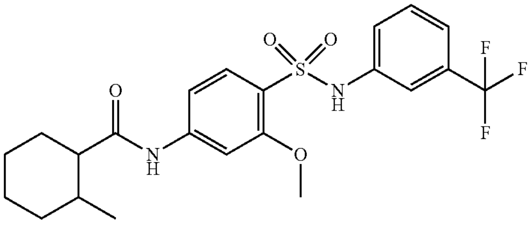 [SMILES: COc1cc(NC(=O)C2CCCCC2C)ccc1S(=O)(=O)Nc1cccc(C(F)(F)F)c1] | ++ |
| 1.418 | 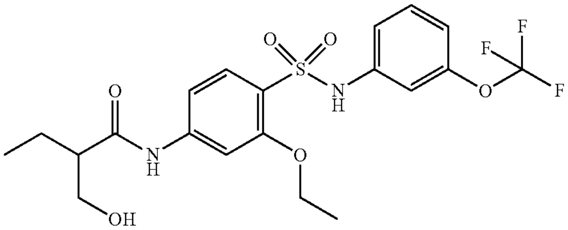 [SMILES: CCOc1cc(NC(=O)C(CC)CO)ccc1S(=O)(=O)Nc1cccc(OC(F)(F)F)c1] | ++++ |
| 1.419 | 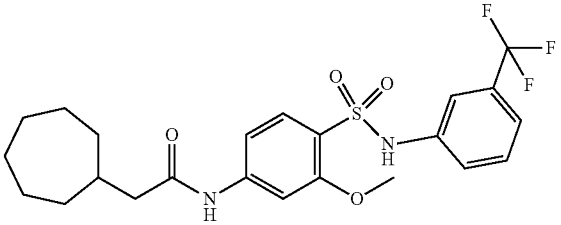 [SMILES: COc1cc(NC(=O)CC2CCCCCC2)ccc1S(=O)(=O)Nc1cccc(C(F)(F)F)c1] | + |
| 1.420 | 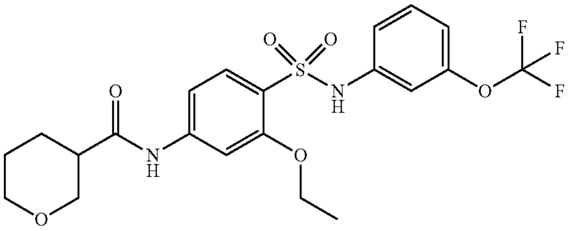 [SMILES: CCOc1cc(NC(=O)C2CCCOC2)ccc1S(=O)(=O)Nc1cccc(OC(F)(F)F)c1] | +++ |
| 1.421 | 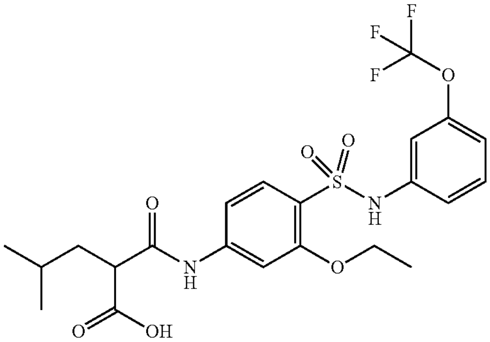 [SMILES: CCOc1cc(NC(=O)C(CC(C)C)C(=O)O)ccc1S(=O)(=O)Nc1cccc(OC(F)(F)F)c1] | ++++ |

-continued
| Compound ID | Structure | Potency |
|---|---|---|
| 1.422 | 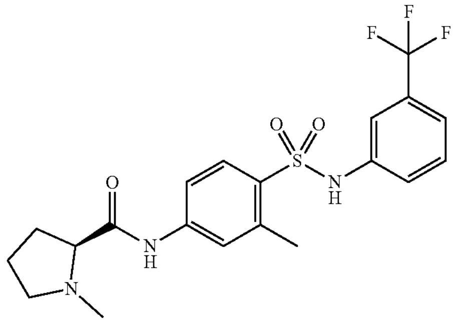 [SMILES: Cc1cc(NC(=O)[C@@H]2CCCN2C)ccc1S(=O)(=O)Nc1cccc(C(F)(F)F)c1] | + |
| 1.423 | 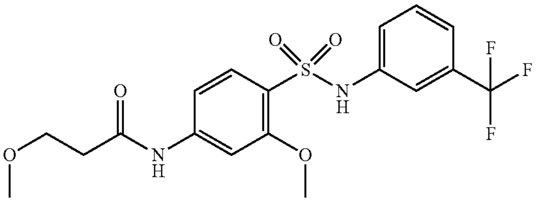 [SMILES: COCCC(=O)Nc1ccc(S(=O)(=O)Nc2cccc(C(F)(F)F)c2)c(OC)c1] | + |
| 1.424 | 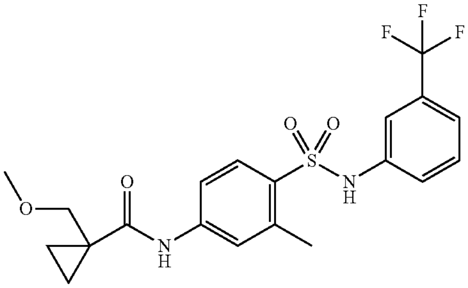 [SMILES: COCC1(C(=O)Nc2ccc(S(=O)(=O)Nc3cccc(C(F)(F)F)c3)c(C)c2)CC1] | + |
| 1.425 | 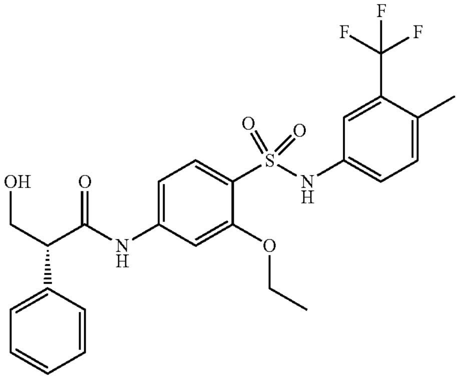 [SMILES: CCOc1cc(NC(=O)[C@@H](CO)c2ccccc2)ccc1S(=O)(=O)Nc1ccc(C)c(C(F)(F)F)c1] | ++++ |

-continued
| Compound ID | Structure | Potency |
|---|---|---|
| 1.426 | 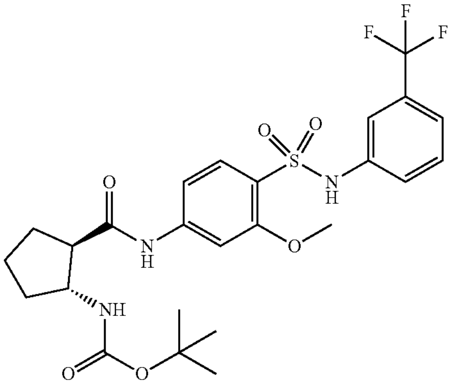 [SMILES: COc1cc(NC(=O)[C@@H]2CCC[C@H]2NC(=O)OC(C)(C)C)ccc1S(=O)(=O)Nc1cccc(C(F)(F)F)c1] | + |
| 1.427 | 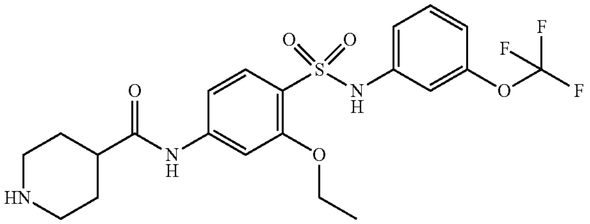 [SMILES: CCOc1cc(NC(=O)C2CCNCC2)ccc1S(=O)(=O)Nc1cccc(OC(F)(F)F)c1] | + |
| 1.428 | 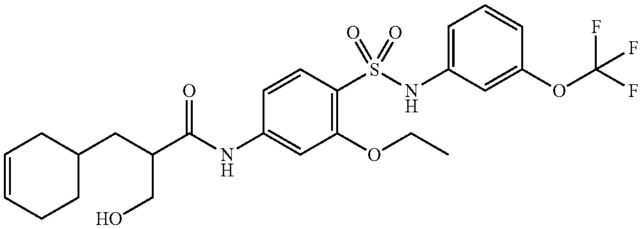 [SMILES: CCOc1cc(NC(=O)C(CO)CC2CC=CCC2)ccc1S(=O)(=O)Nc1cccc(OC(F)(F)F)c1] | ++++ |
| 1.429 | 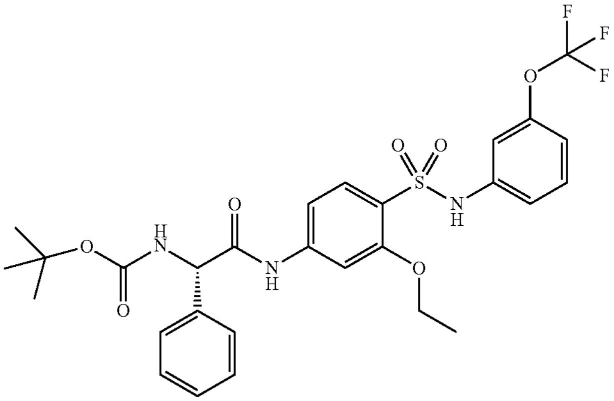 [SMILES: CCOc1cc(NC(=O)[C@@H](NC(=O)OC(C)(C)C)c2ccccc2)ccc1S(=O)(=O)Nc1cccc(OC(F)(F)F)c1] | +++ |
| 1.430 | 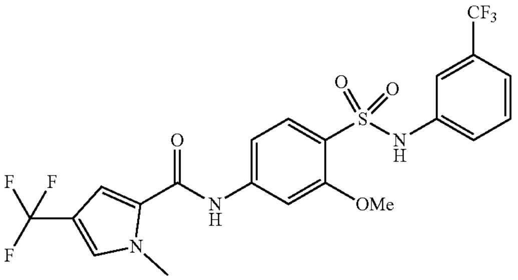 [SMILES: COc1cc(NC(=O)c2cc(C(F)(F)F)cn2C)ccc1S(=O)(=O)Nc1cccc(C(F)(F)F)c1] | ++ |

-continued
| Compound ID | Structure | Potency |
|---|---|---|
| 1.431 | 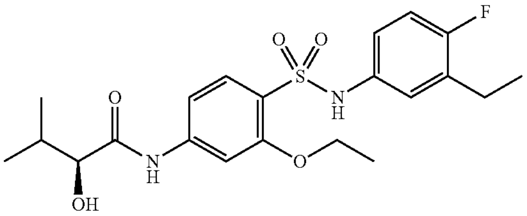 [SMILES: CCOc1cc(NC(=O)[C@@H](O)C(C)C)ccc1S(=O)(=O)Nc1ccc(F)c(CC)c1] | ++++ |
| 1.432 | 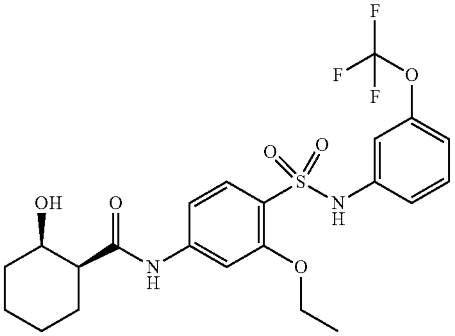 [SMILES: CCOc1cc(NC(=O)[C@H]2CCCC[C@H]2O)ccc1S(=O)(=O)Nc1cccc(OC(F)(F)F)c1] | ++++ |
| 1.433 | 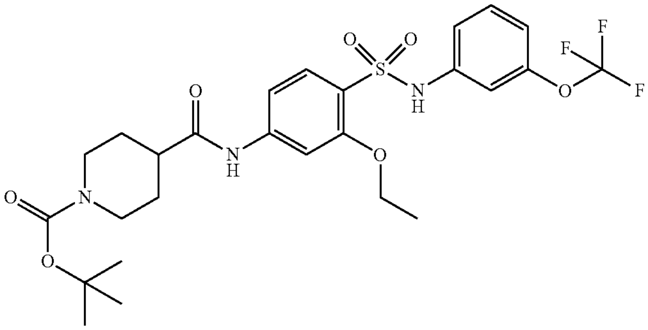 [SMILES: CCOc1cc(NC(=O)C2CCN(C(=O)OC(C)(C)C)CC2)ccc1S(=O)(=O)Nc1cccc(OC(F)(F)F)c1] | + |
| 1.434 | 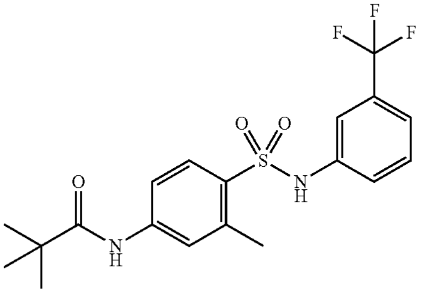 [SMILES: Cc1cc(NC(=O)C(C)(C)C)ccc1S(=O)(=O)Nc1cccc(C(F)(F)F)c1] | + |
| 1.435 | 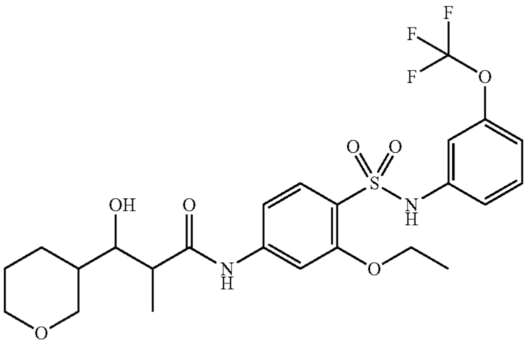 [SMILES: CCOc1cc(NC(=O)C(C)C(O)C2CCCOC2)ccc1S(=O)(=O)Nc1cccc(OC(F)(F)F)c1] | +++ |

-continued
| Compound ID | Structure | Potency |
| --- | --- | --- |
| 1.436 | 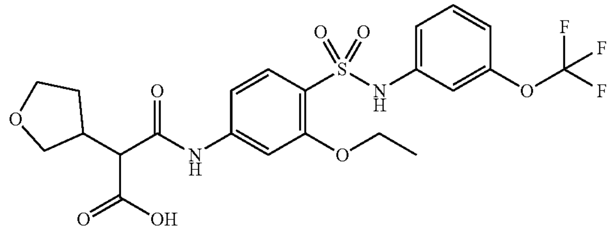 [SMILES: CCOc1cc(NC(=O)C(C(=O)O)C2CCOC2)ccc1S(=O)(=O)Nc1cccc(OC(F)(F)F)c1] | ++++ |
| 1.437 | 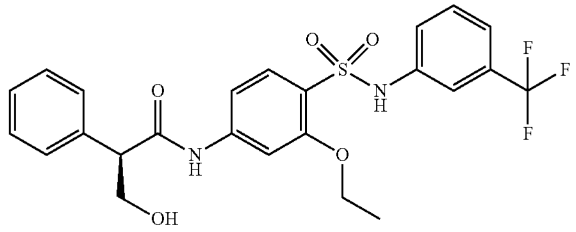 [SMILES: CCOc1cc(NC(=O)[C@@H](CO)c2ccccc2)ccc1S(=O)(=O)Nc1cccc(C(F)(F)F)c1] | ++++ |
| 1.438 | 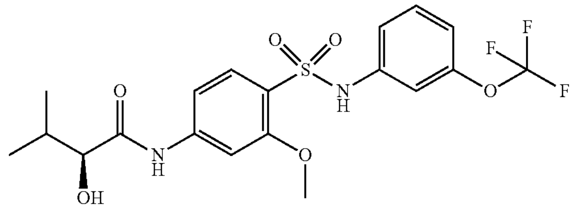 [SMILES: COc1cc(NC(=O)[C@@H](O)C(C)C)ccc1S(=O)(=O)Nc1cccc(OC(F)(F)F)c1] | ++++ |
| 1.439 | 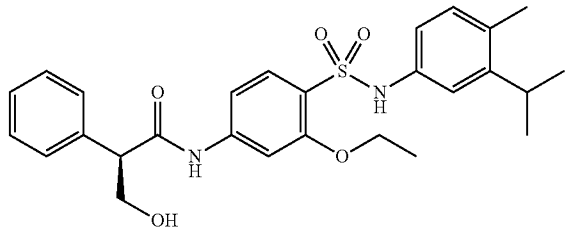 [SMILES: CCOc1cc(NC(=O)[C@@H](CO)c2ccccc2)ccc1S(=O)(=O)Nc1ccc(C)c(C(C)C)c1] | ++++ |
| 1.440 | 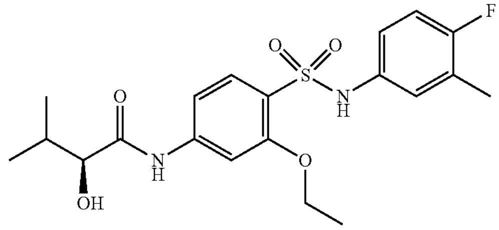 [SMILES: CCOc1cc(NC(=O)[C@@H](O)C(C)C)ccc1S(=O)(=O)Nc1ccc(F)c(C)c1] | +++ |
| 1.441 | 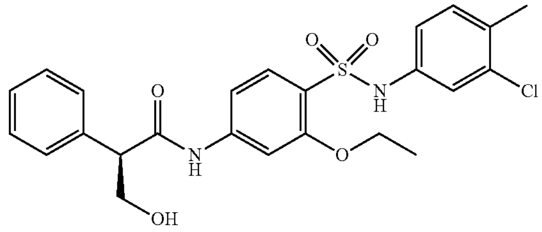 [SMILES: CCOc1cc(NC(=O)[C@@H](CO)c2ccccc2)ccc1S(=O)(=O)Nc1ccc(C)c(Cl)c1] | +++ |

-continued
| Compound ID | Structure | Potency |
|---|---|---|
| 1.442 | 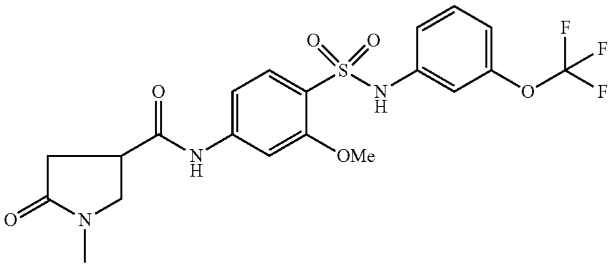 [SMILES: COc1cc(NC(=O)C2CC(=O)N(C)C2)ccc1S(=O)(=O)Nc1cccc(OC(F)(F)F)c1] | + |
| 1.443 | 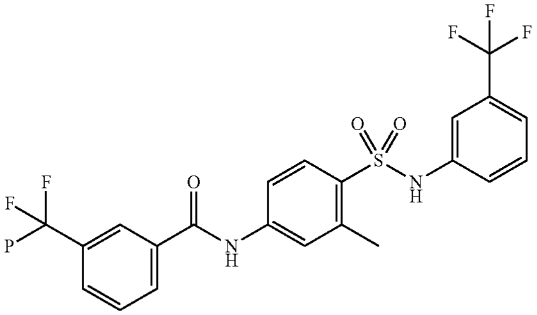 | + |
| 1.444 | 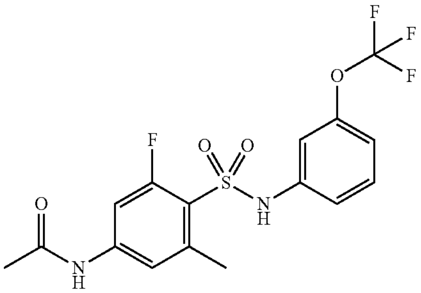 [SMILES: CC(=O)Nc1cc(C)c(S(=O)(=O)Nc2cccc(OC(F)(F)F)c2)c(F)c1] | + |
| 1.445 | 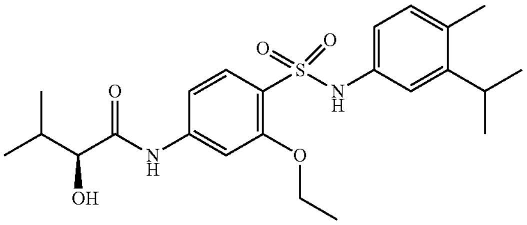 [SMILES: CCOc1cc(NC(=O)[C@@H](O)C(C)C)ccc1S(=O)(=O)Nc1ccc(C)c(C(C)C)c1] | ++++ |
| 1.446 | 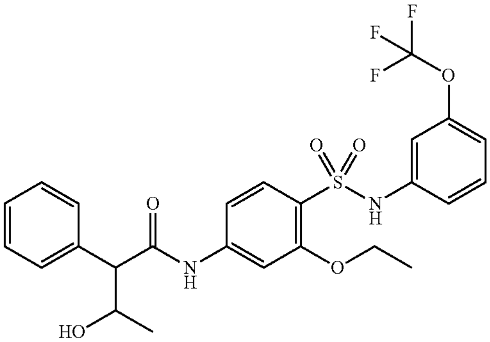 [SMILES: CCOc1cc(NC(=O)C(c2ccccc2)C(C)O)ccc1S(=O)(=O)Nc1cccc(OC(F)(F)F)c1] | ++++ |

-continued
| Compound ID | Structure | Potency |
|---|---|---|
| 1.447 | 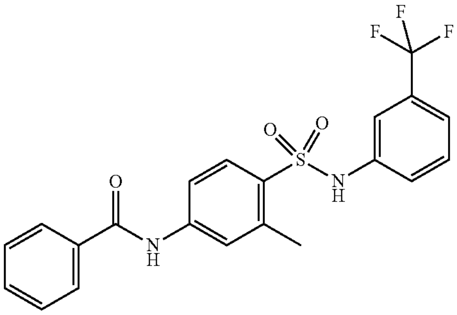 [SMILES: Cc1cc(NC(=O)c2ccccc2)ccc1S(=O)(=O)Nc1cccc(C(F)(F)F)c1] | +++ |
| 1.448 | 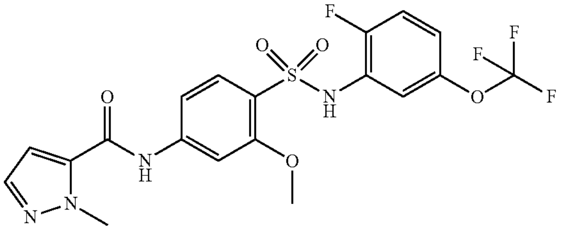 [SMILES: COc1cc(NC(=O)c2ccnn2C)ccc1S(=O)(=O)Nc1cc(OC(F)(F)F)ccc1F] | +++ |
| 1.449 | 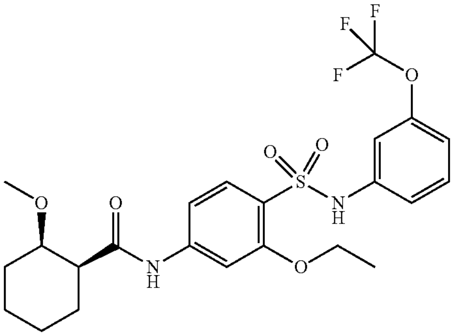 [SMILES: CCOc1cc(NC(=O)[C@H]2CCCC[C@H]2OC)ccc1S(=O)(=O)Nc1cccc(OC(F)(F)F)c1] | + |
| 1.450 | 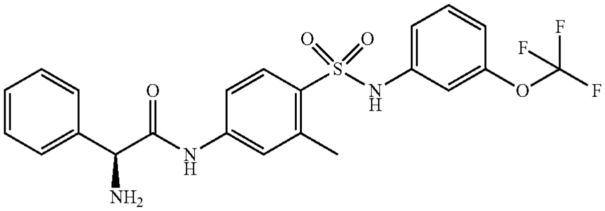 [SMILES: Cc1cc(NC(=O)[C@@H](N)c2ccccc2)ccc1S(=O)(=O)Nc1cccc(OC(F)(F)F)c1] | ++++ |
| 1.451 | 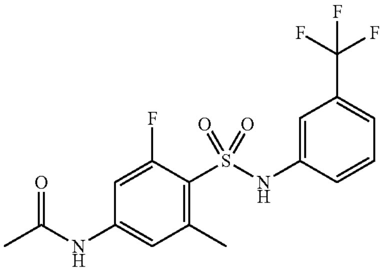 [SMILES: CC(=O)Nc1cc(C)c(S(=O)(=O)Nc2cccc(C(F)(F)F)c2)c(F)c1] | + |

-continued
| Compound ID | Structure | Potency |
|---|---|---|
| 1.452 | 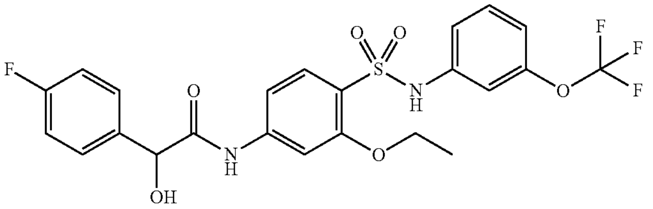 [SMILES: CCOc1cc(NC(=O)C(O)c2ccc(F)cc2)ccc1S(=O)(=O)Nc1cccc(OC(F)(F)F)c1] | ++++ |
| 1.453 | 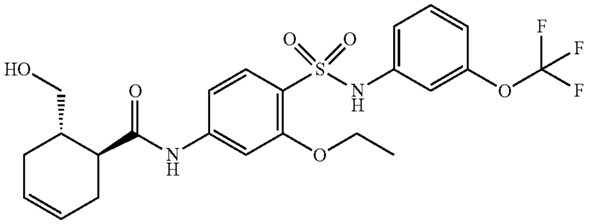 [SMILES: CCOc1cc(NC(=O)[C@H]2CC=CC[C@@H]2CO)ccc1S(=O)(=O)Nc1cccc(OC(F)(F)F)c1] | ++++ |
| 1.454 | 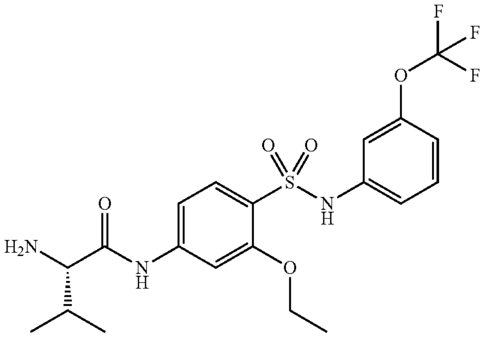 [SMILES: CCOc1cc(NC(=O)[C@@H](N)C(C)C)ccc1S(=O)(=O)Nc1cccc(OC(F)(F)F)c1] | ++++ |
| 1.455 | 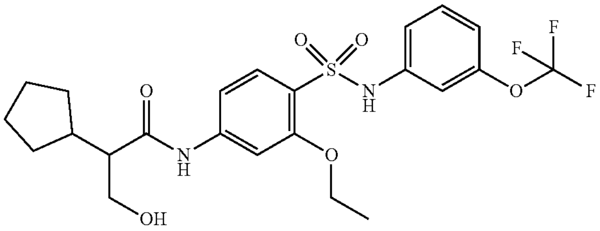 [SMILES: CCOc1cc(NC(=O)C(CO)C2CCCC2)ccc1S(=O)(=O)Nc1cccc(OC(F)(F)F)c1] | ++++ |
| 1.456 | 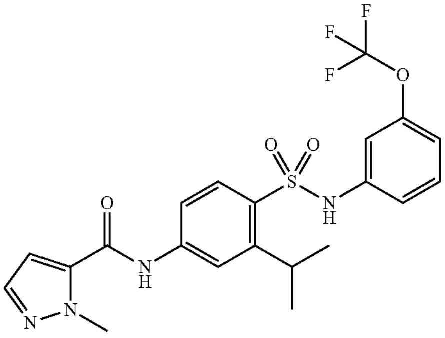 [SMILES: CC(C)c1cc(NC(=O)c2ccnn2C)ccc1S(=O)(=O)Nc1cccc(OC(F)(F)F)c1] | +++ |

-continued
| Compound ID | Structure | Potency |
|---|---|---|
| 1.457 | 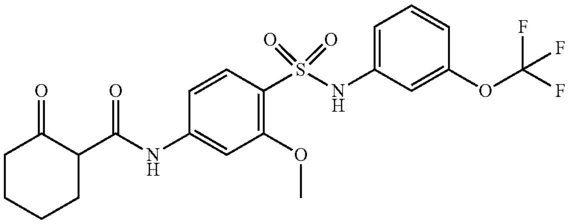 [SMILES: COc1cc(NC(=O)C2CCCCC2=O)ccc1S(=O)(=O)Nc1cccc(OC(F)(F)F)c1] | + |
| 1.458 | 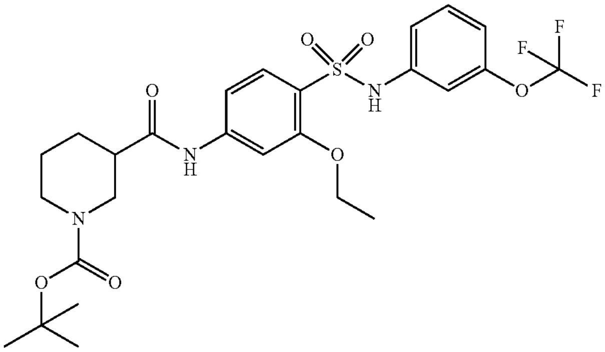 [SMILES: CCOc1cc(NC(=O)C2CCCN(C(=O)OC(C)(C)C)C2)ccc1S(=O)(=O)Nc1cccc(OC(F)(F)F)c1] | + |
| 1.459 | 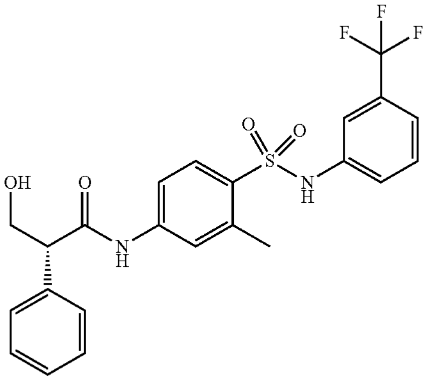 [SMILES: Cc1cc(NC(=O)[C@@H](CO)c2ccccc2)ccc1S(=O)(=O)Nc1cccc(C(F)(F)F)c1] | ++ |
| 1.460 | 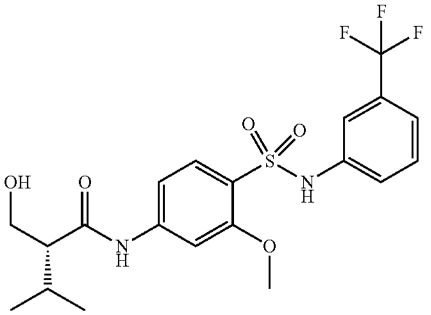 [SMILES: COc1cc(NC(=O)[C@@H](CO)C(C)C)ccc1S(=O)(=O)Nc1cccc(C(F)(F)F)c1] | ++++ |

-continued
| Compound ID | Structure | Potency |
|---|---|---|
| 1.461 | 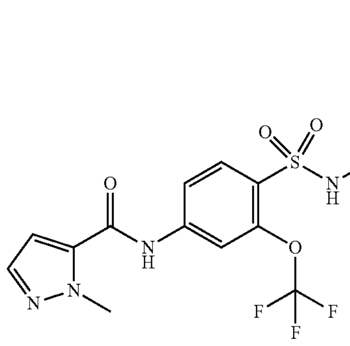 | ++ |
| 1.462 | 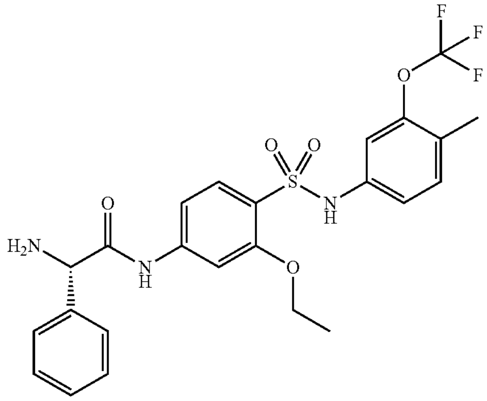 [SMILES: CCOc1cc(NC(=O)[C@@H](N)c2ccccc2)ccc1S(=O)(=O)Nc1ccc(C)c(OC(F)(F)F)c1] | ++++ |
| 1.463 | 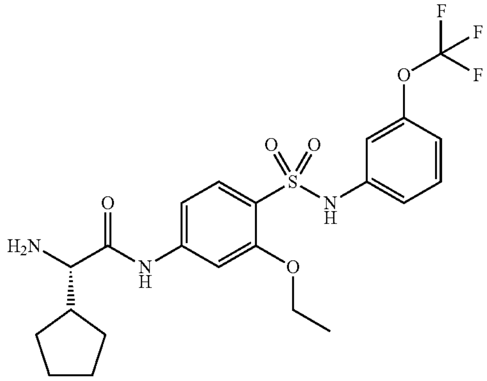 [SMILES: CCOc1cc(NC(=O)[C@@H](N)C2CCCC2)ccc1S(=O)(=O)Nc1cccc(OC(F)(F)F)c1] | ++++ |
| 1.464 | 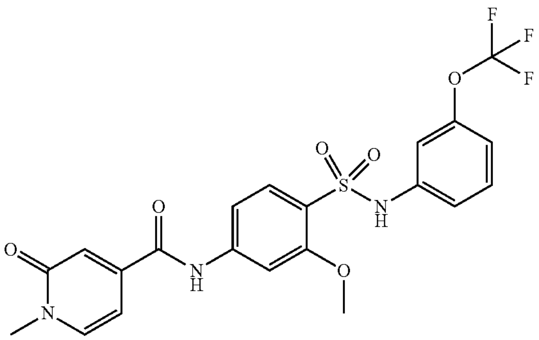 [SMILES: COc1cc(NC(=O)c2ccn(C)c(=O)c2)ccc1S(=O)(=O)Nc1cccc(OC(F)(F)F)c1] | +++ |

-continued
| Compound ID | Structure | Potency |
|---|---|---|
| 1.465 | 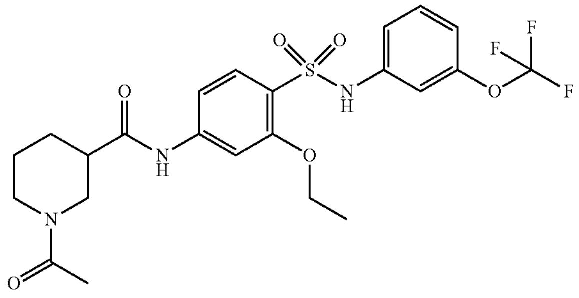 [SMILES: CCOc1cc(NC(=O)C2CCCN(C(C)=O)C2)ccc1S(=O)(=O)Nc1cccc(OC(F)(F)F)c1] | + |
| 1.466 | 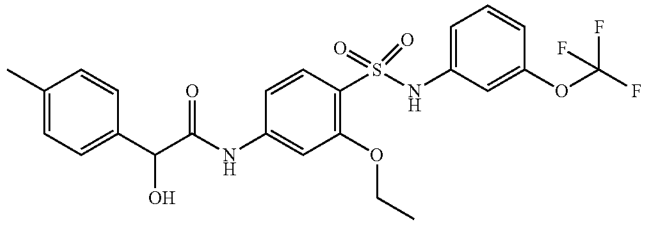 [SMILES: CCOc1cc(NC(=O)C(O)c2ccc(C)cc2)ccc1S(=O)(=O)Nc1cccc(OC(F)(F)F)c1] | +++ |
| 1.467 | 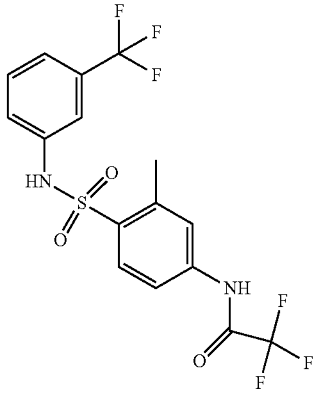 [SMILES: Cc1cc(NC(=O)C(F)(F)F)ccc1S(=O)(=O)Nc1cccc(C(F)(F)F)c1] | + |
| 1.468 | 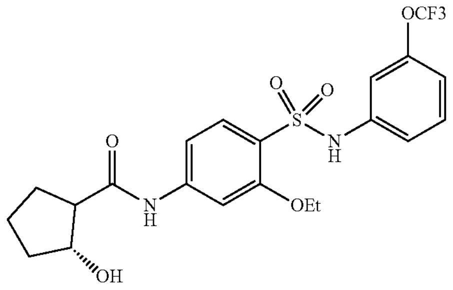 [SMILES: CCOc1cc(NC(=O)C2CCC[C@H]2O)ccc1S(=O)(=O)Nc1cccc(OC(F)(F)F)c1] | +++ |
| 1.469 | 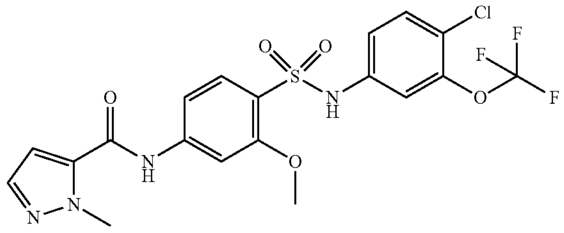 [SMILES: COc1cc(NC(=O)c2ccnn2C)ccc1S(=O)(=O)Nc1ccc(Cl)c(OC(F)(F)F)c1] | ++++ |

-continued
| Compound ID | Structure | Potency |
|---|---|---|
| 1.470 | 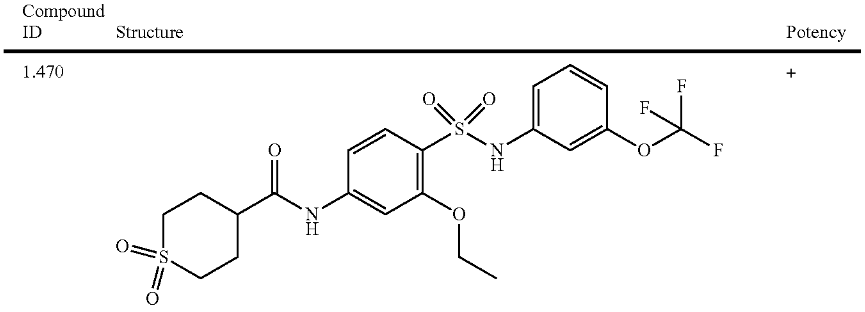 | + |
| 1.471 | 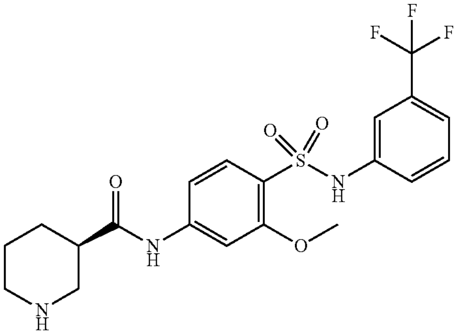 [SMILES: COc1cc(NC(=O)[C@@H]2CCCNC2)ccc1S(=O)(=O)Nc1cccc(C(F)(F)F)c1] | + |
| 1.472 | 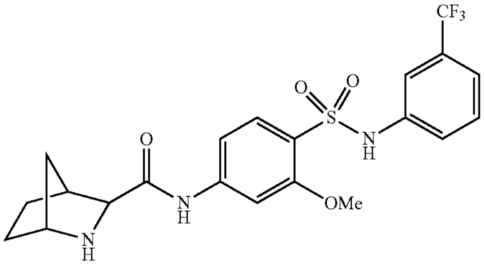 [SMILES: COc1cc(NC(=O)C2NC3CCC2C3)ccc1S(=O)(=O)Nc1cccc(C(F)(F)F)c1] | + |
| 1.473 | 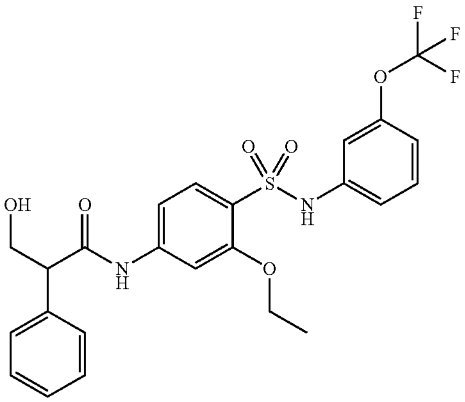 [SMILES: CCOc1cc(NC(=O)C(CO)c2ccccc2)ccc1S(=O)(=O)Nc1cccc(OC(F)(F)F)c1] | ++++ |
| 1.474 | 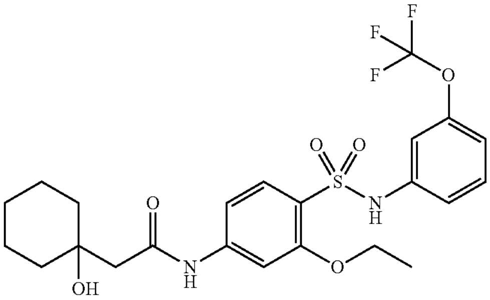 [SMILES: CCOc1cc(NC(=O)CC2(O)CCCCC2)ccc1S(=O)(=O)Nc1cccc(OC(F)(F)F)c1] | +++ |

-continued
| Compound ID | Structure | Potency |
| --- | --- | --- |
| 1.475 | 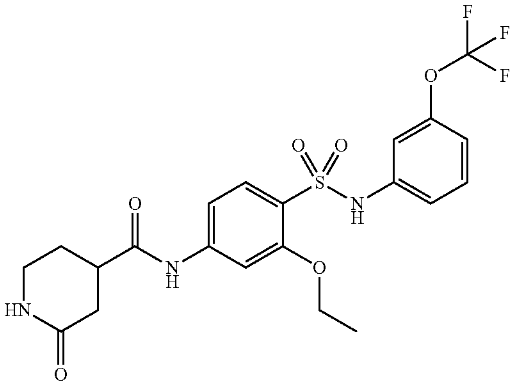 [SMILES: CCOc1cc(NC(=O)C2CCNC(=O)C2)ccc1S(=O)(=O)Nc1cccc(OC(F)(F)F)c1] | + |
| 1.476 | 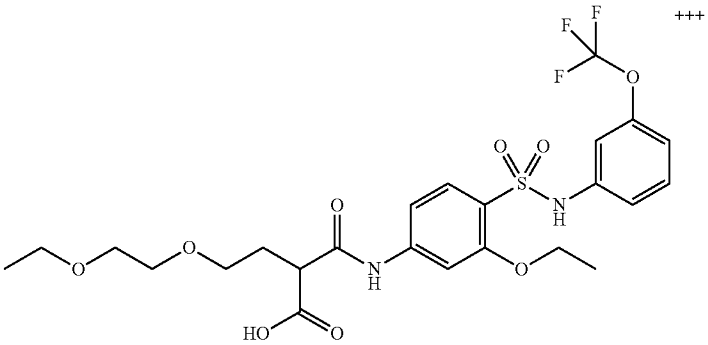 | +++ |
| 1.477 | 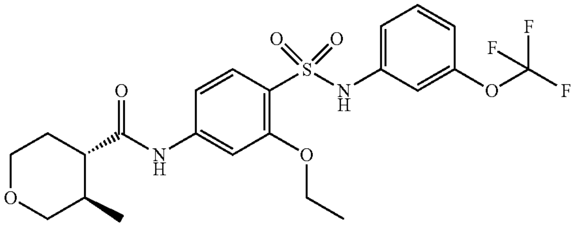 [SMILES: CCOc1cc(NC(=O)[C@H]2CCOC[C@@H]2C)ccc1S(=O)(=O)Nc1cccc(OC(F)(F)F)c1] | ++++ |
| 1.478 | 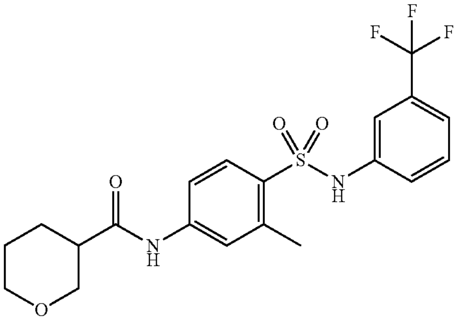 [SMILES: Cc1cc(NC(=O)C2CCCOC2)ccc1S(=O)(=O)Nc1cccc(C(F)(F)F)c1] | ++ |
| 1.479 | 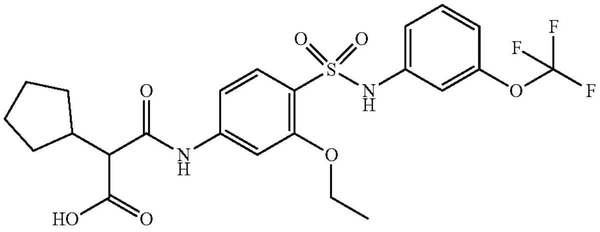 [SMILES: CCOc1cc(NC(=O)C(C(=O)O)C2CCCC2)ccc1S(=O)(=O)Nc1cccc(OC(F)(F)F)c1] | ++++ |

-continued
| Compound ID | Structure | Potency |
|---|---|---|
| 1.480 | 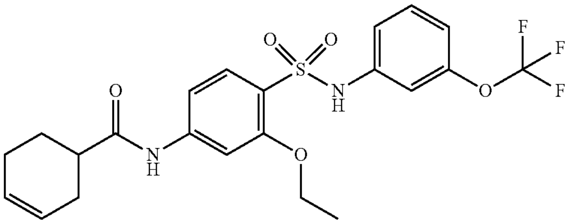 [SMILES: CCOc1cc(NC(=O)C2CC=CCC2)ccc1S(=O)(=O)Nc1cccc(OC(F)(F)F)c1] | +++ |
| 1.481 | 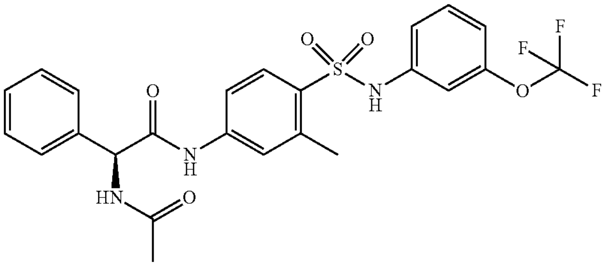 [SMILES: CC(=O)N[C@H](C(=O)Nc1ccc(S(=O)(=O)Nc2cccc(OC(F)(F)F)c2)c(C)c1)c1ccccc1] | ++++ |
| 1.482 | 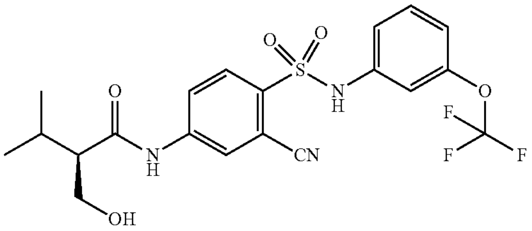 [SMILES: CC(C)[C@H](CO)C(=O)Nc1ccc(S(=O)(=O)Nc2cccc(OC(F)(F)F)c2)c(C#N)c1] | ++++ |
| 1.483 | AND Enantiomer 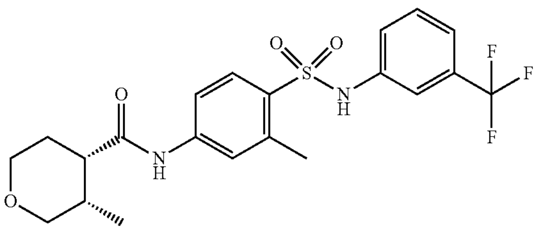 | +++ |
| 1.484 | 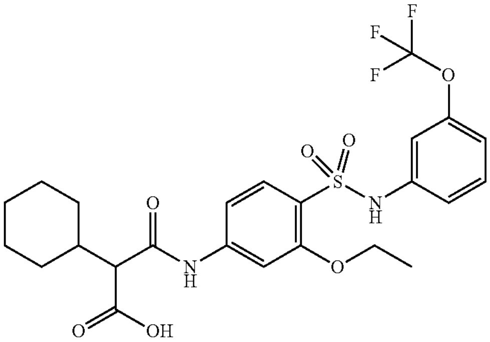 [SMILES: CCOc1cc(NC(=O)C(C(=O)O)C2CCCCC2)ccc1S(=O)(=O)Nc1cccc(OC(F)(F)F)c1] | ++++ |

-continued
| Compound ID | Structure | Potency |
| --- | --- | --- |
| 1.485 | 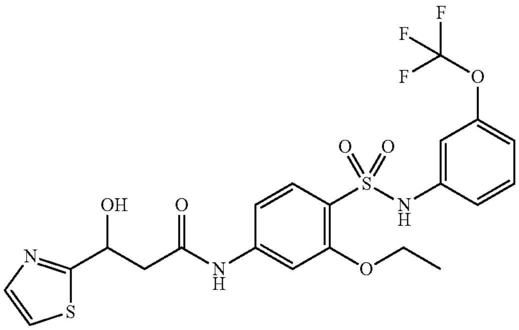 [SMILES: CCOc1cc(NC(=O)CC(O)c2nccs2)ccc1S(=O)(=O)Nc1cccc(OC(F)(F)F)c1] | +++ |
| 1.486 | 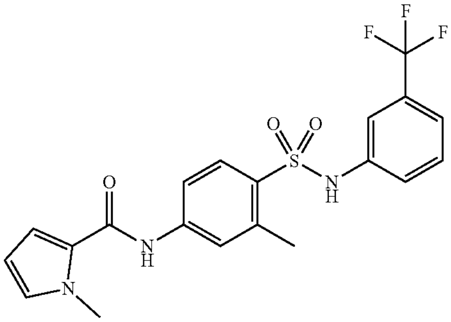 [SMILES: Cc1cc(NC(=O)c2cccn2C)ccc1S(=O)(=O)Nc1cccc(C(F)(F)F)c1] | ++ |
| 1.487 | 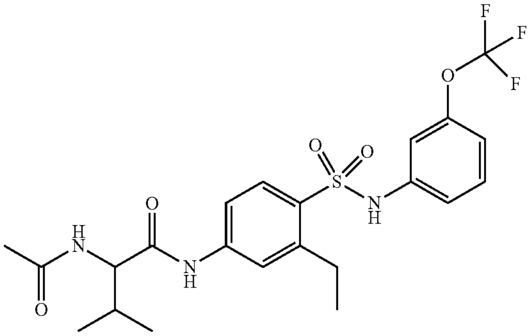 [SMILES: CCc1cc(NC(=O)C(NC(C)=O)C(C)C)ccc1S(=O)(=O)Nc1cccc(OC(F)(F)F)c1] | ++++ |
| 1.488 | 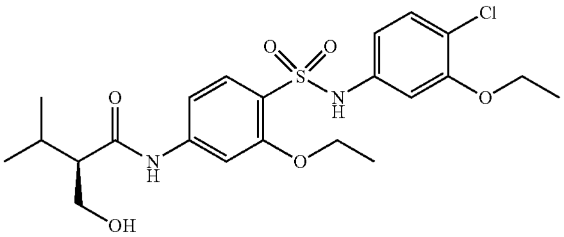 [SMILES: CCOc1cc(NS(=O)(=O)c2ccc(NC(=O)[C@@H](CO)C(C)C)cc2OCC)ccc1Cl] | +++ |
| 1.489 | 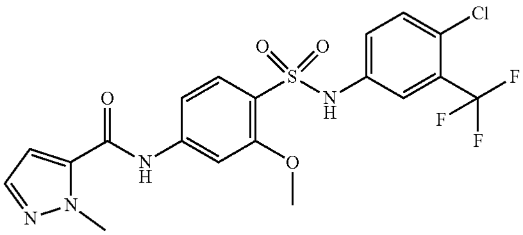 [SMILES: COc1cc(NC(=O)c2ccnn2C)ccc1S(=O)(=O)Nc1ccc(Cl)c(C(F)(F)F)c1] | ++ |

-continued
| Compound ID | Structure | Potency |
|---|---|---|
| 1.490 | 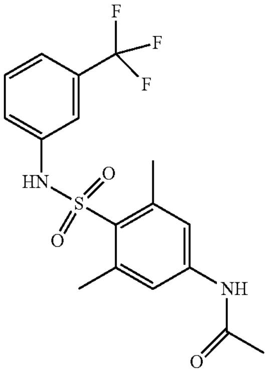 [SMILES: CC(=O)Nc1cc(C)c(S(=O)(=O)Nc2cccc(C(F)(F)F)c2)c(C)c1] | + |
| 1.491 | 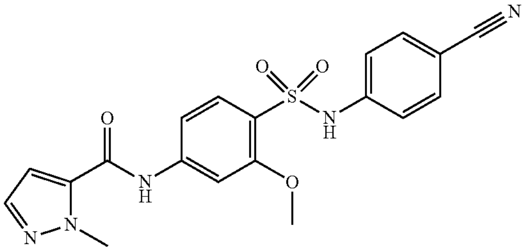 [SMILES: COc1cc(NC(=O)c2ccnn2C)ccc1S(=O)(=O)Nc1ccc(C#N)cc1] | + |
| 1.492 | 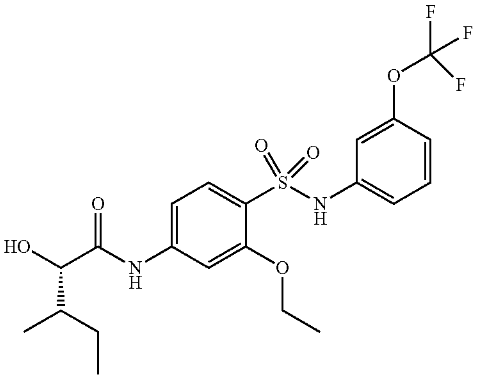 [SMILES: CCOc1cc(NC(=O)[C@@H](O)C(C)CC)ccc1S(=O)(=O)Nc1cccc(OC(F)(F)F)c1] | ++++ |
| 1.493 | 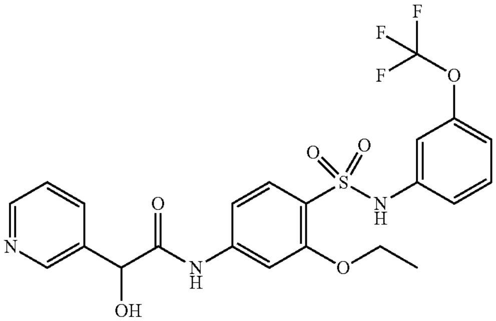 [SMILES: CCOc1cc(NC(=O)C(O)c2cccnc2)ccc1S(=O)(=O)Nc1cccc(OC(F)(F)F)c1] | ++ |
| 1.494 | 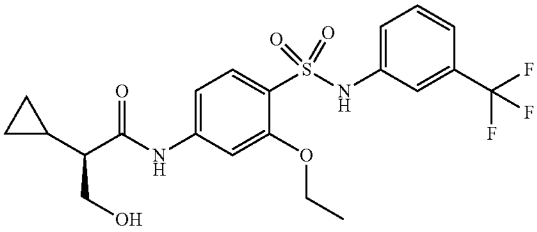 [SMILES: CCOc1cc(NC(=O)[C@@H](CO)C2CC2)ccc1S(=O)(=O)Nc1cccc(C(F)(F)F)c1] | ++++ |

-continued
| Compound ID | Structure | Potency |
|---|---|---|
| 1.495 | 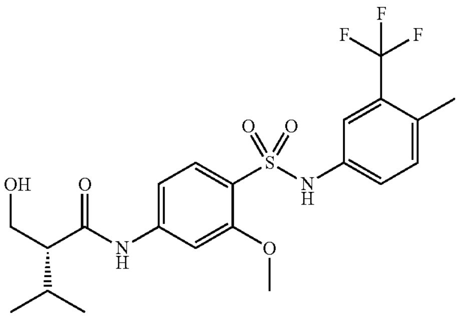 [SMILES: COc1cc(NC(=O)[C@@H](CO)C(C)C)ccc1S(=O)(=O)Nc1ccc(C)c(C(F)(F)F)c1] | +++ |
| 1.496 | 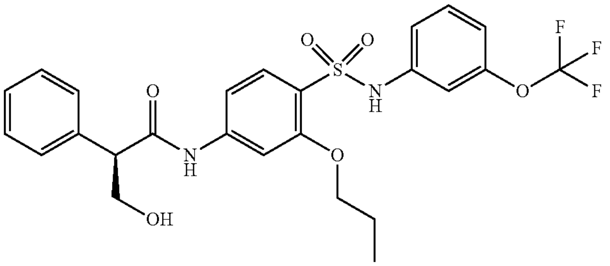 [SMILES: CCCOc1cc(NC(=O)[C@@H](CO)c2ccccc2)ccc1S(=O)(=O)Nc1cccc(OC(F)(F)F)c1] | ++++ |
| 1.497 | 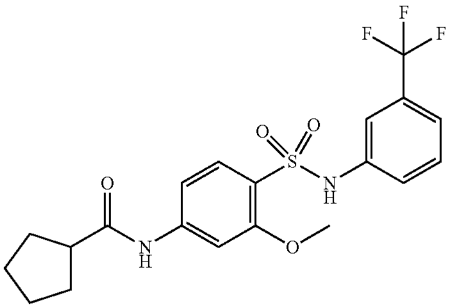 [SMILES: COc1cc(NC(=O)C2CCCC2)ccc1S(=O)(=O)Nc1cccc(C(F)(F)F)c1] | ++ |
| 1.498 | 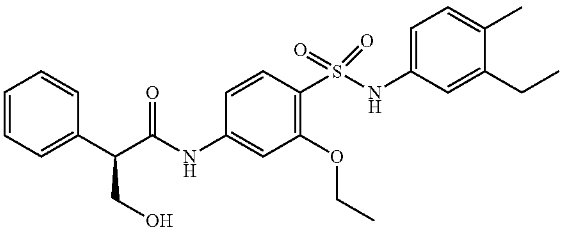 [SMILES: CCOc1cc(NC(=O)[C@@H](CO)c2ccccc2)ccc1S(=O)(=O)Nc1ccc(C)c(CC)c1] | ++++ |
| 1.499 | AND Enantiomer 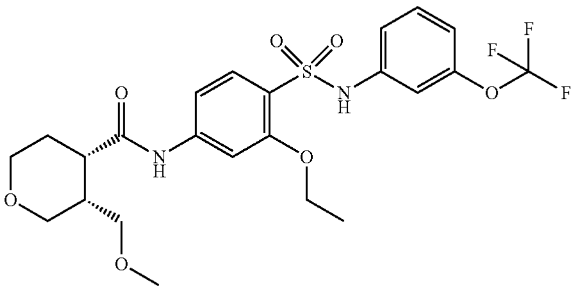 | ++++ |

-continued
| Compound ID | Structure | Potency |
|---|---|---|
| 1.500 | 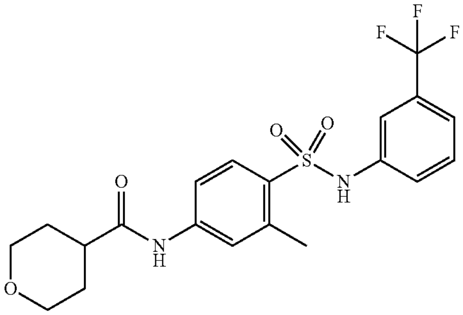 [SMILES: Cc1cc(NC(=O)C2CCOCC2)ccc1S(=O)(=O)Nc1cccc(C(F)(F)F)c1] | +++ |
| 1.501 | 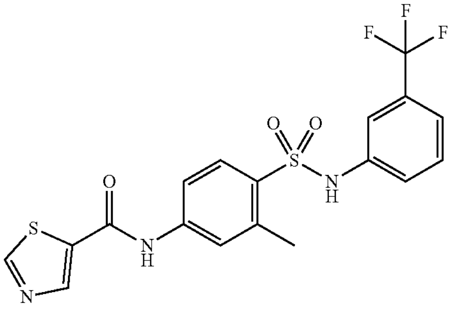 [SMILES: Cc1cc(NC(=O)c2cncs2)ccc1S(=O)(=O)Nc1cccc(C(F)(F)F)c1] | +++ |
| 1.502 | 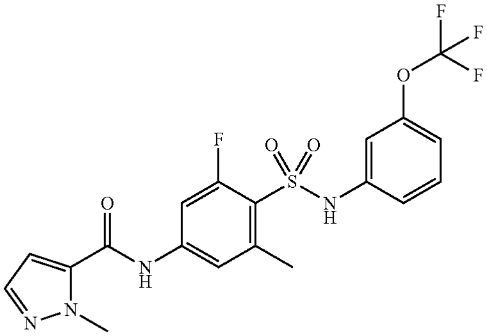 [SMILES: Cc1cc(NC(=O)c2ccnn2C)cc(F)c1S(=O)(=O)Nc1cccc(OC(F)(F)F)c1] | +++ |
| 1.503 | 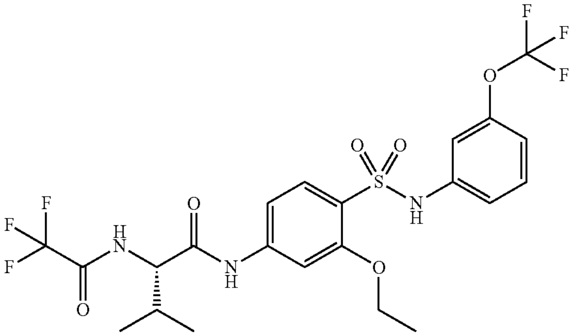 [SMILES: CCOc1cc(NC(=O)[C@@H](NC(=O)C(F)(F)F)C(C)C)ccc1S(=O)(=O)Nc1cccc(OC(F)(F)F)c1] | ++++ |

-continued
| Compound ID | Structure | Potency |
|---|---|---|
| 1.504 | 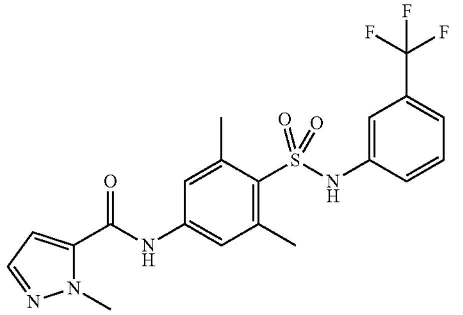 [SMILES: Cc1cc(NC(=O)c2ccnn2C)cc(C)c1S(=O)(=O)Nc1cccc(C(F)(F)F)c1] | +++ |
| 1.505 | 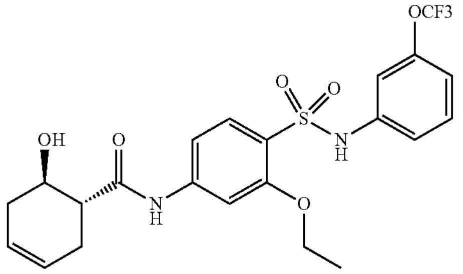 [SMILES: CCOc1cc(NC(=O)[C@@H]2CC=CC[C@H]2O)ccc1S(=O)(=O)Nc1cccc(OC(F)(F)F)c1] | ++++ |
| 1.506 | 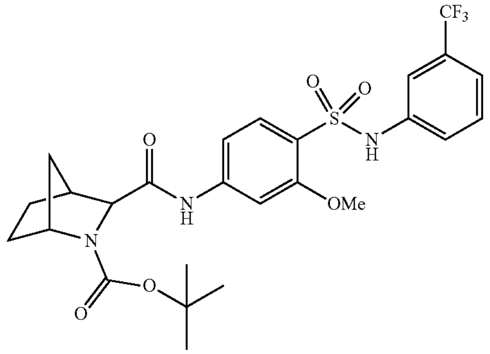 [SMILES: COc1cc(NC(=O)C2C3CCC(C3)N2C(=O)OC(C)(C)C)ccc1S(=O)(=O)Nc1cccc(C(F)(F)F)c1] | ++ |
| 1.507 | 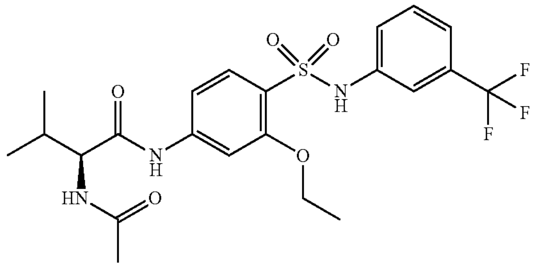 [SMILES: CCOc1cc(NC(=O)[C@@H](NC(C)=O)C(C)C)ccc1S(=O)(=O)Nc1cccc(C(F)(F)F)c1] | ++++ |

-continued
| Compound ID | Structure | Potency |
|---|---|---|
| 1.508 | 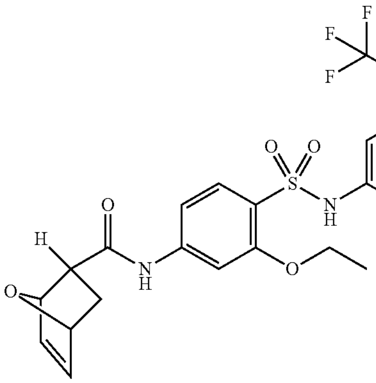 | ++++ |
| 1.509 | 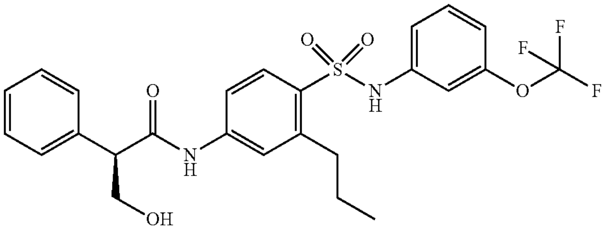 [SMILES: CCCc1cc(NC(=O)[C@@H](CO)c2ccccc2)ccc1S(=O)(=O)Nc1cccc(OC(F)(F)F)c1] | ++++ |
| 1.510 | 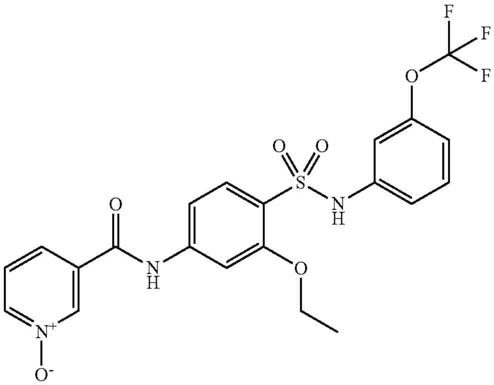 [SMILES: CCOc1cc(NC(=O)c2ccc[n+]([O-])c2)ccc1S(=O)(=O)Nc1cccc(OC(F)(F)F)c1] | ++++ |
| 1.511 | 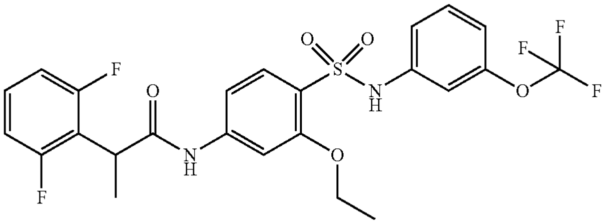 [SMILES: CCOc1cc(NC(=O)C(C)c2c(F)cccc2F)ccc1S(=O)(=O)Nc1cccc(OC(F)(F)F)c1] | ++++ |
| 1.512 | 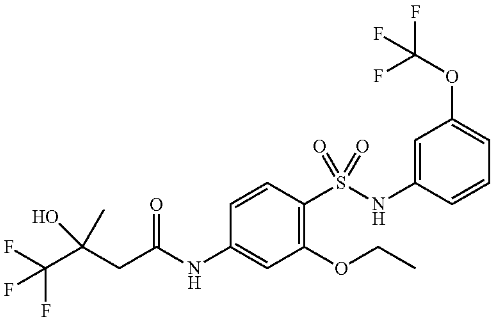 [SMILES: CCOc1cc(NC(=O)CC(C)(O)C(F)(F)F)ccc1S(=O)(=O)Nc1cccc(OC(F)(F)F)c1] | +++ |

-continued
| Compound ID | Structure | Potency |
| --- | --- | --- |
| 1.513 | 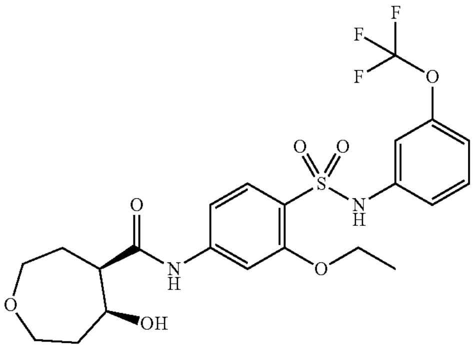 [SMILES: CCOc1cc(NC(=O)[C@@H]2CCOCC[C@@H]2O)ccc1S(=O)(=O)Nc1cccc(OC(F)(F)F)c1] | +++ |
| 1.514 | AND Enantiomer 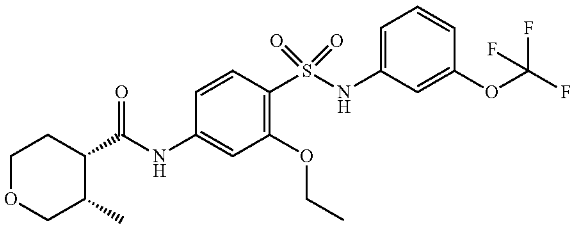 | ++++ |
| 1.515 | 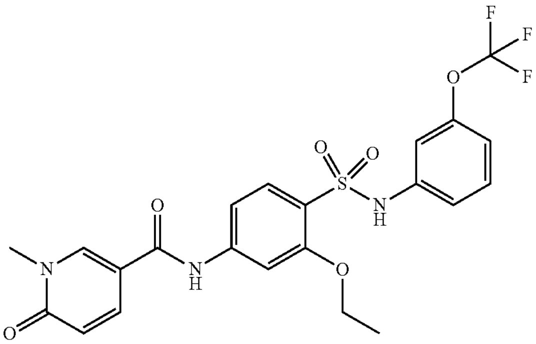 [SMILES: CCOc1cc(NC(=O)c2ccc(=O)n(C)c2)ccc1S(=O)(=O)Nc1cccc(OC(F)(F)F)c1] | ++ |
| 1.516 | 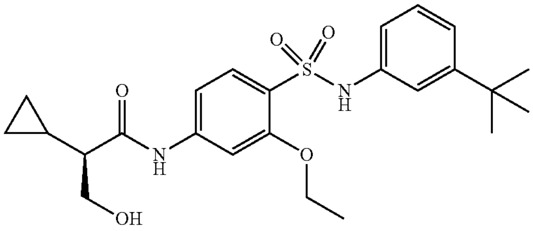 [SMILES: CCOc1cc(NC(=O)[C@@H](CO)C2CC2)ccc1S(=O)(=O)Nc1cccc(C(C)(C)C)c1] | +++ |
| 1.517 | 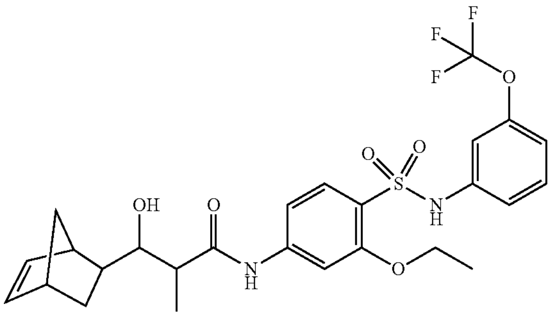 [SMILES: CCOc1cc(NC(=O)C(C)C(O)C2CC3C=CC2C3)ccc1S(=O)(=O)Nc1cccc(OC(F)(F)F)c1] | +++ |

-continued
| Compound ID | Structure | Potency |
|---|---|---|
| 1.518 | 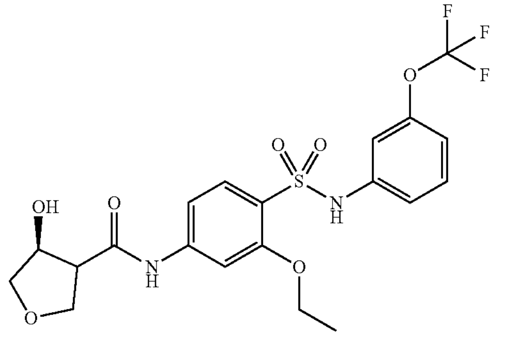 [SMILES: CCOc1cc(NC(=O)C2COC[C@H]2O)ccc1S(=O)(=O)Nc1cccc(OC(F)(F)F)c1] | +++ |
| 1.519 | 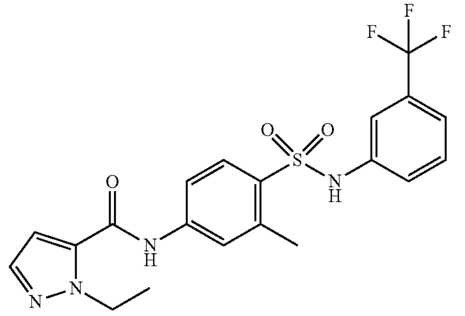 [SMILES: CCn1nccc1C(=O)Nc1ccc(S(=O)(=O)Nc2cccc(C(F)(F)F)c2)c(C)c1] | +++ |
| 1.520 | 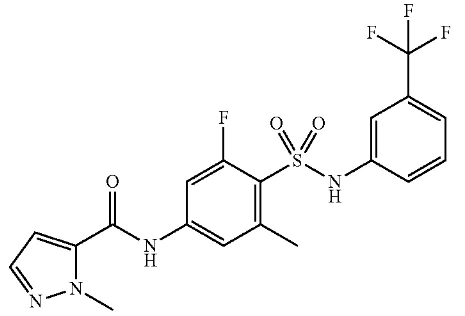 [SMILES: Cc1cc(NC(=O)c2ccnn2C)cc(F)c1S(=O)(=O)Nc1cccc(C(F)(F)F)c1] | ++ |
| 1.521 | 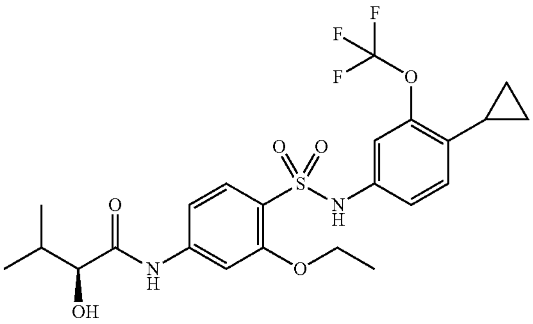 [SMILES: CCOc1cc(NC(=O)[C@@H](O)C(C)C)ccc1S(=O)(=O)Nc1ccc(C2CC2)c(OC(F)(F)F)c1] | ++++ |

-continued
| Compound ID | Structure | Potency |
| --- | --- | --- |
| 1.522 | 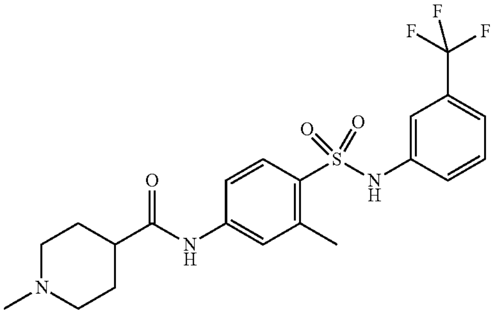 [SMILES: Cc1cc(NC(=O)C2CCN(C)CC2)ccc1S(=O)(=O)Nc1cccc(C(F)(F)F)c1] | + |
| 1.523 | 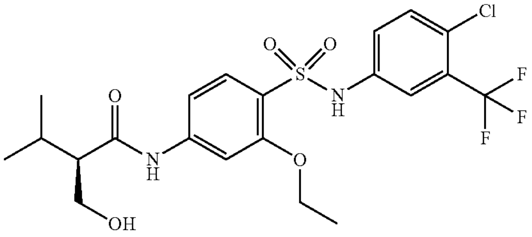 [SMILES: CCOc1cc(NC(=O)[C@@H](CO)C(C)C)ccc1S(=O)(=O)Nc1ccc(Cl)c(C(F)(F)F)c1] | ++++ |
| 1.524 | 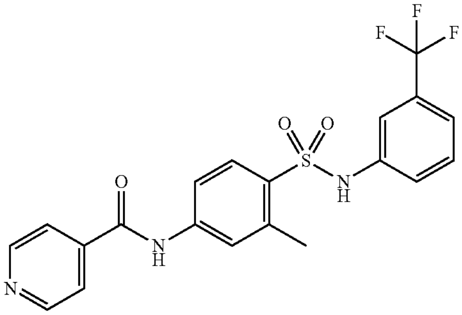 [SMILES: Cc1cc(NC(=O)c2ccncc2)ccc1S(=O)(=O)Nc1cccc(C(F)(F)F)c1] | +++ |
| 1.525 | 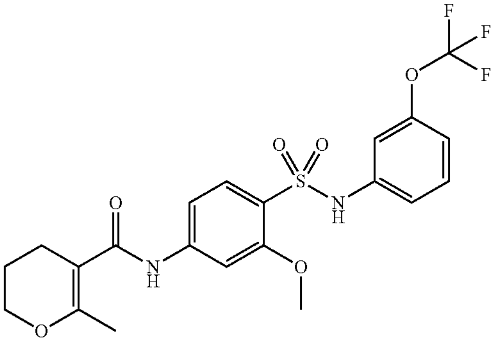 [SMILES: COc1cc(NC(=O)C2=C(C)OCCC2)ccc1S(=O)(=O)Nc1cccc(OC(F)(F)F)c1] | +++ |
| 1.526 | 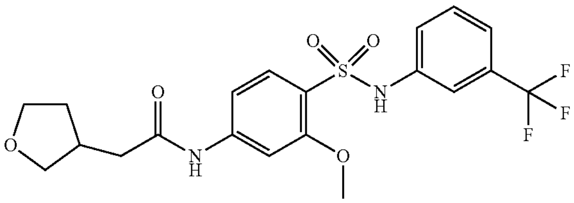 [SMILES: COc1cc(NC(=O)CC2CCOC2)ccc1S(=O)(=O)Nc1cccc(C(F)(F)F)c1] | + |

-continued
| Compound ID | Structure | Potency |
|---|---|---|
| 1.527 | 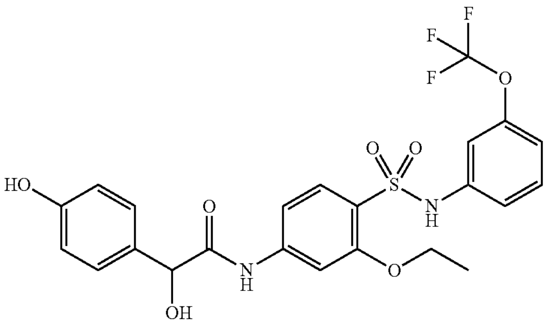 [SMILES: CCOc1cc(NC(=O)C(O)c2ccc(O)cc2)ccc1S(=O)(=O)Nc1cccc(OC(F)(F)F)c1] | +++ |
| 1.528 | 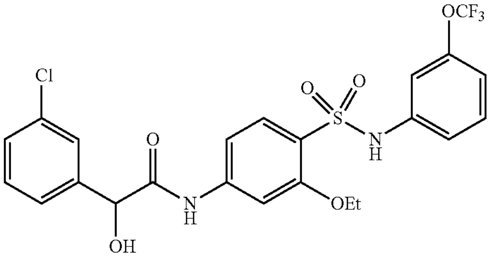 [SMILES: CCOc1cc(NC(=O)C(O)c2cccc(Cl)c2)ccc1S(=O)(=O)Nc1cccc(OC(F)(F)F)c1] | ++++ |
| 1.529 | 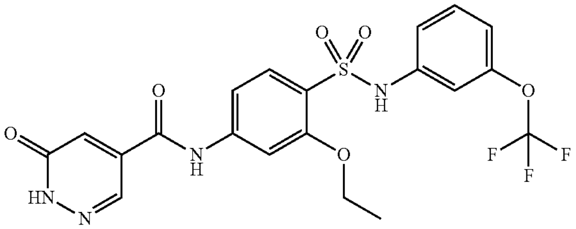 [SMILES: CCOc1cc(NC(=O)c2cn[nH]c(=O)c2)ccc1S(=O)(=O)Nc1cccc(OC(F)(F)F)c1] | ++++ |
| 1.530 | 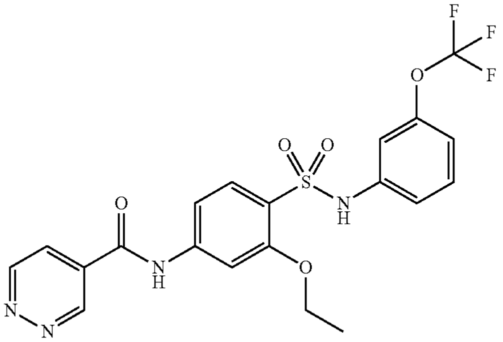 [SMILES: CCOc1cc(NC(=O)c2ccnnc2)ccc1S(=O)(=O)Nc1cccc(OC(F)(F)F)c1] | ++++ |
| 1.531 | AND Enantiomer 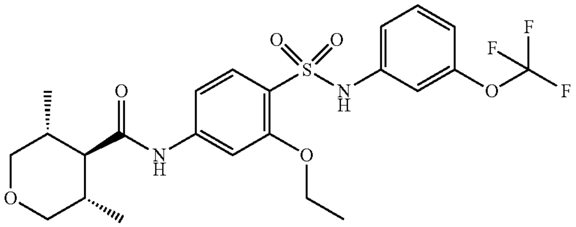 | |

-continued
| Compound ID | Structure | Potency |
|---|---|---|
| 1.532 | 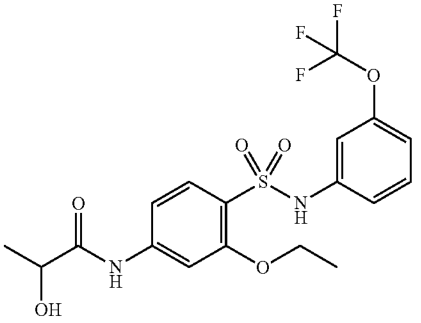 [SMILES: CCOc1cc(NC(=O)C(C)O)ccc1S(=O)(=O)Nc1cccc(OC(F)(F)F)c1] | +++ |
| 1.533 | 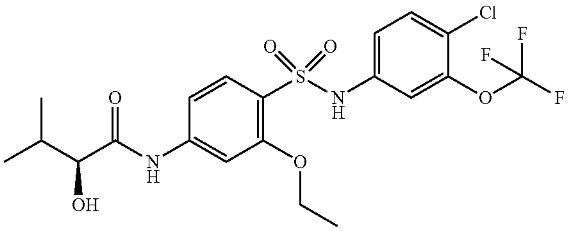 | ++++ |
| 1.534 | 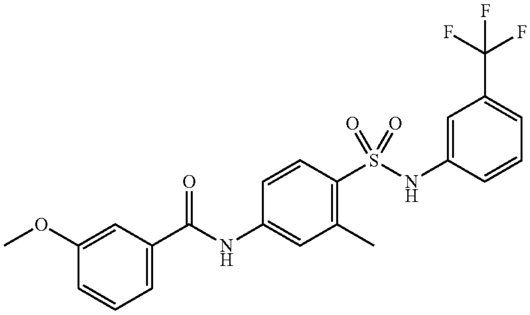 [SMILES: COc1cccc(C(=O)Nc2ccc(S(=O)(=O)Nc3cccc(C(F)(F)F)c3)c(C)c2)c1] | + |
| 1.535 | 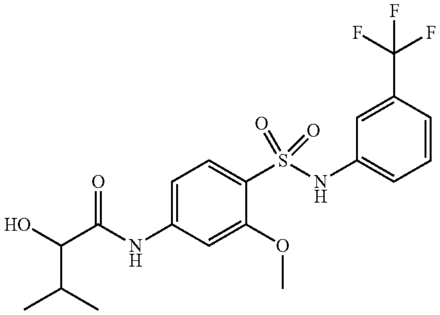 [SMILES: COc1cc(NC(=O)C(O)C(C)C)ccc1S(=O)(=O)Nc1cccc(C(F)(F)F)c1] | ++++ |

-continued
| Compound ID | Structure | Potency |
|---|---|---|
| 1.536 | 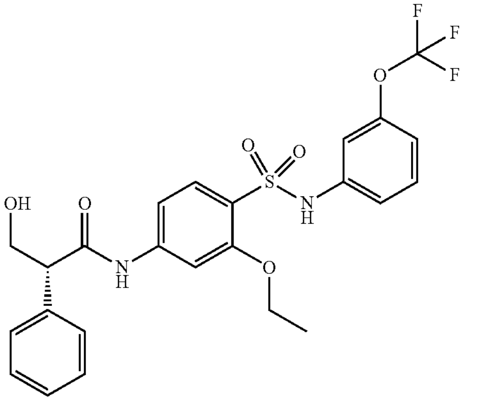 [SMILES: CCOc1cc(NC(=O)[C@@H](CO)c2ccccc2)ccc1S(=O)(=O)Nc1cccc(OC(F)(F)F)c1] | ++++ |
| 1.537 | 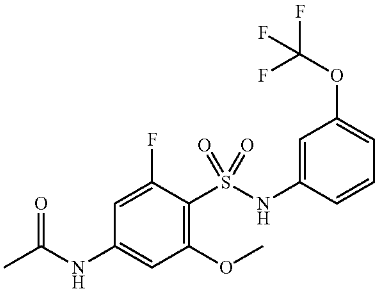 [SMILES: COc1cc(NC(C)=O)cc(F)c1S(=O)(=O)Nc1cccc(OC(F)(F)F)c1] | + |
| 1.538 | 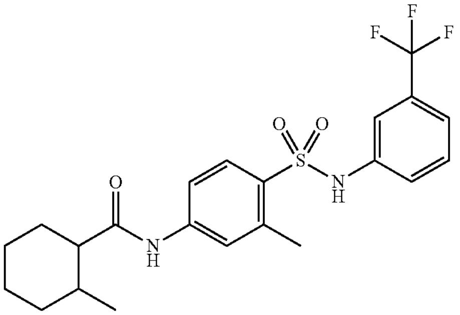 [SMILES: Cc1cc(NC(=O)C2CCCCC2C)ccc1S(=O)(=O)Nc1cccc(C(F)(F)F)c1] | ++ |
| 1.539 | 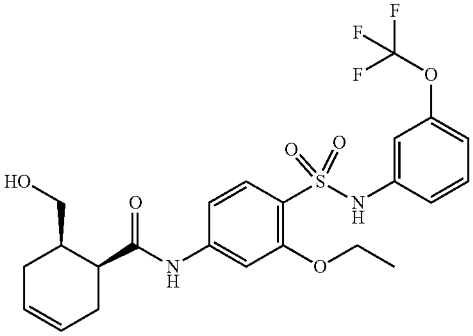 [SMILES: CCOc1cc(NC(=O)[C@H]2CC=CC[C@H]2CO)ccc1S(=O)(=O)Nc1cccc(OC(F)(F)F)c1] | +++ |

-continued
| Compound ID | Structure | Potency |
|---|---|---|
| 1.540 | 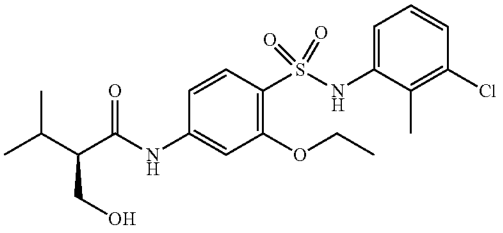 [SMILES: CCOc1cc(NC(=O)[C@@H](CO)C(C)C)ccc1S(=O)(=O)Nc1cccc(Cl)c1C] | +++ |
| 1.541 | 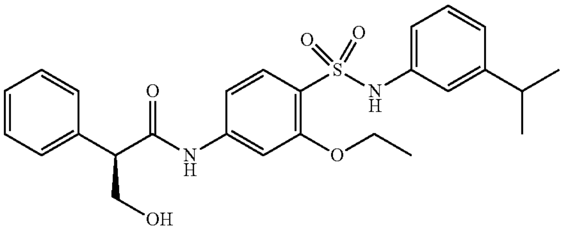 [SMILES: CCOc1cc(NC(=O)[C@@H](CO)c2ccccc2)ccc1S(=O)(=O)Nc1cccc(C(C)C)c1] | ++++ |
| 1.542 | 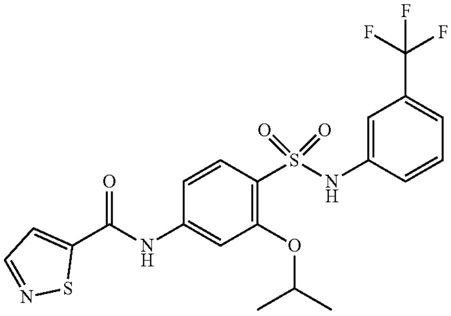 [SMILES: CC(C)Oc1cc(NC(=O)c2ccns2)ccc1S(=O)(=O)Nc1cccc(C(F)(F)F)c1] | + |
| 1.543 | 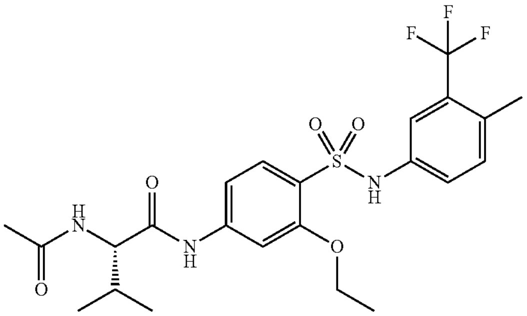 [SMILES: CCOc1cc(NC(=O)[C@@H](NC(C)=O)C(C)C)ccc1S(=O)(=O)Nc1ccc(C)c(C(F)(F)F)c1] | ++++ |
| 1.544 | 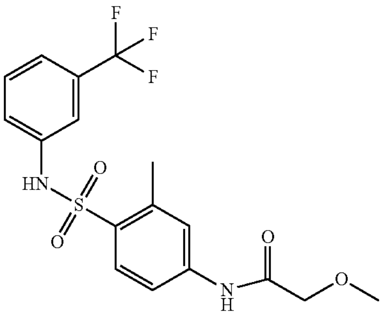 [SMILES: COCC(=O)Nc1ccc(S(=O)(=O)Nc2cccc(C(F)(F)F)c2)c(C)c1] | + |

-continued
| Compound ID | Structure | Potency |
|---|---|---|
| 1.545 | 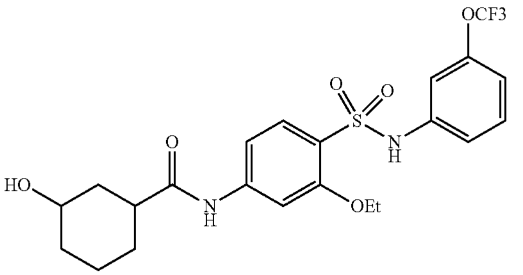 [SMILES: CCOc1cc(NC(=O)C2CCCC(O)C2)ccc1S(=O)(=O)Nc1cccc(OC(F)(F)F)c1] | |
| 1.546 | 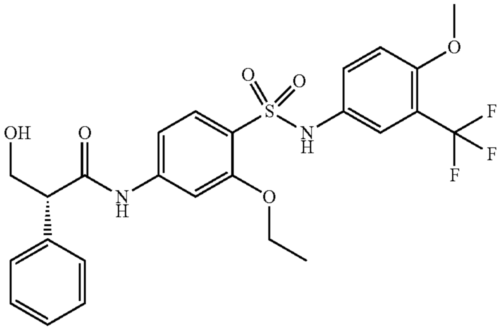 [SMILES: CCOc1cc(NC(=O)[C@@H](CO)c2ccccc2)ccc1S(=O)(=O)Nc1ccc(OC)c(C(F)(F)F)c1] | +++ |
| 1.547 | 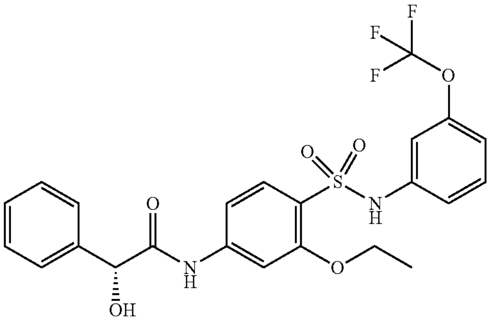 [SMILES: CCOc1cc(NC(=O)[C@H](O)c2ccccc2)ccc1S(=O)(=O)Nc1cccc(OC(F)(F)F)c1] | +++ |
| 1.548 | 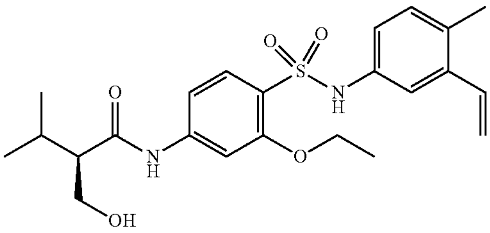 [SMILES: C=Cc1cc(NS(=O)(=O)c2ccc(NC(=O)[C@@H](CO)C(C)C)cc2OCC)ccc1C] | ++++ |
| 1.549 | 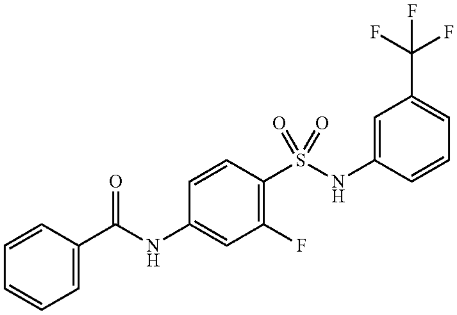 | + |

-continued
| Compound ID | Structure | Potency |
|---|---|---|
| 1.550 | 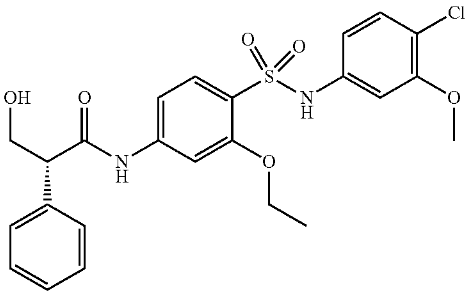 [SMILES: CCOc1cc(NC(=O)[C@@H](CO)c2ccccc2)ccc1S(=O)(=O)Nc1ccc(Cl)c(OC)c1] | +++ |
| 1.551 | 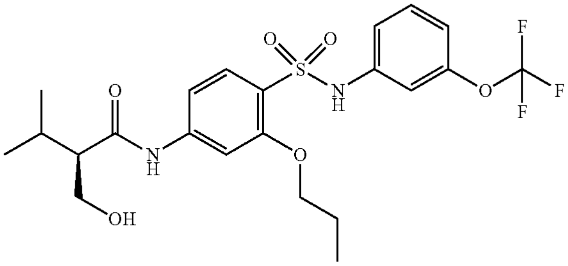 [SMILES: CCCOc1cc(NC(=O)[C@@H](CO)C(C)C)ccc1S(=O)(=O)Nc1cccc(OC(F)(F)F)c1] | ++++ |
| 1.552 | 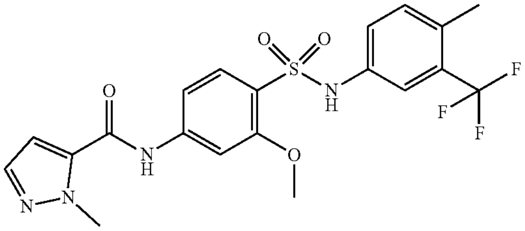 [SMILES: COc1cc(NC(=O)c2ccnn2C)ccc1S(=O)(=O)Nc1ccc(C)c(C(F)(F)F)c1] | ++++ |
| 1.553 | 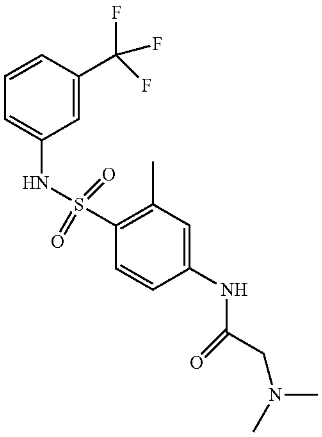 [SMILES: Cc1cc(NC(=O)CN(C)C)ccc1S(=O)(=O)Nc1cccc(C(F)(F)F)c1] | + |

-continued
| Compound ID | Structure | Potency |
| --- | --- | --- |
| 1.554 | 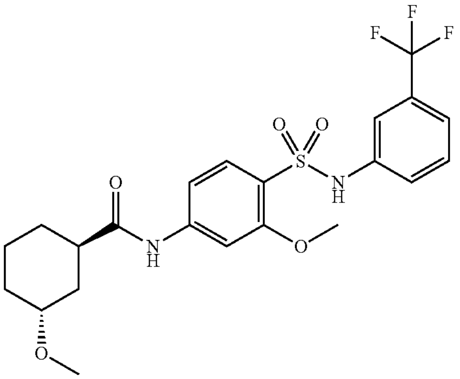 [SMILES: COc1cc(NC(=O)[C@@H]2CCC[C@@H](OC)C2)ccc1S(=O)(=O)Nc1cccc(C(F)(F)F)c1] | + |
| 1.555 | 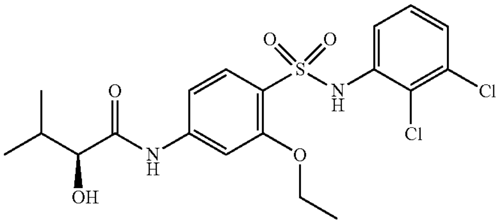 [SMILES: CCOc1cc(NC(=O)[C@@H](O)C(C)C)ccc1S(=O)(=O)Nc1cccc(Cl)c1Cl] | + |
| 1.556 | 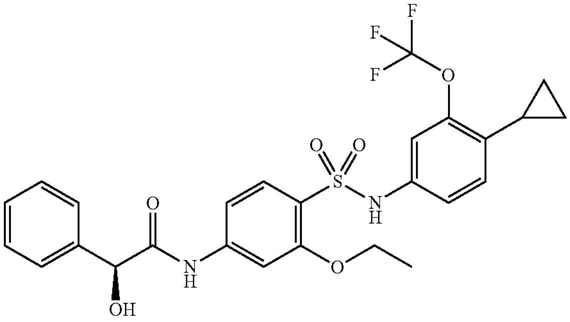 [SMILES: CCOc1cc(NC(=O)[C@@H](O)c2ccccc2)ccc1S(=O)(=O)Nc1ccc(C2CC2)c(OC(F)(F)F)c1] | +++ |
| 1.557 | 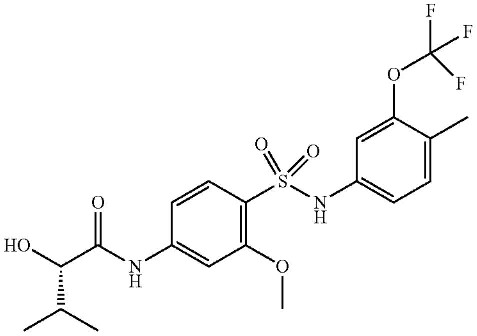 [SMILES: COc1cc(NC(=O)[C@@H](O)C(C)C)ccc1S(=O)(=O)Nc1ccc(C)c(OC(F)(F)F)c1] | ++++ |
| 1.558 | 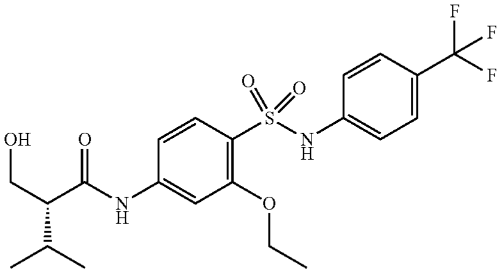 [SMILES: CCOc1cc(NC(=O)[C@@H](CO)C(C)C)ccc1S(=O)(=O)Nc1ccc(C(F)(F)F)cc1] | +++ |

-continued
| Compound ID | Structure | Potency |
|---|---|---|
| 1.559 | 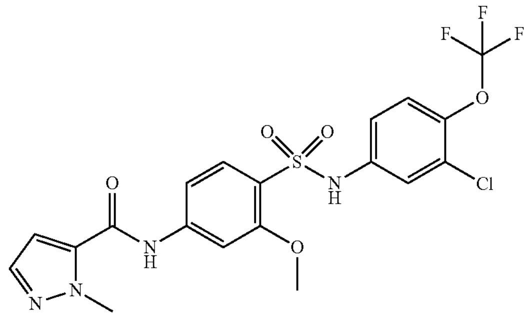 [SMILES: COc1cc(NC(=O)c2ccnn2C)ccc1S(=O)(=O)Nc1ccc(OC(F)(F)F)c(Cl)c1] | ++ |
| 1.560 | 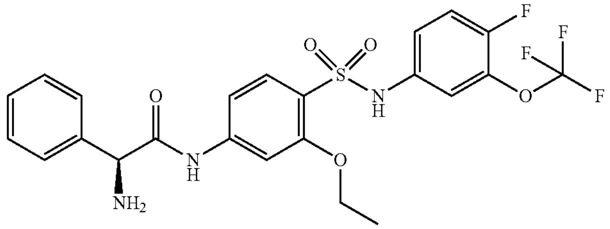 [SMILES: CCOc1cc(NC(=O)[C@@H](N)c2ccccc2)ccc1S(=O)(=O)Nc1ccc(F)c(OC(F)(F)F)c1] | ++++ |
| 1.561 | 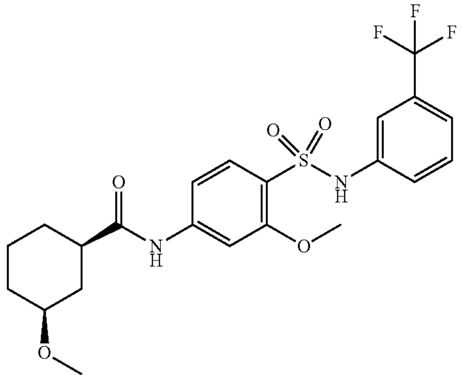 [SMILES: COc1cc(NC(=O)[C@@H]2CCC[C@H](OC)C2)ccc1S(=O)(=O)Nc1cccc(C(F)(F)F)c1] | + |
| 1.562 | 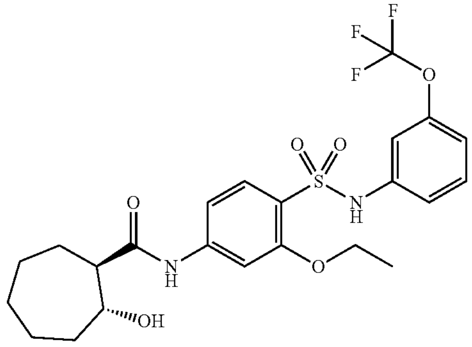 [SMILES: CCOc1cc(NC(=O)[C@@H]2CCCCC[C@H]2O)ccc1S(=O)(=O)Nc1cccc(OC(F)(F)F)c1] | +++ |
| 1.563 | 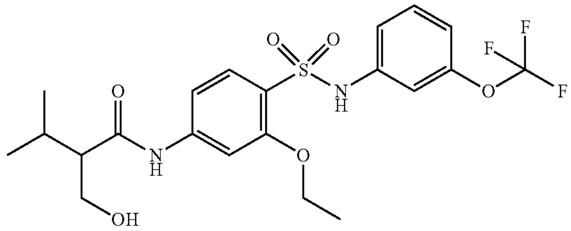 [SMILES: CCOc1cc(NC(=O)C(CO)C(C)C)ccc1S(=O)(=O)Nc1cccc(OC(F)(F)F)c1] | ++++ |

-continued
| Compound ID | Structure | Potency |
| --- | --- | --- |
| 1.564 | 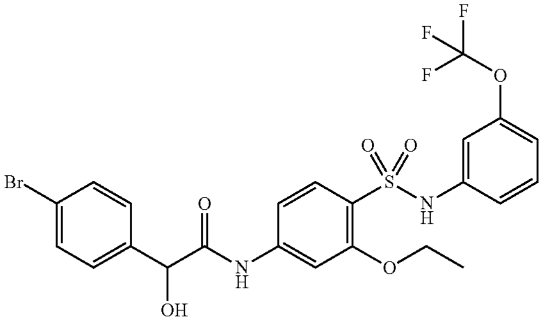 [SMILES: CCOc1cc(NC(=O)C(O)c2ccc(Br)cc2)ccc1S(=O)(=O)Nc1cccc(OC(F)(F)F)c1] | +++ |
| 1.565 | 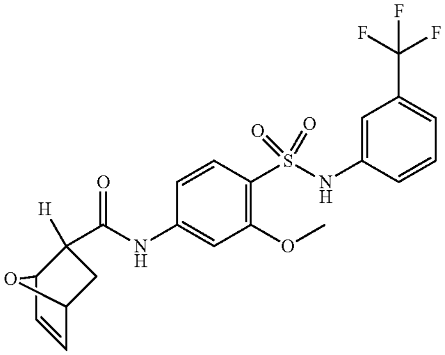 [SMILES: COc1cc(NC(=O)C2CC3C=CC2O3)ccc1S(=O)(=O)Nc1cccc(C(F)(F)F)c1] | +++ |
| 1.566 | 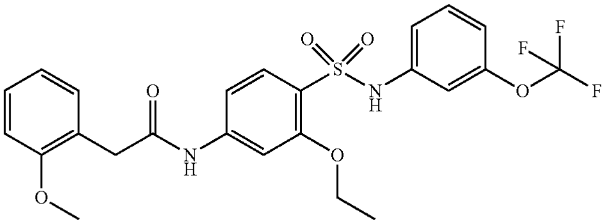 [SMILES: CCOc1cc(NC(=O)Cc2ccccc2OC)ccc1S(=O)(=O)Nc1cccc(OC(F)(F)F)c1] | +++ |
| 1.567 | 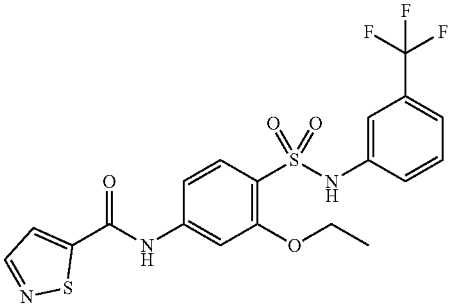 [SMILES: CCOc1cc(NC(=O)c2ccns2)ccc1S(=O)(=O)Nc1cccc(C(F)(F)F)c1] | ++++ |
| 1.568 | 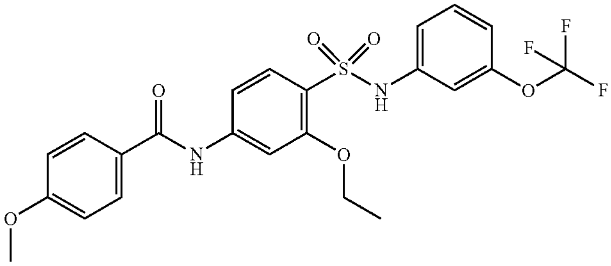 [SMILES: CCOc1cc(NC(=O)c2ccc(OC)cc2)ccc1S(=O)(=O)Nc1cccc(OC(F)(F)F)c1] | ++ |

-continued
| Compound ID | Structure | Potency |
|---|---|---|
| 1.569 | 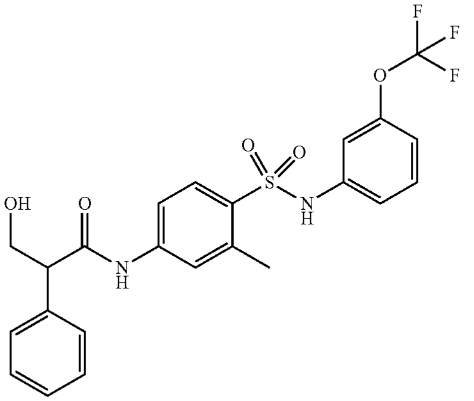 [SMILES: Cc1cc(NC(=O)C(CO)c2ccccc2)ccc1S(=O)(=O)Nc1cccc(OC(F)(F)F)c1] | +++ |
| 1.570 | 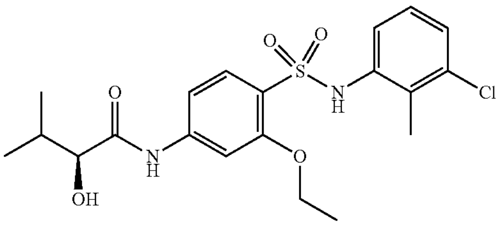 [SMILES: CCOc1cc(NC(=O)[C@@H](O)C(C)C)ccc1S(=O)(=O)Nc1cccc(Cl)c1C] | ++ |
| 1.571 | 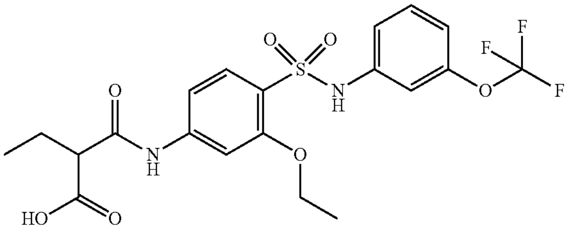 [SMILES: CCOc1cc(NC(=O)C(CC)C(=O)O)ccc1S(=O)(=O)Nc1cccc(OC(F)(F)F)c1] | ++++ |
| 1.572 | 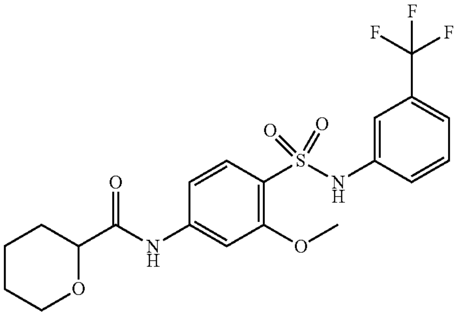 [SMILES: COc1cc(NC(=O)C2CCCCO2)ccc1S(=O)(=O)Nc1cccc(C(F)(F)F)c1] | ++ |
| 1.573 | 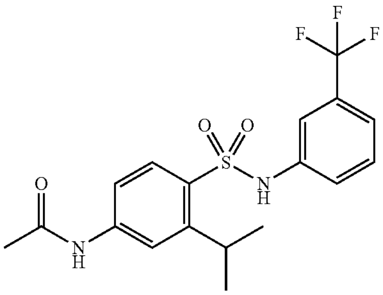 [SMILES: CC(=O)Nc1ccc(S(=O)(=O)Nc2cccc(C(F)(F)F)c2)c(C(C)C)c1] | + |

-continued
| Compound ID | Structure | Potency |
|---|---|---|
| 1.574 | 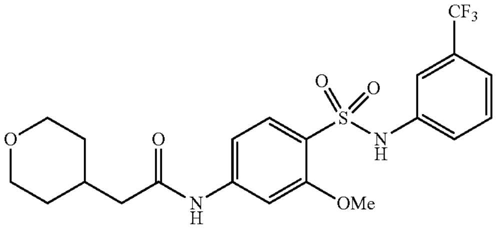 [SMILES: COc1cc(NC(=O)CC2CCOCC2)ccc1S(=O)(=O)Nc1cccc(C(F)(F)F)c1] | + |
| 1.575 | 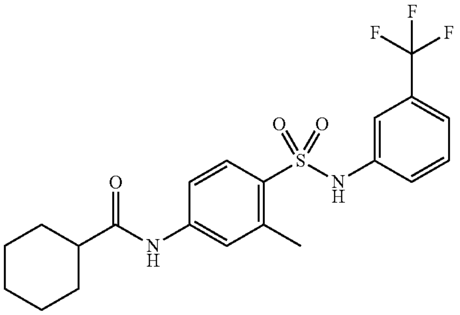 [SMILES: Cc1cc(NC(=O)C2CCCCC2)ccc1S(=O)(=O)Nc1cccc(C(F)(F)F)c1] | ++ |
| 1.576 | 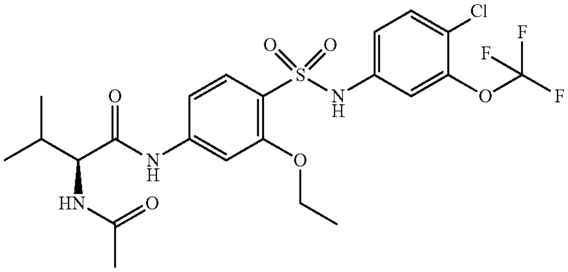 [SMILES: CCOc1cc(NC(=O)[C@@H](NC(C)=O)C(C)C)ccc1S(=O)(=O)Nc1ccc(Cl)c(OC(F)(F)F)c1] | ++++ |
| 1.577 | 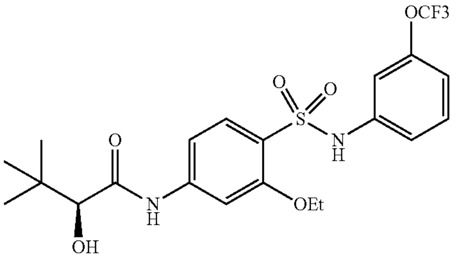 [SMILES: CCOc1cc(NC(=O)[C@@H](O)C(C)(C)C)ccc1S(=O)(=O)Nc1cccc(OC(F)(F)F)c1] | ++++ |
| 1.578 | 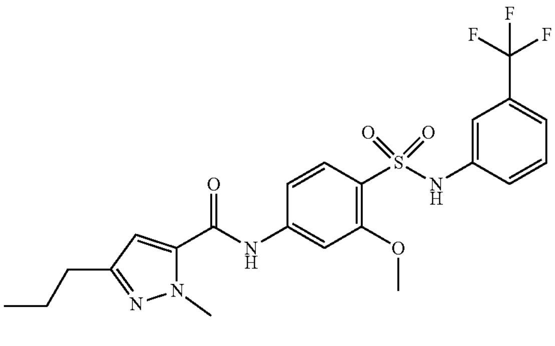 [SMILES: CCCc1cc(C(=O)Nc2ccc(S(=O)(=O)Nc3cccc(C(F)(F)F)c3)c(OC)c2)n(C)n1] | ++ |

-continued
| Compound ID | Structure | Potency |
|---|---|---|
| 1.579 | 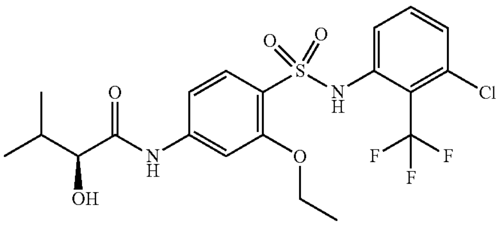 [SMILES: CCOc1cc(NC(=O)[C@@H](O)C(C)C)ccc1S(=O)(=O)Nc1cccc(Cl)c1C(F)(F)F] | + |
| 1.580 | 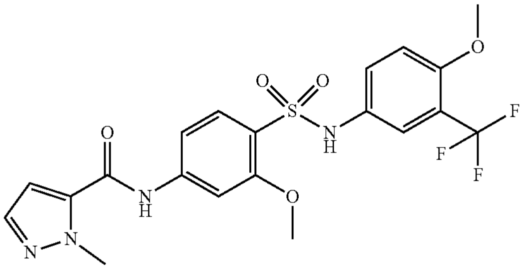 [SMILES: COc1ccc(NS(=O)(=O)c2ccc(NC(=O)c3ccnn3C)cc2OC)cc1C(F)(F)F] | +++ |
| 1.581 | 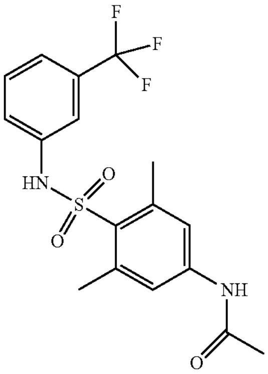 [SMILES: CC(=O)Nc1cc(C)c(S(=O)(=O)Nc2cccc(C(F)(F)F)c2)c(C)c1] | + |
| 1.582 | 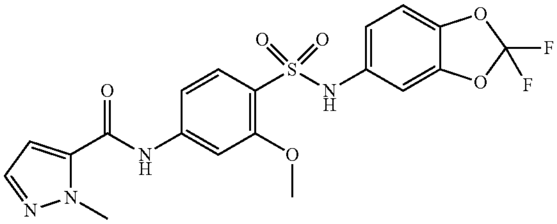 [SMILES: COc1cc(NC(=O)c2ccnn2C)ccc1S(=O)(=O)Nc1ccc2c(c1)OC(F)(F)O2] | ++ |
| 1.583 | 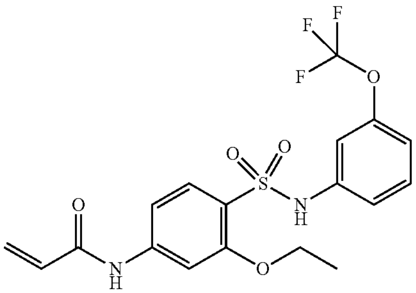 [SMILES: C=CC(=O)Nc1ccc(S(=O)(=O)Nc2cccc(OC(F)(F)F)c2)c(OCC)c1] | +++ |
+ indicates an $IC_{50}$ > 2000 nM and ≤ 20000 nM;
++ indicates an $IC_{50}$ > 750 nM and ≤ 2000 nM;
+++ indicates an $IC_{50}$ > 200 nM and ≤ 750 nM;
++++ indicates an $IC_{50}$ ≤ 200 nM;
*****

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A compound of formula (I):

(I)

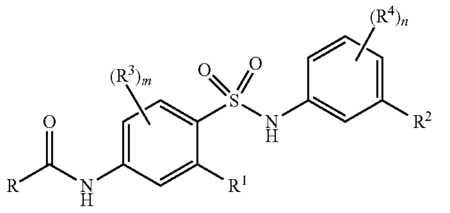

or a pharmaceutically acceptable salt thereof, wherein:

R is a member selected from the group consisting of:

i) $C_{1-8}$ alkyl which is unsubstituted or substituted with $R^5$, $R^6$ and/or $R^7$;

ii) $C_{3-7}$ cycloalkyl, having 0, 1 or 2 double bonds between ring vertices and which is substituted with 0 to 4 $R^d$;

iii) 4- to 7-membered monocyclic heterocyclic ring having 1 or 2 heteroatoms as ring vertices selected from N, O, S and $S(O)_2$, having 0, 1 or 2 double bonds between ring vertices and which is substituted with 0 to 4 $R^d$;

iv) 6- to 12-membered fused or bridged carbocyclic or heterocyclic ring having 1 to 2 heteroatoms as ring vertices selected from N, O, S and $S(O)_2$, each of which has 0, 1 or 2 double bonds between ring vertices and is substituted with 0 to 4 $R^d$;

(v) phenyl or —CO-phenyl, each of which is substituted with 0 to 4 $R^a$;

(vi) 5- or 6-membered heteroaryl ring, substituted with 0 to 3 $R^a$;

$R^1$ is a member selected from the group consisting of CN, $C_{1-8}$ haloalkyl, $C_{1-4}$ alkoxy$C_{1-4}$ alkyl, $C_{2-8}$ alkenyl, $C_{2-8}$ alkynyl, $C_{3-8}$ cycloalkyl, OH, and O—$R^{1a}$, wherein each $R^{1a}$ is independently selected from the group consisting of $C_{1-8}$ alkyl, $C_{1-8}$ haloalkyl, and $C_{3-8}$ cycloalkyl, and wherein each $R^{1a}$ is substituted with 0 to 4 members selected from the group consisting of halogen, CN, OH, amino, $C_{1-4}$ alkylamino, and di$C_{1-4}$ alkylamino;

$R^2$ is a member selected from the group consisting of H, halogen, CN, $C_{1-8}$ alkyl, $C_{1-8}$ haloalkyl, $C_{1-8}$ hydroxyalkyl, $C_{2-8}$ alkenyl, $C_{2-8}$ alkynyl, $C_{3-8}$ cycloalkyl, —$NH_2$, —NH($C_{1-4}$ alkyl), —N($C_{1-4}$ alkyl)$_2$, OH, and O—$R^{2a}$, wherein each $R^{2a}$ is independently selected from the group consisting of $C_{1-8}$ alkyl, $C_{1-8}$ haloalkyl, and $C_{3-8}$ cycloalkyl, and wherein each $R^{2a}$ is substituted with 0 to 4 members selected from the group consisting of halogen, CN, OH, amino, $C_{1-4}$ alkylamino, and di$C_{1-4}$ alkylamino;

the subscript m is 0, 1, 2 or 3;

each $R^3$ is a member selected from the group consisting of CN, $C_{1-6}$ alkyl, $C_{1-6}$ haloalkyl, $C_{1-6}$ hydroxyalkyl, $C_{3-6}$ cycloalkyl, $C_{1-6}$ alkoxy, and $C_{1-6}$ haloalkoxy;

the subscript n is 0, 1, 2, 3 or 4;

each $R^4$ is a member selected from the group consisting of halogen, CN, $C_{1-6}$ alkyl, $C_{2-8}$ alkenyl, $C_{1-6}$ haloalkyl, $C_{1-6}$ hydroxyalkyl, $C_{3-6}$ cycloalkyl, $C_{1-6}$ alkoxy, and $C_{1-6}$ haloalkoxy;

and when $R^2$ is H, then n is 1, 2, 3 or 4;

$R^5$, $R^6$ and $R^7$ are each independently selected from the group consisting of OH, $C_{1-6}$ alkyl, $C_{1-6}$ haloalkyl, $C_{1-6}$ hydroxyalkyl, $C_{1-6}$ alkoxy, $C_{2-8}$ alkenyl, $C_{2-8}$ alkynyl, $C_{1-4}$ alkoxy$C_{1-4}$ alkoxy, —X—Y, —X—$CO_2R^b$, —X—$NR^bR^c$, —X—$NR^bCOR^c$, —X—$NR^bCO_2R^c$, —X—$NR^bS(O)_2R^c$, —X—$NR^bCONR^bR^c$, and —X—$CONR^bR^c$, wherein each X is a bond or $C_{1-4}$ alkylene, and each Y is phenyl, $C_{3-7}$ cycloalkyl, $C_{5-7}$ cycloalkenyl, $C_{6-8}$ bridged cycloalkyl, $C_{6-8}$ bridged cycloalkenyl, a 4- to 7-membered heterocyclic ring having 1 or 2 heteroatoms as ring vertices selected from N, O, S and $S(O)_2$, and having 0 or 1 double bonds between ring vertices, a 6- to 12-membered fused or bridged heterocyclic ring having 1 to 2 heteroatoms as ring vertices selected from N, O, S and $S(O)_2$, and having 0, 1 or 2 double bonds between ring vertices, or a 5- or 6-membered heteroaryl ring having 1 to 3 heteroatoms as ring vertices selected from N, O, and S; and wherein each Y is unsubstituted or substituted with 1 to 4 $R^d$; or two of $R^5$, $R^6$ and $R^7$ are joined to form $C_{3-6}$ cycloalkyl;

each $R^a$ is independently selected from the group consisting of halogen, cyano, OH, $C_{1-4}$ alkyl, $C_{1-4}$ alkoxy, $C_{1-4}$ haloalkyl, $C_{1-4}$ haloalkoxy, $C_{1-4}$ hydroxyalkyl, —$NH_2$, —NH($C_{1-4}$ alkyl), —N($C_{1-4}$ alkyl)$_2$, —$CO_2H$, —$CO_2C_{1-4}$ alkyl, and $C_{3-6}$ cycloalkyl;

each $R^b$ and $R^c$ is independently selected from the group consisting of hydrogen, $C_{1-4}$ alkyl, $C_{1-4}$ haloalkyl, $C_{1-4}$ hydroxyalkyl, and $C_{3-6}$ cycloalkyl; and each $R^d$ is independently selected from the group consisting of hydroxyl, oxo, halogen, cyano, $C_{1-4}$ alkyl, $C_{1-4}$ haloalkyl, $C_{1-4}$ alkoxy, $C_{1-4}$ haloalkoxy, $C_{1-4}$ hydroxyalkyl, $C_{1-4}$ alkoxy$C_{1-4}$ alkyl, —$NH_2$, —NH($C_{1-4}$ alkyl), —N($C_{1-4}$ alkyl)$_2$, —$CO_2H$, —$CO_2C_{1-4}$ alkyl, —$COC_{1-4}$ alkyl, —$NHCO_2C_{1-4}$ alkyl, and $C_{3-6}$ cycloalkyl.

2. The compound of claim 1, or a pharmaceutically acceptable salt thereof, wherein R is $C_{1-4}$ alkyl which is unsubstituted or substituted with $R^5$, $R^6$ and/or $R^7$.

3. The compound of claim 1, or a pharmaceutically acceptable salt thereof, wherein R is $C_{3-7}$ cycloalkyl, having 0, 1 or 2 double bonds between ring vertices and which is substituted with 0 to 4 $R^d$.

4. The compound of claim 1, or a pharmaceutically acceptable salt thereof, wherein R is a 4- to 7-membered monocyclic heterocyclic ring having 1 or 2 heteroatoms as ring vertices selected from N, O, S and $S(O)_2$, having 0, 1 or 2 double bonds between ring vertices and which is substituted with 0 to 4 $R^d$.

5. The compound of claim 4, wherein R is selected from the group consisting of pyrrolidinyl, piperidinyl, tetrahydropyranyl, morpholinyl, and tetrahydrofuranyl, each of which is substituted with 0 to 4 $R^d$.

6. The compound of claim 1, or a pharmaceutically acceptable salt thereof, wherein R is phenyl or —CO-phenyl, each of which is substituted with 0 to 4 $R^a$.

7. The compound of claim 1, or a pharmaceutically acceptable salt thereof, wherein R is a 5- or 6-membered heteroaryl ring, substituted with 0 to 3 $R^a$.

8. The compound of claim 7, wherein R is selected from the group consisting of pyrrolyl, furanyl, thienyl, pyrazolyl, imidazolyl, triazolyl, 1,2-oxazolyl, 1,3-oxazolyl, 1,2-thiazolyl, 1,3-thiazolyl, 1,3-thiazolyl, pyridyl, pyrimidinyl, and pyrazinyl, each of which is substituted with 0 to 3 $R^a$.

9. The compound of claim 1, or a pharmaceutically acceptable salt thereof, wherein $R^3$ and $R^4$ are independently selected from the group consisting of CN, $C_{1-4}$ alkyl, $C_{1-4}$ haloalkyl, $C_{1-4}$ hydroxyalkyl, $C_{3-6}$ cycloalkyl, $C_{1-4}$ alkoxy, and $C_{1-4}$haloalkoxy.

10. The compound of claim 1, having formula (Ia):

(Ia)

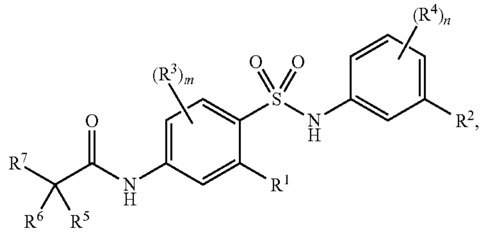

or a pharmaceutically acceptable salt thereof, wherein m is 0 or 1; and n is 0 or 1.

11. The compound of claim 1, having formula (Ia1):

(Ia1)

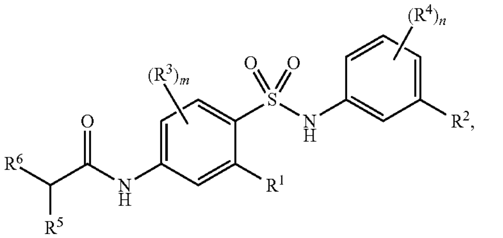

or a pharmaceutically acceptable salt thereof, wherein m is 0 or 1; and n is 0 or 1.

12. The compound of claim 1, having formula (Ia2):

(Ia2)

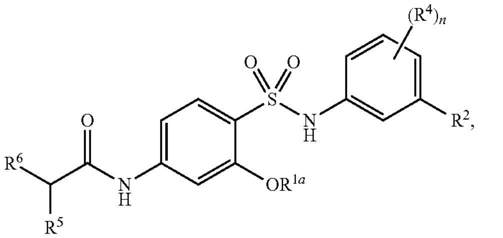

or a pharmaceutically acceptable salt thereof.

13. The compound of claim 1, having formula (Ia3):

(Ia3)

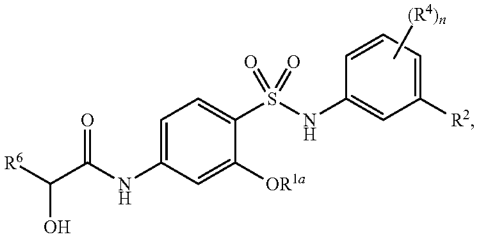

or a pharmaceutically acceptable salt thereof, wherein $R^6$ is selected from the group consisting of $C_{1-6}$ alkyl, $C_{1-6}$ haloalkyl, $C_{1-6}$ hydroxyalkyl, $C_{2-8}$ alkenyl, —X—Y, —X—$CO_2R^b$, —X—$NR^bR^c$, —X—$NR^bCOR^c$, —X—$NR^bCO_2R^c$, —X—$NR^bS(O)_2R^c$, —X—$NR^bCONR^bR^c$, and —X—$CONR^bR^c$.

14. The compound of claim 1, having formula (Ia4):

(Ia4)

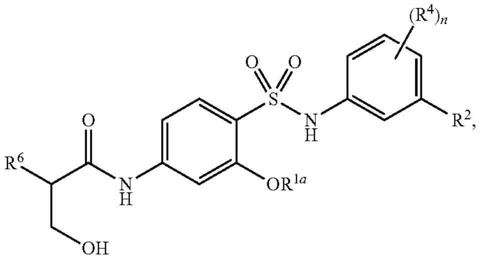

or a pharmaceutically acceptable salt thereof, wherein $R^6$ is selected from the group consisting of $C_{1-6}$ alkyl, $C_{1-6}$ haloalkyl, $C_{1-6}$ hydroxyalkyl, $C_{2-8}$ alkenyl, —X—Y, —X—$CO_2R^b$, —X—$NR^bR^c$, —X—$NR^bCOR^c$, —X—$NR^bCO_2R^c$, —X—$NR^bS(O)_2R^c$, —X—$NR^bCONR^bR^c$, and —X—$CONR^bR^c$.

15. The compound of claim 14, or a pharmaceutically acceptable salt thereof, wherein $R^6$ is selected from the group consisting of $C_{1-6}$ alkyl, $C_{1-6}$ haloalkyl, $C_{1-6}$ hydroxyalkyl, $C_{2-8}$ alkenyl, and —X—Y.

16. The compound of claim 14, or a pharmaceutically acceptable salt thereof, wherein $R^{1a}$ is methyl, ethyl or propyl; $R^2$ is $CF_3$, $OCF_3$, or cyclopropyl; the subscript n is 0 or 1; $R^4$ is halogen, $C_{1-4}$ alkyl or $C_{1-4}$ haloalkyl; and $R^6$ is selected from the group consisting of $C_{1-6}$ alkyl, $C_{1-6}$ haloalkyl, $C_{1-6}$ hydroxyalkyl, $C_{2-8}$ alkenyl, and —X—Y.

17. The compound of claim 1, wherein said compound is optically enriched (from 60-99.8% single isomer) or optically pure (>99.8% single isomer).

18. The compound of claim 1, or a pharmaceutically acceptable salt thereof, wherein $R^1$ is methoxy or ethoxy; $R^2$ is cyclopropyl, $OCF_3$, or $CF_3$; and R is selected from the group consisting of

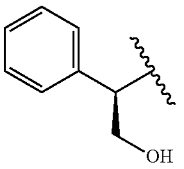
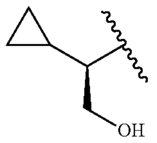
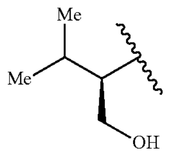
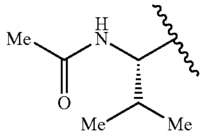
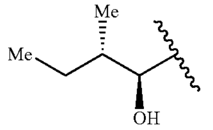

and

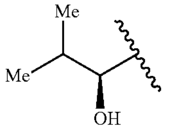

wherein the wavy line indicates the position of attachment to the remainder of the compound.

19. The compound of claim 1, selected from the group consisting of:

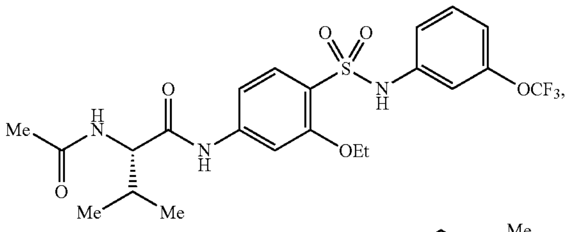

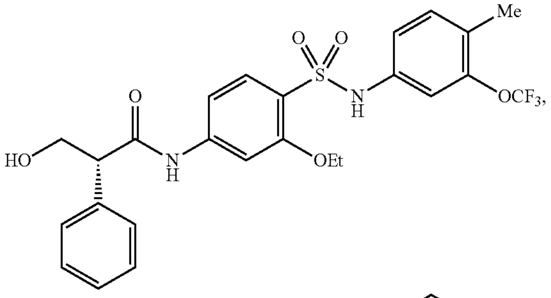

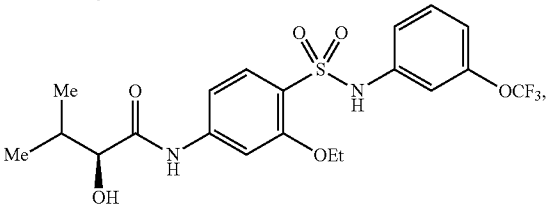

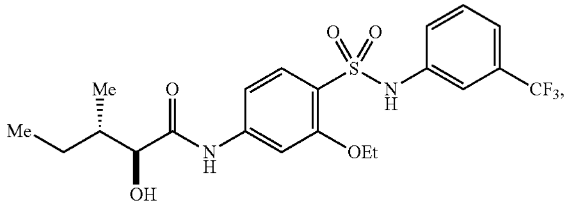

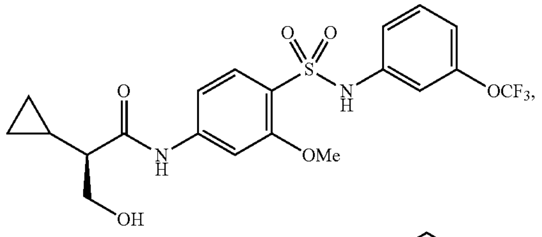

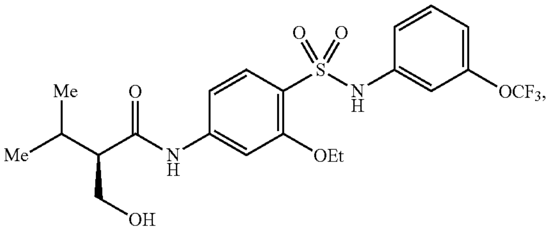

-continued

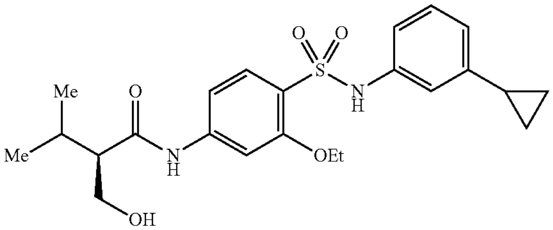

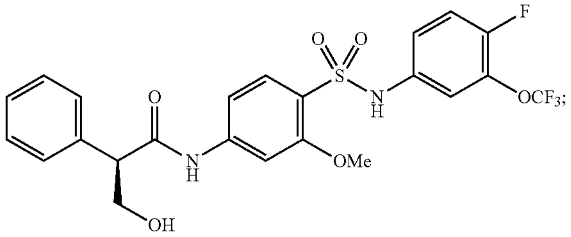

or a pharmaceutically acceptable salt thereof.

20. A pharmaceutical composition comprising a pharmaceutically acceptable excipient and a compound of claim 1.

21. A method of treating a disease or condition mediated by CXCR6 in a subject in need thereof comprising administering to said subject a therapeutically effective amount of a compound of claim 1.

22. A method of treating cancer in a subject in need thereof comprising administering to said subject a therapeutically effective amount of a compound of claim 1.

23. A method of treating autoimmune hepatitis in a subject in need thereof comprising administering to said subject a therapeutically effective amount of a compound of claim 1.

24. A method of treating myocardial ischemia or reperfusion injury in a subject in need thereof comprising administering to said subject a therapeutically effective amount of a compound of claim 1.

25. A method of treating a Th17-mediated autoimmune disease in a subject in need thereof, comprising administering to said subject a therapeutically effective amount of a compound of claim 1.

26. A method of treating inflammation in a subject in need thereof comprising administering to said subject a therapeutically effective amount of a compound of claim 1.

* * * * *